US011787836B2

(12) United States Patent
Nomura et al.

(10) Patent No.: US 11,787,836 B2
(45) Date of Patent: *Oct. 17, 2023

(54) METHOD FOR SYNTHESIZING PEPTIDE CONTAINING N-SUBSTITUTED AMINO ACID

(71) Applicant: Chugai Seiyaku Kabushiki Kaisha, Tokyo (JP)

(72) Inventors: Kenichi Nomura, Shizuoka (JP); Terushige Muraoka, Shizuoka (JP); Mikimasa Tanada, Shizuoka (JP); Takashi Emura, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/976,942

(22) Filed: Oct. 31, 2022

(65) Prior Publication Data

US 2023/0138226 A1 May 4, 2023

Related U.S. Application Data

(63) Continuation of application No. 16/619,388, filed as application No. PCT/JP2018/021998 on Jun. 8, 2018, now Pat. No. 11,542,299.

(30) Foreign Application Priority Data

Jun. 9, 2017 (JP) ................................. 2017-114073

(51) Int. Cl.
*C07K 11/02* (2006.01)
*C07K 1/06* (2006.01)

(52) U.S. Cl.
CPC .............. *C07K 1/061* (2013.01); *C07K 11/02* (2013.01)

(58) Field of Classification Search
CPC .......... C07K 1/061; C07K 11/02; C07K 7/64; C07K 1/04; C07K 1/06; Y02P 20/55
See application file for complete search history.

(56) References Cited

U.S. PATENT DOCUMENTS

| | | |
|---|---|---|
| 4,670,607 A | 6/1987 | Maeda et al. |
| 4,859,736 A | 8/1989 | Rink |
| 4,950,418 A | 8/1990 | Yajima et al. |
| 5,057,415 A | 10/1991 | Schuetz et al. |
| 5,059,679 A | 10/1991 | Yajima et al. |
| 6,127,550 A | 10/2000 | Grondard et al. |
| 7,288,372 B2 | 10/2007 | Olejnik et al. |
| 7,439,222 B2 | 10/2008 | Guinn et al. |
| 8,518,666 B2 | 8/2013 | Wang et al. |
| 8,809,280 B2 | 8/2014 | Strom et al. |
| 9,133,245 B2 | 9/2015 | Gao et al. |
| 9,409,952 B2 | 8/2016 | Kariyuki et al. |
| 9,701,993 B2 | 7/2017 | Suga et al. |
| 10,711,268 B2 | 7/2020 | Murakami et al. |
| 11,542,299 B2* | 1/2023 | Nomura ............... C07K 11/02 |
| 2003/0219780 A1 | 11/2003 | Olejnik et al. |
| 2005/0065068 A1 | 3/2005 | Kumagai et al. |
| 2005/0165217 A1 | 7/2005 | Guinn et al. |
| 2008/0044854 A1 | 2/2008 | Wang et al. |
| 2008/0221303 A1 | 9/2008 | Katzhendler et al. |
| 2010/0137561 A1 | 6/2010 | Chen |
| 2010/0197891 A1 | 8/2010 | Giraud et al. |
| 2010/0292435 A1 | 11/2010 | Chen et al. |
| 2013/0035296 A1 | 2/2013 | Strom et al. |
| 2013/0217599 A1 | 8/2013 | Suga et al. |
| 2014/0194369 A1 | 7/2014 | Gao et al. |
| 2015/0080549 A1 | 3/2015 | Kariyuki et al. |
| 2016/0272964 A1 | 9/2016 | Murakami et al. |
| 2016/0311858 A1 | 10/2016 | Kariyuki et al. |
| 2018/0127761 A1 | 5/2018 | Ohta et al. |
| 2019/0338050 A1 | 11/2019 | Nakano et al. |
| 2020/0040372 A1 | 2/2020 | Tanaka et al. |
| 2020/0131669 A1 | 4/2020 | Muraoka et al. |
| 2020/0277327 A1 | 9/2020 | Nomura et al. |
| 2020/0339623 A1 | 10/2020 | Nomura et al. |

(Continued)

FOREIGN PATENT DOCUMENTS

| | | |
|---|---|---|
| CN | 1317011 A | 10/2001 |
| CN | 103764666 A | 4/2014 |

(Continued)

OTHER PUBLICATIONS

U.S. Appl. No. 14/368,564, filed Dec. 28, 2012, Kariyuki, et al.
U.S. Appl. No. 15/166,550, filed May 27, 2016, Kariyuki, et al.
U.S. Appl. No. 15/557,532, filed Sep. 12, 2017, Ohta, et al.
U.S. Appl. No. 16/081,522, filed Mar. 3, 2017, Nakano, et al.
U.S. Appl. No. 16/479,736, filed Jan. 31, 2018, Tanaka, et al.
U.S. Appl. No. 16/771,335, filed Dec. 14, 2018, Nomura, et al.
U.S. Appl. No. 17/011,815, filed Sep. 3, 2020, Kariyuki, et al.
U.S. Appl. No. 17/024,944, filed Sep. 18, 2020, Ohta, et al.

(Continued)

*Primary Examiner* — Sudhakar Katakam

(74) *Attorney, Agent, or Firm* — Nixon & Vanderhye P.C.

(57) ABSTRACT

Methods of producing a peptide containing an N-substituted amino acid or N-substituted amino acid analog of the present invention include the steps of: preparing an Fmoc-protected amino acid, an Fmoc-protected amino acid analog, or an Fmoc-protected peptide; deprotecting a protecting group which have an Fmoc skeleton of the Fmoc-protected amino acid and such by using a base; and forming an amide bond by adding a new Fmoc-protected amino acid and such; and when the peptide is produced by a solid-phase method, the obtained peptide is cleaved off from the solid phase under conditions of weaker acidity than TFA. Furthermore, at least one side chain of the obtained peptide has a protecting group that is not deprotected under basic conditions and is deprotected under conditions of weaker acidity than TFA.

12 Claims, 16 Drawing Sheets

(56) References Cited

U.S. PATENT DOCUMENTS

| | | |
|---|---|---|
| 2021/0061860 A1 | 3/2021 | Kariyuki et al. |
| 2021/0087572 A1 | 3/2021 | Ohta et al. |

FOREIGN PATENT DOCUMENTS

| | | |
|---|---|---|
| EP | 1277755 A1 | 1/2003 |
| EP | 1424395 A1 | 6/2004 |
| EP | 1964916 A1 | 9/2008 |
| EP | 2088202 A1 | 8/2009 |
| EP | 2141175 A1 | 1/2010 |
| EP | 2177533 A1 | 4/2010 |
| EP | 2380596 A1 | 10/2011 |
| EP | 2492344 A1 | 8/2012 |
| EP | 2610348 A1 | 7/2013 |
| EP | 2615455 A1 | 7/2013 |
| EP | 2088202 B1 | 8/2013 |
| EP | 2647720 A1 | 10/2013 |
| EP | 2813512 A1 | 12/2014 |
| EP | 2492344 B1 | 4/2016 |
| EP | 3031915 A1 | 6/2016 |
| EP | 2141175 B1 | 7/2016 |
| EP | 3031915 B1 | 3/2019 |
| JP | S57159747 A | 10/1982 |
| JP | S60169451 A | 9/1985 |
| JP | S62289 A | 1/1987 |
| JP | S62143698 A | 6/1987 |
| JP | S63260946 A | 10/1988 |
| JP | H01222795 A | 9/1989 |
| JP | H01250396 A | 10/1989 |
| JP | H0259146 B2 | 12/1990 |
| JP | H0681759 B2 | 10/1994 |
| JP | 2513775 B2 | 7/1996 |
| JP | 2001048866 A | 2/2001 |
| JP | 2003508408 A | 3/2003 |
| JP | 2003531199 A | 10/2003 |
| JP | 2005095013 A | 4/2005 |
| JP | 2007319064 A | 12/2007 |
| JP | 2008125396 A | 6/2008 |
| JP | 2009096791 A | 5/2009 |
| JP | 2009528824 A | 8/2009 |
| JP | 4490663 B2 | 6/2010 |
| JP | 4502293 B2 | 7/2010 |
| JP | 2011139667 A | 7/2011 |
| JP | 2012506909 A | 3/2012 |
| JP | 2012510486 A | 5/2012 |
| JP | 2012525348 A | 10/2012 |
| JP | 5200241 B2 | 6/2013 |
| JP | 5592893 B2 | 9/2014 |
| JP | 5808882 B2 | 11/2015 |
| JP | 2018509172 A | 4/2018 |
| WO | WO9831700 A1 | 7/1998 |
| WO | WO0002898 A1 | 1/2000 |
| WO | WO0181325 A2 | 11/2001 |
| WO | WO02085923 A2 | 10/2002 |
| WO | WO03014354 A1 | 2/2003 |
| WO | WO03068990 A1 | 8/2003 |
| WO | WO03089454 A2 | 10/2003 |
| WO | WO2005063791 A2 | 7/2005 |
| WO | WO2007066627 A1 | 6/2007 |
| WO | WO2007103307 A2 | 9/2007 |
| WO | WO2007120614 A2 | 10/2007 |
| WO | WO2008117833 A1 | 10/2008 |
| WO | WO2010053050 A1 | 5/2010 |
| WO | WO2010062590 A2 | 6/2010 |
| WO | WO2010063604 A1 | 6/2010 |
| WO | WO2010125079 A2 | 11/2010 |
| WO | WO2011049157 A1 | 4/2011 |
| WO | WO2011051692 A1 | 5/2011 |
| WO | WO2011058122 A1 | 5/2011 |
| WO | WO2012026566 A1 | 3/2012 |
| WO | WO2012033154 A1 | 3/2012 |
| WO | WO2012074130 A1 | 6/2012 |
| WO | WO2012122059 A1 | 9/2012 |
| WO | WO2012171982 A1 | 12/2012 |
| WO | WO2013100132 A1 | 7/2013 |
| WO | WO2014033466 A1 | 3/2014 |
| WO | WO2014181888 A1 | 11/2014 |
| WO | WO2015019192 A2 | 2/2015 |
| WO | WO2015019999 A1 | 2/2015 |
| WO | WO2015155676 A1 | 10/2015 |
| WO | WO2015179434 A1 | 11/2015 |
| WO | WO2015185162 A1 | 12/2015 |
| WO | WO2016115168 A1 | 7/2016 |
| WO | WO2016148044 A1 | 9/2016 |
| WO | WO2016154675 A1 | 10/2016 |
| WO | WO2017150732 A1 | 9/2017 |
| WO | WO2017181061 A1 | 10/2017 |
| WO | WO2018100561 A1 | 6/2018 |
| WO | WO2018143145 A1 | 8/2018 |
| WO | WO2018225864 A1 | 12/2018 |
| WO | WO2019117274 A1 | 6/2019 |
| WO | WO2020095983 A1 | 5/2020 |
| WO | WO2020111238 A1 | 6/2020 |
| WO | WO2020122182 A1 | 6/2020 |
| WO | WO2020138336 A1 | 7/2020 |
| WO | WO2020189540 A1 | 9/2020 |
| WO | WO2021132545 A1 | 7/2021 |

OTHER PUBLICATIONS

U.S. Appl. No. 17/291,099, filed Jun. 3, 2021, Ishizawa.
U.S. Appl. No. 17/297,231, filed May 26, 2021, Iwasaki et al.
U.S. Appl. No. 17/312,296, filed Jun. 9, 2021, Muraoka et al.
U.S. Appl. No. 17/417,822, filed Jun. 24, 2021, Shinohara et al.
U.S. Appl. No. 17/437,535, filed Sep. 9, 2021, Wadamoto.
Albericio, F., et al., "Fmoc Methodology: Cleavage from the Resin and Final Deprotection," Amino Acids, Peptides and Proteins in Organic Chemistry, 3:349-369 (2011).
Behrendt, R., et al., "Advances in Fmoc solid-phase peptide synthesis," J Pept Sci., 22:4-27 (2016).
Bock, J. E., et al., "Getting in Shape: Controlling Peptide Bioactivity and Bioavailability Using Conformational Constraints," ACS Chem Biol., 8:488-499 (2013).
Carpino, L. A., et al., "Dramatically enhanced N → O acyl migration during the trifluoroacetic acid-based deprotection step in solid phase peptide synthesis," Tetrahedron Letters, 46:1361-1364 (2005).
Chatterjee, J., et al., "N-Methylation of Peptides: A New Perspective in Medicinal Chemistry," Acc Chem Res., 41(10):1331-1342 (2008).
Eberhard, H. and Seitz, O., "N → O-Acyl shift in Fmoc-based synthesis of phosphopeptides," Org Biomol Chem., 6:1349-1355 (2008).
Fang, W.-J., et al., "Deletion of Ac-NMePhe From [NMePhe]arodyn Under Acidic Conditions, Part 1: Effects of Cleavage Conditions and N-Terminal Functionality," PeptideScience, 96(1):97-102 (2011).
Gracia, S. R., et al., "Synthesis of chemically modified bioactive peptides: recent advances, challenges and developments for medicinal chemistry," Future Med Chem., 1(7):1289-1310 (2009).
International Search Report dated Sep. 4, 2018 in International Application No. PCT/JP2018/021998.
Josephson, K., et al., "mRNA display: from basic principles to macrocycle drug discovery," Drug Discov Today, 19(4):388-399 (2014).
Marcucci, E., et al., "Solid-Phase Synthesis of NMe-IB-01212, a Highly N-Methylated Cyclic Peptide," Org Lett., 14(2):612-615 (2012).
Rodriguez, H., et al., "A convenient microwave-enhanced solid-phase synthesis of short chain N-methyl-rich peptides," J Pept Sci., 16:136-140 (2010).
Roodbeen, R., et al., "Microwave Heating in the Solid-Phase Synthesis of N-Methylated Peptides: When Is Room Temperature Better?" Eur J Org Chem., 2012:7106-7111 (2012).
Teixidó, M., et al., "Solid-phase synthesis and characterization of N-methyl-rich peptides," J Peptide Res., 65:153-166 (2005).
Urban, J., et al., "Lability of N-alkylated peptides towards TFA cleavage," Int J Peptide Protein Res., 47:182-189 (1996).
Wenschuh, H., et al., "Stepwise Automated Solid Phase Synthesis of Naturally Occurring Peptaibols Using FMOC Amino Acid Fluorides," J Org Chem., 60:405-410 (1995).

(56) References Cited

OTHER PUBLICATIONS

Alvaro, et al., "A Novel Activity of Immobilized Penicillin G Acylase: Removal of Benzyloxycarbonyl Amino Protecting Group," Biocatalysis and Biotransformation, 18(3):253-238 (2000).
Beck, J.G., et al., "Intestinal Permeability of Cyclic Peptides: Common Key Backbone Motifs Identified," Journal of the American Chemical Society, 134(29):12125-12133 (2012).
Brunner, J., "Biosynthetic Incorporation of Non-natural Amino Acids into Proteins," Chemical Society Reviews, 22(3):183-189 (1993).
Chen, J.F., et al., "Effect of Alanine-293 Replacement on the Activity, ATP Binding, and Editing of *Escherichia coli* Leucyl-tRNA Synthetase," Biochemistry, 40(5):1144-1149 (2001).
Chen, S., et al., "Structurally Diverse Cyclisation Linkers Impose Different Backbone Conformations in Bicyclic Peptides," Chembiochem, 13(7):1032-1038 (2012).
Cusack, S., et al., "The 2 A Crystal Structure of Leucyl-tRNA Synthetase and Its Complex With a Leucyl-Adenylate Analogue," The EMBO Journal, 19(10):2351-2361 (2000).
Dawson, P.E., et al., "Synthesis of Proteins by Native Chemical Ligation," Science, 266(5186):776-779 (1994).
Doi, Y., et al., "Elongation Factor Tu Mutants Expand Amino Acid Tolerance of Protein Biosynthesis System," Journal of the American Chemical Society, 129(46):14458-14462 (2007).
Doublie, S., et al., "Tryptophanyl-tRNA Synthetase Crystal Structure Reveals an Unexpected Homology to Tyrosyl-tRNA Synthetase," Structure, 3(1):17-31 (1995).
Frankel, A., et al., "Encodamers: Unnatural Peptide Oligomers Encoded in RNA," Chemistry & Biology, 10(11):1043-1050 (2003).
Fujino, T., et al., "Reevaluation of the D-Amino Acid Compatibility With the Elongation Event in Translation," Journal of the American Chemical Society, 135(5):1830-1837 (2013).
Fujino, T., et al., "Ribosomal Synthesis of Peptides with Multiple beta-Amino Acids," Journal of the American Chemical Society, 138(6):1962-1969 (2016).
Fukai, S., et al., "Mechanism of Molecular Interactions for tRNA(Val) Recognition by Valyl-tRNA Synthetase," RNA, 9(1):100-111 (2003).
Fukai, S., et al., "Structural Basis for Double-Sieve Discrimination of L-Valine From L-Isoleucine and L-Threonine by the Complex of tRNA(Val) and Valyl-tRNA Synthetase," Cell, 103(5):793-803 (2000).
Fukunaga, R. and Yokoyama, S., "Structural Basis for Non-Cognate Amino Acid Discrimination by the Valyl-tRNA Synthetase Editing Domain," The Journal of Biological Chemistry, 280(33):29937-29945 (2005).
Ganesan, A., "The Impact of Natural Products Upon Modern Drug Discovery," Current Opinion in Chemical Biology, 12(3):306-317 (2008).
Genbank, "Valine-tRNA ligase [Thermus thermophilus]," Accession No. P96142, accessed on Jan. 27, 2021.
Gilon, C., et al., "Backbone Cyclization: A New Method for Conferring Conformational Constrainton Peptides," Biopolymers, 31(6):745-750 (1991).
Goto, et al., "Ribosomal Synthesis of Combinatorial Polypeptides containing unusual amino acid blocks," Kagaku Kogyo, 58(4):255-62 (2007).
Goto, Y. and Suga, H., "Translation Initiation With Initiator tRNA Charged With Exotic Peptides," Journal of the American Chemical Society, 131(14):5040-5041 (2009).
Goto, Y., et al., "Flexizymes for Genetic Code Reprogramming," Nature Protocols, 6(6):779-790 (2011).
Hartman, M.C., et al., "An Expanded Set of Amino Acid Analogs for the Ribosomal Translation of Unnatural Peptides," PLoS One, 2(10):e972 (2007).
Hartman, M.C., et al., "Enzymatic Aminoacylation of tRNA With Unnatural Amino Acids," Proceedings of the National Academy of Sciences of the United States of America, 103(12):4356-4361 (2006).
Hayashi, G., et al., "Ribosomal Synthesis of Nonstandard Cyclic Peptides and Its Application to Drug Discovery," The Journal of Japanese Biochemical Society, 82(6):505-514 (2010).

Hecht, S.M., et al., ""Chemical Aminoacylation" of tRNA's," The Journal of Biological Chemistry, 253(13):4517-4520 (1978).
Heinis, C., et al., "Phage-Encoded Combinatorial Chemical Libraries Based on Bicyclic Peptides," Nature Chemical Biology, 5(7):502-507 (2009).
Higuchi, T. and Suga, H., "Programmed Synthesis of Natural Product-Like Non-Standard Peptides Using the Translation System and Its Application," Journal of Synthetic Organic Chemistry, 68(3):217-227 (2010).
Hoogenboom, H.R., "Selecting and Screening Recombinant Antibody Libraries," Nature Biotechnology, 23(9):1105-1116 (2005).
Hountondji, C., et al., "Crucial Role of Conserved Lysine 277 in the Fidelity of tRNA Aminoacylation by *Escherichia coli* Valyl-tRNA Synthetase," Biochemistry, 41(50):14856-14865 (2002).
Hountondji, C., et al., "Valyl-tRNA Synthetase From *Escherichia coli* MALDI-MS Identification of the Binding Sites for L-Valine or for Noncognate Amino Acids Upon Qualitative Comparative Labeling With Reactive Amino-Acid Analogs," European Journal of Biochemistry, 267(15):4789-4798 (2000).
Hruby, V.J., et al., "Emerging Approaches in the Molecular Design of Receptor-Selective Peptide Ligands: Conformational, Topographical and Dynamic Considerations," The Biochemical Journal, 268(2):249-262 (1990).
Itoh, Y., et al., "Crystallographic and Mutational Studies of Seryl-tRNA Synthetase From the Archaeon Pyrococcus Horikoshii," RNA Biology, 5(3):169-177 (2008).
Josephson, K., et al., "Ribosomal Synthesis of Unnatural Peptides," Journal of the American Chemical Society, 127(33):11727-11735 (2005).
Kato, et al., "Enzymes Involved in Drug Metabolism and Reaction Mechanisms Thereof," Yakubutsutaishagaku, 2nd edition, 9-13 (2000).
Kato, et al., "Enzymes Involved in Drug Metabolism and Reaction Mechanisms Thereof," Yakubutsutaishaga, 3rd edition, 43-46 (2010).
Katoh, T., et al., "Ribosomal Synthesis of Backbone Macrocyclic Peptides," Chemical Communications, 47(36):9946-9958 (2011).
Kawakami, et al., "Incorporation of electrically charged N-alkyl amino acids into ribosomally synthesized peptides via post-translational conversion," Chemical Science, 5(3):887-93 (2014).
Kawakami, T. and Aimoto, S., "Sequential Peptide Ligation by Using a Controlled Cysteinyl Prolyl Ester (CPE) Autoactivating Unit," Tetrahedron Letters, 48(11):1903-1905 (2007).
Kawakami, T., et al., "Diverse Backbone-Cyclized Peptides via Codon Reprogramming," Nature Chemical Biology, 5(12):888-890 (2009).
Kawakami, T., et al., "In Vitro Selection of Multiple Libraries Created by Genetic Code Reprogramming to Discover Macrocyclic Peptides That Antagonize VEGFR2 Activity in Living Cells," ACS Chemical Biology, 8(6):1205-1214 (2013).
Kawakami, T., et al., "Messenger RNA-Programmed Incorporation of Multiple N-Methyl-Amino Acids Into Linear and Cyclic Peptides," Chemistry & Biology, 15(1):32-42 (2008).
Kawakami, T., et al., "Ribosomal Synthesis of Polypeptoids and Peptoid-Peptide Hybrids," Journal of the American Chemical Society, 130(50):16861-16863 (2008).
Kleineweischede, R. and Hackenberger, C.P., "Chemoselective Peptide Cyclization by Traceless Staudinger Ligation," Angew Chem Int Ed., 47(32):5984-5988 (2008).
Kobayashi, T., et al., "Recognition of Non-Alpha-Amino Substrates by pyrrolysyl-tRNA Synthetase," Journal of Molecular Biology, 385(5):1352-1360 (2009).
Lassak, J., et al., "Stall No More at Polyproline Stretches With the Translation Elongation Factors EF-P and IF-5A," Molecular Microbiology, 99(2):219-235 (2016).
Laufer, B., et al., "The Impact of Amino Acid Side Chain Mutations in Conformational Design of Peptides and Proteins," Chemistry, 16(18):5385-5390 (2010).
Lee, K.W. and Briggs, J.M., "Molecular Modeling Study of the Editing Active Site of *Escherichia coli* leucyl-tRNA Synthetase: Two Amino Acid Binding Sites in the Editing Domain," Proteins, 54(4):693-704 (2004).
Li, S., et al., "In Vitro Selection of mRNA Display Libraries Containing an Unnatural Amino Acid," Journal of the American Chemical Society, 124(34):9972-9973 (2002).

(56) References Cited

OTHER PUBLICATIONS

Li, X., et al., "Salicylaldehyde Ester-Induced Chemoselective Peptide Ligations: Enabling Generation of Natural Peptidic Linkages at the Serine/Threonine Sites," Organic Letters, 12(8):1724-1727 (2010).
Liu, D.R., et al., "Engineering a tRNA and aminoacyl-tRNA Synthetase for the Site-Specific Incorporation of Unnatural Amino Acids Into Proteins in Vivo," Proceedings of the National Academy of Sciences of the United States of America, 94(19):10092-10097 (1997).
Lodder, M., et al., "The N-Pentenoyl Protecting Group for Aminoacyl-tRNAs," Methods, 36(3):245-251 (2005).
Loos, P., et al., "Unified Azoline and Azole Syntheses by Optimized Aza-Wittig Chemistry," European Journal of Organic Chemistry, 2013(16):3290-3315 (2013).
Low, K. E., et al., "Rational Design of Calpain Inhibitors Based on Calpastatin Peptidomimetics," J Med Chem., 59:5403-5415 (2016).
Lundquist, J.T. and Pelletier, J.C., "Improved Solid-Phase Peptide Synthesis Method Utilizing Alpha-Azide-Protected Amino Acids," Organic Letters, 3(5):781-783 (2001).
Maini, R., et al., "Protein Synthesis With Ribosomes Selected for the Incorporation of beta-Amino Acids," Biochemistry, 54(23):3694-3706 (2015).
Maini, R., et al., "Ribosome-Mediated Synthesis of Natural Product-Like Peptides via Cell-Free Translation," Current Opinion in Chemical Biology, 34:44-52 (2016).
Mas-Moruno, C., et al., "Cilengitide: The First Anti-Angiogenic Small Molecule Drug Candidate Design, Synthesis, and Clinical Evaluation," Anti-Cancer Agents in Medicinal Chemistry, 10(10):753-768 (2010).
Meinnel, T., et al., "Methionine as Translation Start Signal: A Review of the Enzymes of the Pathway in *Escherichia coli*," Biochimie, 75(12):1061-1075 (1993).
Mermershtain, I., et al., "Idiosyncrasy and Identity in the Prokaryotic Phe-system: Crystal Structure of *E. coli* phenylalanyl-tRNA Synthetase Complexed With Phenylalanine and AMP," Protein Science, 20(1):160-167 (2011).
Merryman, C. and Green, R., "Transformation of Aminoacyl tRNAs for the in Vitro Selection of "Drug-Like" Molecules," Chemistry & Biology, 11(4):575-582 (2004).
Millward, S.W., et al., "A General Route for Post-Translational Cyclization of mRNA Display Libraries," Journal of the American Chemical Society, 127(41):14142-14143 (2005).
Millward, S.W., et al., "Design of Cyclic Peptides That Bind Protein Surfaces With Antibody-Like Affinity," ACS Chemical Biology, 2(9):625-634 (2007).
Montalbetti, C.A.G.N. and Falque, V., "Amide Bond Formation and Peptide Coupling," Tetrahedron, 61 (46):10827-10852 (2005).
Ohta, A., et al., "Synthesis of Polyester by Means of Genetic Code Reprogramming," Chemistry & Biology, 14(12):1315-1322 (2007).
Ohtsuki, T., et al., "Phototriggered Protein Syntheses by Using (7-diethylaminocoumarin-4-yl)Methoxycarbonyl-Caged Aminoacyl tRNAs," Nature Communications, 7:12501 (2016).
Ovadia, O., et al., "Improvement of Drug-Like Properties of Peptides: The Somatostatin Paradigm," Expert Opinion on Drug Discovery, 5(7):655-671 (2010).
Parthasarathy, R., et al., "Sortase A as a Novel Molecular "Stapler" for Sequence-Specific Protein Conjugation," Bioconjugate Chemistry, 18(2):469-476 (2007).
Peacock, J.R., et al., "Amino Acid-Dependent Stability of the Acyl Linkage in aminoacyl-tRNA," RNA, 20(6):758-764 (2014).
Perona, J.J. and Hadd, A., "Structural Diversity and Protein Engineering of the aminoacyl-tRNA Synthetases," Biochemistry, 51(44):8705-8729 (2012).
Reddy, P.R., et al., "Synthesis of Small Cyclic Peptides via Intramolecular Heck Reactions," Tetrahedron Letters, 44(2):353-356 (2003).
Rezai, T., et al., "Testing the Conformational Hypothesis of Passive Membrane Permeability Using Synthetic Cyclic Peptide Diastereomers," Journal of the American Chemical Society, 128(8):2510-2511 (2006).

Sankaranarayanan, R., et al., "The Structure of threonyl-tRNA synthetase-tRNA(Thr) Complex Enlightens Its Repressor Activity and Reveals an Essential Zinc Ion in the Active Site," Cell, 97(3):371-381 (1999).
Satyanarayanajois, S.D. and Hill, R.A., "Medicinal Chemistry for 2020," Future Medicinal Chemistry, 3(14):1765-1786 (2011).
Schlippe, Y.V.G., et al., "In Vitro Selection of Highly Modified Cyclic Peptides That Act as Tight Binding Inhibitors," Journal of the American Chemical Society, 134(25):10469-10477, (2012).
Sever, S., et al., "*Escherichia coli* tryptophanyl-tRNA Synthetase Mutants Selected for Tryptophan Auxotrophy Implicate the Dimer Interface in Optimizing Amino Acid Binding," Biochemistry, 35(1):32-40 (1996).
Shimizu, Y., et al., "Cell-Free Translation Reconstituted With Purified Components," Nature Biotechnology, 19(8):751-755 (2001).
Shukla, G.S. and Krag, D.N., "Phage-Displayed Combinatorial Peptide Libraries in Fusion to Beta-Lactamase as Reporter for an Accelerated Clone Screening: Potential Uses of Selected Enzyme-Linked Affinity Reagents in Downstream Applications," Combinatorial Chemistry & High Throughput Screening, 13(1):75-87 (2010).
Starosta, A.L., et al., "A Conserved Proline Triplet in Val-tRNA Synthetase and the Origin of Elongation Factor P," Cell Reports, 9(2):476-483 (2014).
Subtelny, A.O., et al., "Optimal Codon Choice Can Improve the Efficiency and Fidelity of N-methyl Amino Acid Incorporation Into Peptides by In-Vitro Translation," Angewandte Chemie, 50(14):3164-3167 (2011).
Subtelny, A.O., et al., "Ribosomal Synthesis of N-Methyl Peptides," Journal of the American Chemical Society, 130(19):6131-6136 (2008).
Tan, Z., et al., "Amino Acid Backbone Specificity of the *Escherichia coli* Translation Machinery," Journal of the American Chemical Society, 126(40):12752-12753 (2004).
Terasaka, et al., "Construction of Nonstandard Peptide Library by Genetic Code Reprogramming and Bioactive Peptide Discovery," Experimental Medicine, 29(7):1063-1070 (2011).
Terasaka, N., et al., "Recent Developments of Engineered Translational Machineries for the Incorporation of Non-Canonical Amino Acids Into Polypeptides," International Journal of Molecular Sciences, 16(3):6513-6531 (2015).
Tsukiji, S. and Nagamune, T., "Sortase-mediated Ligation: A Gift From Gram-positive Bacteria to Protein Engineering," Chembiochem, 10(5):787-798 (2009).
Wang, J., et al., "Kinetics of Ribosome-Catalyzed Polymerization Using Artificial Aminoacyl-tRNA Substrates Clarifies Inefficiencies and Improvements," ACS Chemical Biology, 10(10):2187-2192 (2015).
Wells, J.A. and McClendon, C.L., "Reaching for High-Hanging Fruit in Drug Discovery at Protein-Protein Interfaces," Nature, 450(7172):1001-1009 (2007).
White, C.J. and Yudin, A.K., "Contemporary Strategies for Peptide Macrocyclization," Nature Chemistry, 3(7):509-524 (2011).
White, T.R., et al., "On-Resin N-methylation of Cyclic Peptides for Discovery of Orally Bioavailable Scaffolds," Nature Chemical Biology, 7(11):810-817 (2011).
Wu, N., et al., "A Genetically Encoded Photocaged Amino Acid," Journal of the American Chemical Society, 126(44):14306-14307 (2004).
Yamagishi, Y., et al., "Natural Product-Like Macrocyclic N-Methyl-Peptide Inhibitors Against a Ubiquitin Ligase Uncovered From a Ribosome-Expressed De Novo Library," Chemistry & Biology, 18(12):1562-1570 (2011).
Yanagisawa, T., et al., "Multistep Engineering of Pyrrolysyl-tRNA Synthetase to Genetically Encode N(epsilon)-(o-azidobenzyloxycarbonyl) Lysine for Site-Specific Protein Modification," Chemistry & Biology, 15(11):1187-1197 (2008).
Yang, Y., "Redundant Amino Acid Coupling Side Reactions," Side Reactions in Peptide Synthesis, 246 (2016).
Zhai, Y. and Martinis, S.A., "Two Conserved Threonines Collaborate in the *Escherichia coli* Leucyl-tRNA Synthetase Amino Acid Editing Mechanism," Biochemistry, 44(47):15437-15443 (2005).

(56) References Cited

OTHER PUBLICATIONS

Zhang, B., et al., "Specificity of Translation for N-Alkyl Amino Acids," Journal of the American Chemical Society, 129(37):11316-11317 (2007).
U.S. Appl. No. 07/171,049, filed Mar. 21, 1988, Hans.
U.S. Appl. No. 10/345,664, filed Jan. 16, 2003, Olejnik, et al.
U.S. Appl. No. 11/682,272, filed Mar. 5, 2007, Wang, et al.
U.S. Appl. No. 13/505,625, filed Nov. 2, 2010, Strom, et al.
U.S. Appl. No. 14/125,906, filed May 24, 2012, Gao, et al.
U.S. Appl. No. 14/368,564, filed Dec. 28, 2012, Kariyuki, et al., related application.
U.S. Appl. No. 15/166,550, filed May 27, 2016, Kariyuki, et al., related application.
U.S. Appl. No. 15/557,532, filed Sep. 12, 2017, Ohta, et al., related application.
U.S. Appl. No. 16/081,522, filed Mar. 3, 2017, Nakano, et al., related application.
U.S. Appl. No. 16/479,736, filed Jan. 31, 2018, Tanaka, et al., related application.
U.S. Appl. No. 16/771,335, filed Dec. 14, 2018, Nomura, et al., related application.
U.S. Appl. No. 17/011,815, filed Sep. 3, 2020, Kariyuki, et al., related application.
U.S. Appl. No. 17/024,944, filed Sep. 18, 2020, Ohta, et al., related application.
U.S. Appl. No. 251,176, filed Sep. 30, 1988, Hans-Jurgen, et al.
Afonso, A., et al., "Solid-Phase Synthesis of Biaryl Cyclic Peptides Containing a 3-Aryltyrosine," European Journal of Organic Chemistry, 2012(31):6204-6211 (2012).
Alakhov, Y.B., et al., "Butylation of the Tryptophan Indole Ring: A Side Reaction During the Removal of t-butyloxycarbonyl and t-butyl Protecting Groups in Peptide Synthesis," Journal of the Chemical Society D: Chemical Communications, 7:406b-407 (1970).
Alex, A., et al., "Intramolecular Hydrogen Bonding to Improve Membrane Permeability and Absorption in Beyond Rule of Five Chemical Space," Medicinal Chemistry Communication 2(7):669-674 (2011).
Bastiaans, et al., "Flexible and Convergent Total Synthesis of Cyclotheonamide B," The Journal of Organic Chemistry, 62(12):3880-3889 (1997).
Bockus, A.T., et al., "Form and Function in Cyclic Peptide Natural Products: A Pharmacokinetic Perspective," Current Topics in Medicinal Chemistry 13(7):821-836 (2013).
Bolek, S. and Ignatowska, J., "Ring opening reactions of cyclic sulfamidates. Synthesis of β-fluoroaryl alanines and derivatives of 4,4-difluoroglutamic acid," Journal of Fluorine Chemistry, 27:13-21 (2019).
Burkholder, T. P., et al., "Acid-Catalyzed O-Allylation of β-Hydroxy-α-Amino Acids: an Entry into Conformationally Constrained Dipeptide Surrogates," Bioorganic & Medicinal Chemistry Letters, 2(6):579-582 (1992).
Chen, C.C., et al., "A Mild Removal of Fmoc Group Using Sodium Azide," Amino Acids, 46(2):367-374 (2014).
Cornella, J., et al., "Practical Ni-Catalyzed Aryl-Alkyl Cross-Coupling of Secondary Redox-Active Esters," Journal of the American Chemical Society 138(7):2174-2177 (2016).
Cox, A.D., et al., "Drugging the undruggable RAS: Mission possible?," Nature Reviews Drug Discovery, 13(11):828-851 (2014).
Creighton, C.J., et al., "Mechanistic Studies of an Unusual Amide Bond Scission," Journal of the American Chemical Society 121(29):6786-6791, American Chemical Society, United States (Apr. 1999).
Cudic, M. and Fields, G.B., "Solid-Phase Peptide Synthesis," Molecular Biomethods Handbook 515-546, Springer Protocols Handbooks (2008).
Dailler, et al., "Divergent Synthesis of Aeruginosins Based on a C(sp(3))-H Activation Strategy," Chemistry 21 (26):9370-9379 (2015).
Fujii, N., et al., "Trimethylsilyl Trifluoromethanesulphonate as a Useful Deprotecting Reagent in Both Solution and Solid Phase Peptide Syntheses," Journal of the Chemical Society 4:274-275, Chemical Communications, (1987).
Fujino, M., et al., "Further Studies on the Use of Multi-substituted Benzenesulfonyl Groups for Protection of the Guanidino Function of Arginine," Chemical and Pharmaceutical Bulletin 29(10):2825-2831 (1981).
Gravestock, D., et al., "Novel branched isocyanides as useful building blocks in the Passerini-amine deprotection-acyl migration (PADAM) synthesis of potential HIV-1 protease inhibitors," Tetrahedron Letters, 53(26):3225-3229 (2012).
Grosjean, H. and Bjork, G.R., "Enzymatic Conversion of Cytidine to Lysidine in Anticodon of Bacterial Isoleucyl-tRNA-an Alternative Way of RNA Editing," Trends in Biochemical Sciences 29(4):165-168 (2004).
Huihui, K.M.M., et al., "Decarboxylative Cross-Electrophile Coupling of N-Hydroxyphthalimide Esters With Aryl Iodides," Journal of the American Chemical Society 138(15):5016-5019 (2016).
Ikeuchi, Y., et al., "Agmatine-conjugated Cytidine in a tRNA Anticodon Is Essential for AUA Decoding in Archaea," Nature Chemical Biology 6(4):277-282 (2010).
Ikeuchi, Y., et al., "Molecular Mechanism of Lysidine Synthesis That Determines tRNA Identity and Codon Recognition," Molecular Cell 19(2):235-246 (2005).
Isidro-Llobet, A., et al., "Amino Acid-Protecting Groups," Chemical Reviews 109(6):2455-2504 (2009).
Iwane, Y., et al., "Expanding the Amino Acid Repertoire of Ribosomal Polypeptide Synthesis via the Artificial Division of Codon Boxes," Nature Chemistry 8(4):317-325 (2016).
Jaradat, D.M.M., "Thirteen Decades of Peptide Synthesis: Key Developments in Solid Phase Peptide Synthesis and Amide Bond Formation Utilized in Peptide Ligation," Amino Acids 50(1):39-68 (2018).
Jones, A.B., et al., "A Formal Synthesis of FK-506. Exploration of Some Alternatives to Macrolactamization," The Journal of Organic Chemistry 55(9):2786-2797 (1990).
Kiho, T., et al., "Total Synthesis of Pleofugin A, a Potent Inositol Phosphorylceramide Synthase Inhibitor," Organic Letters 20(15):4637-4640 (2018).
Kopina, B.J. and Lauhon, C.T., "Efficient Preparation of 2,4-diaminopyrimidine Nucleosides: Total Synthesis of Lysidine and Agmatidine," Organic Letters 14(16):4118-4121 (2012).
Kuhn, B., et al., "Intramolecular Hydrogen Bonding in Medicinal Chemistry," Journal of Medicinal Chemistry 53(6):2601-2611 (2010).
Lajoie, M.J., et al., "Overcoming Challenges in Engineering the Genetic Code," Journal of Molecular Biology, 428(5 Pt B):1004-1021 (2016).
Lejeune, V., et al., "Towards a Selective Boc Deprotection on Acid Cleavable Wang Resin," Tetrahedron Letters 44(25):4757-4759 (2003).
Lenzi, A., et al., "Synthesis of N-Boc-α-amino Acids With Nucleobase Residues as Building Blocks for the Preparation of Chiral PNA (Peptidic Nucleic Acids)," Tetrahedron Letters 36(10):1713-1716 (1995).
Li, H., et al., "Ni-Catalyzed Electrochemical Decarboxylative C—C Couplings in Batch and Continuous Flow," Organic letters 20(5):1338-1341 (2018).
Liniger, M., et al., "Total Synthesis and Characterization of 7-Hypoquinuclidonium Tetrafluoroborate and 7-Hypoquinuclidone BF3 Complex," Journal of the American Chemical Society 138(3):969-974 (2016).
Liu, Z., et al., "N-Boc Deprotection and Isolation Method for Water-soluble Zwitterionic Compounds," The Journal of Organic Chemistry 79(23):11792-11796 (2014).
Luo, D., et al., "Total Synthesis of the Potent Marine-Derived Elastase Inhibitor Lyngbyastatin 7 and in Vitro Biological Evaluation in Model Systems for Pulmonary Diseases," The Journal of Organic Chemistry 81(2):532-544 (2016).
Malhotra, R., et al., "Efficient Asymmetric Synthesis of N-Protected-B-Aryloxyamino Acids Via Regioselective Ring Opening of Serine Sulfamidate Carboxylic Acid," Organic & Biomolecular Chemistry, 12(33):6507-6515 (2014).
Manfredini, S., et al., "Design And Synthesis of Phosphonoacetic Acid (PPA) Ester and Amide Bioisosters of Ribofuranosylnucleoside

(56) References Cited

OTHER PUBLICATIONS

Diphosphates as Potential Ribonucleotide Reductase Inhibitors and Evaluation of Their Enzyme Inhibitory, Cytostatic and Antiviral Activity," Antiviral Chemistry and Chemotherapy 14(4):183-194 (2003).
Mangold, S.L., et al., "Z-Selective Olefin Metathesis on Peptides: Investigation of Side-Chain Influence, Preorganization, and Guidelines in Substrate Selection," Journal of the American Chemical Society, 136(35):12469-12478 (2014).
Miyake, A., et al., "Design and Synthesis of N-[N-[(S)-1-ethoxycarbonyl-3-phenylpropyl]-l-alanyl]-N-(Indan-2-yl)glycine (CV-3317), a New, Potent Angiotensin Converting Enzyme Inhibitor," Chemical and Pharmaceutical Bulletin 34(7):2852-2858 (1986).
Morieux, P., et al., "The Structure-Activity Relationship of the 3-Oxy Site in the Anticonvulsant (R)-N-Benzyl 2-Acetamido-3-Methoxypropionamide," Journal of Medicinal Chemistry, 53(15):5716-5726 (2010).
Muramatsu, T., et al., "A Novel Lysine-Substituted Nucleoside in The First Position of the Anticodon of Minor Isoleucine tRNA from *Escherichia coli*," The Journal of Biological Chemistry 263(19):9261-9267 (1988).
Murashige, R., et al., "Asymmetric and Efficient Synthesis of Homophenylalanine Derivatives via Friedel-Crafts Reaction With Trifluoromethanesulfonic Acid," Tetrahedron Letters 49(46):6566-6568 (2008).
Navo, C.D., et al., "Oxygen by Carbon Replacement at the Glycosidic Linkage Modulates the Sugar Conformation in Tn Antigen Mimics," ACS Omega, 3(12):18142-18152 (2018).
Niida, A., et al., "Investigation of the Structural Requirements of K-Ras(G12D) Selective Inhibitory Peptide KRpep-2d Using Alanine Scans and Cysteine Bridging," Bioorganic & Medicinal Chemistry Letters 27(12):2757-2761 (2017).
Ohwada, T., et al., "On the Planarity of Amide Nitrogen. Intrinsic Pyramidal Nitrogen of N-acyl-7-azabicyclo[2.2.1]heptanes," Tetrahedron Letters 39(8):865-868 (1998).
Orain, D., et al., "Protecting Groups in Solid-Phase Organic Synthesis," Journal of Combinatorial Chemistry 4(1):1-16 (2002).
Osawa, T., et al., "Structural Basis of tRNA Agmatinylation Essential for AUA Codon Decoding," Nature Structural & Molecular Biology 18(11):1275-1280 (2011).
Ostrem, J.M.L., et al., "Direct Small-Molecule Inhibitors of KRAS: From Structural Insights to Mechanism-Based Design," Nature reviews. Drug discovery, 15(11):771-785 (2016).
Peschke, B., et al., "New Highly Potent Dipeptidic Growth Hormone Secretagogues with Low Molecular Weight," European Journal of Medicinal Chemistry 35(6):599-618 (2000).
Piszkiewicz, D., et al., "Anomalous Cleavage of Aspartyl-Proline Peptide Bonds During Amino Acid Sequence Determinations," Biochemical and Biophysical Research Communications 40(5):1173-1178 (1970).
Rader, A.F.B., et al., "Orally Active Peptides: Is There a Magic Bullet?," Angewandte Chemie 57(44):14414-14438 (2018).
Rafi, S.B., et al., "Predicting and Improving The Membrane Permeability of Peptidic Small Molecules," Journal of Medicinal Chemistry 55(7):3163-3169 (2012).
Sakamoto, K., et al., "K-Ras(G12D)-Selective Inhibitory Peptides Generated by Random Peptide T7 Phage Display Technology," Biochemical and Biophysical Research Communications 484(3):605-611 (2017).
Salowe, S.P.,. et al., "The Catalytic Flexibility of Trnaile-Lysidine Synthetase can Generate Alternative tRNA Substrates for Isoleucyl-tRNA Synthetase," The Journal of Biological Chemistry 284(15):9656-9662 (2009).
Samatar, A.A., et al., "Targeting RAS-ERK Signalling in Cancer: Promises and Challenges," Nature reviews. Drug Discovery, 13(12):928-942 (2014).
Sang-Aroon, W., et al., "Theoretical Study on Isomerization and Peptide Bond Cleavage at Aspartic Residue," Journal of Molecular Modeling 19(9):3627-3636 (2013).

Sogabe, S., et al., "Crystal Structure of a Human K-Ras G12D Mutant in Complex with GDP and the Cyclic Inhibitory Peptide KRpep-2d," ACS Medicinal Chemistry Letters 8(7):732-736 (2017).
Stetsenko, D.A., et al., "Removal of Acid-Labile Protecting or Anchoring Groups in the Presence of Polyfluorinated Alcohol: Application to Solid-Phase Peptide Synthesis," Russian Journal of Bioorganic Chemistry 42(2):143-152, Pleiades Publishing, Ltd., (2016).
Struck, A., et al., "An Enzyme Cascade for Selective Modification of Tyrosine Residues in Structurally Diverse Peptides and Proteins," Journal of the American Chemical Society 138(9):3038-3045 (2016).
Suenaga, K., et al., "Aurilide, A Cytotoxic Depsipeptide From the Sea Hare Dolabella Auricularia: Isolation, Structure Determination, Synthesis, and Biological Activity," Tetrahedron 60(38):8509-8527 (2004).
Suenaga, K., et al., "Synthesis and Cytotoxicity of Aurilide Analogs," Bioorganic & Medicinal Chemistry Letters, 18(14);3902-3905 (2008).
Suzuki, T., et al., "Discovery and Characterization of tRNAIIe Lysidine Synthetase (TilS)," FEBS Letters 584(2):272-277 (2010).
Suzuki, T., "How to Decipher AUA Codon in Archaea," Kagaku to Seibutsu 50(1):36-43 (2012).
Tam, J.P., et al., "Cyclohexyl Ester as a New Protecting Group for Aspartyl Peptides to Minimize Aspartimide Formation in Acidic and Basic Treatments," Tetrahedron Letters 20(42):4033-4036 (1979).
Toriyama, F., et al., "Redox-Active Esters in Fe-catalyzed C—C Coupling," Journal of the American Chemical Society, 138(35):11132-11135 (2016).
Tsuda, et al., Amino Acids, Peptides and Proteins in Organic Chemistry, 3:201-406, 495-517, 549-569 (2011).
Vaisar, T. and Urban, J., "Gas-Phase Fragmentation of Protonated Mono-n-Methylated Peptides. Analogy With Solution-Phase Acid-Catalyzed Hydrolysis," Journal of Mass Spectrometry 33(6):505-524 (1998).
Van Der Auwera, C., et al., "Easy Cleavage of C'-Terminal Iminoacids from Peptide Acids through Acidic Hydrolysis," International Journal of Peptide and Protein Research 31(2):186-191 (1988).
Wang, S., et al., "Iridium/f-Amphox-Catalyzed Asymmetric Hydrogenation of Styrylglyoxylamides," Synlett 29(16):2203-2207 (2018).
Wang, T., et al., "Revisiting Oxytocin through the Medium of Isonitriles," Journal of the American Chemical Society 134(32):13244-13247 (2012).
Watanabe, E., et al., "A Practical Method for Continuous Production of Sp3-Rich Compounds From (Hetero)Aryl Halides and Redox-Active Esters," Chemistry, 26(1):186-191 (2020).
Weber, F., et al., "A Potato Mitochondrial Isoleucine tRNA is Coded for by a Mitochondrial Gene Possessing a Methionine Anticodon," Nucleic Acids Research 18(17):5027-5030 (1990).
Wermuth, C. G., editor, "The Practice of Medicinal Chemistry," 2nd Edition, 52-53, 87-88 (2003).
Wu, J., et al., "Intrinsic Basicity of Oligomeric Peptides that Contain Glycine, Alanine, and Valine-the Effects of the Alkyl Side Chain on Proton Transfer Reactions," Journal of the American Society for Mass Spectrometry 6(2):91-101 (1995).
Yajima, et al., "New Strategy for the Chemical Synthesis of Proteins," Tetrahedron 44(3):805-819 (1988).
Yamanoi, K., et al., "Synthesis of Trans and cis-α-(carboxycyclopropyl)Glycines. Novel Neuroinhibitory Amino Acids as L-Glutamate Analogue," Tetrahedron Letters 29(10):1181-1184, Pergamon Press plc, United Kingdom (1988).
Yang, Y., Side Reactions in Peptide Synthesis, pp. 1-31 (2015).
Yao, G., et al., "Efficient Synthesis and Stereochemical Revision of Coibamide A," Journal of American Chemical Society 137(42);13488-13491 (2015).
Zhang, A.J., et al., "A Method for Removal of N-BOC Protecting Groups from Substrates on TFA-Sensitive Resins," Tetrahedron Letters 39(41):7439-7442 (1998).
Zhang, K., et al., "Ab Initio Studies of Neutral and Protonated Triglycines: Comparison of Calculated and Experimental Gas-Phase Basicity," Journal of the American Chemical Society 116(25):11512-11521 (1994).
U.S. Appl. No. 07/331,292, filed Mar. 30, 1989, Yajima et al.
U.S. Appl. No. 13/816,911, filed Feb. 13, 2013, Suga et al.

(56) References Cited

OTHER PUBLICATIONS

U.S. Appl. No. 14/889,868, filed Mar. 7, 2016, Murakami et al.
U.S. Appl. No. 16/619,014, filed Dec. 3, 2019, Muraoka et al.
U.S. Appl. No. 17/291,099, filed Jun. 3, 2021, Ishizawa, related application.
U.S. Appl. No. 17/297,231, filed May 26, 2021, Iwasaki et al., related application.
U.S. Appl. No. 17/312,296, filed Jun. 9, 2021, Muraoka et al., related application.
U.S. Appl. No. 17/417,822, filed Jun. 24, 2021, Shinohara et al., related application.
U.S. Appl. No. 17/437,535, filed Sep. 9, 2021, Wadamoto, related application.
Bodanszky, M., et al., "Coupling in the absence of tertiary amines," Int J Peptide Res., 26:550-556 (1985).
Chatterjee, J., et al., "N-Methylated Cyclic Pentaalanine Peptides as Template Structures," J Am Chem Soc., 128:15164-15172 (2006).
Merrifield, R. B., "Solid Phase Peptide Synthesis. I. The Synthesis of a Tetrapeptide," J Am Chem Soc., 85:2149-2154 (1963).

* cited by examiner

METHOD FOR SYNTHESIZING PEPTIDE CONTAINING N-SUBSTITUTED AMINO ACID

CROSS-REFERENCE TO RELATED APPLICATIONS

This application is a continuation of U.S. application Ser. No. 16/619,388, 371(c) date Dec. 4, 2019, which is a U.S. National Phase of PCT Application No. PCT/JP2018/021998, filed Jun. 8, 2018, which claims the benefit of Japanese Patent Application No. 2017-114073, filed Jun. 9, 2017, each of which is incorporated herein by reference in its entirety.

TECHNICAL FIELD

The present invention relates to novel methods for synthesizing peptides which allow for the synthesis with high purity and high synthesis efficiency, in synthesizing peptides comprising N-substituted amino acids.

BACKGROUND ART

Peptides are highly valuable chemical species, and 40 or more types of peptides have been placed on the market as pharmaceuticals (NPL 1). Among them, for cyclic peptides and N-methylated (or N-alkylated) unnatural peptides, improvement of membrane permeability for the improved lipophilicity and improvement of metabolic stability for the acquisition of resistance to hydrolytic enzymes (hydrolases) have been anticipated (NPL 2). Recently, investigation on cyclic peptides that are drug-like (drug-likeness: preferably, it indicates that both membrane permeable and metabolically stable characteristics are achieved), the drug-likeness being the key to accomplish transfer into cells and to allow formulation as oral agents, is progressing (NPLs 3 and 4). Furthermore, a patent document elucidating the conditions necessary for drug-like cyclic peptides was published (PTL 1), and the importance and awareness of such peptides in drug development have been increasing.

On the other hand, progresses in the development of methods of synthesizing peptides comprising many unnatural amino acids such as those represented by N-alkyl amino acids are relatively narrow. In most cases, techniques established for natural peptides have been directly applied to unnatural peptides.

The Fmoc method and the Boc method are widely known as peptide synthesis methods, and most of the findings regarding these methods have been obtained from the development of methods for synthesizing natural peptides. An Fmoc group is stable to acids; therefore, when an N-terminal amino group is protected by an Fmoc group, its deprotection reaction is performed using bases such as DBU and piperidine. Thus, for example, protecting groups that can be deprotected (deprotectable) by acids are used as protecting groups for peptide side chain functional groups, and peptide chain is elongated by selectively deprotecting N-terminal amino group. As protecting groups often used, t-butyl (tBu), trityl (Trt), and such groups deprotectable by acids at the level of trifluoroacetic acid (TFA) can be employed for protecting amino acid side chains in the Fmoc method, and the step of cleaving the peptide from the resin and deprotection of protecting groups of the side chain functional groups can be performed under milder conditions compared to the Boc method.

However, even in a solid-phase synthesis method by the Fmoc method, which allows cleavage from resins and deprotection of protecting groups of side-chain functional groups under relatively mild conditions, the following problems have been revealed in the synthesis of N-alkylated peptides during the step of cleavage from resins or deprotection of protecting groups on the side-chain functional groups using TFA.

When synthesizing peptides by the usual Fmoc method, it is common to use TFA for the step of cleavage from the resin and deprotection of protecting groups of side-chain functional groups. In most cases, cleavage reaction from the resin and deprotection reaction of the side-chain functional groups are performed simultaneously using an aqueous 90% TFA solution. However, it has been known that in the case of N-methylated peptides, particularly peptides with sequences having consecutive N-methyl amino acids, a side reaction occurs where acid hydrolysis via oxazolonium proceeds and the peptide chain is cleaved (NPLs 5 and 6). Furthermore, it has been known that in the case of peptides comprising in their sequences amino acids having an □-hydroxy group such as serine and threonine, N- to O-acyl shift reaction can also proceed as a side reaction in addition to the acid hydrolysis in these steps that use TFA, which results in the depsipeptide formation (NPLs 7 and 8).

Measures to avoid this problem of hydrolysis in the cleavage step and deprotection step using acids are being taken, such as using a low-concentration TFA solution and controlling the reaction time to be short. For example, according to the report by Albericio et al., in the solid-phase synthesis of a peptide named NMe-IB-01212, peptide degradation at the N-Me site was observed when deprotection of Boc group on an amino group included in an N-methylated cyclic hexapeptide is carried out in a TFA-DCM (1:1) solution. Although attempts for improvement have been made to avoid degradation by using lower concentrations of TFA and reducing the reaction time to a minimum, sufficient improvement has not been attained (NPL 9). In the first place, protecting groups widely used in conventional peptide synthesis have shown cases where the deprotection step using a low-concentration TFA solution results in deprotection reaction on the side chains proceeding extremely slowly or not proceeding whereas cleavage reaction of peptides from the resin proceeding at a satisfactory speed.

Furthermore, to prevent cleavage of Ac-MePhe at the N terminus which proceeds via the same reaction mechanism as hydrolysis of highly N-methylated peptides, Fang et al. used TFA and decreased the reaction temperature to 4° C. to deprotect the Pbf group, which is a protecting group for the Arg side chain (NPL 10). However, even by using this method which decreases the temperature, complete prevention of Ac-MePhe cleavage was difficult, and the method could just stop the reaction when the generated level of the desired product reaches its maximum.

In addition to the problem during deprotection, the problem of low reactivity in the elongation step is also known. When an N-methyl amino acid comes to the N terminus of the amide bond which is newly formed, the amide formation reaction (elongation reaction) with a subsequent amino acid may not proceeds sufficiently because of the bulkiness of its secondary amine (NPLs 2 and 5).

For this problem in the elongation step, measures to decrease unreacted site by repeating identical reaction condition twice or more times have been taken (the method repeating twice is called double coupling). Furthermore, regarding activation of the amino acid to be condensed, effort has been made to improve condensation efficiency, for example, by changing to highly active acid halides (NPL 11). However, repeating the same reaction condition as in the double coupling will double or more the time and reagent cost spent; and performing the condensation using acid halides will require preparation of the acid halides at the time of use, and it also adds an unattended concern of whether the generated acid halides can exist stably during the peptide synthesis step. Furthermore, generation of HCl and HF by the reaction invites a possibly problematic concern that deprotection reaction may unintendedly proceed.

Other measures for improving low reactivity in the elongation step have been tried such as increasing the condensation efficiency by decreasing the amount loaded onto the resin to reduce the density of the peptide chains on the solid phase and by increasing the concentration of the reaction solution (NPL 9). Recently, there have been efforts to improve the condensation efficiency by increasing the reaction temperature through irradiation of microwaves (NPLs 12 and 13).

However, in N-methylated peptide syntheses, there are no reports of radical solutions for concerns for the decreased purity and yield of the peptides to be synthesized, and that the desired product will not be obtained at all in some cases.

PRIOR ART REFERENCES

Patent Literature

[PTL 1] WO 2013/100132 A1

SUMMARY OF THE INVENTION

Problems to be Solved by the Invention

The present inventors focused on cyclic peptides comprising N-alkylated amino acids, which may become drug-like peptides, and examined methods of synthesizing peptide compounds having such features by parallel synthesis. As a result, the present inventors have discovered that when conventional synthesis methods using TFA is applied for cyclic peptides comprising N-alkylated amino acids which may become drug-like peptides, the above-mentioned problems which have been discovered for the compounds described in known documents appeared prominently and can cause the failure in isolating the cyclic peptides. Specifically, the present inventors have found that obtaining the desired peptide is difficult in the case of peptides comprising N-alkylated amino acids, since the side reaction in which the peptide chain is cleaved becomes the major reaction during the reaction performed under acidic conditions using TFA as steps for cleaving off from the solid phase or for deprotecting the protecting groups of the side chain functional groups. The present inventors have further discovered that when amino acids having a β-hydroxy group are included in a peptide, N- to O-acyl shift reaction also proceeds during the reaction under the acidic conditions using TFA, and obtaining the desired peptide was difficult. These problems were found in the compounds of the known documents mentioned above, but the present inventors newly discovered that these

| | Non-patent Literature |
|---|---|
| [NPL 1] | S. R. Gracia, ei al., Synthesis of chemically modified bioactive peptides: recent advances, challenges and developments for medicinal chemistry. Future Med. Chem., 2009, 1, 1289. |
| [NPL 2] | J. Chatterjee, et al., N-Methylation of peptides: A new perspective in medicinal chemistry. Acc. Chem. Res., 2008, 41, 1331. |
| [NPL 3] | J. E. Bock, et al.. Getting in Shape: Controlling Peptide Bioactivity and Bioavailability Using Conformational Constraints. ACS Chem. Biol., 2013, 8, 488. |
| [NPL 4] | K. Jpsephson, et al., mRNA display: from basic principles to macrocycle drug discovery. Drug Discovery Today, DOI: 10.1016/j.drudis.2013.10.011 |
| [NPL 5] | M. Teixido, et al., Solid-phase synthesis and characterization of N-methyl-rich peptides. J. Peptide Res., 2005, 65, 153. |
| [NPL 6] | J. Urban, et al., Lability of N-alkylated peptides towards TFA cleavage. Int. J. Pept. Prot. Res., 1996, 47, 182. |
| [NPL 7] | L. A. Carpino, et al.. Dramatically enhanced N→O acyl migration during the trifluoroacetic acid-based deprotection step in solid phase peptide synthesis. Tetrahedron Lett., 2005, 46, 1361. |
| [NPL 8] | H. Eberhard, et al., N→O-Acyl shift in Fmoc-based synthesis of phosphopeptides. Org. Biomol. Chern., 2008, 6, 1349. |
| [NPL 9] | E. Marcucci, et al., Solid-Phase Synthesis of NMe-IB-01212, a Highly N-Methylated Cyclic Peptide. Org. Lett., 2012, 14, 612. |
| [NPL 10] | W.-J. Fang, et al., Deletion of Ac-NMePhe¹ From [NMePhe']arodyn Under Acidic Conditions, Part 1: Effects of Cleavage Conditions and N-Terminal Functionality. Peptide Science Vol. 96, 97 |
| [NPL 11] | L. A. Carpino, et al., Stepwise Automated Solid Phase Synthesis of Naturally Occurring Peptaibols Using FMOC Amino Acid Fluorides. J. Org. Chern., 1995, 60, 405. |
| [NPL 12] | H. Rodriguez, et al., A convenient microwave-enhanced solid-phase synthesis of short chain N-methyl-rich peptides. J. Pept. Sci., 2010, 16, 136. |
| [NPL 13] | R. Roodbeen, et al., Microwave Heating in the Solid-Phase Synthesis of N-Methylated Peptides: When Is Room Temperature Better? Eur. J. Org. Chem., 2012, 7106. | problems are similarly observed in many other peptides. In addition to these problems, the present inventors have also discovered a problem that when peptides comprising an amino acid that has a hydroxy group in its skeleton (not necessarily at the β position) are subjected to reaction under acidic conditions using TFA, its hydroxy group was esterified with TFA.

Furthermore, the present inventors have discovered that, when considering industrialization of peptide synthesis comprising N-alkylated amino acids which may become drug-like peptides, the conventional TFA-utilizing deprotection method gives considerable difficulty in realizing industrialization not only from the viewpoint of deprotection reaction or elongation reaction itself, but also the subsequent work-up processes and large-scale synthesis. For example, when the solvent of a TFA/DCM solution is removed by condensation, the TFA concentration increases as the condensation progresses, and problems such as hydrolysis and N- to O-acyl shift arise simultaneously with the condensation. This could lead to the failure in obtaining the desired compound, or cause remarkable decrease in yield. The condensation step needs to be performed at low temperature. Furthermore, even with low concentration of TFA, a large excess amount of TFA compared to that of the target molecule is included; therefore, a large excess amount of base to be added is necessary in order to stop reactions by neutralizing TFA, causing a large excess of salt to remain together with the desired peptide, and this could lead to trouble to the purification step. Furthermore, although TFA itself is a solvent that effectively dissolves peptides, with only a lowered concentration of TFA solution, solubility of the peptide will lead to become low. Regarding solubility, a solvent that has high solubility to a group of peptides needs to be selected, not only when considering industrialization, but also in parallel synthesis which handles many different peptide compounds at once.

In addition, the present inventors focused on improvement of reactivity by decreasing the steric size of the protecting group of an Fmoc-amino acid which has a protecting group-bearing functional group on its side chain, which had so far not been undertaken with great effort. For example, since threonine (Thr) has a hydroxyl group, to allow the subsequent acylation reaction to occur selectively at the amino group, a protecting group for the hydroxyl group is necessary. However, since Thr has a branched secondary alcohol at the β-position as its side chain functional group, condensation efficiency of the protected Thr is relatively low due to its bulkiness. Protecting groups generally used for Thr in peptide synthesis include an acetyl (Ac) group, tBu group, Trt group, benzyl (Bn) group, and t-butyldimethylsilyl (TBS) group (Albert Isidro-Llobet, et al., Amino Acid-Protecting Groups. Chem. Rev., 2009, 109, 2455; Watanabe Chemical Industries, Ltd. Reagent Catalog, Amino acids & chiral building blocks to new medicine 2012-14). However, regarding Trt group and TBS group, their bulkiness leads to decreased condensation efficiency. Furthermore, even in the case of tBu group which is deprotectable with acids, condition of high TFA concentration is necessary for the deprotection; therefore, the already mentioned problems during deprotection become obvious. Other protecting groups are not recognized as protecting groups that can be easily removed using acids. To sum, it is necessary to discover protecting groups that are sterically small enough to not reduce the condensation efficiency and can also easily be deprotected by acids that can avoid the above-mentioned problems of acid hydrolysis and N- to O-acyl shift. The same broadly applies to other cases for N-methyl serine (MeSer), which does not have a branched site at the β-position but has higher bulkiness due to N-substitution, and for amino acids having hydroxy groups as their functional groups.

More specifically, an objective of the present invention is to discover novel reaction processes that can reduce the problems of side reactions such as peptide acid hydrolysis and N- to O-acyl shift, and TFA esterification of hydroxy groups in the deprotection step using TFA, which are found to become conspicuous during parallel syntheses of peptides comprising N-substituted amino acids, and that can also secure peptide solubility. Furthermore, an objective of the present invention is to provide methods of obtaining peptides comprising N-substituted amino acids with high purity and high synthetic yield by using appropriate protecting groups for the side-chain functional groups (appropriate protecting groups from the viewpoint of reducing the bulkiness of the protecting groups to improve the low reactivity during elongation, and being deprotectable under deprotection conditions of the present invention).

Specifically, objectives are:
(1) to find reaction conditions necessary for suppressing hydrolysis during acid addition (during cleavage reaction from a solid phase and during side chain deprotection reaction), particularly hydrolysis derived from N-substituted amino groups;
(2) to find reaction conditions that enable practical work-up upon acid addition;
(3) to find reaction conditions including solvents, with consideration on the characteristic solubility of unnatural peptide compounds; and
(4) to suppress side-reactions after deprotection (N- to O-acyl shift and side-reactions between hydroxyl groups and the reaction reagents, for example, TFA acylation reaction when using TFA as the reagent) when the unnatural peptide compounds comprise functional groups such as hydroxyl groups, in performing parallel syntheses of N-substituted amino acid-comprising peptide compounds having various sequences.

In addition, an objective is to discover protecting groups that satisfy the four conditions mentioned above for various functional groups in amino acid side chains.

Furthermore, considering industrial production of peptide compounds comprising N-substituted amino acids, an objective of the present invention is to find production methods applicable to optimization of specific sequences.

Means for Solving the Problems

In order to realize efficient synthesis of cyclic peptides comprising N-substituted amino acids, the present inventors discovered novel methods that can solve many problems, for example by achieving suppression of hydrolysis and N- to O-acyl shift progression, establishment of practical work-up methods, suppression of TFA ester formation when hydroxyl group is present, and selection of solvents that can secure peptide solubility, which could not have been sufficiently solved by generally performed improvement methods, such as the methods of decreasing the TFA concentration or the methods of lowering the reaction temperature, in addition to problems observed when using conventional peptide synthesis methods that use TFA to synthesize compounds described in known literatures. In the novel methods, TFA used in conventional peptide synthesis is not used at all, and the present inventors succeeded in obtaining target molecules with high selectivity.

In one embodiment of the present invention, TFA is not used in the step of cleavage from a solid phase, and a weaker acid, for example 2,2,2-trifluoroethanol (TFE) or hexafluoro-2-propanol (HFIP) is used. Additionally, in another embodiment of the present invention, protecting groups for side chain functional groups which are not deprotected in the cleavage step are used. In the cleavage step using an acid weaker than TFA, such as TFE or HFIP, the rates of side reactions such as amide-bond hydrolysis are sufficiently low, unlike the case using TFA, even during concentration step after reaction. In particular, when using an acid weaker than TFA, such as TFE or HFIP, the rates of side reactions are low even for peptides comprising highly N-substituted amino acids and cyclic peptides which are susceptible to side reactions. Therefore, the desired compounds can be obtained as the major products. In another embodiment of the present invention, reagents satisfying the following conditions are used in the cleavage step: (1) the reaction of cleavage from the solid phase proceeds smoothly while peptide side reactions (such as hydrolysis) are suppressed; (2) rate of side reactions is sufficiently slow even when work-up such as concentration is performed; (3) high solubility is secured also for highly lipid-soluble unnatural peptides; and (4) cleavage is possible while the protecting groups of the side chain functional groups are retained. By using a reagent that satisfies such conditions, synthesis of peptides comprising many N-substituted amino acids, particularly synthesis of drug-like peptides comprising many N-alkyl groups becomes possible. Reagents satisfying such conditions can be used not only during parallel syntheses but also when industrially synthesizing specific peptides.

An embodiment of the present invention provides peptide synthesis methods which can suppress hydrolysis and N- to O-acyl shift, and can deprotect side chain protecting groups so that the major reaction, the desired deprotection reaction, is promoted. For the progression of hydrolysis and N- to O-acyl shift, acid strength (proton concentration) alone may be important. And, the inventors have found that by using a weak acid having weakened acidity instead of a strong acid such as TFA, progression of hydrolysis and N- to O-acyl shift can be suppressed. Furthermore, for the progression of desired deprotection, a step of dissociation of the protecting groups as cationic species (carbocation or oxonium cation) from the protected functional groups may be important, in addition to acid strength (proton concentration). Therefore, as a solvent that promotes the step of dissociation of protecting groups as cationic species, the inventors have found that the use of solvents having ionization ability can promote deprotection by the above-mentioned weak acid.

In addition, to establish highly efficient methods for synthesizing the drug-like peptides described in PTL 1, the inventors discovered protecting groups for the side-chain functional groups of amino acids having side chains with small ionization degree under neutral conditions, which protecting groups are not deprotected under the weakly acidic conditions used when cleaving the peptides off from resins but can be deprotected under the above-mentioned weak acid conditions, and which functional groups are, for example, hydroxyl groups which are side chain functional groups of amino acids such as Ser and Thr: alkylalcohol groups having hydroxy groups in the side chains; phenol groups which are side chain functional groups of amino acids such as Tyr; imidazole groups which are side chain functional groups of amino acids such as His; side chain carboxylic acids which are side chain functional groups of amino acids such as Asp and Glu; and main chain carboxylic acid of peptides or amino acids.

Furthermore, the inventors found protecting groups that can be deprotected under the above-mentioned weak acid conditions and can improve the low reactivity during elongation reaction, for cases where amino acids such as β-hydroxy-α-amino acids (for example, Thr, Ser, and derivatives thereof) for which low reactivity during elongation reaction is concerned have protecting groups.

More specifically, the present invention is:

[1] a method of producing a peptide comprising at least one N-substituted amino acid or N-substituted amino acid analog, wherein the method comprises the steps of:
1) preparing an amino acid (Fmoc-protected amino acid) comprising at least one each of following functional groups i) and ii), an amino acid analog (Fmoc-protected amino acid analog) comprising at least one each of following i) and ii), or a peptide (Fmoc-protected peptide) comprising either one or both of the Fmoc-protected amino acid and the Fmoc-protected amino acid analog:
   i) a main chain amino group protected by at least one protecting group having an Fmoc skeleton: and
   ii) at least one free carboxylic acid group or active esterified carboxylic acid group;
2) making the Fmoc-protected amino acid, the Fmoc-protected amino acid analog, or the Fmoc-protected peptide prepared in step 1) to be supported onto a solid phase;
3) deprotecting the protecting group having the Fmoc skeleton of the Fmoc-protected amino acid, the Fmoc-protected amino acid analog, or the Fmoc-protected peptide, which is supported onto the solid phase, by using a base to expose its amino group;
4) forming an amide bond by adding a new Fmoc-protected amino acid, a new Fmoc-protected amino acid analog, or a new Fmoc-protected peptide; and
5) cleaving the peptide obtained in step 4) off from the solid phase under a condition of weaker acidity than TFA;

[2] the production method of [1], wherein at least one side chain of the amino acid or amino acid analog constituting the peptide obtained in step 4) is protected by a protecting group that is not deprotected under a basic condition but is deprotected by a first acid, and wherein the method further comprises before or after step 5), a step of deprotecting the protecting group using the first acid; and wherein in step 5, the peptide is cleaved off using a second acid, and wherein the first acid and the second acid are both weaker acids than TFA and the acidity of the first acid is higher than the acidity of the second acid;

[3] a method of producing a peptide comprising at least one N-substituted amino acid or N-substituted amino acid analog, wherein the method comprises the steps of:
1) preparing an amino acid (Fmoc-protected amino acid) comprising at least one each of following functional groups i) and ii), an amino acid analog (Fmoc-protected amino acid analog) comprising at least one each of following i) and ii), or a peptide (Fmoc-protected peptide) comprising either one or both of the Fmoc-protected amino acid and the Fmoc-protected amino acid analog:
   i) a main chain amino group protected by at least one protecting group having an Fmoc skeleton: and ii) at least one free carboxylic acid group or active esterified carboxylic acid group;

2) deprotecting the protecting group having the Fmoc-skeleton of the Fmoc-protected amino acid, the Fmoc-protected amino acid analog, or the Fmoc-protected peptide, by using a base to expose its amino group;

3) forming an amide bond by adding a new Fmoc-protected amino acid, a new Fmoc-protected amino acid analog, or a new Fmoc-protected peptide, wherein at least one side chain of the amino acid or amino acid analog constituting a peptide obtained in this step has a protecting group that is not deprotected under a basic condition and is deprotected under a condition having weaker acidity than TFA; and 4) deprotecting the protecting group of the side chain under the condition having weaker acidity than TFA;

[4] the production method of [3], wherein peptide production is carried out by a solid phase method;

[5] the production method of [4], which further comprises before or after step 4), a step of cleaving the peptide obtained in step 3) off from the solid phase under a condition further weaker than the weakly-acidic condition used in step 4);

[6] the production method of [3], wherein peptide production is carried out by a liquid phase method;

[7] the production method of any one of [1] to [6], wherein step 4) of [1] or step 3) of [3] further comprises the steps of:

deprotecting the protecting group having the Fmoc skeleton on the newly added
  Fmoc-protected amino acid, the newly added Fmoc-protected amino acid analog, or the newly added Fmoc-protected peptide, by using a base to expose its amino group; and
  forming an amide bond by further adding a new Fmoc-protected amino acid, a new Fmoc-protected amino acid analog, or a new Fmoc-protected peptide, and wherein these steps are repeated once or multiple times;

[8] the production method of any one of [1] to [7], wherein the produced peptide comprises on its C-terminal side an amino acid residue or an amino acid analogue residue comprising one reactive site, and comprises on its N-terminal side an amino acid residue, an amino acid analogue residue, or a carboxylic acid analog comprising the other reactive site;

[9] the production method of [8], which further comprises the step of bonding said reactive site and said other reactive site to cyclize the peptide;

[10] the production method of [9], wherein the amino acid residue, the amino acid analogue residue, or the carboxylic acid analog having said other reactive site is at the N terminus and the bonding is an amide bonding;

[11] the production method of [9], wherein the amino acid residue, the amino acid analogue residue, or the carboxylic acid analog having said other reactive site is at the N terminus and the bonding is a carbon-carbon bonding;

[12] the production method of any one of [1] to [11], wherein the step performed under a condition having weaker acidity than TFA is performed using a weakly acidic solution comprising a weak acid having an aqueous pKa value of 0 to 9 in a solvent having an aqueous pKa value of 5 to 14 and whose ionization ability value YOTs is positive;

[13] the production method of [12], wherein the solvent is fluoroalcohol;

[14] the production method of [13], wherein the fluoroalcohol is TFE or HFIP;

[15] the production method of any one of [2] to [14], wherein the side chain protecting group is a protecting group which is deprotected in the range of pH 1 to pH 7, or a protecting group which is deprotected in 10% or lower concentration of TFA; and

[16] the production method of any one of [2] to [15], wherein the side chain protecting group is selected from following a) to d):

a) when the side chain protecting group is a protecting group for the side chain hydroxyl group of Ser, Thr, Hyp (hydroxyproline), and derivatives thereof, any one protecting group selected from a MOM skeleton, a Bn skeleton, a Dpm skeleton, a Trt skeleton, a silyl skeleton, and a Boc skeleton represented by the general formulae below;

b) when the side chain protecting group is a protecting group for the side chain hydroxyl group of Tyr and derivatives thereof, any one protecting group selected from a MOM skeleton, a Bn skeleton, a Dpm skeleton, a Trt skeleton, a silyl skeleton, a Boc skeleton, and a tBu skeleton represented by the general formulae below;

c) when the side chain protecting group is a protecting group for the side chain imidazole ring of His and derivatives thereof, any one protecting group selected from a MOM skeleton, a Bn skeleton, and a Trt skeleton represented by the general formulae below; and d) when the side chain protecting group is a protecting group for the side chain carboxylic acid group of Asp, Glu, and derivatives thereof, any one protecting group selected from a MOM skeleton, a Bn skeleton, a Dpm skeleton, a Trt skeleton, a tBu skeleton, a phenyl-EDOTn skeleton, which are represented by the following general formulae, and an orthoester skeleton in which a carbon atom of the carboxylic acid group to be protected is substituted with three alkoxy groups:

<a protecting group having a MOM skeleton>

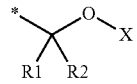

(wherein
  R1 is H, R2 is H, and X is methyl, benzyl, 4-methoxybenzyl, 2,4-dimethoxybenzyl, 3,4-dimethoxybenzyl, or 2-trimethylsilylethyl;
  R1 is methyl. R2 is H, and X is ethyl;
  R1, R2, and R3 are all methyl; or
  R1 and X together form —CH$_2$—CH$_2$—CH$_2$— or —CH$_2$—CH$_2$—CH$_2$—CH$_2$—, and R2 is H,
wherein when any one of R1, R2, and X is methyl or ethyl, these groups may further be substituted with alkyl, benzyl, or aryl);

<a protecting group having a Bn skeleton>

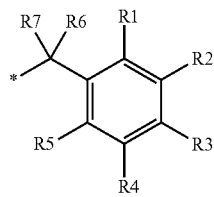

(wherein
R1 to R5 are each independently H, alkyl, aryl, or halogen, and R6 and R7 are alkyl;
R1, R2, R4, and R5 are each independently H, alkyl, aryl, or halogen, R3 is methoxy, and R6 and R7 are H;
R1 and R3 are methoxy, R2, R4, and R5 are each independently H, alkyl, aryl, or halogen, and R6 and R7 are H; or
R1, R4, and R5 are each independently H, alkyl, aryl, or halogen, and R2 and R3 together form —O—CH2-O—);

<a protecting group having a Dpm skeleton>

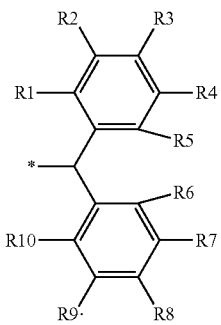

(wherein
R1 to R10 are each independently H, alkyl, aryl, alkoxy, or halogen; or
R1 to R4 and R7 to R10 are each independently H, alkyl, aryl, alkoxy, or halogen, and R5 and R6 together form —O— or —CH2-CH2-);

<a protecting group having a Trt skeleton>

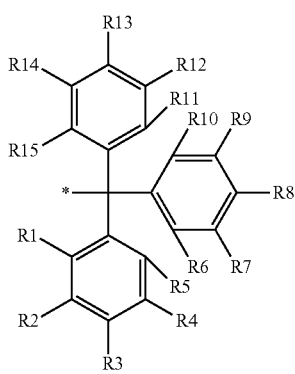

(wherein
R1 to R15 are each independently H, alkyl, aryl, alkoxy, or halogen;
R1, R2, and R4 to R15 are each independently H, alkyl, aryl, alkoxy, or halogen, and R3 is methyl or methoxy;
R1 is Cl, and R2 to R15 are each independently H, alkyl, aryl, alkoxy, or halogen; or
R1 to R4 and R7 to R15 are each independently H, alkyl, aryl, alkoxy, or halogen, and R5 and R6 together form —O—);

<a protecting group having a silyl skeleton>

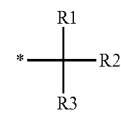

(wherein R1 to R3 are each independently alkyl or aryl);

<a protecting group having a Boc skeleton>

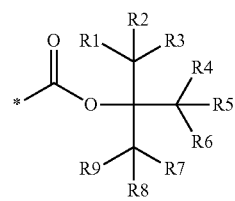

(wherein R1 to R9 are each independently H, alkyl, or aryl);

<a protecting group having a tBu skeleton>

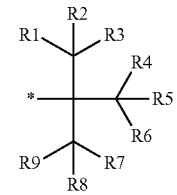

(wherein
R1 to R9 are each independently H, alkyl, or aryl); and

<a protecting group having a phenyl-EDOTn skeleton>

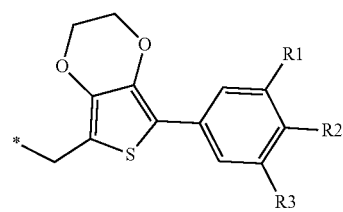

(wherein R1 to R3 are each independently H or methoxy).

Effects of the Invention

Peptides comprising N-substituted amino acids can be obtained with high synthesis efficiency and high purity by the present invention.

For example, in the case of peptide sequences comprising amino acids having protecting groups on their side chains,
(1) the combination of an acid weaker than TFA and a solvent showing ionizing ability discovered by the present invention can allow deprotection to be carried out with minimized acid hydrolysis of the peptide chains, and with minimized N- to O-acyl shift, TFA esterification, and such which may occur for sequences comprising β-hydroxy-α-amino acids (for example, Ser, Thr, and derivatives thereof), and
(2) when elongating the amino acids by amide bond-forming reactions, the reaction rate and reaction efficiency can be improved in comparison to when amino acids have protecting groups used for general peptide synthesis.

MODE FOR CARRYING OUT THE INVENTION

Figure 1:
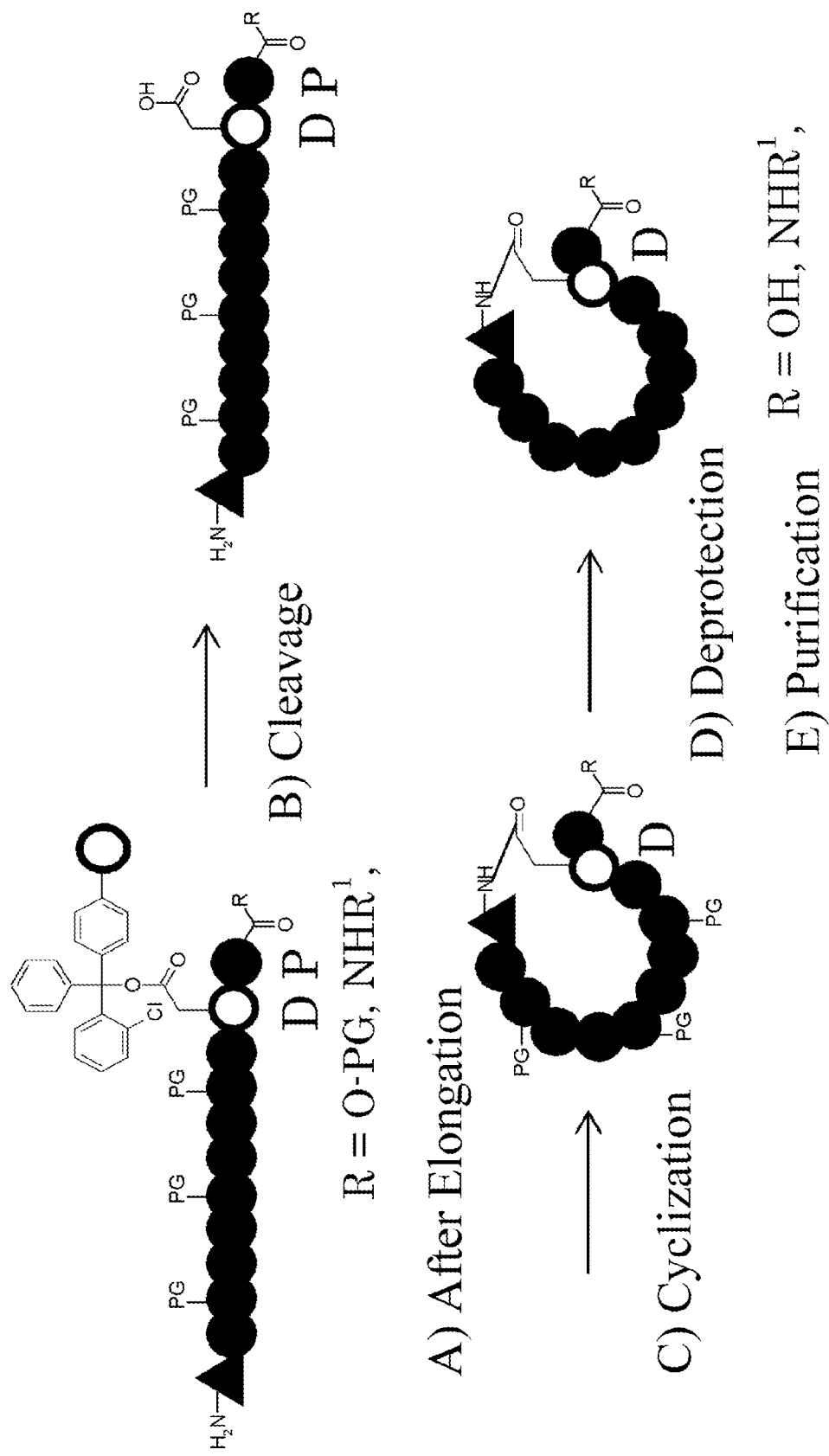
FIG. 1 shows the basic synthetic route for a cyclic peptide comprising an N-methyl amino acid in its sequence.

In a certain embodiment, the present invention relates to methods of producing a peptide comprising at least one N-substituted amino acid or N-substituted amino acid analog, wherein the method comprises the steps of:
1) preparing an amino acid (Fmoc-protected amino acid) having at least one each of following functional groups i) and ii), an amino acid analog (Fmoc-protected amino acid analog) having at least one each of following i) and ii), or a peptide (Fmoc-protected peptide) comprising either one or both of the Fmoc-protected amino acid and the Fmoc-protected amino acid analog:
   i) a main chain amino group protected by at least one protecting group having an Fmoc skeleton; and
   ii) at least one free carboxylic acid group or active esterified carboxylic acid group;
2) making the Fmoc-protected amino acid, the Fmoc-protected amino acid analog, or the Fmoc-protected peptide prepared in step 1) to be supported onto a solid phase;
3) deprotecting the protecting group having an Fmoc skeleton of the Fmoc-protected amino acid, the Fmoc-protected amino acid analog, or the Fmoc-protected peptide, which is supported onto the solid phase, by using a base to expose its amino group;
4) forming an amide bond by adding a new Fmoc-protected amino acid, a new Fmoc-protected amino acid analog, or a new Fmoc-protected peptide; and
5) cleaving the peptide obtained in step 4) off from the solid phase under a condition of weaker acidity than TFA.

In another embodiment, the present invention relates to a method of producing a peptide comprising at least one N-substituted amino acid or N-substituted amino acid analog, wherein the method comprises the steps of:
1) preparing an amino acid (Fmoc-protected amino acid) having at least one each of following functional groups i) and ii), an amino acid analog (Fmoc-protected amino acid analog) having at least one each of following functional groups i) and ii), or a peptide (Fmoc-protected peptide) comprising either one or both of the Fmoc-protected amino acid and the Fmoc-protected amino acid analog:
   i) a main chain amino group protected by at least one protecting group having an Fmoc skeleton; and
   ii) at least one free carboxylic acid group or active esterified carboxylic acid group;
2) deprotecting the protecting group having an Fmoc skeleton of the Fmoc-protected amino acid, the Fmoc-protected amino acid analog, or the Fmoc-protected peptide, by using a base to expose its amino group;
3) forming an amide bond by adding a new Fmoc-protected amino acid, a new Fmoc-protected amino acid analog, or a new Fmoc-protected peptide, wherein at least one side chain of the amino acid or amino acid analog constituting a peptide obtained in this step has a protecting group that is not deprotected under a basic condition and is deprotected under a condition having weaker acidity than TFA; and
4) deprotecting the protecting group of the side chain under a condition having weaker acidity than TFA.

The above-mentioned peptide production may be performed by a solid phase method or a liquid phase method.

"Peptide" in the present invention is not particularly limited as long as it is a peptide formed by amide bonding or ester bonding of amino acids and/or amino acid analogs, and is preferably a peptide of 5 to 30 residues, more preferably 7 to 15 residues, and even more preferably 9 to 13 residues. Peptides synthesized in the present invention comprise at least one or more amino acids or amino acid analogs which have been N-substituted (also called N-substituted amino acids), and preferably comprise two or more, more preferably three or more, and even more preferably five or more N-substituted amino acids, in a single peptide. These N-substituted amino acids may be present consecutively or non-consecutively in a peptide.

Peptides in the present invention may be linear peptides or cyclic peptides, and are preferably cyclic peptides.

A "cyclic peptide" in the present invention can be obtained by synthesizing a linear peptide according to methods of the present invention, and then cyclizing it. The cyclization may be in any form such as cyclization by a carbon-nitrogen bonding such as an amide bonding, cyclization by a carbon-oxygen bonding such as an ester bonding or an ether bonding, cyclization by a carbon-sulfur bonding such as a thioether bonding, cyclization by a carbon-carbon bonding, or cyclization by construction of a heterocycle. While not particularly limited thereto, cyclization via a covalent bonding such as a carbon-carbon bonding or an amide bonding is preferred, and cyclization via an amide bonding formed by a side chain carboxylic acid group and an N-terminal main chain amino group is particularly preferred. The sites of the carboxylic acid group, amino group, and such used in the cyclization may be on the main chain or on the side chain, and are not particularly limited as long as they are at sites where cyclization is possible.

An "N-substituted amino acid" in the present invention means an amino acid or an amino acid analog in which the main chain amino group of the later described "amino acid" or "amino acid analog" is N-substituted, and an amino acid or amino acid analog that is N-alkylated, such as N-methylated, is preferred. Specific examples of an N-substituted amino acid include amino acids or amino acid analogs in which the main chain amino group is an NHR group, wherein R is an optionally substituted alkyl group, optionally substituted alkenyl group, optionally substituted alkynyl group, optionally substituted aryl group, optionally substituted heteroaryl group, optionally substituted aralkyl group, or optionally substituted cycloalkyl group, or alternatively those in which a carbon atom bonded to the N atom forms a ring with a carbon atom from the $\alpha$ position such as proline. The substituent of each of the optionally substituted groups is not particularly limited, and examples include a halogen group, an ether group, and a hydroxyl group.

Specifically, for such N-substituted amino acids, an alkyl group, an aralkyl group, a cycloalkyl group, or such are preferably used.

An "amino acid" in the present invention is $\alpha$-, $\beta$-, and $\gamma$-amino acids, and is not limited to natural amino acids and may be unnatural amino acids. (In the present invention, "natural amino acids" refer to the 20 types of amino acids included in proteins. Specifically, they refer to Gly, Ala, Ser, Thr, Val, Leu, Ile. Phe, Tyr, Trp, His, Glu, Asp. Gln, Asn, Cys, Met, Lys, Arg, and Pro.) In the case of $\alpha$-amino acids, they may be L-amino acids or D-amino acids, or may be $\alpha,\alpha$-dialkylamino acids. Selection of amino acid side chains are not particularly limited, but examples include a hydrogen atom, alkyl groups, alkenyl groups, alkynyl groups, aryl groups, heteroaryl groups, aralkyl groups, and cycloalkyl groups. The amino acid side chains may be respectively attached with substituent groups, and substituent groups are freely selected from among any functional groups including, for example, an N atom, an O atom, an S atom, a B atom, a Si atom, or a P atom. The number of substituent groups is not particularly limited and the amino acid side chains may have one or two or more substituent groups.

The term "amino acid analog" in the present invention preferably means α-hydroxycarboxylic acids. Like amino acids, the side chains of α-hydroxycarboxylic acids are not particularly limited, and examples include a hydrogen atom, alkyl groups, alkenyl groups, alkynyl groups, aryl groups, heteroaryl groups, aralkyl groups, and cycloalkyl groups. The steric structures of α-hydroxycarboxylic acids may be those that correspond to the L- or D-form of amino acids. The side chains are not particularly limited, and are freely selected from among arbitrary functional groups carrying, for example, an N atom, an O atom, an S atom, a B atom, a Si atom, or a P atom. They may have one or two or more substituent groups, and the number of substituent groups is not particularly limited. For example, they may have an S atom, and may also have functional groups such as amino groups or halogen groups. Similarly to the case with α-amino acids, arbitrary steric configurations are accepted in the case of β- and γ-amino acids as well, and selection of their side chains is also not particularly limited.

The "amino acids" or "amino acid analogs" constituting the peptides synthesized in the present invention includes all their respective corresponding isotopes. The isotope in the "amino acids" or "amino acid analogs" refers to one in which at least one atom is replaced with an atom of the same atomic number (number of protons is the same) and of different mass number (sum of the number of protons and neutrons is different). Examples of the isotope contained in the "amino acids" or "amino acid analogs" constituting the peptide compounds of the present invention include a hydrogen atom, a carbon atom, a nitrogen atom, an oxygen atom, a phosphorus atom, a sulfur atom, a fluorine atom and a chlorine atom, and specific examples include 2H, 3H, 13C, 14C, 15N, 17O, 18O, 31P, 32P, 35S, 18F, and 36Cl.

The amino acids or the amino acid analogs may have one or two or more substituent groups. Examples of such substituent groups include those derived from an O atom, an N atom, an S atom, a B atom, a P atom, a Si atom, and a halogen atom.

Examples of halogen-derived substituents include fluoro (—F), chloro (—Cl), bromo (—Br), and iodo (—I).

Examples of O atom-derived substituents include hydroxyl (—OH), oxy (—OR), carbonyl (—C=O—R), carboxyl (—CO2H), oxycarbonyl (—C=O—OR), carbonyloxy (—O—C=O—R), thiocarbonyl (—C=O—SR), carbonylthio group (—S—C=O—R), aminocarbonyl (—C=O—NHR), carbonylamino (—NH—C=O—R), oxycarbonylamino (—NH—C=O—OR), sulfonylamino (—NH—SO2-R), aminosulfonyl (—SO2-NHR), sulfamoylamino (—NH—SO2-NHR), thiocarboxyl (—C(=O)—SH), and carboxylcarbonyl (—C(=O)—CO2H).

Examples of oxy (—OR) include alkoxy, cycloalkoxy, alkenyloxy, alkynyloxy, aryloxy, heteroaryloxy, and aralkyloxy.

Examples of carbonyl (—C=O—R) include formyl (—C=O—H), alkylcarbonyl, cycloalkylcarbonyl, alkenylcarbonyl, alkynylcarbonyl, arylcarbonyl, heteroarylcarbonyl, and aralkylcarbonyl.

Examples of oxycarbonyl (—C=O—OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.
(—C=O—OR)

Examples of carbonyloxy (—O—C=O—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of thiocarbonyl (—C=O—SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of carbonylthio (—S—C=O—R) include, alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of aminocarbonyl (—C=O—NHR) include alkylaminocarbonyl, cycloalkylaminocarbonyl, alkenylaminocarbonyl, alkynylaminocarbonyl, arylaminocarbonyl, heteroarylaminocarbonyl, and aralkylaminocarbonyl. Additional examples include compounds produced by further substitution of an alkyl, a cycloalkyl, an alkenyl, an alkynyl, an aryl, a heteroaryl, or an aralkyl for the H atom bonded to the N atom in —C=O—NHR.

Examples of carbonylamino (—NH—C=O—R) include alkylcarbonylamino, cycloalkylcarbonylamino, alkenylcarbonylamino, alkynylcarbonylamino, arylcarbonylamino, heteroarylcarbonylamino, and aralkylcarbonylamino. Additional examples include compounds produced by further substitution of an alkyl, a cycloalkyl, an alkenyl, an alkynyl, an aryl, a heteroaryl, or an aralkyl for the H atom bonded to the N atom in —NH—C=O—R.

Examples of oxycarbonylamino (—NH—C=O—OR) include alkoxycarbonylamino, cycloalkoxycarbonylamino, alkenyloxycarbonylamino, alkynyloxycarbonylamino, aryloxycarbonylamino, heteroaryloxycarbonylamino, and aralkyloxycarbonylamino. Additional examples include compounds produced by further substitution of an alkyl, a cycloalkyl, an alkenyl, an alkynyl, an aryl, a heteroaryl, or an aralkyl for the H atom bonded to the N atom in —NH—C=O—OR.

Examples of sulfonylamino (—NH—SO2-R) include alkylsulfonylamino, cycloalkylsulfonylamino, alkenylsulfonylamino, alkynylsulfonylamino, arylsulfonylamino, heteroarylsulfonylamino, and aralkylsulfonylanino. Additional examples include compounds produced by further substitution of an alkyl, a cycloalkyl, an alkenyl, an alkynyl, an aryl, a heteroaryl, or an aralkyl for the H atom bonded to the N atom in —NH—SO2-R, Examples of aminosulfonyl (—SO2-NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. Additional examples include compounds produced by further substitution of an alkyl, a cycloalkyl, an alkenyl, an alkynyl, an aryl, a heteroaryl, or an aralkyl for the H atom bonded to the N atom in —SO2-NHR.

Examples of sulfamoylamino (—NH—SO2-NHR) include alkylsulfamoylamino, cycloalkylsulfamoylamino, alkenylsulfamoylanino, alkynylsulfamoylamino, arylsulfamoylamino, heteroarylsulfamoylamino, and aralkylsulfamoylamino. Additionally, the two H atoms bonded to the N atoms in —NH—SO2-NHR may be substituted with a substituent independently selected from the group consisting of an alkyl, a cycloalkyl, an alkenyl, an alkynyl, an aryl, a heteroaryl, and an aralkyl; or these two substituents may form a ring.

For S atom-derived substituents, examples include thiol (—SH), thio (—S—R), sulfinyl (—S=O—R), sulfonyl (—S(O)2-R), and sulfo (—SO3H).

Examples of thio (—S—R) are selected from alkylthio, cycloalkylthio, alkenylthio, alkynylthio, arylthio, heteroarylthio, aralkylthio, and such.

Examples of sulfinyl (—S=O—R) include alkylfulfinyl, cycloalkylsulfinyl, alkenylsulfinyl, alkynylsulfinyl, arylsulfinyl, heteroarylsulfinyl, and aralkylsulfinyl.

Examples of sulfonyl (—S(O)2-R) include alkylsulfonyl, cycloalkylsulfonyl, alkenylsulfonyl, alkynylsulfonyl, arylsulfonyl, heteroarylsulfonyl, and aralkylsulfonyl.

For N atom-derived substituents, examples include azide (—N3, also called "azido group"), cyano (—CN), primary amino (—NH2), secondary amino (—NH—R), tertiary amino (—NR(R')), amidino (—C(=NH)—NH2), substituted amidino (—C(=NR)—NR'R"), guanidino (—NH—C(=NH)—NH2), substituted guanidino (—NR—C(=NR'—)—NR'R"), and aminocarbonylamino (—NR—CO—NR'R").

Examples of secondary amino (—NH—R) include alkylamino, cycloalkylamino, alkenylamino, alkynylamino, arylamino, heteroarylamino, and aralkylamino.

Examples of tertiary amino (—NR(R')) include amino groups, such as alkyl(aralkyl)amino, having any two substituents each independently selected from alkyl, cycloalkyl, alkenyl, alkynyl, aryl, heteroaryl, and aralkyl; and these two arbitrary substituents may form a ring.

Examples of substituted amidino (—C(=NR)—NR'R") include groups in which each of the three substituents R, R', and R" on the N atoms is independently selected from among alkyl, cycloalkyl, alkenyl, alkynyl, aryl, heteroaryl, and aralkyl; and such examples include alkyl(aralkyl)(aryl) amidino.

Examples of substituted guanidino (—NR—C(=NR''')—NR'R") include groups in which each of R, R', R", and R''' is independently selected from alkyl, cycloalkyl, alkenyl, alkynyl, aryl, heteroaryl, and aralkyl; or groups in which they form a ring.

Examples of aminocarbonylamino (—NR—CO—NR'R") include groups in which each of R, R', and R" is independently selected from a hydrogen atom, alkyl, cycloalkyl, alkenyl, alkynyl, aryl, heteroaryl, and aralkyl; or groups in which they form a ring.

Examples of B atom-derived substituents include boryl (—BR(R')) and dioxyboryl (—B(OR)(OR')). These two substituents. R and R', are each independently selected from alkyl, cycloalkyl, alkenyl, alkynyl, aryl, heteroaryl, and aralkyl; or they may form a ring.

This way, the amino acids or amino acid analogs of the present invention may have one or two or more of the various substituent groups including an O atom, an N atom, an S atom, a B atom, a P atom, an Si atom, and a halogen atom, which are ordinarily used in small molecule compounds. These substituent groups may further be substituted with other substituent groups.

Herein, the "amino acid" and "amino acid analog" constituting the peptides synthesized in the present invention are also referred to as "amino acid residue" and "amino acid analogue residue", respectively.

In the present invention, "Fmoc-protected amino acid" and "Fmoc-protected amino acid analog" are an amino acid and an amino acid analog respectively having at least one each of following functional groups i) and ii):
  i) a main chain amino group protected by at least one protecting group having an Fmoc skeleton; and
  ii) at least one free carboxylic acid group or active esterified carboxylic acid group.

"Protecting group having an Fmoc skeleton" in the present invention means an Fmoc group or a group formed by introducing arbitrary substituent group(s) into arbitrary position(s) in the skeleton constituting the Fmoc group. Specific examples of protecting groups having an Fmoc skeleton include 9-fluorenytmethyloxycarbonyl (Fmoc) group, 2,7-di-tert-butyl-Fmoc (Fmoc*) group. 2-fluoro-Fmoc (Fmoc (2F)) group, 2-monoisooctyl-Fmoc (mio-Fmoc) group, and 2,7-diisooctyl-Fmoc (dio-Fmoc) group. In the present invention, protecting groups that are deprotectable (that can be deprotected) under basic conditions or by nucleophiles showing basicity (for example, piperidine or hydrazine) may also be used in place of protecting groups having an Fmoc skeleton. Specific examples of such protecting groups include 2-(4-nitrophenylsulfonyl)ethoxycarbonyl (Nsc) group, (1,1-dioxobenzo[b]thiphene-2-yl)methyloxycarbonyl (Bsmoc) group, (1,1-dioxonaphtho[1,2-b]thiophene-2-yl)methyloxycarbonyl (α-Nsmoc) group, 1-(4,4-dimethyl-2,6-dioxocyclohex-1-ylidine)-3-methylbutyl (ivDde) group, tetrachlorophthaloyl (TCP) group, 2-[phenyl(methyl)sulfonio]ethyloxycarbonyl tetrafluoroborate (Pms) group, ethanesulfonylethoxycarbonyl (Esc) group, and 2-(4-sulfophenylsulfonyl)ethoxycarbonyl (Sps) group. Furthermore, protecting groups that are deprotectable by means other than acids or bases may also be used. Specific examples of such protecting groups include benzyloxycarbonyl (Z) group which are deprotectable by hydrogenation in the presence of a transition metal catalyst such as palladium, allyloxycarbonyl (Alloc) group which are deprotectable by a combination of a palladium catalyst and a scavenger (for example, the combination of tetrakis(triphenylphosphine)palladium (0) (Pd(PPh3)4) and phenylsilane), o-nitrobenzenesulfonyl (oNBS, Ns) group which are deprotectable by a combination of an alkylthiol or arylthiol with a base, 2,4-dinitrobenzenesulfonyl (dNBS) group, and dithiasuccinoyl (Dts) group, and p-nitrobenzyloxycarbonyl (pNZ) group which are deprotectable reductively by a reducing agent such as sodium dithionite (Na2S2O4) or by hydrogenation in the presence of a transition metal catalyst (Reference Document: Amino Acid-Protecting Groups, Chem. Rev. 2009, 109, 2455-2504).

In the present invention which uses the Fmoc method, Fmoc-protected amino acids or Fmoc-protected amino acid analogs that may preferably be used are, for example, those in which the main chain amino group is protected by the Fmoc group, side chain functional group(s) are protected when necessary by protecting group(s) that are not cleaved by bases such as piperidine or DBU, and the main chain carboxylic acid group is not protected. Fmoc-protected amino acids or Fmoc-protected amino acid analogs, which have an amino group protected with a protecting group that has the Fmoc skeleton and a carboxylic acid group without a protecting group, may also be preferably used.

In the present invention, when an Fmoc-protected amino acid, an Fmoc-protected amino acid analog, or an Fmoc-protected peptide has side-chain functional group(s), such functional group(s) are preferably protected by protecting group(s). When side-chain functional groups are protected by protecting groups, well-known protecting groups that can be deprotected under conditions of choice can be used. Such protecting groups are preferably protecting groups that are not cleaved under basic conditions and are deprotected under conditions having weaker acidity than TFA. Protecting groups that are deprotectable under acidic conditions include protecting groups that can be deprotected in the range of, for example, pH 1 to pH 7, and preferably pH 2 to pH 6. Alternatively, protecting groups that are deprotectable by 10% or lower TFA, or protecting groups having the later-described structures can be used. In the present invention, well-known protecting groups can be used as the side-chain protecting groups. For example, from among the protecting groups described in the following documents i) and ii), those that satisfy the above-mentioned conditions can be employed as the side-chain protecting groups.

NPL i) Greene's Protective Groups in Organic Synthesis, Fourth Edition

NPL ii) Chemical Reviews, 2009, 109(6), 2455-2504

The methods of the present invention can be used in peptide synthesis by parallel synthesis. In such cases, protecting groups are not always necessary for the amino acid side chains, but when protecting groups are necessary for the side chains, it is preferable that the protecting groups used be deprotected quickly under the deprotection conditions of the present invention. It is preferable that the side chain protecting groups be 50% deprotected in 24 hours or less, and it is particularly preferable that the side chain protecting groups be 90% deprotected in 4 hours or less. As protecting groups that satisfy such conditions, protecting groups having the later-described Trt skeleton, THP skeleton, THF skeleton, or TBS skeleton are preferred. To enable easy deprotection by an acid and to secure high reactivity during elongation, protecting groups having at least one hydrogen-atom substituent on the protecting-group atom which directly bonds to the functional group (three-dimensional bulkiness is smaller than protecting groups having a Trt skeleton) are preferred. Among them, protecting groups in which substituent groups other than hydrogen form a ring are more preferred, and THP and THF are particularly preferred.

The methods of the present invention can be used for industrial peptide synthesis as well. In such cases too, the amino acid side chain(s) do not always need to have protecting group(s) as in the case of parallel synthesis, but when the side chains have protecting groups, they preferably have the same protecting groups as in parallel synthesis. If there is no problem with hydrolysis and N- to O-acyl shift during deprotection for the sequence of a peptide to be synthesized, but elongation reaction is problematic due to the bulkiness of the protecting groups, strong acids generally used for deprotection such as TFA may be used in deprotection. Furthermore, when there is no problem with elongation reaction of the peptide to be synthesized, bulky protecting groups may also be used.

In the present invention, "a condition of weaker acidity than TFA" preferably includes conditions that use a weakly acidic solution containing a weak acid which has an aqueous pKa value of 0 to 9 in a solvent which has an aqueous pKa value of 5 to 14 and whose ionization ability value YOTs is positive.

The "weak acid having an aqueous pKa value of 0 to 9" is more preferably weak acids having an aqueous pKa of 1 to 5. Such weak acids specifically include tetramethylammonium hydrogensulfate (aqueous pKa=2.0), oxalic acid (aqueous pKa=1.23), and maleic acid (aqueous pKa=1.92). The concentration of the weak acid dissolved in a solvent may be any concentration as long as the condition of showing weaker acidity than TFA is satisfied.

A "solvent having an aqueous pKa value of 5 to 14 and whose ionization ability value YOTs is positive" preferably includes fluoroalcohols. Fluoroalcohol is a generic term for an alcohol in which a fluorine atom(s) is bonded to carbon atom(s) of the alcohol-constituting carbon atoms excluding the carbon atom to which a hydroxyl group is bonded. In the present invention, alcohols in which a hydroxyl group is bonded to an aromatic ring such as 2,3,4,5,6-pentafluorophenol are also included in the fluoroalcohols. The preferred fluoroalcohols are 2,2-trifluoroethanol (TFE) and hexafluoro-2-propanol (HFIP).

In the present invention, as long as the condition of yielding weaker acidity than TFA is satisfied, other organic solvents (for example, dichloromethane or 1.2-dichloroethane) and cationic scavengers (for example, triisopropylsilane), and such may further be added to the aforementioned weakly acid solution.

In the present invention, when Fmoc-protected amino acids or Fmoc-protected amino acid analogs have protecting groups on their side chains, preferable examples of such side-chain protecting groups are as described below.

When the side-chain protecting groups are those for the hydroxyl groups of Ser, Thr, Hyp, and derivatives thereof, protecting groups having a MOM skeleton, Bn skeleton. Dpm skeleton, Trt skeleton, silyl skeleton, or Boc skeleton each of which is represented by the following general formulae are preferred.

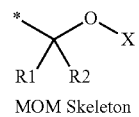

MOM Skeleton

Representative examples of protecting groups having a MOM skeleton include MOM (R1=H, R2=H, X=Me), EE (R1=Me, R2=H, X=Et), MIP (R1=Me, $R^2$=Me, X=Me), THP (R2=H, having a cyclic structure of four carbon atoms by R1 and X), THF (R2=H, having a cyclic structure of three carbon atoms by R1 and X), and SEM (R1=H, R2=H, X=2-trimethylsilylethyl). Regarding the Me and Et substituents on the skeleton, the skeleton substituted with other substituents such as alkyl groups, benzyl groups, and aryl groups may be used.

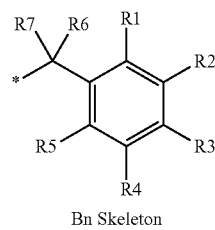

Bn Skeleton

Representative examples of protecting groups having a Bn skeleton include Pis (R6=Me, R7=Me, other Rs=H), PMB (R3=OMe, other Rs=H), and DMB (R1=OMe, R3=OMe, other Rs=H). Instead of the Me substituent group, another alkyl group may be used. Furthermore, the benzene ring may have substituents such as alkyl groups, aryl groups, and halogen groups.

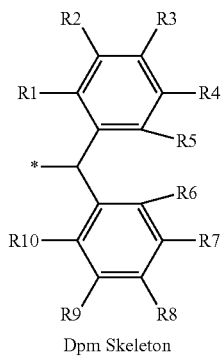

Dpm Skeleton

Representative examples of protecting groups having a Dpm skeleton include Dpm (all Rs=H). The aromatic ring may have substituents such as alkyl groups, aryl groups, alkoxy groups, and halogen groups.

Groups in which R5 and R6 are bridged, such as the Xan group in which R5 and R6 are bridged through an oxygen atom or a dibenzosuberyl group in which R5 and R6 are bridged through two carbon atoms may also be used.

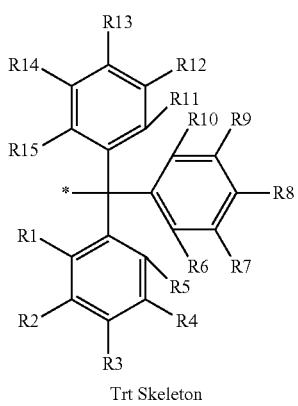

Trt Skeleton

Representative examples of protecting groups having a Trt skeleton include Trt (all Rs=H), Mint (R3=Me, other Rs=H), Mtt (R3=OMe, other Rs=H), Dnt (R3=OMe, R8=OMe, other Rs=H), and Clt (R1=Cl, other Rs=H). The aromatic rings may have substituents such as alkyl groups, aryl groups, alkoxy groups, and halogen groups.

Furthermore, groups in which R5 and R6 are bridged, such as the Pixyl group in which R5 and R6 are bridged through an oxygen atom may also be used.

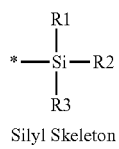

Silyl Skeleton

Representative examples of protecting groups having a silyl skeleton include TBS (R1=Me, R2=Me, R3=tBu). Instead of Me and tBu, other groups such as alkyl groups and aryl groups may be the substituents.

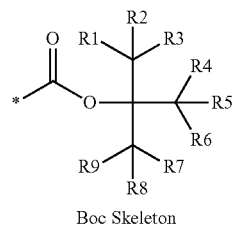

Boc Skeleton

Representative examples of protecting groups having a Boc skeleton include Boc (all Rs=H), but it may be substituted with other alkyl groups, aryl groups, and such.

Additionally, protecting groups shown below may also be used.

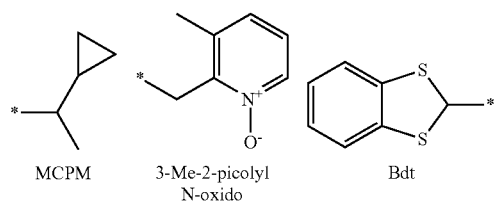

MCPM     3-Me-2-picolyl N-oxido     Bdt

Among these protecting groups, THP and Trt are particularly preferred. Furthermore, THP and Trt are particularly preferred as the side-chain protecting groups when the amino acid residue is Ser, and THP is particularly preferred as the side-chain protecting group when the amino acid residue is Thr.

When the side-chain protecting groups are those for amino acids having an aryl group with a hydroxyl group substituent, such as Tyr, D-Tyr, or Tyr(3-F), for example, protecting groups having a MOM skeleton, Bn skeleton, Dpm skeleton, Trt skeleton, silyl skeleton, Boc skeleton, or tBu skeleton which are represented by the following general formula are preferred.

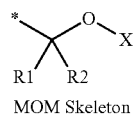

MOM Skeleton

Representative examples of protecting groups having a MOM skeleton include MOM (R1=H. R2=H, X=Me), BOM (R1=H, R2=H, X=Bn), EE (R1=Me. R2=H, X=Et), THP (R2=H, having a cyclic structure of four carbon atoms by R1 and X), THF (R2=H, having a cyclic structure of three carbon atoms by R1 and X), and SEM (R1=H, R2=H, X=2-trimethylsilylethyl). Regarding the Me and Et substituent groups on the skeletons, a skeleton substituted with other substituents such as alkyl groups, benzyl groups, or aryl groups may also be used.

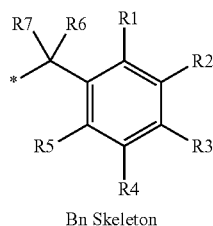

Bn Skeleton

Representative examples of protecting groups having a Bn skeleton include Pis (R6=Me, R7=Me, other Rs=H), PMB (R3=OMe, other Rs=H), and DMB (R1=OMe, R3=OMe, other Rs=H). Instead of the Me substituent group, other alkyl groups may be used. Furthermore, the benzene ring may have substituents such as alkyl groups, aryl groups, and halogen groups.

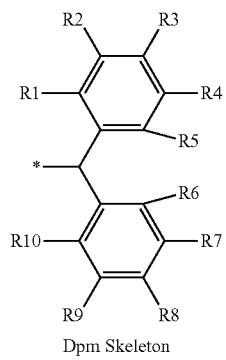

Dpm Skeleton

Representative examples of protecting groups having a Dpm skeleton include Dpm (all Rs=H). The aromatic ring may have substituents such as alkyl groups, aryl groups, alkoxy groups, and halogen groups.

Groups in which R5 and R6 are bridged, such as the Xan group in which R5 and R6 are bridged through an oxygen atom or a dibenzosuberyl group in which R5 and R6 are bridged through two carbon atoms may also be used.

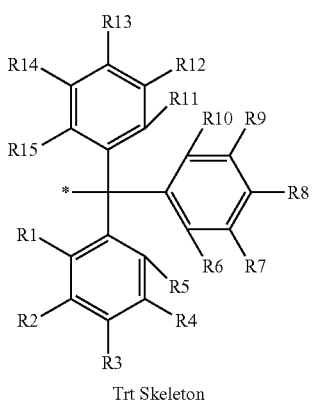

Trt Skeleton

Representative examples of protecting groups having a Trt skeleton include Trt (all Rs=H), Mmt (R3=Me, other Rs=H), Mtt (R3=OMe, other Rs=H), and Clt (R1=Cl, other Rs=H). The aromatic ring may have substituents such as alkyl groups, aryl groups, alkoxy groups, and halogen groups.

Furthermore, groups in which R5 and R6 are bridged, such as the Pixyl group in which R5 and R6 are bridged through an oxygen atom may also be used.

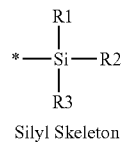

Silyl Skeleton

Representative examples of protecting groups having a silyl skeleton include TBS (R1=Me, R2=Me, R3=tBu). Instead of the Me and tBu, other groups such as alkyl groups and aryl groups may be the substituents.

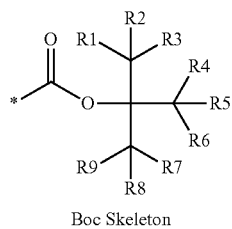

Boc Skeleton

Representative examples of protecting groups having a Boc skeleton include Boc (all Rs=H), but it may be substituted with other groups such as alkyl groups, aryl groups.

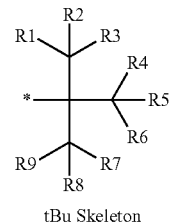

tBu Skeleton

Representative examples of protecting groups having a tBu skeleton include tBu (all Rs=H). Instead of H, it may have substituents such as alkyl groups and aryl groups.

Among these protecting groups, tBu, Pis, Trt, Clt, THP, and THF are particularly preferred. Furthermore, when the amino acid residue is Tyr or D-Tyr, the side-chain protecting group is particularly preferably tBu, Trt, Clt, or THP, and when the amino acid residue is Tyr(3-F), the side-chain protecting group is particularly preferably tBu or Pis.

When the side-chain protecting groups are those for an amino acid that has an imidazole on its side chain, such as His or MeHis, use of protecting groups having, for example, a MOM skeleton, Bn skeleton, or Trt skeleton which are represented by the following general formulae is preferred.

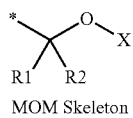

MOM Skeleton

Representative examples of protecting groups having a MOM skeleton include MBom (R1=H. R2=H, X=4- methoxybenzyl), 2,4-DMBom (R1=H, R2=H, X=2,4-dimethoxybenzyl), 3,4-DMBom (R1=H, R2=H, X=3,4-dimethoxybenzyl), EE (R1=Me, R2=H, X=Et). THP (R2=H, having a cyclic structure of four carbon atoms by R1 and X), and THF (R2=H, having a cyclic structure of three carbon atoms by R1 and X). Regarding the Me and Et substituents on the skeleton, the skeleton having protecting groups substituted with other substituents such as alkyl groups, benzyl groups, or aryl groups may also be used.

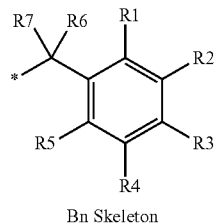

Bn Skeleton

Representative examples of protecting groups having a Bn skeleton include Pis (R6=Me, R7=Me, other Rs=H), PMB (R3=OMe, other Rs=H), and DMB (R1=OMe, R3=OMe, other Rs=H). Instead of the Me substituent group, other alkyl groups may be used. Furthermore, the benzene ring may have substituents such as alkyl groups, aryl groups, and halogen groups.

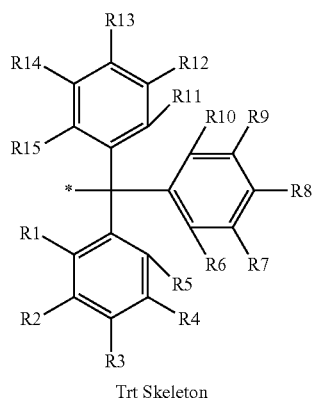

Trt Skeleton

Representative examples of protecting groups having a Trt skeleton include Trt (all Rs=H), Mmt (R3=Me, other Rs=H), Mtt (R3=OMe, other Rs=H), and Clt (R1=Cl, other Rs=H). The aromatic ring may have substituents such as alkyl groups, aryl groups, alkoxy groups, and halogen groups.

Among them, Trt is particularly preferred. Furthermore, when the amino acid residue is His or MeHis, the side-chain protecting group is particularly preferably Trt.

Furthermore, protecting groups having a MOM skeleton, Bn skeleton, Dpm skeleton, Trt skeleton, tBu skeleton, or phenyl-EDOTn skeleton represented by the following general formulae can be used, for example, as the protecting group for the side-chain carboxylic acid group of Asp, Glu, and derivatives thereof when the main-chain carboxylic acid group is used as a "free carboxylic acid group or active esterified carboxylic acid group", or as the protecting group for the main-chain carboxylic acid group when the side-chain carboxylic acid group of Asp, Glu, and derivatives thereof as a "free carboxylic acid group or active esterified carboxylic acid group". Furthermore, protecting groups having an orthoester skeleton in which three alkoxy groups are bonded to a carboxylic acid group-derived carbon atom can also be used as protecting groups for carboxylic acids. Carbon atoms forming such protecting groups may have substitutions.

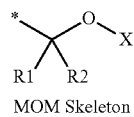

MOM Skeleton

Representative examples of protecting groups having a MOM skeleton include BOM (R1=H, R2=H, X=Bn), THP (R2=H, having a cyclic structure of four carbon atoms by R1 and X), and THF (R2=H, having a cyclic structure of three carbon atoms by R1 and X). For the substituent groups on the skeleton, a skeleton having other substituents such as alkyl groups, benzyl groups, or aryl groups may also be used.

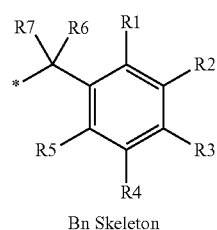

Bn Skeleton

Representative examples of protecting groups having a Bn skeleton include Pis (R6=Me, R7=Me, other Rs=H), PMB (R3=OMe, other Rs=H), DMB (R1=OMe, R3=OMe, other Rs=H), and piperonyl (R2 and R3 are both substituted with oxygen atoms, and those oxygen atoms are bridged through a single carbon atom; other Rs=H). Instead of the Me substituent group, other alkyl groups may be used. Furthermore, the benzene ring may have substituents such as alkyl groups, aryl groups, and halogen groups.

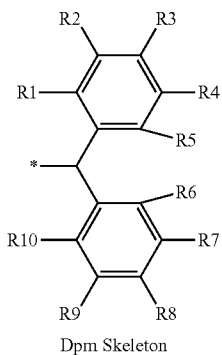

Dpm Skeleton

Representative examples of protecting groups having a Dpm skeleton include Dpm (all Rs=H). The aromatic ring may have substituents such as alkyl groups, aryl groups, alkoxy groups, and halogen groups.

Furthermore, groups in which R5 and R6 are bridged, such as a dibenzosuberyl group in which R5 and R6 are bridged through two carbon atoms may also be used.

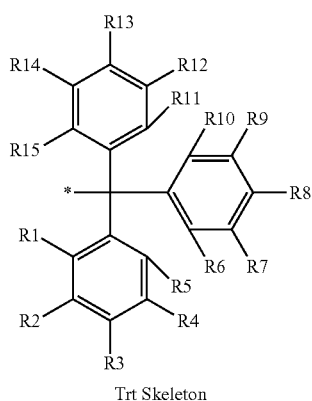

Trt Skeleton

Representative examples of protecting groups having a Trt skeleton include Trt (all Rs=H), Mmt (R3=Me, other Rs=H), Mtt (R3=OMe, other Rs=H), and Clt (R1=Cl, other Rs=H). The aromatic ring may have substituents such as alkyl groups, aryl groups, alkoxy groups, and halogen groups.

Furthermore, groups in which R5 and R6 are bridged, such as the Pixyl group in which R5 and R6 are bridged through an oxygen atom may also be used.

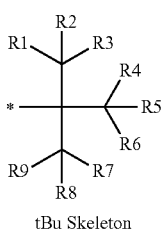

tBu Skeleton

Representative examples of protecting groups having a tBu skeleton include tBu (all Rs=H), and Mpe (R1=Me, R4=Me, other Rs=H). It may have substituents such as other alkyl groups and aryl groups.

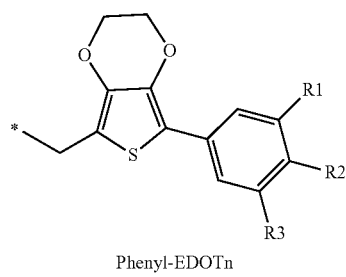

Phenyl-EDOTn

Phenyl-EDOTn having the following combination of substituent groups can be used: (i) R1=R2=R3=OMe; (ii) R1=R2=OMe, R3=H; (iii) R1=R2=H, R3=OMe; or (iv) R1=R2=R3=H.

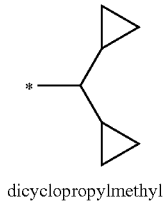

dicyclopropylmethyl

A dicyclopropylmethyl group may also be used.

Among them, tBu, Pis, and Trt are particularly preferred.

In the present invention, "Fmoc-protected peptide" means a peptide comprising either one or both of the aforementioned "Fmoc-protected amino acid" and "Fmoc-protected amino acid analog". Examples of such peptides include dipeptides and oligopeptides comprising a total of two or more molecules including either one or both of the aforementioned Fmoc-protected amino acids and Fmoc-protected amino acid analogs.

In peptide synthesis by the solid-phase methods of the present invention, Fmoc-protected amino acids, Fmoc-protected amino acid analogs, or Fmoc-protected peptides (also referred to as Fmoc-protected amino acids and the like) can be supported onto a solid phase using resins. The groups in the employed resin, which are used for bonding to the Fmoc-protected amino acids and the like (resin bonding group) are not particularly limited as long as they allow peptides to be cleaved off by acids. The supported amount and the supported ratio of the Fmoc-protected amino acids and the like are not particularly limited either. In the present invention, for example, a tritylchloride resin (Trt resin), a 2-chlorotritylchloride resin (Clt resin), a 4-methyltritylchloride resin (Mtt resin), and 4-methoxytritylchloride resin (Mmt) can be used. It is particularly preferred that the resins have resin bonding groups which are described and have been evaluated to be "H (<5% TFA in DCM)" as acid sensitivity in the Solid-phase Synthesis Handbook (published by Merck Co. on May 1, 2002), and they can be selected appropriately according to the functional groups on the amino acids to be used. For example, when using a carboxylic acid (main-chain carboxylic acid or side-chain carboxylic acid represented by Asp or Glu) or a hydroxy group on an aromatic ring (phenol group represented by Tyr) as the functional group on the amino acid, use of trityl chloride resin (Trt resin) or 2-chlorotritylchloride resin (Clt resin) as the resin is preferred. When using an aliphatic hydroxy group (aliphatic alcohol group represented by Ser or Thr) as the functional group on the amino acid, use of tritylchloride resin (Trt resin), 2-chlorotritylchloride resin (Clt resin), or 4-methyltritylchloride resin (Mtt) as the resin is preferred.

Furthermore, the types of polymers constituting the resins are also not particularly limited. For resins composed of polystyrenes, either 100 to 200 mesh or 200 to 400 mesh may be used. The cross-link percentage is also not particularly limited, but those cross-linked with 1% divinylbenzene (DVB) are preferred.

Fmoc-protected amino acids, Fmoc-protected amino acid analogs, or Fmoc-protected peptides are supported onto resins by performing chemical reactions between the bonding groups on the resins and the free carboxylic acid groups or the active esterified carboxylic acid groups of Fmoc-protected amino acids, or Fmoc-protected amino acid analogs, or amino acids positioned at the C terminus of the Fmoc-protected peptides. In this case, the free carboxylic acid may be the main-chain carboxylic acid of the amino acids or amino acid analogs, or the side-chain carboxylic acids (Asp and such). Instead of the carboxylic acid groups, free OH groups or free SH groups of the side chains or main chains of Fmoc-protected amino acids, Fmoc-protected amino acid analogs, or amino acids positioned at the C-terminus of the Fmoc-protected peptides, may also be used for supporting onto the solid phase.

The protecting groups having an Fmoc skeleton, which are carried by Fmoc-protected amino acids, Fmoc-protected amino acid analogs, or Fmoc-protected peptides supported onto the solid phase, are deprotected by bases to expose their amino groups. The bases used here is not particularly limited, and deprotecting agents generally used in peptide synthesis may be used (for example, Amino Acid-Protecting Groups (Chem. Rev. 2009, 109, 2455-2504)). Examples of such deprotecting agents are preferably secondary amines, bases having an amidine skeleton, and bases having a guanidine skeleton. Specific examples of the secondary amines include piperidine, morpholine, pyrrolidine, and piperidine. Specific examples of bases having an amidine skeleton include 1,8-diazabicyclo[5.4.0]undeca-7-en (DBU) and 1,5-diazabicyclo[4.3.0]-5-nonen (DBN). Specific examples of the bases having a guanidine skeleton include 1,1,3,3-tetramethylguanidine.

The aforementioned exposed amino groups and the free or active esterified carboxylic acid groups of newly added Fmoc-protected amino acids, Fmoc-protected amino acid analogs, or Fmoc-protected peptides are condensed to form peptide bonds.

The condensing agents used when condensing amino groups and carboxylic acid groups are not particularly limited as long as they can form amide bonds, and condensing agents generally used in peptide synthesis are preferred (for example, Peptide Coupling Reagents, More than a Letter Soup (Chem. Rev. 2011, 111, 6557-6602)). Specific examples of such condensing agents include condensing agents having a carbodiimide skeleton. For example, condensing agents having a carbodiimide skeleton can be used for condensation reactions by combining them with hydroxy compounds that can form active esters. Examples of the condensing agents having a carbodiimide skeleton include N,N'-dicyclohexylcarbodiimide (DCC). N,N'-diisopropylcarbodiimide (DIC), and 1-ethyl-3-(3-dimethylaminopropyl)carbodiimide hydrochloride (WSCI·HCl) (see for example, the catalog of Watanabe Chemical: Amino Acids and Chiral Building Blocks to New Medicine). Examples of the hydroxy compounds that can form active esters include 1-hydroxy-1H-benzotriazole (HOBt), 1-hydroxy-7-azabenzotriazole (HOAt), ethyl 2-cyano-2-(hydroxyimino)acetate (oxyma), 3,4-dihydro-3-hydroxy-4-oxo-1,2,3-benzotriazin (HOOBt or HODhbt), N-hydroxy-5-norbornene-2,3-dicarboximide (HONB), 2,3,4,5,6-pentafluorophenol (HOPfp), N-hydroxysuccinimide (HOSu), and 6-chloro-1-hydroxy-1H-benzotriazole (Cl-HOBt) (see for example, the catalog of Watanabe Chemical: Amino Acids and Chiral Building Blocks to New Medicine). Furthermore, salts having such skeletons such as K-oxyma, which is the potassium salt of oxyma, can also be used. Among them, HOBt, HOAt, oxyma, and HOOBt are particularly preferred. Even among them, combined use of DIC and HOAt, or combined use of DIC and oxyma are preferred. In addition, the following agents can be used in combination in the condensation reaction:

as phosphonium condensing agents and uronium condensing agents, any one of: O-(1H-benzotriazol-1-yl)-N,N,N',N'-tetramethyluronium hexafluorophosphate (HBTU); O-(7-aza-1H-benzotriazol-1-yl)-N,N,N',N'-tetramethyluronium hexafluorophosphate (HATU); N-[1-(cyano-2-ethoxy-2-oxoethylideneaminooxy)dimethylamino(morpho-lino)]uronium hexafluorophosphate (COMU); O-[(ethoxycarbonyl)cyanomethylene-amino]-N,N,N',N'-tetramethyluronium hexafluorophosphate (HOTU): O-(1H-benzotriazol-1-yl)-N,N,N',N'-tetramethyluronium tetrafluoroborate (TBTU); O-(7-azabenzotriazol-1-yl)-N,N,N',N'-tetramethyluronium tetrafluoroborate (TATU); 1H-benzotriazol-1-yloxy-tri(pyrolidino)phosphonium hexafluorophosphate (PyBOP); 1H-benzotriazol-1-yloxy-tris(dimethylamino)phosphonium hexafluorophosphate (BOP); bromotri(pyrolidino)phosphonium hexafluorophosphate (PyBroP); chlorotri(pyrolid-ino)phosphonium hexafluorophosphate (PyCloP); (7-azabenzotriazol-1-yloxy) tripyrrolid-inophosphonium hexafluorophosphate (PyAOP); bromotris(dimethylamino)phosphonium hexafluorophosphate (Brop); 3-(diethoxyphosphoryloxy)-1,2,3-benzotriazin-4(3H)-one (DEPBT): N,N,N',N'-tetramethyl-O—(N-succinimidyl)uronium tetrafluoroborate (TSTU); N,N,N',N'-tetramethyl-O—(N-succinimidyl)uronium hexafluorophosphate (HSTU); O-(3,4-dihydro-4-oxo-1,2,3-benzotriazin-3-yl)-N,N,N',N'-tetramethyluronium tetrafluoroborate (TDBTU); tetramethylthiuronium S-(1-oxide-2-pyridyl)-N,N,N',N'-tetrafluoroborate (TOTT); and O-(2-oxo-1(2H)pyridyl)-N,N,N',N'-tetramethyluronium tetrafluoroborate (TPTU), and any one of the bases, N,N-diisopropylethylamine (DIPEA); triethylamine (TEA); 2,4,6-trimethylpyridine (2,4,6-colidine); and 2,6-dimethylpyridine (2,6-lutidine). Combined use of HATU and DIPEA, or combined use of COMU and DIPEA is particularly preferred. In addition, N,N'-carbonyldiimidazole (CDI), 1,1'-carbonyl-di-(1,2,4-triazole) (CDT), 4-(4,6-dimethoxy-1,3,5-triazin-2-yl)-4-methylmorpholinium chloride (DMT-MM), propylphosphonic acid anhydride (T3P), and such may also be used as condensing agents.

The production methods of the present invention further comprises the steps of: deprotecting the protecting group having an Fmoc skeleton of the added new Fmoc-protected amino acid, the new Fmoc-protected amino acid analog, or the new Fmoc-protected peptide, by using a base to expose its amino group: and forming an amide bond by further adding a new Fmoc-protected amino acid, a new Fmoc-protected amino acid analog, or a new Fmoc-protected peptide.

These steps may be repeated once or several times. With the methods of the present invention, repeating deprotection of the protecting group having the Fmoc skeleton and the condensation reaction with a next, new Fmoc-protected amino acid, new Fmoc-protected amino acid analog, or new Fmoc-protected peptide, a desired peptide sequence can be obtained.

When the present invention is performed by solid-phase methods, the desired peptide once obtained is cleaved off from the solid phase (cleavage step). Furthermore, structural conversion and cyclization of the peptide can be carried out before the cleavage step. In the present invention, the side chain functional groups that have been protected by protecting groups may be deprotected or may not be deprotected at the time of cleavage, and only a part of the protecting groups may be deprotected. Preferably, the cleavage step is carried out while the side-chain functional groups are still protected.

Specifically, the reaction conditions for the cleavage step of the present invention are preferably weakly acidic conditions, and particularly preferably conditions of weaker acidity than TFA. Specifically, for such weak acids, acids showing an aqueous pKa value higher than that of TFA are preferred. More specifically, acids having the pKa value in the range of 0 to 15 are preferred, and those having an aqueous pKa value in the range of 6 to 15 are more preferred. Examples of acids having weaker acidity than TFA, which are used in this step, include TFE and HFIP. Two or more weak acids can be used in combination, such as TFE/acetic acid, in any ratios. Furthermore, a solvent such as DCM, DCE, and water can be mixed in any ratios. For such combinations of weak acids and solvents, the combination of TFE and DCM is particularly preferred. For the solutions used for cleavage, other organic solvents and reagents (for example, DIPEA), and cation scavengers (for example, triisopropylsilane) may be added.

When the cleavage step is performed before deprotecting the side-chain protecting groups of the synthesized peptides, the weak acid used for the cleavage is preferably an acid weaker than the acid used for the deprotection reaction. In this case, two types of acids having different acidities which are weaker than TFA are prepared in advance, and the weaker acid of the two is used for the cleavage.

When the cleavage step is performed after deprotecting the side-chain protecting groups of the synthesized peptides, the weak acids used for the cleavage are not particularly limited as long as they are acids weaker than TFA.

In the step of deprotecting the side-chain protecting groups of the present invention, desired deprotection reactions can be performed selectively by reducing side reactions such as hydrolysis and N- to O-acyl shift. Deprotection of the side-chain protecting groups is preferably performed under conditions of weaker acidity than TFA. The deprotection reaction can be performed at any temperature, and performing the reaction at 0° C. to 40° C. is preferred. When deprotection is completed, or when stopping the reaction during deprotection, bases such as ammonia and primary anines to tertiary amines can be used. Furthermore, basic heterocyclic compounds (for example, pyridine, imidazole, and analogs thereof) and such may also be used.

When further altering or modifying the peptides synthesized by the production methods of the present invention, those steps can be performed either before or after the cleavage step.

Peptides produced by the production methods of the present invention may be a peptide comprising on its C-terminal side an amino acid residue or an amino acid analogue residue having one reactive site on a side chain, and on its N-terminal side an amino acid residue, an amino acid analogue residue, or a carboxylic acid analog having another reactive site. Such peptides can be produced, for example, by selecting the raw material Fmoc-protected amino acids, Fmoc-protected amino acid analogs, and Fmoc-protected peptides so that an amino acid residue or an amino acid analogue residue having one reactive site on its side chain is comprised at the C-terminal side and an amino acid residue, an amino acid analogue residue, or a carboxylic acid analog having another reactive site is comprised at the N-terminal side.

This peptide can be cyclized by forming a bond between one reactive site and another reactive site. Production methods of the present invention can comprise such a cyclization step. Specifically, the cyclization step can be performed based on the description in WO 2013/100132.

When performing the cyclization step after the cleavage step, a concentrated residue obtained under reduced pressure from reacted solution of the cleavage step (cleavage solution) may be used in the cyclization step, or the cleavage solution may be used as is in the cyclization step.

In the present invention, "carboxylic acid analog" includes compounds having both an amino group and a carboxyl group and having three or more atoms between the two groups; various carboxylic acid derivatives which do not have amino groups: peptides formed from two to four residues; and amino acids in which the main chain amino group has been chemically modified by formation of an amide bond or such with a carboxylic acid. Furthermore, "carboxylic acid analog" may have a borate or borate ester moiety which can be used for cyclization. Furthermore, "carboxylic acid analog" may be carboxylic acids having a double bonded portion or a triple bonded portion, or may be carboxylic acids having a ketone or a halide. In these compounds, portions other than the specified functional groups may be substituted, and for example, such substituents can be selected from among alkyl groups, aralkyl groups, aryl groups, cycloalkyl groups, heteroaryl groups, alkenyl groups, alkynyl groups, and such (freely selected substituents).

The cyclization step comprises the step of cyclizing by forming, for example, an amide bond, a disulfide bond, an ether bond, a thioether bond, an ester bond, a thioester bond, or a carbon-carbon bond by the above-mentioned two reactive sites, but is not limited thereto.

Cyclizations by amide bond formation are, for example, cyclizations by forming an amide bond between a reactive site on the N-terminal amino acid residue, N-terminal amino acid analogue residue, or N-terminal carboxylic acid analog (a main-chain amino group or an amino group present on the side chain) and a reactive site on the amino acid residue or amino acid analog having one carboxylic acid on its side chain. As the condensing agents for these reactions, agents similar to those used in the above-described peptide bonding may be used. Specifically, for example, the side-chain carboxylic acid and the N-terminal main-chain amino group, or the side-chain amino group and the C-terminal main-chain carboxylic acid can be condensed by using the combination of HATU and DIPEA or the combination of COMU and DIPEA. In this case, it is preferable that the protecting group for the carboxylic acid on the C-terminal side and the protecting group for the carboxylic acid on the side chain which is subjected to cyclization, or the protecting group for the main-chain amino group on the N-terminal side and the protecting group for the amino group on the side chain which is subjected to cyclization are selected by considering their orthogonality. The preferred protecting groups in this series of peptide syntheses are as described above.

Cyclization by carbon-carbon bond formation is, for example, cyclization by forming a carbon-carbon bond between a reactive site on the N-terminal amino acid residue, N-terminal amino acid analogue residue, or N-terminal carboxylic acid analog, and a reactive site on the amino acid residue or amino acid analog having one reactive site on its side chain. Specifically, for example, by selecting an alkenyl group as the reactive site on the N-terminal amino acid residue, N-terminal amino acid analogue residue, or N-terminal carboxylic acid analog, and selecting an alkenyl group as the reactive site on the amino acid residue or amino acid analogue residue having one reactive site on its side chain, a cyclization reaction can be carried out by a transition metal-catalyzed carbon-carbon bonding reaction. In this case, examples of the transition metals used as the catalyst include ruthenium, molybdenum, titanium, and tungsten. For example, when using ruthenium, the cyclization reactions can be carried out by metathesis reactions. Furthermore, the cyclization reactions can be carried out by transition metal-catalyzed carbon-carbon bonding reactions by employing the combination of arylhalide and boronic acid or boronic acid analog as the combination of reactive site on the N-terminal amino acid residue, N-terminal amino acid analogue residue, or N-terminal carboxylic acid analog and the reactive site on the amino acid residue or amino acid analogue residue having one reactive site on its side chain. In this case, the transition metals used as the catalyst include palladium, nickel, and iron. For example, when using palladium, the cyclization reactions can be carried out by the Suzuki reaction. Furthermore, the cyclization reactions can be carried out by a transition metal-catalyzed carbon-carbon bonding reaction by employing the combination of an alkenyl group and an aryl halide or alkenyl halide as the combination of reactive site on the N-terminal amino acid residue, N-terminal amino acid analogue residue, or N-terminal carboxylic acid analog, and the reactive site on the amino acid residue or amino acid analogue residue having one reactive site on its side chain. In this case, the transition metals used as the catalyst include palladium and nickel. For example, when using palladium, the cyclization reactions can be carried out by the Heck-type chemical reactions. Furthermore, the cyclization reactions can be carried out by transition metal-catalyzed carbon-carbon bonding reactions by selecting the combination of an acetylene group and an aryl halide or alkenyl halide as the combination of reactive site on the N-terminal amino acid residue, N-terminal amino acid analogue residue, or N-terminal carboxylic acid analog and the reactive site on the amino acid residue or amino acid analogue residue having one reactive site on its side chain. In this case, the transition metals used as the catalyst include palladium, copper, gold, and iron. For example, when using the combination of palladium and copper, the cyclization reactions can be carried out by the Sonogashira reaction.

In the present invention, the obtained products can be purified as necessary. For example, general peptide purification methods such as reverse-phase columns or molecular sieve columns may be used. Furthermore, the obtained products can also be purified by crystallization or solidification using appropriate solvents. Concentration under reduced pressure before purification is also possible.

All prior art references cited herein are incorporated by reference into this description.

EXAMPLES

The present invention will be further illustrated with reference to the following Examples but is not limited thereto.

The following abbreviations are used in the Examples.
DCM Dichloromethane
DCE 1,2-Dichloroethane
DMF N,N-dimethylformamide
DIC N,N'-diisopropylcarbodiimide
DIPEA N,N-diisopropylethylamine
DBU 1,8-Diazabicyclo[5.4.0]-7-undecene
NMP N-Methyl-2-pyrrolidone
FA Formic acid
TFA Trifluoroacetic acid
TFE 2,2,2-Trifluoroethanol
HFIP 1,1,1,3,3,3-Hexafluoroisopropyl alcohol
HOAt 1-Hydroxy-7-azabenzotriazole
HOBt 1-Hydroxybenzotriazole
WSCI·HCl 1-Ethyl-3-(3-dimethylaminopropyl)carbodiimide hydrochloride
TBME t-Butyl methyl ether
TIPS Triisopropyl silane
HATU O-(7-aza-1H-benzotriazol-1-yl)-N,N,N',N'-tetramethyluronium hexafluorophosphate The reaction solvents used for peptide synthesis and solid-phase synthesis were those for peptide synthesis (purchased from Watanabe Chemical Industries and Wako Pure Chemical Industries). Examples include DCM, DMF, NMP, 2% DBU in DMF, and 20% piperidine in DMF. Furthermore, for reactions to which water was not added as solvent, dehydrated solvents, super-dehydrated solvents, and anhydrous solvents (purchased from Kanto Chemical Co., Wako Pure Chemical Industries, and such) were used.

Conditions for LCMS analyses are as shown in Table 1.

TABLE 1

| Analysis Condition | Device | Column (I.D. × Length) (mm) | Mobile Phase | Gradient (A/B) | Flow Rate (mL/min) | Column Temperature (° C.) | Wavelength |
|---|---|---|---|---|---|---|---|
| SQDAA05 | Acquity UPLC/SQD | Ascentis Express C18 (2.1 × 50) | A) 10 mM AcONH$_4$, H$_2$O B) MeOH | 95/5 => 0/100 (1.0 min) 0/100 (0.4 min) | 1 | 35 | 210-400 nm; PDA total |
| SQDAA50 | Acquity UPLC/SQD | Ascentis Express C18 (2.1 × 50) | A) 10 mM AcONH$_4$, H$_2$O B) MeOH | 50/50 => 0/100 (0.7 min) 0/100 (0.7 min) | 1 | 35 | 210-400 nm; PDA total |
| SQDFA05 | Acquity UPLC/SQD | Ascentis Express C18 (2.1 × 50) | A) 0.1% FA, H$_2$O B) 0.1% FA, MeCN | 95/5 => 0/100 (1.0 min) 0/100 (0.4 min) | 1 | 35 | 210-400 nm; PDA total |
| SQDFA50 | Acquity UPLC/SQD | Ascentis Express C18 (2.1 × 50) | A) 0.1% FA, H$_2$O B) 0.1% FA, MeCN | 50/50 => 0/100 (0.7 min) 0/100 (0.7 min) | 1 | 35 | 210-400 nm; PDA total |

Example 1 Basic Synthetic Route for Cyclic Peptides Comprising N-Methyl Amino Acids in their Sequences Solid-phase synthesis by the Fmoc method was employed for synthesizing cyclic peptides comprising N-methyl amino acids in their sequences, and the synthesis was performed by the synthetic route described in FIG. 1, which involves the following five-steps:

A) elongating the peptide from the N terminus of Asp supported onto a 2-chlorotrityl resin through its side-chain carboxylic acid, by an Fmoc method using a peptide synthesizer;
B) cleaving the peptide off from the 2-chlorotrityl resin;
C) cyclizing the cleaved peptide by amide bonding through condensation of the side-chain carboxylic acid of Asp (open circular unit) and the amino group at the N terminus of the peptide chain (triangular unit);
D) deprotecting the protecting groups of side-chain functional groups included in the peptide chain; and
E) purifying the compound by fractionation HPLC.

In the Example, unless otherwise particularly stated, the cyclic peptides were synthesized based on this basic synthetic route.

Fmoc-Amino Acids Used in Peptide Synthesis by a Peptide Synthesizer

In the peptide syntheses described in the Examples, the following Fmoc-amino acids were used for the synthesis by a peptide synthesizer (the aforementioned step A).

Fmoc-Pro-OH, Fmoc-Thr(Trt)-OH, Fmoc-Ile-OH, Fmoc-Trp-OH, Fmoc-D-Tyr(tBu)-OH, Fmoc-D-Tyr(Clt)-OH, Fmoc-Ser(Trt)-OH, Fmoc-Ala-OH, Fmoc-Gly-OH, Fmoc-Leu-OH, Fmoc-His(Trt)-OH, Fmoc-MePhe-OH, Fmoc-MeAla-OH, Fmoc-MeGly-OH, Fmoc-MeLeu-OH, Fmoc-Phe(4-CF3)-OH, Fmoc-b-Ala-OH. Fmoc-b-MeAla-OH, Fmoc-Nle-OH, Fmoc-Met(O2)-OH, Fmoc-Phe(3-Cl)—OH, Fmoc-MeVal, and Fmoc-Val-OH were purchased from Watanabe Chemical Industries, Chempep Inc., Chem-Impex International Inc., or such.

Fmoc-MeSer(DMT)-OH, Fmoc-MePhe(3-Cl)—OH, Fmoc-MeAla(4-Thz)-OH, Fmoc-Hyp(Et)-OH, and Fmoc-γEtAbu-OH, Fmoc-nPrGly-OH were synthesized by methods described in the literature (Document: WO 2013/100132 A1).

Fmoc-Ser(THP)—OH (Compound 1), Fmoc-Thr(THP)—OH (Compound 2), Fmoc-MeSer(THP)—OH (Compound 6), Fmoc-MeHis(Trt)-OH (Compound 7), Fmoc-D-Tyr(THP)—OH (Compound 8), Fmoc-D-Tyr(Pis)-OH (Compound 11), Fmoc-Tyr(3-F,tBu)-OH (Compound 13), Fmoc-MePhe(4-Cl)—OH (Compound 16), and Fmoc-Tyr(3-F,Pis)-OH (Compound 22) were synthesized as follows. These synthesized Fmoc-amino acids were used not only for synthesizing peptides but also for examining deprotection of protecting groups of side-chain functional groups and protecting groups of C-terminal carboxylic acid groups.

Example 1-1

Synthesis of (2S)-2-((((9H-fluoren-9-yl)methoxy) carbonyl)amino)-3-((tetrahydro-2H-pyran-2-yl)oxy) propanoic acid (Compound 1, Fmoc-Ser(THP)—OH)

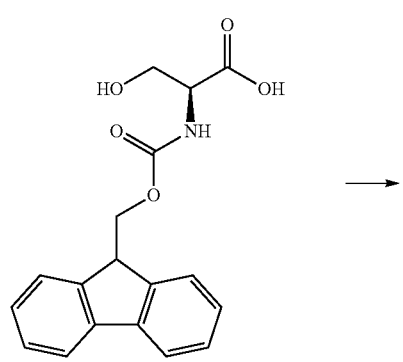

→

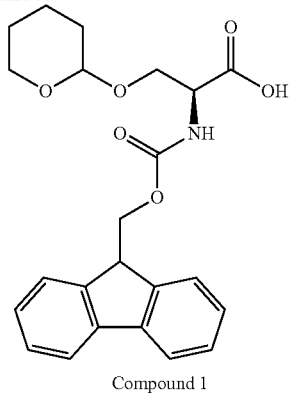

Compound 1

Toluene (10 mL) was added to a mixture of (2S)-2-((((9H-fluoren-9-yl)methoxy)carbonyl)amino)-3-hydroxypropanoic acid (Fmoc-Ser-OH; purchased from Watanabe Chemical Industries; 1.0 g, 3.06 mmol) and pyridinium p-toluenesulfonate (PPTS: 0.038 g, 0.153 mmol), and the moisture included was removed by azeotropically distilling off toluene under reduced pressure. Super-dehydrated tetrahydrofuran (THF, 6.1 mL) and 3,4-dihydro-2H-pyran (1.9 mL, 21.3 mmol) were added to the obtained residue, and this was stirred under nitrogen atmosphere at 50° C. for four hours. After confirming disappearance of the raw materials by LCMS (SQDFA05), the mixture was cooled to 25° C., and ethyl acetate (6 ml) was added. Next, saturated aqueous sodium chloride solution (6 mL) was added to wash the organic layer, and the aqueous layer was extracted using ethyl acetate (6 mL). All of the obtained organic layers were mixed, and this was further washed twice with saturated aqueous sodium chloride solution (6 mL). The organic layer was dried over sodium sulfate and the solvent was distilled off under reduced pressure.

The obtained residue was dissolved in tetrahydrofuran (THF, 12.2 mL), and then 1.0 M phosphate buffer solution (12.2 mL; adjusted to pH 8.0) was added. This mixture was stirred at 50° C. for three hours. After cooling it to 25° C., ethyl acetate (12.2 mL) was added, and the organic and aqueous layers were separated. Ethyl acetate (12.2 mL) was added to the aqueous layer for extraction, and then all of the obtained organic layers were mixed, and this mixture was washed twice with saturated aqueous sodium chloride solution (12.2 mL). The organic layer was then dried over sodium sulfate, the solvent was distilled off under reduced pressure, and the resulting material was further dried at 25° C. for 30 minutes under reduced pressure using a pump.

The obtained residue was dissolved in dichloromethane (7 mL), and then heptane (16.6 mL) was added. Under a controlled reduced pressure (approximately 100 hPa), dichloromethane alone was distilled off, and the obtained mixture was filtered to obtain solid. This washing operation using heptane was repeated twice. The obtained solid was dried at 25° C. for two hours under reduced pressure using a pump, and 1.40 g of residue was obtained.

t-Butyl methyl ether (TBME, 25 mL) and 0.05 M aqueous phosphoric acid solution (70 nL; pH 2.1) were added to the obtained residue, and after stirring this at 25° C. for five minutes, the organic and aqueous layers were separated. t-Butylmethyl ether (TBME, 25 mL) was added to the aqueous layer for extraction, and this was followed by mixing all of the obtained organic layers, and washing this mixture twice with saturated aqueous sodium chloride solution (25 mL). The organic layer was then dried over sodium sulfate, and the solvent was distilled off under reduced pressure. The residue was dried at 25° C. for two hours under reduced pressure using a pump to yield (2S)-2-((((9H-fluoren-9-yl)methoxy)carbonyl)amino)-3-((tetrahydro-2H-pyran-2-yl)oxy)propanoic acid (Compound 1, Fmoc-Ser (THP)—OH, 1.22 g, 30 mol % t-butyl methyl ether (TBME) remained). The obtained Fmoc-Ser(THP)—OH was stored in a −25° C. freezer.

LCMS (ESI) m/z=410.2 (M−H)−

Retention time: 0.81 minutes (analysis condition SQDFA05)

Example 1-2

Synthesis of (2S,3R)-2-((((9H-fluoren-9-yl)methoxy)carbonyl)amino)-3-((tetrahydro-2H-pyran-2-yl)oxy)butanoic acid (Compound 2, Fmoc-Thr(THP)—OH)

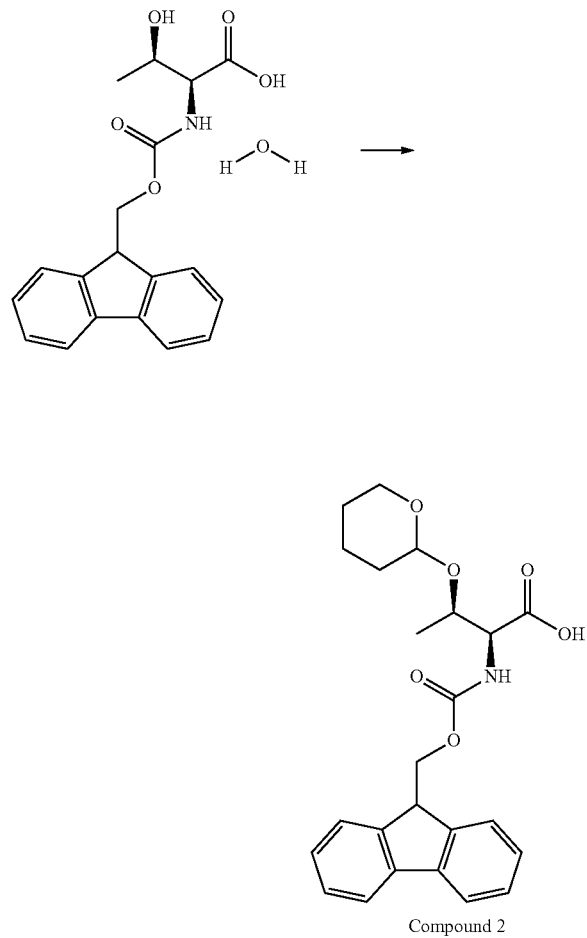

Compound 2

Toluene (50 mL) was added to a mixture of (2S,3R)-2-((((9H-fluoren-9-yl)methoxy)carbonyl)amino)-3-hydroxybutanoic acid monohydrate (monohydrate of Fmoc-Thr-OH; purchased from Tokyo Chemical Industry; 5.0 g, 13.9 mmol) and pyridinium p-toluenesulfonate (PPTS; 0.175 g, 0.70 mmol), and the moisture included was removed by azeotropically distilling off toluene under reduced pressure. Super-dehydrated tetrahydrofuran (THF, 28 mL) and 3,4-dihydro-2H-pyran (8.8 mL, 97 mmol) were added to the obtained residue, and this was stirred under nitrogen atmosphere at 50° C. for four hours. After confirming disappearance of the raw materials by LCMS (SQDFA05), the mixture was cooled to 25° C., and ethyl acetate (30 mL) was added. Next, saturated aqueous sodium chloride solution (30 mL) was added to wash the organic layer, and the aqueous layer was extracted with ethyl acetate (30 mL). All of the obtained organic layers were mixed, and this was further washed twice with saturated aqueous sodium chloride solution (30 mL). The organic layer was dried over sodium sulfate and the solvent was distilled off under reduced pressure to yield 9.3 g of a crude product.

4.65 g of the obtained crude product was dissolved in tetrahydrofuran (THF, 30 mL), and 1.0 M phosphate buffer solution (30 mL: adjusted to pH 8.0) was added to it. This mixture was stirred at 50° C. for four hours. After cooling to 25° C., ethyl acetate (30 mL) was added, and the organic and aqueous layers were separated. After adding ethyl acetate (30 mL) to the aqueous layer for extraction, all of the obtained organic layers were mixed and washed twice with saturated aqueous sodium chloride solution (30 mL). The organic layer was then dried over sodium sulfate, the solvent was distilled off under reduced pressure. This was further dried at 25° C. for 30 minutes under reduced pressure using a pump.

The obtained residue was dissolved in diethyl ether (50 mL), and then heptane (50 ml) was added. Under a controlled reduced pressure (approximately 100 hPa), diethyl ether alone was distilled off, and the obtained mixture was filtered to yield a solid. This washing operation using heptane was repeated twice. The obtained solid was dried at 25° C. for two hours under reduced pressure using a pump, and the sodium salt of Fmoc-Thr(THP)—OH (2.80 g, 6.26 mmol) was obtained.

To the total amount of the obtained sodium salt of Fmoc-Thr(THP)—OH, ethyl acetate (50 mL) and 0.05 M aqueous phosphoric acid solution (140 mL; pH 2.1) were added. After stirring this at 25° C. for five minutes, the organic and aqueous layers were separated. Ethyl acetate (50 mL) was added to the aqueous layer for extraction, and all of the obtained organic layers were mixed and this mixture was washed twice with saturated aqueous sodium chloride solution (50 mL). The organic layer was then dried over sodium sulfate, and the solvent was distilled off under reduced pressure. The residue was dried at 25° C. for two hours under reduced pressure using a pump, and then the obtained solid was dissolved in t-butyl methyl ether (TBME, 50 mL), and the solvent was distilled off under reduced pressure. This was further dried at 25° C. for one hour under reduced pressure using a pump, and (2S,3R)-2-((((9H-fluoren-9-yl)methoxy)carbonyl)amino)-3-((tetrahydro-2H-pyran-2-yl)oxy)butanoic acid (Compound 2, Fmoc-Thr(THP)—OH, 2.70 g, 30 mol % t-butyl methyl ether (TBME) remained) was yielded as a diastereomer formed due to the asymmetric carbon on the THP protecting group. The obtained Fmoc-Thr(THP)—OH was stored in a −25° C. freezer.

LCMS (ESI) m/z=424.2 (M−H)−

Retention time: 0.84 minutes, 0.85 minutes (analysis condition SQDFA05)

Example 1-3

Synthesis of (2S)-2-((((9H-fluoren-9-yl)methoxy)carbonyl)(methyl)amino)-3-((tetrahydro-2H-pyran-2-yl)oxy)propanoic acid (Compound 6, Fmoc-MeSer(THP)—OH)

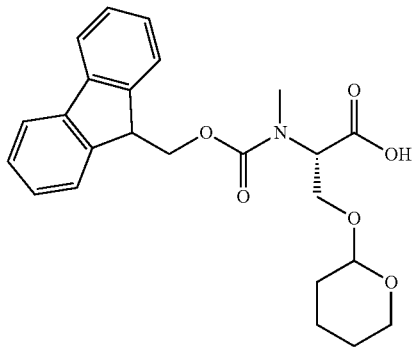

Compound 6

(S)-2-((((9H-fluoren-9-yl)methoxy)carbonyl)(methyl)amino)-3-hydroxypropanoic acid (Fmoc-MeSer-OH) was synthesized by a method described in the literature (Document: WO 2013/100132 A1). To a solution of (S)-2-((((9H-fluoren-9-yl)methoxy)carbonyl)(methyl)amino)-3-hydroxypropanoic acid (Fmoc-MeSer-OH; 15 g, 43.9 mmol) in tetrahydrofuran (88 mL), pyridinium p-toluenesulfonate (PPTS: 0.552 g, 2.197 mmol) and 3,4-dihydro-2H-pyran (23.85 mL) were added, and this was stirred at 50° C. for four hours. The mixture was cooled to 25° C., and ethyl acetate (90 mL) was added. Next, the organic layer was washed with saturated aqueous sodium chloride solution (90 mL), and the aqueous layer was extracted with ethyl acetate (90 mL). All of the obtained organic layers were mixed, and this was further washed twice with saturated aqueous sodium chloride solution (90 mL). The organic layer was dried over sodium sulfate, and the solvent was distilled off under reduced pressure.

15.0 g of the obtained residue was dissolved in tetrahydrofuran (175 mL), and 1.0 M phosphate buffer (175 mL; adjusted to pH 8.0) was added to it. This mixture was stirred at 50° C. for three hours. After cooling to 25° C., ethyl acetate (175 mL) was added, and the organic and aqueous layers were separated. Ethyl acetate (175 mL) was added to the aqueous layer for extraction, and all of the obtained organic layers were mixed and washed twice with saturated aqueous sodium chloride solution (175 mL). The organic layer was then dried over sodium sulfate, and the solvent was distilled off under reduced pressure.

The obtained residue was dissolved in dichloromethane (100 mL), and then heptane (250 mL) was added. Under a controlled reduced pressure (approximately 100 hPa), dichloromethane alone was distilled off, and the obtained mixture was filtered to yield a solid. This washing operation using heptane was repeated twice. The obtained solid was dried at 25° C. for two hours under reduced pressure using a pump.

t-Butyl methyl ether (TBME, 250 mL) and 0.05 M aqueous phosphoric acid solution (700 mL: pH 2.1) were added to the obtained residue. After stirring this at 25° C. for five minutes, the organic and aqueous layers were separated. t-Butyl methyl ether (TBME, 250 mL) was added to the aqueous layer for extraction, and all of the obtained organic layers were mixed and washed twice with saturated aqueous sodium chloride solution (250 mL). The organic layer was then dried over sodium sulfate, and the solvent was distilled off under reduced pressure. The residue was dried at 25° C. for two hours under reduced pressure using a pump to yield (2S)-2-((((9H-fluoren-9-yl)methoxy)carbonyl)(methyl)amino)-3-((tetrahydro-2H-pyran-2-yl)oxy)propanoic acid (Compound 6, Fmoc-MeSer(THP)—OH, 9.0 g, 30 mol % t-butylmethyl ether (TBME) remained). The obtained Fmoc-MeSer(THP)—OH was stored in a −25° C. freezer.

LCMS (ESI) m/z=426.4 (M+H)+

Retention time: 0.86 minutes (analysis condition SQDFA05)

Example 1-4

Synthesis of (S)-2-((((9H-fluoren-9-yl)methoxy)carbonyl)(methyl)amino)-3-(1-trityl-1H-imidazol-4-yl)propanoic acid (Compound 7, Fmoc-MeHis(Trt)-OH)

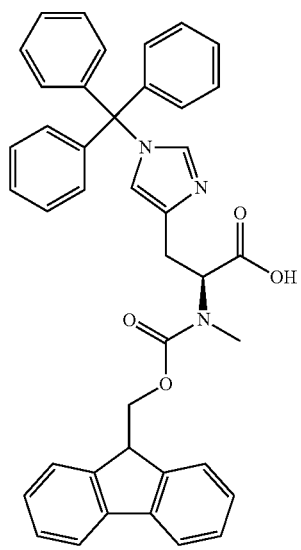

Compound 7

A solution of (S)-3-(1H-imidazol-4-yl)-2-(methylamino)propanoic acid hydrochloride (75 g, 364.71 mmol) in dichloromethane (1000 mL), dichlorodimethylsilane (51 g, 395.16 mmol), and triethylamine (40 g, 395.30 mmol) were added to a 3000-mL flask. Next a solution of (chloromethanetrityl)tribenzene (Trt-Cl; 111 g, 398.17 mmol) in dichloromethane (500 mL) and triethylamine (40 g, 395.30 mmol) were added. The obtained reaction solution was stirred while heating under reflux for four hours, and further stirred at 20° C. for two hours. The reaction was stopped by adding methanol to the reaction solution, and then the solvent was distilled off under reduced pressure. pH was adjusted to 8 to 8.5 using triethylamine and 125 g of solid was obtained.

1,4-Dioxane (1000 mL), potassium carbonate (84 g, 603.39 mmol) and water (1000 mL) were added to the obtained solid. In addition, (2,5-dioxopyrrolidin-1-yl) (9H-fluoren-9-yl)methyl carbonate (Fmoc-OSu; 102 g, 302.38 mmol) was added, and the mixture was stirred at 0° C. for two hours. The obtained reaction solution was washed with diethyl ether (2000 mL), and then the pH of the solution was adjusted to 6 to 7 using acetic acid. The obtained solid was filtered to obtain (S)-2-((((9H-fluoren-9-yl)methoxy)carbonyl)(methyl)amino)-3-(1-trityl-1H-imidazol-4-yl)propanoic acid (Compound 7, Fmoc-MeHis(Trt)-OH, 155 g).

LCMS (ESI) m/z=634.4 (M+H)+

Retention time: 1.07 minutes (analysis condition SQDAA05)

Example 1-5

Synthesis of (2R)-2-((((9H-fluoren-9-yl)methoxy)carbonyl)amino)-3-(4-((tetrahydro-2H-pyran-2-yl)oxy)phenyl)propanoic acid (Compound 8, Fmoc-D-Tyr(THP)—OH)

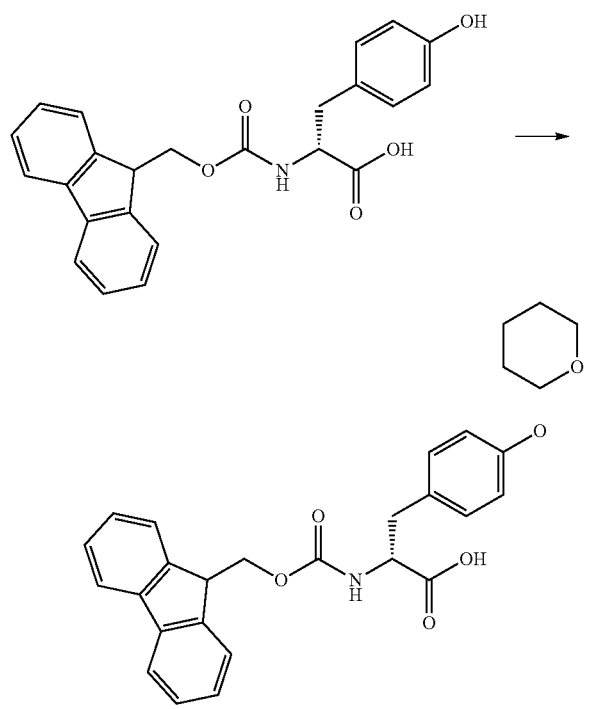

Compound 8

Toluene (5.0 mL) was added to (R)-2-((((9H-fluoren-9-yl)methoxy)carbonyl)amino)-3-(4-hydroxyphenyl)propanoic acid (Fmoc-D-Tyr-OH, purchased from Watanabe Chemical Industries: 500 mg, 1.24 mmol) and a catalytic amount of pyridinium para-toluene sulfonate (PPTS; 15.6 mg, 0.062 mmol), and the included moisture was removed azeotropically by distilling off toluene under reduced pressure. The obtained residue was dissolved in tetrahydrofuran (THF) (2.5 mL), 3,4-dihydro-2H-pyran (785 μL, 8.68 mmol) was added, and this was stirred under nitrogen atmosphere at 50° C. for four hours. The reaction solution was cooled to 25° C., and ethyl acetate (3 mL) was added. Next, saturated aqueous sodium chloride solution (3 ml-) was added to wash the organic layer, and the aqueous layer was extracted with ethyl acetate (3 mL). All of the obtained organic layers were mixed, and this was further washed twice with saturated aqueous sodium chloride solution (3 mL). The organic layer was dried over sodium sulfate, the solvent was distilled off under reduced pressure, and further the resulting material was dried under reduced pressure using a pump, which yielded 596 mg of residue.

The obtained residue (300 mg) was dissolved in tetrahydrofuran (THF) (2.5 mL), and then 1.0 M aqueous phosphoric acid solution (pH 8.0, 2.5 mL) was added and stirred at 50° C. for three hours. Ethyl acetate (3 mL) was added to the reaction solution, the organic and aqueous layers were separated, and the aqueous layer was extracted with ethyl acetate (3 mL). All of the obtained organic layers were mixed, and this was washed twice with saturated aqueous sodium chloride solution (3 mL). The organic layer was dried over sodium sulfate, then the solvent was distilled off under reduced pressure, and the resulting material was further dried for 30 minutes under reduced pressure using a pump.

The obtained residue was dissolved in dichloromethane (DCM) (2 mL), and then heptane (5 mL) was added. Dichloromethane (DCM) alone was removed using an evaporator, and the obtained white solid was collected by filtration. Similar operations were repeated twice on the obtained white solid. White solid obtained in this manner was dried under reduced pressure using a pump for two hours.

To the above white solid, t-butyl methyl ether (TBME) (4.6 mL) and 0.05 M aqueous phosphoric acid solution (pH 2.1, 13 mL) were added, and this was stirred at 25° C. for five minutes. After separating the organic layer, the aqueous layer was extracted with t-butyl methyl ether (TBME) (4.6 mL). The obtained organic layers were combined, and this was washed twice with saturated aqueous sodium chloride solution (4.6 mL). The organic layer was dried over sodium sulfate, and the solvent was distilled off under reduced pressure. The obtained residue was purified by reverse-phase chromatography (Wakosil 25C18, 10 g, water/acetonitrile) to obtain (2R)-2-((((9H-fluoren-9-yl)methoxy)carbonyl)amino)-3-(4-((tetrahydro-2H-pyran-2-yl)oxy)phenyl)propanoic acid (Compound 8, Fmoc-D-Tyr(THP)—OH, 173 mg) in 57% yield as a diastereomer formed due to the asymmetric carbon on the THP protecting group.

LCMS (ESI) m/z=488.4 (M+H)+

Retention time: 0.92 minutes (analysis condition SQDFA05)

Example 1-6

Synthesis of 2-phenylpropan-2-yl) 2,2,2-trichloroacetoimidate (Compound 9)

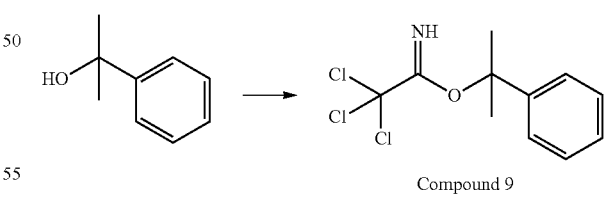

Compound 9

A 1.9 M solution of NaHMDS in tetrahydrofuran (THF) (850 μL, 1.62 mmol) was added dropwise at 22° C. to a solution of 2-phenylpropan-2-ol (purchased from Wako Pure Chemical Industries; 2.0 g, 14.7 mmol) in diethyl ether (Et2O) (4.8 mL). The reaction solution was stirred at the same temperature for 20 minutes, then cooled to 0° C. and 2,2,2-trichloroacetonitrile (1.47 mL, 14.7 mmol) was added dropwise. After stirring the reaction solution at 0° C. for ten minutes, the temperature was raised to 15° C., and this was stirred for another hour. The reaction solution was concentrated using an evaporator, hexane (1.8 mL) and methanol (65 µL) were added to the obtained residue, and this was stirred at 15° C. for 15 minutes. The obtained solids were filtered and washed three times with hexane (2.0 mL) to obtain 4.19 g of 2-phenylpropan-2-yl 2,2,2-trichloroacetoimidate (Compound 9). This was used in reactions without further purification.

1H NMR (Varian 400-MR, 400 MHz, CDCl3) δ 1.89 (6H, s), 7.28 (1H, m), 7.36 (2H, m), 7.43 (2H, m), 8.20 (1H, brs)

Example 1-7

Synthesis of (R)-methyl 2-((((9H-fluoren-9-yl)methoxy)carbonyl)amino)-3-(4-hydroxyphenyl)propanoate (Compound 10, Fmoc-D-Tyr-OMe)

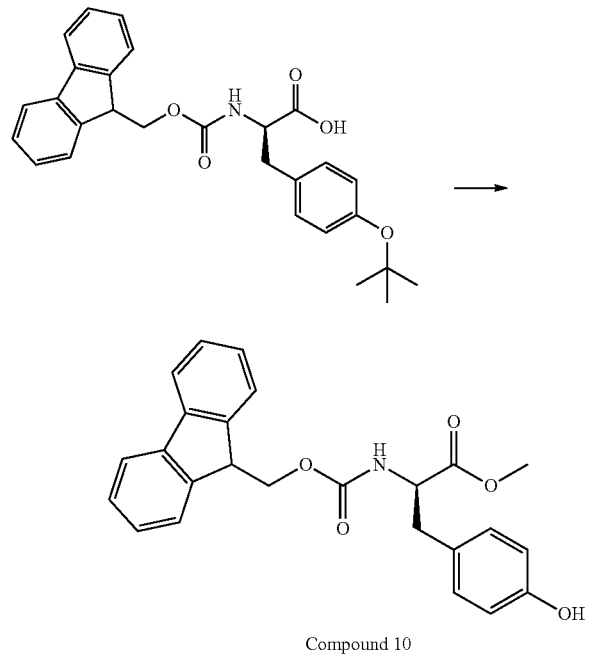

Compound 10

Under nitrogen atmosphere, thionyl chloride (1.59 mL, 21.76 mmol) was added dropwise at 0° C. to a mixture of (R)-2-((((9H-fluoren-9-yl)methoxy)carbonyl)amino)-3-(4-(tert-butoxy)phenyl)propanoic acid (Fmoc-D-Tyr(tBu)-OH, purchased from Watanabe Chemical Industries; 5.0 g, 10.88 mmol) and methanol (8.80 mL, 218 mmol). The obtained reaction solution was stirred at 25° C. for three hours, and then the solvent was distilled off under reduced pressure. The obtained residue was dissolved in ethyl acetate, and this solution was washed twice with saturated aqueous sodium chloride solution. The organic layer was dried over sodium sulfate, solids were removed by filtration, and the solvent was distilled off under reduced pressure to obtain (R)-methyl 2-((((9H-fluoren-9-yl)methoxy)carbonyl)amino)-3-(4-hydroxyphenyl)propanoate (Compound 10, Fmoc-D-Tyr-OMe, 4.50 g).

LCMS (ESI) m/z=418.3 (M+H)+

Retention time: 0.81 minutes (analysis condition SQDFA05)

Example 1-8

Synthesis of (R)-2-((((9H-fluoren-9-yl)methoxy)carbonyl)amino)-3-(4-((2-phenylpropan-2-yl)oxy)phenyl)propanoic acid (Compound 11, Fmoc-D-Tyr(Pis)-OH)

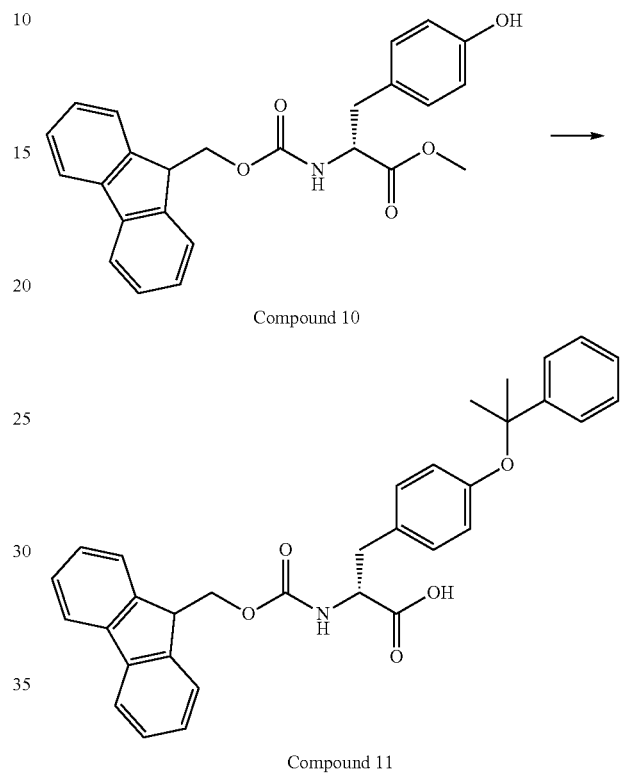

Compound 11

To a solution of (R)-methyl 2-((((9H-fluoren-9-yl)methoxy)carbonyl)amino)-3-(4-hydroxyphenyl)propanoate (Compound 10, Fmoc-D-Tyr-OMe; 100 mg, 0.24 mmol) in tetrahydrofuran (THF) (240 µL), a separately prepared 10 M solution of 2-phenylpropan-2-yl 2,2,2-trichloroacetoimidate (Compound 9) in cyclohexane (60 µL) and a catalytic amount of boron trifluoride-ethyl ether complex (BF3-OEt, 4.55 µL, 0.036 mmol) was added dropwise at 0° C. After stirring the reaction solution at 25° C. for one hour, the equivalent amount of the 10 M solution of 2-phenylpropan-2-yl 2,2,2-trichloroacetoimidate (Compound 9) in cyclohexane (60 µL) and boron trifluoride-ethyl ether complex (BF3-OEt, 4.55 µL, 0.036 mmol) were added again, and this reaction solution was stirred at 25° C. for another 30 minutes. The reaction solution was diluted with dichloromethane (DCM), and a saturated aqueous sodium bicarbonate solution was added. After extraction with dichloromethane, the organic layer was washed with saturated aqueous sodium chloride solution. This organic layer was dried over sodium sulfate, the solvent was distilled off under reduced pressure, and the resulting material was further dried using a pump. A solution of dichloromethane (DCM)/hexane=1/1 was added to the obtained residue, and precipitates were removed by filtration. The filtrate was concentrated using an evaporator, the obtained residue was purified by flash column chromatography (purif pack (registered trademark) SIZE 20, hexane/ethyl acetate), and (R)-methyl 2-((((9H-fluoren-9-yl)methoxy)carbonyl)amino)-3-(4-((2-phenylpropan-2-yl)oxy)phenyl)propanoate (Fmoc-D-Tyr(Pis)-OMe) was obtained as a mixture.

The obtained mixture described above was dissolved in dichloroethane (DCE) (535 μL), trimethyltin(IV) hydroxide (Me3SnOH, 58.1 mg, 0.321 mmol) was added, and this was stirred at 60° C. for seven hours. Trimethyltin(IV) hydroxide (Me3SnOH, 29.1 mg, 0.161 mmol) was further added to the reaction solution, and this was stirred at 60° C. for 15 hours. The reaction solution was concentrated using an evaporator, t-butyl methyl ether (TBME, 1 mL) and 0.05 M aqueous phosphoric acid solution (pH 2.1, 2 mL) were added, and this was stirred at 25° C. for five minutes. After separating the organic layer, the aqueous layer was extracted twice with t-butyl methyl ether (TBME, 1 mL). The organic layer was dried over sodium sulfate, the solvent was distilled off under reduced pressure, and the resulting material was further dried using a pump. The obtained residue was purified by column chromatography (purif pack (registered trademark) SIZE 20, dichloromethane/methanol), and (R)-2-((((9H-fluoren-9-yl)methoxy)carbonyl)amino)-3-(4-((2-phenylpropan-2-yl)oxy)phenyl)propanoic acid (Compound 11, Fmoc-D-Tyr(Pis)-OH, 33 mg) was obtained in a two-step yield of 39%.

LCMS (ESI) m/z=522.4 (M+H)+

Retention time: 1.00 minutes (analysis condition SQDFA05)

Example 1-9

Synthesis of (S)-methyl 2-((((9H-fluoren-9-yl)methoxy)carbonyl)amino)-3-(3-fluoro-4-hydroxyphenyl)propanoate (Compound 12, Fmoc-Tyr(3-F)—OMe)

were added, and the reaction solution was washed three times with diethyl ether. The pH of the aqueous layer was adjusted to 2 to 3 using an aqueous 5N hydrochloric acid solution, and then this was extracted three times with ethyl acetate (100 mL×3). The organic layer was dried over magnesium sulfate, the solvent was distilled off under reduced pressure, and the resulting material was further dried using a pump. The obtained residue (4.08 g) was used in the next reaction without further purification.

The above residue (1.04 g) was dissolved in methanol (10 mL), and thionyl chloride (SOCl2, 539 μL, 7.38 mmol) was added dropwise at 0° C. The reaction solution was stirred at 60° C. for one hour and then cooled to room temperature, and the solvent was distilled off using an evaporator. Ethyl acetate and water were added to the obtained residue, and extraction was performed twice using ethyl acetate. The organic layer was washed with saturated aqueous sodium chloride solution and dried over magnesium sulfate, and the solvent was distilled off under reduced pressure and further dried using a pump. The obtained residue was purified by flash column chromatography (purif pack (registered trademark) SIZE 200, hexane/ethyl acetate), and (S)-methyl 2-((((9H-fluoren-9-yl)methoxy)carbonyl)amino)-3-(3-fluoro-4-hydroxyphenyl)propanoate (Compound 12, Fmoc-Tyr(3-F)—OMe: 900 mg, 2.07 mmol) was obtained in a two-step yield of 84%.

LCMS (ESI) m/z=436.4 (M+H)+

Retention time: 0.82 minutes (analysis condition SQDFA05)

Example 1-10

Synthesis of (S)-2-((((9H-fluoren-9-yl)methoxy)carbonyl)amino)-3-(4-(tert-butoxy)-3-fluorophenyl)propanoic acid (Compound 13. Fmoc-Tyr(3-F,tBu)-OH)

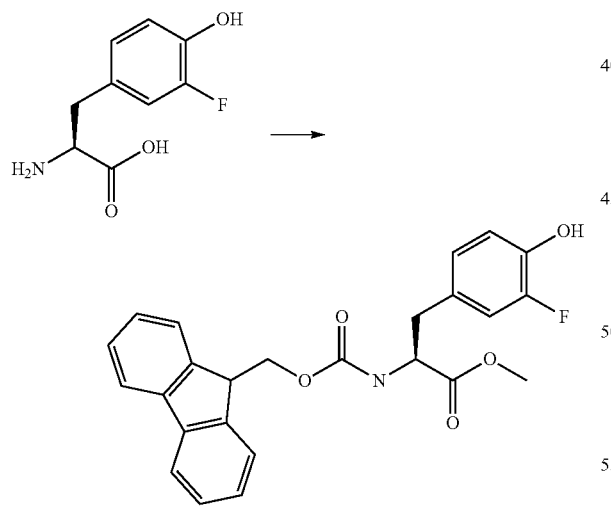

Compound 12

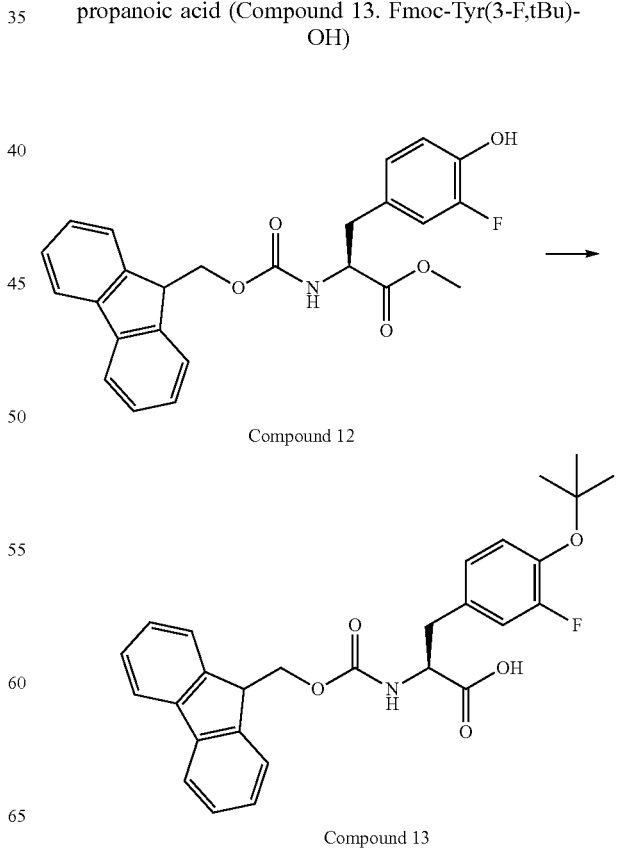

Compound 12

Compound 13

(S)-2-amino-3-(3-fluoro-4-hydroxyphenyl)propanoic acid (H2N-Tyr(3-F)—OH, purchased from Astatech; 2.0 g, 10.0 mmol) was dissolved in 10% aqueous sodium carbonate solution, and then, using a dropping funnel, a solution of (2,5-dioxopyrrolidin-1-yl) (9H-fluoren-9-yl)methyl carbonate (Fmoc-OSu, 3.39 g, 10.0 mmol) in 1,4-dioxane (35 mL) was added at 0° C. After stirring the reaction solution at 25° C. for 40 minutes, water (35 mL) and diethyl ether (70 mL)

To a solution of (S)-methyl 2-((((9H-fluoren-9-yl)methoxy)carbonyl)amino)-3-(3-fluoro-4-hydroxyphenyl)propanoate (Compound 12, Fmoc-Tyr(3-F)—OMe; 300 mg, 0.689 mmol) in tetrahydrofuran (THF) (690 μL), tert-butyl 2,2,2-trichloroacetimidate (308 μL, 1.72 mmol) and a catalytic amount of boron trifluoride-ethyl ether complex (BF3-OEt, 13.1 μL, 0.103 mmol) was added dropwise at 0° C. After stirring the reaction solution at 25° C. for one hour, the equivalent amount of tert-butyl 2,2,2-trichloroacetoimidate (308 μL, 1.72 mmol) and boron trifluoride-ethyl ether complex (BF3-OEt, 13.1 μL, 0.103 mmol) were added again, and this reaction solution was stirred at 25° C. for another hour. The reaction solution was diluted with dichloromethane (DCM), and a saturated aqueous sodium bicarbonate solution was added. After extraction with dichloromethane, the organic layer was washed with saturated aqueous sodium bicarbonate solution and saturated aqueous sodium chloride solution. The organic layer was dried over sodium sulfate, the solvent was distilled off under reduced pressure, and the resulting material was further dried using a pump. The obtained residue was purified by flash column chromatography (purif pack (registered trademark) SIZE 60, hexane/ethyl acetate), and (S)-methyl 2-((((9H-fluoren-9-yl)methoxy)carbonyl)amino)-3-(4-(tert-butoxy)-3-fluorophenyl)propanoate (Fmoc-Tyr(3-F,tBu)-OMe) was obtained as a mixture.

The obtained mixture (40 mg) described above was dissolved in dichloroethane (DCE) (810 μL), trimethyltin (IV) hydroxide (Me3SnOH, 29.4 mg, 0.163 mmol) was added to this, and the mixture was stirred at 60° C. for one hour. After adding formic acid (15.35 μL, 0.407 mmol) to the reaction solution, this was purified by reverse-phase chromatography (Wakosil 25C18, 10 g, 0.1% aqueous formic acid solution/0.1% solution of formic acid in acetonitrile) to obtain (S)-2-((((9H-fluoren-9-yl)methoxy)carbonyl)amino)-3-(4-(tert-butoxy)-3-fluorophenyl)propanoic acid (Compound 13, Fmoc-Tyr(3-F,tBu)-OH; 27 mg, 56.5 μmol) in a two-step yield of 93%.

LCMS (ESI) m/z=478.3 (M+H)+

Retention time: 0.94 minutes (analysis condition SQDFA05)

Example 1-11

Synthesis of 2-(2-phenylpropan-2-yl) (S)-1-((9H-fluoren-9-yl)methyl) pyrrolidine-1,2-dicarboxylate (Compound 14. Fmoc-Pro-OPis)

Compound 14

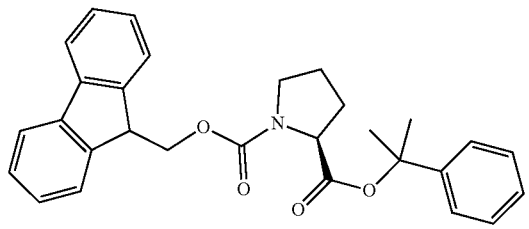

To a mixture of 2-phenyl-2-propanol (14.2 g, 104 mmol) and dehydrated diethyl ether (35 mL), 1.9 M NaHMDS (solution in tetrahydrofuran: 0.85 mL, 1.62 mmol) was added dropwise over a period of three minutes or more under nitrogen atmosphere at room temperature, and then this was stirred at room temperature for 30 minutes.

Subsequently, the reaction solution was cooled on ice to 0° C., and trichloroacetonitrile (11.5 mL, 115 mmol) was added dropwise over a period of five minutes or more. The mixture was stirred at 0° C. for ten minutes, then removed from its ice-bath, and was further stirred at room temperature for one hour. The obtained mixture was cooled on ice to 0° C., and a mixture of (S)-1-(((9H-fluoren-9-yl)methoxy)carbonyl)pyrrolidine-2-carboxylic acid (Fmoc-Pro-OH; 42.3 g, 125 mmol) and dichloromethane (100 mL) was added over a period of 15 minutes. This was stirred at 0° C. for 30 minutes, then filtered, and washed with a hexane-dichloromethane (5/1) solution. Then, the solvent was distilled off under reduced pressure. The obtained residue was purified by silica gel column chromatography (hexane-ethyl acetate) to yield 2-(2-phenylpropan-2-yl) (S)-1-((9H-fluoren-9-yl)methyl) pyrrolidine-1,2-dicarboxylate (Compound 14, Fmoc-Pro-OPis; 26.3 g, 57.7 mmol).

LCMS (ESI) m/z=456.4 (M+H)+

Retention time: 0.76 minutes (analysis condition SQDAA50)

Example 1-12

Synthesis of (S)-2-((((9H-fluoren-9-yl)methoxy)carbonyl)(methyl)amino)-3-(4-chlorophenyl)propanoic acid (Compound 16. Fmoc-MePhe(4-Cl)—OH)

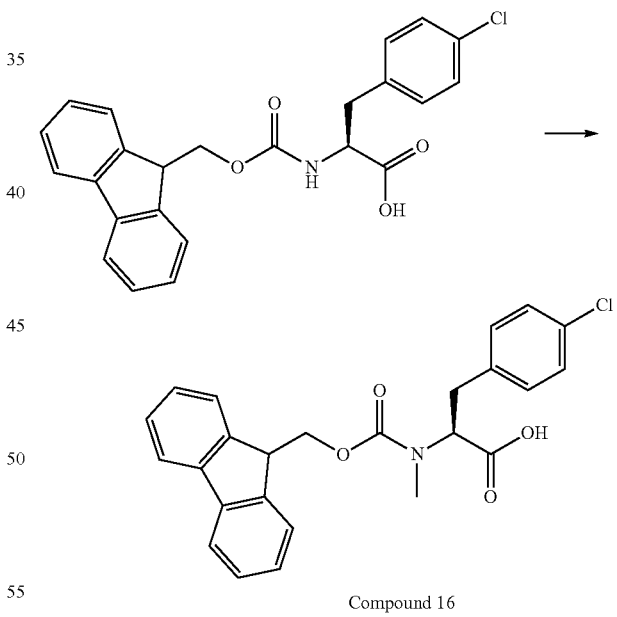

Compound 16

To a solution of (S)-2-((((9H-fluoren-9-yl)methoxy)carbonyl)amino)-3-(4-chlorophenyl)propanoic acid (Fmoc-Phe(4-Cl)—OH; 170 g, 402.96 mmol) in toluene (2.5 L), paraformaldehyde (48 g, 1.60 mol) and 10-camphorsulfonic acid (CSA; 4.6 g, 19.83 mmol) were added, and this was stirred at 110° C. for 16 hours. Subsequently, the reaction solution was washed twice with saturated aqueous sodium bicarbonate solution (0 L), and twice with saturated aqueous sodium chloride solution (1 L). The organic layer was dried over sodium sulfate, solids were removed by filtration, and the solvent was distilled off under reduced pressure to obtain 160 g of (S)-(9H-fluoren-9-yl)methyl 4-(4-chlorobenzyl)-5-oxooxazoline-3-carbonate.

To a solution of (S)-(9H-fluoren-9-yl)methyl 4-(4-chlorobenzyl)-5-oxooxazoline-3-carbonate prepared by mixing a separate lot prepared by similar operations (230 g, 530.10 mmol) in dichloromethane (2.5 L), triethylsilane (881 g, 7.58 mol) and trifluoroacetic acid (TFA; 2518 g, 22.28 mol) were mixed, and the mixture was stirred at 30° C. for 12 hours. Subsequently, the solvent was distilled off under reduced pressure, and by recrystallizing the obtained residue in dichloromethane/hexane (1/10, v/v), (S)-2-((((9H-fluoren-9-yl)methoxy)carbonyl)(methyl)amino)-3-(4-chlorophenyl)propanoic acid (Compound 16. Fmoc-MePhe(4-Cl)—OH, 205 g) was obtained.

LCMS (ESI) m/z=436.3 (M+H)+

Retention time: 0.99 minutes (analysis condition SQDAA05)

Example 1-13

Synthesis of (S)-methyl 2-((((9H-fluoren-9-yl)methoxy)carbonyl)amino)-3-(3-fluoro-4-((2-phenylpropan-2-yl)oxy)phenyl)propanoate (Compound 21. Fmoc-Tyr(3-F,Pis)-OMe)

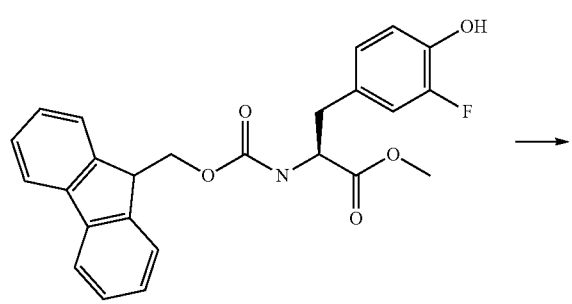

Compound 12

(S)-methyl 2-((((9H-fluoren-9-yl)methoxy)carbonyl)amino)-3-(3-fluoro-4-hydroxyphenyl)propanoate (Compound 12. Fmoc-Tyr(3-F)—OMe; 200 mg, 0.459 mmol) was dissolved in THF (460 μL), and then a separately prepared 2-phenylpropan-2-yl 2,2,2-trichloroacetoimidate (Compound 9; 322 mg, 1.15 mmol) and a catalytic amount of boron trifluoride-ethyl ether complex (BF3-OEt, 8.73 μL, 0.069 mmol) were added dropwise at 0° C. After stirring the reaction solution at room temperature for 30 minutes, the equivalent amount of 2-phenylpropan-2-yl 2,2,2-trichloroacetoimidate (322 mg, 1.15 mmol) and a catalytic amount of boron trifluoride-ethyl ether complex (BF3-OEt, 8.73 μL, 0.069 mmol) were added dropwise at 0° C. After the reaction solution was stirred at room temperature for another 30 minutes, it was diluted with dichloromethane and a saturated aqueous sodium bicarbonate solution was added while cooling on ice. After extraction with dichloromethane, the organic layer was washed with saturated aqueous sodium chloride solution. This organic layer was dried over sodium sulfate, the solvent was distilled off under reduced pressure, and the resulting material was further dried using a pump. The obtained residue was washed twice with dichloromethane/hexane=1/1 (20 mL, 10 mL), and white solids were removed by filtration. The obtained filtrate was concentrated, the residue was purified by flash column chromatography (purif pack (registered trademark) SIZE 20, hexane/ethyl acetate, 0.1% diisopropylethyl amine (DIPEA)), and (S)-methyl 2-((((9H-fluoren-9-yl)methoxy)carbonyl)amino)-3-(3-fluoro-4-((2-phenylpropan-2-yl)oxy)phenyl)propanoate (Compound 21 Fmoc-Tyr(3-F,Pis)-OMe: 210 mg, 0.379 mmol) was obtained in 83% yield.

LCMS (ESI) m/z=554.4 (M+H)+

Retention time: 1.09 minutes (analysis condition SQDFA05)

Example 1-14

Synthesis of (S)-2-((((9H-fluoren-9-yl)methoxy)carbonyl)amino)-3-(3-fluoro-4-((2-phenylpropan-2-yl)oxy)phenyl)propanoic acid (Compound 22, Fmoc-Tyr(3-F,Pis)-OH) Compound 21 Compound 22

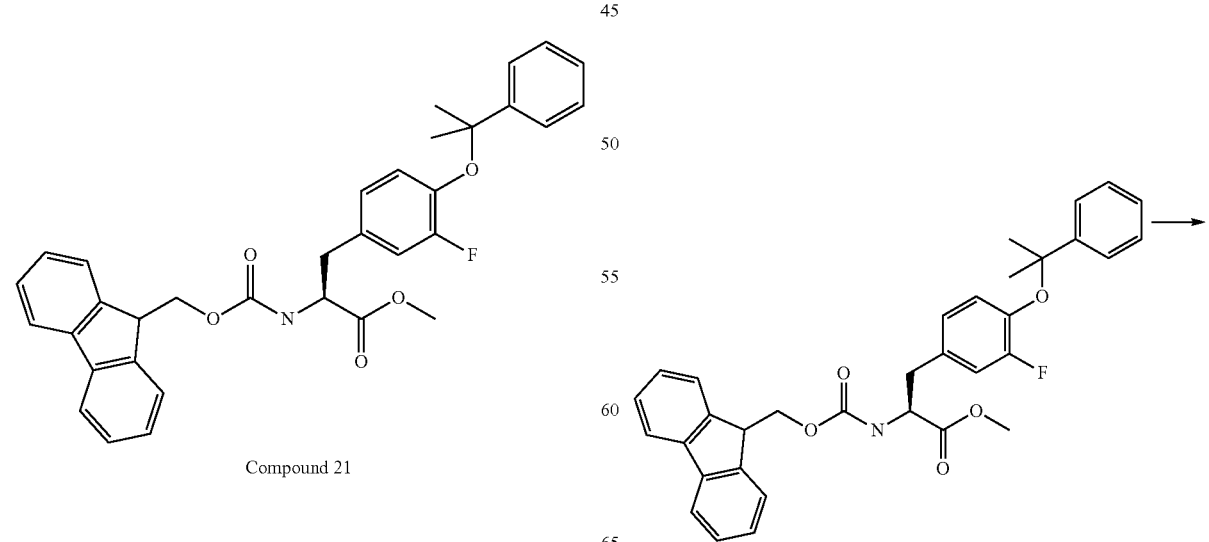

Compound 21

Compound 21

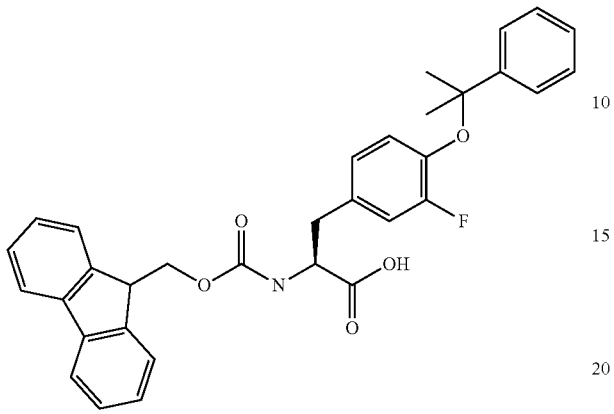

Compound 22

(S)-methyl 2-((((9H-fluoren-9-yl)methoxy)carbonyl) amino)-3-(3-fluoro-4-((2-phenylpropan-2-yl)oxy)phenyl) propanoate (Compound 21, Fmoc-Tyr(3-F,Pis)-OMe: 210 mg, 0.379 mmol) was dissolved in dichloroethane (DCE) (1.26 mL), trimethyltin(IV) hydroxide (Me3SnOH, 137 mg, 0.379 mmol) was added, and this was stirred at 60° C. for three hours. After the reaction solution was concentrated using an evaporator, t-butyl methyl ether (TBME, 2.0 mL) and 0.05 M aqueous phosphoric acid solution (pH 2.1, 4.0 mL) were added, and this was stirred at 25° C. for 15 minutes. After separating the organic layer, the aqueous layer was extracted twice with t-butyl methyl ether (TBME, 1 mL). The organic layer was dried over sodium sulfate, the solvent was distilled off under reduced pressure, and the resulting material was further dried using a pump. The obtained residue was dissolved in a solution of 0.1% formic acid in acetonitrile, stirred for 15 minutes, and then the obtained solution was purified by reverse-phase chromatography (Wakosil 25C18, 30 g, 0.1% aqueous formic acid solution/0.1% formic acid in acetonitrile) to obtain (S)-2-((((9H-fluoren-9-yl)methoxy)carbonyl)amino)-3-(3-fluoro-4-((2-phenylpropan-2-yl)oxy)phenyl)propanoic acid (Compound 22, Fmoc-Tyr(3-F,Pis)-OH: 190 mg, 0.352 mmol) in 93% yield.

LCMS (ESI) m/z=538.2 (M−H)−

Retention time: 1.00 minutes (analysis condition SQDFA05)

Synthesis of Conjugates Formed Between Fmoc-Amino Acids and Resins Used for Peptide Synthesis by a Peptide Synthesizer Conjugates formed between Fmoc-amino acids and resins used for peptide synthesis by a peptide synthesizer were synthesized as follows.

Example 1-15

Synthesis of (S)-3-((((9H-fluoren-9-yl)methoxy) carbonyl)amino)-4-oxo-4-(piperidin-1-yl)butanoic acid-2-chlorotrityl resin (Compound 50, Fmoc-Asp (O-Trt(2-Cl)-resin)-pip)

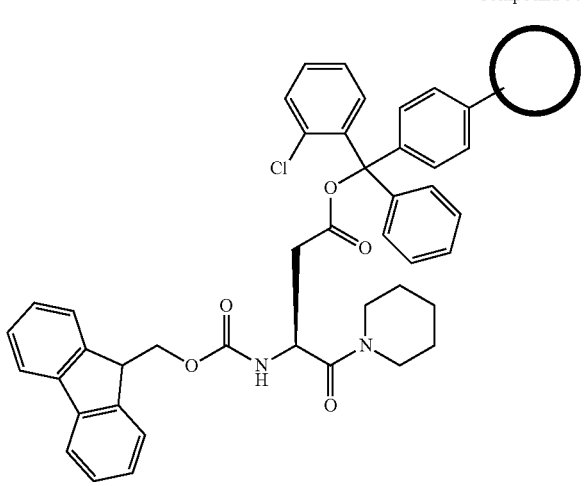

Compound 50

(S)-3-((((9H-fluoren-9-yl)methoxy)carbonyl)amino)-4-oxo-4-(piperidin-1-yl)butanoic acid-2-chlorotrityl resin (Compound 50, Fmoc-Asp(O-Trt(2-Cl)-resin)-pip) was synthesized by a method described in the literature (Document: WO 2013/100132 A1).

Herein, when a polymer or resin binds with a compound, the polymer or resin moiety may be represented by "○" (open circle). Furthermore, to clarify the reaction point of the resin moiety, the chemical structure of the reaction site may be shown by connecting it to the open circle. For example, in the above-mentioned structure (Fmoc-Asp(O-Trt(2-Cl)-resin)-pip (Compound 50)), the 2-chlorotrityl group of the resin is linked to the side-chain carboxylic acid of Asp through an ester bond. Furthermore, pip means piperidine, and in the above-mentioned structure, the C-terminal carboxylic acid group forms an amide bond with piperidine.

Example 1-16

Synthesis of a compound (Compound 52) in which the side-chain carboxylic acid of Fmoc-Asp-piptBu (Compound 51) was linked to a resin

Example 1-16-1

Synthesis of (S)-tert-butyl 3-((((9H-fluoren-9-yl)methoxy)carbonyl)amino)-4-(4-(tert-butyl)piperidin-1-yl)-4-oxobutanoate (Compound 53, Fmoc-Asp(OtBu)-piptBu) (piptBu Means 4-(Tert-Butyl) Piperidine, and Here, it Shows that the C-Terminal Carboxylic Acid Group Forms an Amide Bond with 4-(tert-butyl)piperidine.)

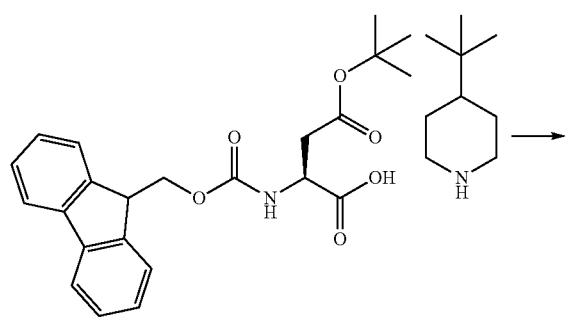

Compound 53

(S)-2-((((9H-fluoren-9-yl)methoxy)carbonyl)amino)-4-(tert-butoxy)-4-oxobutanoic acid (10 g, 24.30 mmol), 4-(tert-butyl)piperidine hydrochloride (4.10 g, 23.09 mmol), and 1-hydroxybenzotriazole monohydrate (HOBt, 3.61 g) were dissolved in DMF (80 mL), then 1-ethyl-3-(3-dimethylaminopropyl)carbodiimide hydrochloride (WSCI·HCl, 5.59 g) was added at 0° C., and this was stirred at 0° C. for 30 minutes. Subsequently, 4-methylmorpholine (2.54 mL) was added, and this was stirred at room temperature for one hour. Hexane-ethyl acetate (1/1, v/v, 500 mL) was added to the reaction solution, and the organic layer was washed twice with saturated aqueous ammonium chloride solution, twice with saturated aqueous sodium bicarbonate solution, and once with saturated aqueous sodium chloride solution. The obtained organic layer was dried over sodium sulfate, solids were removed by filtration, and the solvent was distilled off under reduced pressure. The obtained residue was purified by silica gel column chromatography (mobile phase: hexane-ethyl acetate) to yield (S)-tert-butyl 3-((((9H-fluoren-9-yl)methoxy)carbonyl)amino)-4-(4-(tert-butyl)piperidin-1-yl)-4-oxobutanoate (Compound 53, Fmoc-Asp(OtBu)-piptBu; 11.5 g, 21.51 mmol).

LCMS (ESI) m/z=535.4 (M+H)+

Retention time: 1.17 minutes (analysis condition SQDAA05)

Example 1-16-2

Synthesis of (S)-3-((((9H-fluoren-9-yl)methoxy)carbonyl)amino)-4-(4-(tert-butyl)piperidin-1-yl)-4-oxobutanoic acid (Compound 51, Fmoc-Asp-piptBu)

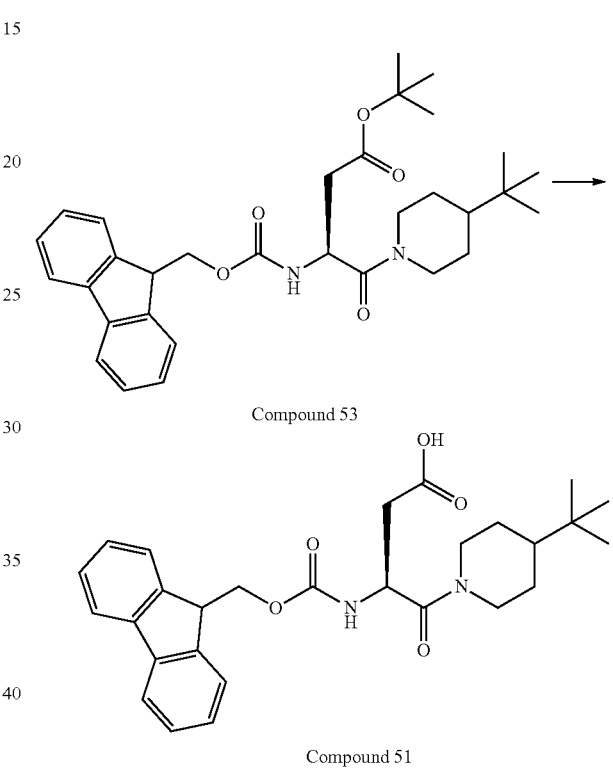

Compound 53

Compound 51

Toluene was added to (S)-tert-butyl 3-((((9H-fluoren-9-yl)methoxy)carbonyl)amino)-4-(4-(tert-butyl)piperidin-1-yl)-4-oxobutanoate (Compound 53, Fmoc-Asp(OtBu)-piptBu; 2.0 g, 3.74 mmol), and the included moisture was removed azeotropically by distilling off the solvent under reduced pressure. The obtained residue was dissolved in dichloromethane (1.66 mL), and the included amount of moisture was confirmed to be 110 ppm by the Karl Fischer titration. Subsequently, the solution was stirred at 0° C. for five minutes, trifluoroacetic acid (TFA, 1.66 mL) was added dropwise at 0° C., and this was stirred for five minutes. The temperature of the reaction solution was brought back to room temperature, and stirring was continued for four hours. The mixture was cooled to 0° C., and triethylamine (3.1 mL) was added dropwise. The mixture was diluted with dichloromethane (30 mL), and this was washed with 5% aqueous sodium dihydrogenphosphate solution (5% NaH2PO4aq. pH 4.4). The organic layer was dried over sodium sulfate, solids were removed by filtration, and the solvent was distilled off under reduced pressure at 20° C. Since 19FNMR (DMSO-d6) measurement on the obtained residue confirmed the presence of residual TFA, the residue was diluted again in dichloromethane (30 mL), and this was washed with 5% aqueous sodium dihydrogenphosphate solution (5% NaH2PO4aq, pH 4.4). The organic layer was dried over sodium sulfate, the solids were removed by filtration, and then the solvent was distilled off under reduced pressure at 20° C. to obtain (S)-3-((((9H-fluoren-9-yl)methoxy)carbonyl)amino)-4-(4-(tert-butyl)piperidin-1-yl)-4-oxobutanoic acid (Compound 51, Fmoc-Asp-piptBu: 1.73 g). Residual TFA was confirmed to be below the detection limit by 19FNMR.

LCMS (ESI) m/z=479.4 (M+H)+

Retention time: 1.00 minutes (analysis condition SQDAA05)

Example 1-16-3

Synthesis of (S)-3-((((9H-fluoren-9-yl)methoxy)carbonyl)amino)-4-(4-(tert-butyl)piperidin-1-yl)-4-oxobutanoic acid-2-chlorotrityl resin (Compound 52. Fmoc-Asp(O-Tr(2-Cl)-resin)-piptBu)

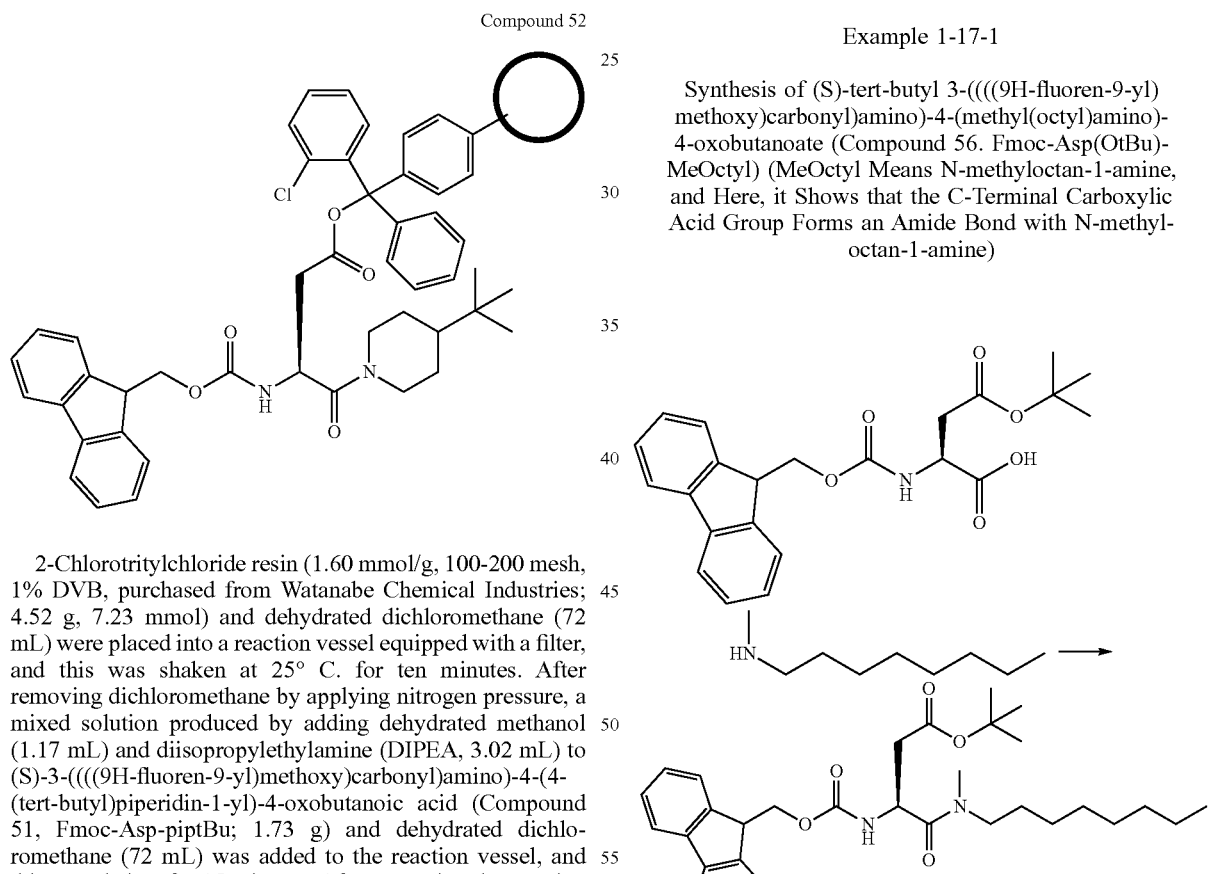

Compound 52

2-Chlorotritylchloride resin (1.60 mmol/g, 100-200 mesh, 1% DVB, purchased from Watanabe Chemical Industries; 4.52 g, 7.23 mmol) and dehydrated dichloromethane (72 mL) were placed into a reaction vessel equipped with a filter, and this was shaken at 25° C. for ten minutes. After removing dichloromethane by applying nitrogen pressure, a mixed solution produced by adding dehydrated methanol (1.17 mL) and diisopropylethylamine (DIPEA, 3.02 mL) to (S)-3-((((9H-fluoren-9-yl)methoxy)carbonyl)amino)-4-(4-(tert-butyl)piperidin-1-yl)-4-oxobutanoic acid (Compound 51, Fmoc-Asp-piptBu; 1.73 g) and dehydrated dichloromethane (72 mL) was added to the reaction vessel, and this was shaken for 15 minutes. After removing the reaction solution by applying nitrogen pressure, a mixed solution produced by adding dehydrated methanol (9.0 mL) and diisopropylethylamine (DIPEA, 3.02 mL) to dehydrated dichloromethane (72 mL) was added to a reaction vessel, and this was shaken for 90 minutes. After removing the reaction solution by applying nitrogen pressure, dichloromethane was placed into the vessel, and this was shaken for five minutes. The reaction solution was removed by applying nitrogen pressure. This operation of washing the resin with dichloromethane was repeated five times, and the obtained resin was dried overnight under reduced pressure to yield (S)-3-((((9H-fluoren-9-yl)methoxy)carbonyl)amino)-4-(4-(tert-butyl)piperidin-1-yl)-4-oxobutanoic acid-2-chlorotrityl resin (Compound 52, Fmoc-Asp(O-Trt(2-Cl)-resin)-piptBu, 5.23 g).

The obtained Fmoc-Asp(O-Trt(2-Cl)-resin)-piptBu (Compound 52, 16.5 mg) was placed into a reaction vessel, 20% piperidine/DMF solution (1 mL) was added, and this was shaken at 25° C. for 30 minutes. From the mixed reaction solution, 30 μL was drawn out and diluted using DMF (2.97 mL), its absorbance (301.2 nm) was measured (Shimadzu, UV-1600PC (cell length: 1.0 cm) was used for the measurement), and the loading rate of Fmoc-Asp(O-Trt (2-Cl)-resin)-piptBu (Compound 52) was calculated to be 0.356 mmol/g.

Different lots synthesized similarly but having different loading rates were also used for peptide synthesis.

Example 1-17

Synthesis of a compound (Compound 55) in which Fmoc-Asp-MeOctyl (Compound 54) was linked to a resin at its side-chain carboxylic acid Example 1-17-1

Synthesis of (S)-tert-butyl 3-((((9H-fluoren-9-yl)methoxy)carbonyl)amino)-4-(methyl(octyl)amino)-4-oxobutanoate (Compound 56. Fmoc-Asp(OtBu)-MeOctyl) (MeOctyl Means N-methyloctan-1-amine, and Here, it Shows that the C-Terminal Carboxylic Acid Group Forms an Amide Bond with N-methyl-octan-1-amine)

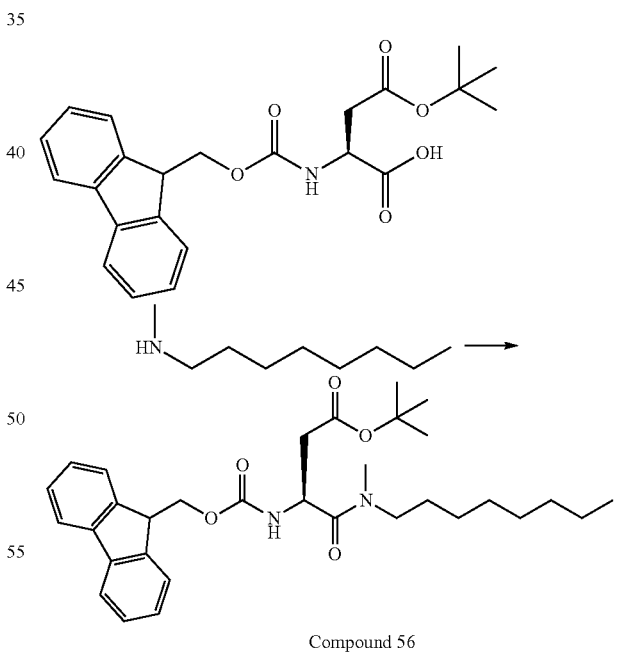

Compound 56

(S)-2-((((9H-fluoren-9-yl)methoxy)carbonyl)amino)-4-(tert-butoxy)-4-oxobutanoic acid (Fmoc-Asp(OtBu)-OH; 8.00 g, 19.44 mmol) and DMF (65 mL) were added to a 300-mL flask and stirred at room temperature for five minutes. Next, 4-methylmorpholine (2.57 mL) and O-(7-aza-1H-benzotriazol-1-yl)-N,N,N',N'-tetramethyluronium hexafluorophosphate (HATU; 8.87 g, 23.33 mmol) were added, and this was stirred at 0° C. for five minutes. Furthermore, N-methyloctan-1-amine (3.35 mL, 18.47 mmol) was added dropwise over a period of two minutes, and the obtained reaction solution was stirred at 0° C. for 30 minutes. To this reaction solution, hexane-ethyl acetate (1/1, v/v, 400 mL) was added, and this was washed with water (400 mL), saturated aqueous ammonium chloride solution (400 mL), 50% aqueous sodium bicarbonate solution (400 mL), water (400 mL×2), and then saturated aqueous sodium chloride solution (400 mL). The obtained organic layer was dried over sodium sulfate, solids were removed, and the solvent was distilled off under reduced pressure. The obtained residue was purified by silica gel column chromatography (hexane-ethyl acetate) to yield (S)-tert-butyl 3-((((9H-fluoren-9-yl)methoxy)carbonyl)amino)-4-(methyl (octyl)amino)-4-oxobutanoate (Compound 56. Fmoc-Asp (OtBu)-MeOctyl; 10.2 g, 19.00 mmol).

LCMS (ESI) m/z=537.5 (M+H)+

Retention time: 0.84 minutes (analysis condition SQDFA50)

Example 1-17-2

Synthesis of (S)-3-((((9H-fluoren-9-yl)methoxy) carbonyl)amino)-4-(methyl(octyl)amino)-4-oxobutanoic acid (Compound 54, Fmoc-Asp-MeOctyl)

Toluene was added to (S)-tert-butyl 3-((((9H-fluoren-9-yl)methoxy)carbonyl)amino)-4-(methyl(octyl)amino)-4-oxobutanoate (Compound 56, Fmoc-Asp(OtBu)-MeOctyl; 8.1 g, 15.09 mmol), and the included moisture was removed azeotropically by distilling off the solvent under reduced pressure. The obtained residue was dissolved in dichloromethane (dehydrated, 6.7 mL), and the included amount of moisture was confirmed to be 380 ppm by the Karl Fischer titration. Subsequently, the solution was stirred at 0° C. for five minutes, trifluoroacetic acid (TFA, 6.7 mL) was added dropwise at 0° C. over a period of five minutes, and then this was stirred for five minutes. The temperature of the reaction solution was brought back to room temperature, and stirring was continued for four hours. The mixture was cooled to 0° C., and triethylamine (12.62 mL) was added dropwise. The mixture was diluted with dichloromethane (100 mL), and this was washed with 5% aqueous sodium dihydrogenphosphate solution (5% NaH2PO4aq). The organic layer was dried over sodium sulfate, solids were removed by filtration, and then the solvent was distilled off under recued pressure at 20° C. Since 19FNMR (DMSO-d6) measurement on the obtained residue confirmed the presence of residual TFA, the residue was dissolved again in dichloromethane, and this was washed with 5% aqueous sodium dihydrogenphosphate solution (5% NaH2PO4aq). The organic layer was dried over sodium sulfate, the solids were removed by filtration, and then the solvent was distilled off under reduced pressure at 20° C. to obtain (S)-3-((((9H-fluoren-9-yl)methoxy)carbonyl)amino)-4-(methyl(octyl) amino)-4-oxobutanoic acid (Compound 54, Fmoc-Asp-MeOctyl; 6.61 g, 13.75 mmol). Residual TFA was confirmed to be below the detection limit by 19FNMR.

LCMS (ESI) m/z=481.4 (M+H)+

Retention time: 0.65 minutes (analysis condition SQDAA50)

Example 1-17-3

Synthesis of (S)-3-((((9H-fluoren-9-yl)methoxy) carbonyl)amino)-4-(methyl(octyl)amino)-4-oxobutanoic acid-2-chlorotrityl resin (Compound 55. Fmoc-Asp(O-Trt(2-Cl)-resin)-MeOctyl)

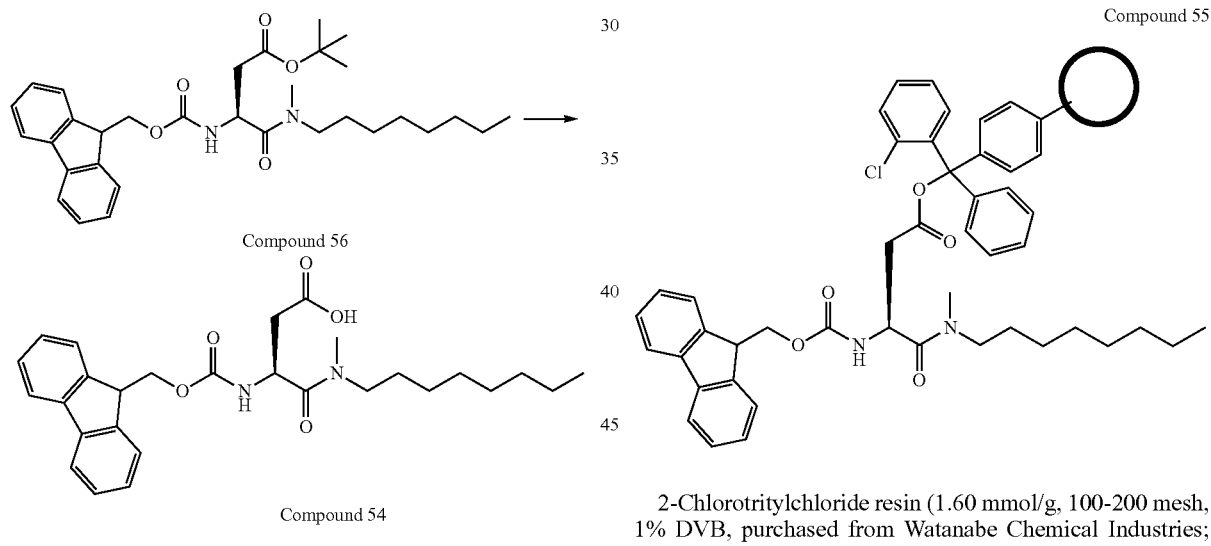

2-Chlorotritylchloride resin (1.60 mmol/g, 100-200 mesh, 1% DVB, purchased from Watanabe Chemical Industries; 16.3 g, 26.1 mmol) and dehydrated dichloromethane (261 mL) were placed into a reaction vessel equipped with a filter, and this was shaken at 25° C. for ten minutes. After removing dichloromethane by applying nitrogen pressure, a mixed solution produced by adding dehydrated methanol (4.23 mL) and diisopropylethylamine (DIPEA, 10.9 mL) to (S)-3-((((9H-fluoren-9-yl)methoxy)carbonyl)amino)-4-(methyl(octyl)amino)-4-oxobutanoic acid (Compound 54, Fmoc-Asp-MeOctyl; 6.28 g, 13.07 mmol) and dehydrated dichloromethane (261 mL) was added to the reaction vessel, and this was shaken for 15 minutes. After removing the reaction solution by applying nitrogen pressure, a mixed solution produced by adding dehydrated methanol (32.4 mL) and diisopropylethylamine (DIPEA, 10.9 mL) to dehydrated dichloromethane (261 mL) was added to the reaction vessel, and this was shaken for 90 minutes. After removing the reaction solution by applying nitrogen pressure, dichloromethane (261 mL) was placed into the vessel, and this was shaken for five minutes. The reaction solution was removed by applying nitrogen pressure. This operation of washing the resin with dichloromethane was repeated twice, and the obtained resin was dried overnight under reduced pressure to yield (S)-3-((((9H-fluoren-9-yl)methoxy)carbonyl)amino)-4-(methyl(octyl)amino)-4-oxobutanoic acid-2-chlorotrityl resin (Compound 55, Fmoc-Asp(O-Trt(2-Cl)-resin)-MeOctyl; 18.2 g).

Loading rate: 0.366 mmol/g

Different lots synthesized similarly but having different loading rates were also used for peptide synthesis.

Example 1-18

Synthesis of a compound (Compound 58) in which Fmoc-Asp-Pro-OPis (Compound 57) was Linked to a Resin at its Side-Chain Carboxylic Acid Example 1-18-1

Synthesis of (S)-2-phenylpropan-2-yl 1-((S)-2-((((9H-fluoren-9-yl)methoxy)carbonyl)amino)-4-(allyloxy)-4-oxobutanoyl)pyrrolidine-2-carboxylate (Compound 59. Fmoc-Asp(OAll)-Pro-OPis)

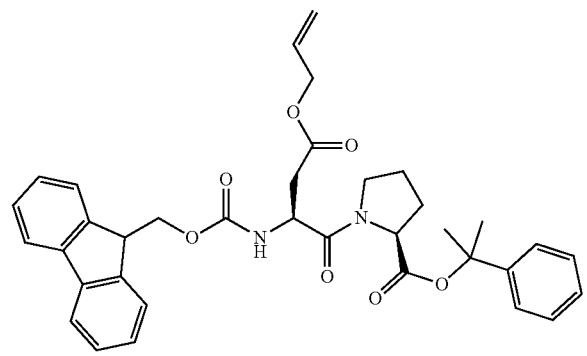

Compound 59

A solution of 2-(2-phenylpropan-2-yl) (S)-1-((9H-fluoren-9-yl)methyl) pyrrolidine-1,2-dicarboxylate (Compound 14, Fmoc-Pro-OPis; 20.0 g, 43.9 mmol) prepared by the already described method in dehydrated DMF (40 mL) was cooled to 20° C. using a water bath, 1,8-Diazabicyclo[5.4.0]-7-undecene (DBU; 6.57 mL, 43.9 mmol) was added to this solution dropwise over a period of seven minutes, and this was stirred at room temperature for five minutes. Subsequently, the reaction solution was cooled to 0° C., pyridine hydrochloride (5.07 g, 43.9 mmol) was added, and this was stirred at 0° C. for ten minutes. Thereafter, a mixture of (S)-2-((((9H-fluoren-9-yl)methoxy)carbonyl)amino)-4-(allyloxy)-4-oxobutanoic acid (Fmoc-Asp(OAll)-OH; 17.35 g, 43.9 mmol), 1-ethyl-3-(3-dimethylaminopropyl)carbodiimide hydrochloride (WSCI·HCl; 11.8 g, 61.4 mmol), and 1-hydroxy-7-azabenzotriazol (HOAt: 7.17 g, 52.7 mmol) was added, and additionally, diisopropylethylamine (DIPEA; 7.6 mL, 43.9 mmol) was added dropwise at 0° C. over a period of seven minutes. The reaction solution was stirred at room temperature for 20 minutes. To the obtained reaction solution, hexane (50 mL), diethyl ether (50 mL), saturated aqueous sodium bicarbonate solution (10 mL), and saturated aqueous sodium chloride solution (50 mL) were added, and the aqueous layer was extracted twice using diethyl ether. All of the obtained organic layers were combined, and washed three times with saturated aqueous sodium chloride solution (50 mL), and then this was dried over sodium sulfate. The solvent was removed under reduced pressure, and the obtained residue was purified by silica gel column chromatography (mobile phase: hexane-ethyl acetate) to yield (S)-2-phenylpropan-2-yl 1-((S)-2-((((9H-fluoren-9-yl)methoxy)carbonyl)amino)-4-(allyloxy)-4-oxobutanoyl)pyrrolidine-2-carboxylate (Compound 59, Fmoc-Asp(OAll)-Pro-OPis; 24.5 g, 40.1 mmol).

LCMS (ESI) m/z=611.4 (M+H)+

Retention time: 1.03 minutes (analysis condition SQDFA05)

Example 1-18-2

Synthesis of (S)-3-((((9H-fluoren-9-yl)methoxy)carbonyl)amino)-4-oxo-4-((S)-2-(((2-phenylpropan-2-yl)oxy)carbonyl)pyrrolidin-1-yl)butanoic acid (Compound 57, Fmoc-Asp-Pro-OPis)

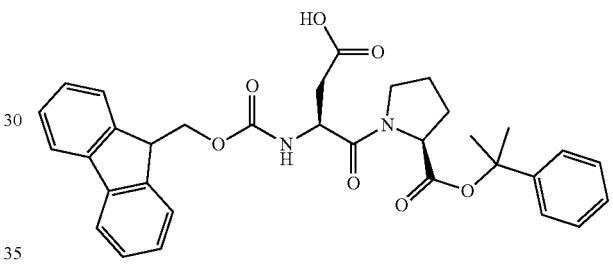

Compound 57

(S)-2-phenylpropan-2-yl 1-((S)-2-((((9H-fluoren-9-yl)methoxy)carbonyl)amino)-4-(allyloxy)-4-oxobutanoyl)pyrrolidine-2-carboxylate (Compound 59, Fmoc-Asp(OAll)-Pro-OPis; 24.16 g, 39.6 mmol) and tetrakis(triphenylphosphine)palladium(0) (Pd(PPh3)4; 0.114 g, 0.099 mmol) were placed in a 300-mL two-necked flask, and the interior of the flask was nitrogen substituted. Subsequently, dichloromethane (40 mL) was added, this was stirred at room temperature, and then this was cooled to 14° C. in a water bath. Phenylsilane (3.30 mL, 26.7 mmol) was added dropwise over a period of five minutes, and the reaction solution was stirred under nitrogen atmosphere at 14° C. to 17° C. for 35 minutes. Next, SH silica (manufactured by Fuji Silysia; 5 g) and methanol (32.1 mL) were added, and then Kieselgel 60 (15 g) was added. Methanol (30 mL), SH silica (manufactured by Fuji Silysia; 5 g) and Kieselgel 60 (25 g) were further added, and the mixture was stirred at 17° C. to 24° C. until the liquid phase became colorless. The obtained mixture was filtered through Celite and washed with dichloromethane-methanol (10/1, v/v), and the solvent was distilled off under reduced pressure to yield (S)-3-((((9H-fluoren-9-yl)methoxy)carbonyl)amino)-4-oxo-4-((S)-2-(((2-phenylpropan-2-yl)oxy)carbonyl)pyrrolidin-1-yl)butanoic acid (Compound 57. Fmoc-Asp-Pro-OPis) as a crude product (25.38 g). The obtained crude product was used without purification in the subsequent process of making the resins support the compound.

LCMS (ESI) m/z=571.3 (M+H)+

Retention time: 0.88 minutes (analysis condition SQDFA05)

Example 1-18-3

Synthesis of (S)-3-((((9H-fluoren-9-yl)methoxy) carbonyl)amino)-4-oxo-4-((S)-2-(((2-phenylpropan-2-yl)oxy)carbonyl)pyrrolidine-1-yl)butanoic acid-2-chlorotrityl resin (Compound 58. Fmoc-Asp(O-Trt (2-Cl)-resin)-Pro-OPis)

Compound 58

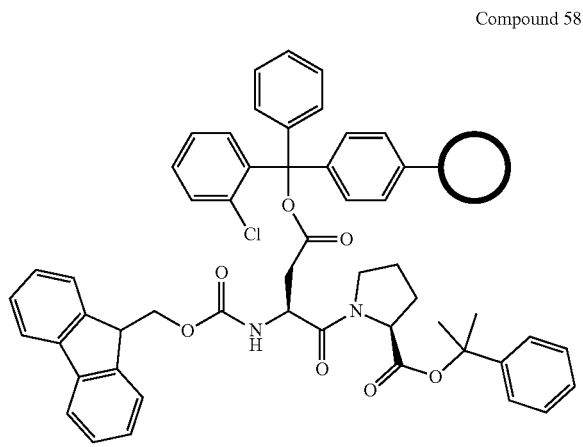 [SMILES: Cc1ccc(C(OC(=O)C[C@H](NC(=O)OCC2c3ccccc3-c3ccccc32)C(=O)N2CCC[C@H]2C(=O)OC(C)(C)c2ccccc2)(c2ccccc2)c2ccccc2Cl)cc1]

2-Chlorotritylchloride resin (1.60 mmol/g, 100-200 mesh, 1% DVB, purchased from Watanabe Chemical Industries; 47.8 g, 76.48 mmol) and dehydrated dichloromethane (150 mL) were placed into a reaction vessel equipped with a filter, and this was shaken at 25° C. for 35 minutes. After removing dichloromethane by applying nitrogen pressure, a mixed solution produced by adding dehydrated methanol (3.11 mL) and diisopropylethylamine (DIPEA, 32.1 mL) to a prepared solution of (S)-3-((((9H-fluoren-9-yl)methoxy)carbonyl) amino)-4-oxo-4-((S)-2-(((2-phenylpropan-2-yl)oxy)carbonyl)pyrrolidin-1-yl)butanoic acid (Compound 57, Fmoc-Asp-Pro-OPis; 21.94 g, 38.4 mmol) in dehydrated dichloromethane (115 mL) was added to a reaction vessel, and this was shaken for 45 minutes. After removing the reaction solution by applying nitrogen pressure, a mixed solution produced by adding dehydrated methanol (55 mL) and diisopropylethylamine (DIPEA, 25 mL) to dehydrated dichloromethane (100 mL) was added to the reaction vessel, and this was shaken for 90 minutes. After removing the reaction solution by applying nitrogen pressure, dichloromethane (100 mL) was placed into the vessel, and this was shaken for five minutes. The reaction solution was removed by applying nitrogen pressure. This operation of washing the resin with dichloromethane (100 mL) was repeated four times, and the obtained resin was dried for 15.5 hours under reduced pressure to yield (S)-3-((((9H-fluoren-9-yl) methoxy)carbonyl)amino)-4-oxo-4-((S)-2-(((2-phenylpropan-2-yl)oxy)carbonyl)pyrrolidine-1-yl)butanoic acid-2-chlorotrityl resin (Compound 58, Fmoc-Asp(O-Trt(2-Cl)-resin)-Pro-OPis; 61.55 g).

The obtained Fmoc-Asp(O-Trt(2-Cl)-resin)-Pro-OPis (Compound 58, 12.3 mg) was placed into a reaction vessel, DMF (0.2 mL) and piperidine (0.2 mL) were added, and this was shaken at 25° C. for 30 minutes. DMF (1.6 mL) was added to the reaction vessel, then 0.4 mL of the reaction mixture solution was drawn out, this was diluted with DMF (9.6 mL), and its absorbance (301.2 nm) was measured (Shimadzu, UV-1600PC (cell length: 1.0 cm) was used for the measurement). From the following calculation formula, the loading rate of Fmoc-Asp(O-Trt(2-Cl)-resin)-Pro-OPis (Compound 58) was calculated to be 0.3736 mmol/g.

(Absorption (301.2 nm)×1000×50)/(resin weight (mg)× 7800)=(0.717×1000×50)/(12.3×7800)=0.3736 mmol/g Different lots synthesized similarly but having different loading rates were also used for peptide synthesis.

Example 2 Chemical Synthesis of Peptides by a Peptide Synthesizer (Steps a to C)

Unless otherwise stated particularly, peptide synthesis by the above-mentioned basic synthetic route was performed by the following methods.

Example 2-1: Solid-Phase Synthesis of Peptides by an Automated Synthesizer (Step A)

Peptide synthesis by the Fmoc method was performed using a peptide synthesizer (Multipep RS: manufactured by Intavis). Specific procedures for the operation were performed according to the instructions attached to the synthesizer.

A solution of 2-chlorotritylresin (100 mg per column) linked to the side-chain carboxylic acid portion of an aspartic acid in which its N terminus is protected with Fmoc, various Fmoc-amino acids (0.6 mol/L, 0.5 mol/L in the case of Fmoc-MeHis(Trt)-OH), and 1-hydroxy-7-azabenzotriazole (HOAt) or oxyma (0.375 mol/L) in NMP, and a solution of diisopropylcarbodiimide (DIC) in N,N-dimethylformaldehyde (DMF) (10% v/v) were placed into the synthesizer. Furthermore, when the Fmoc-amino acid used was Fmoc-Ser(THP)—OH (Compound 1), Fmoc-Thr(THP)—OH (Compound 2), or Fmoc-MeSer(THP)—OH (Compound 6), such an Fmoc-amino acid was made to coexist with oxyma in the NMP solution, and it was placed into the synthesizer after further adding Molecular Sieves 4A 1/8 (Wako Pure Chemical Industries) or Molecular Sieves 4A 1/16 (Wako Pure Chemical Industries).

A solution of diazabicycloundecene (DBU) in DMF (2% v/v) was used as an Fmoc deprotection solution. After washing the resin with DMF, the Fmoc groups were deprotected, and then condensation reaction with new Fmoc amino acid was performed. This was defined as a single cycle, and by repeating this cycle multiple times, the peptides were elongated on the surface of the resin.

Example 2-2: Cleavage of the Elongated Peptides from the Resin (Step B)

The Fmoc groups of the N terminus of the peptides elongated by the above-mentioned method were removed on the peptide synthesizer, and then the resin was washed with DMF. This was followed by swelling the resin again in DCM, and then after adding TFE/DCM (1/1, v/v, 2 mL) to the resin, and this was shaken at room temperature for two hours. Subsequently, the solution in the tube was filtered through a column for synthesis to remove the resin, and the remaining resin was further washed twice with TFE/DCM (1/1, v/v, 1 mL). All the cleavage solutions obtained were mixed, and this was concentrated under reduced pressure.

Example 2-3: Cyclization of the Cleaved Peptides (Step C)

The residue resulting from cleavage followed by concentration under reduced pressure was dissolved in DMF/DCM (1/1, v/v, 8 mL). A 0.5 M O-(7-aza-1H-benzotriazol-1-yl)-

N,N,N,N-tetramethyluronium hexafluorophosphate (HATU)/DMF solution (volume corresponding to 1.5 equivalents with respect to the number of moles on the resin used (loading rate (mmol/g) multiplied by the amount of resin used (normally 0.10 g)) and DIPEA (1.8 equivalents with respect to the number of moles on the resin used) were added, and this was shaken at room temperature for two hours. Thereafter, the solvent was distilled off under reduced pressure. Generation of the desired cyclic peptides was confirmed by LCMS analyses.

Peptides Pep1 to Pep7 to be used for examination of the later-described deprotection reactions were synthesized by the above-mentioned methods. The sequences, structures, and LCMS data of Pep1 to Pep7 are shown in Tables 2-1, 2-2, and 2-3, respectively. Examinations of deprotection conditions (degrees of hydrolysis and N- to O-acyl shift problems observed during deprotection, or peptides to be coexisted in the solution which are to be examined) carried out later were evaluated using residues containing the cyclic peptides obtained in this process.

TABLE 2-1

| | | MW (Cyclized) | EM (Cyclized) | 11 | 10 | 9 | 8 | 7 |
|---|---|---|---|---|---|---|---|---|
| Pep-1 | Compound 101 | 1490.2 | 1478.75 | Ala | Trp | Nle | Trp | D-Tyr(tBu) |
| Pep-2 | Compound 102 | 1852.4 | 1581.11 | MePhe | MePhe | Leu | MeLeu | Thr(THP) |
| Pep-3 | Compound 103 | 2018.8 | 2016.97 | g-EtAbu | MeSer(DMT) | Hyp(Et) | Ile | MePhe(3-Cl) |
| Pep-4 | Compound 104 | 1344.0 | 1342.66 | Ala | Trp | Nle | Trp | MeAla |
| Pep-5 | Compound 105 | 1574.3 | 1572.74 | Ala | Trp | Nle | Trp | Ser(Trt) |
| Pep-6 | Compound 106 | 1775.1 | 1773.56 | g-EtAbu | Hyp(Et) | MeAla(4-Th) | MeAla | MeSer(DMT) |
| Pep-7 | Compound 107 | 1734.0 | 1732.37 | Ala | Phe(4-CF3) | Trp | Trp | MeLeu |

| | 6 | 5 | 4 | 3 | 2 | 1 | H-1 | Used Resin | Resin Loading Amount |
|---|---|---|---|---|---|---|---|---|---|
| Pep-1 | MeGly | MeAla | MePhe(3-Cl) | MeGly | nPrGly | Asp | pip | Compound 50 | 0.342 mmol/g |
| Pep-2 | MeLeu | MeLeu | His(Trt) | MePhe | MeLeu | Asp | pip | Compound 50 | 0.368 mmol/g |
| Pep-3 | Ser(Trt) | Trp | Trp | Pro | MeGly | Asp | pip | Compound 50 | 0.318 mmol/g |
| Pep-4 | MeGly | MeAla | MePhe(3-Cl) | MeGly | Pro | Asp | pip | Compound 50 | 0.342 mmol/g |
| Pep-5 | Gly | MeAla | MePhe(3-Cl) | MeGly | Pro | Asp | pip | Compound 50 | 0.342 mmol/g |
| Pep-6 | Hyp(Et) | Trp | Trp | Pro | MeGly | Asp | pip | Compound 50 | 0.318 mmol/g |
| Pep-7 | MeGly | MeGly | Pro | Hyp(Et) | Ser(Trt) | Asp | piptBU | Compound 52 | 0.358 mmol/g |

TABLE 2-2

Pep-1 Compound 101

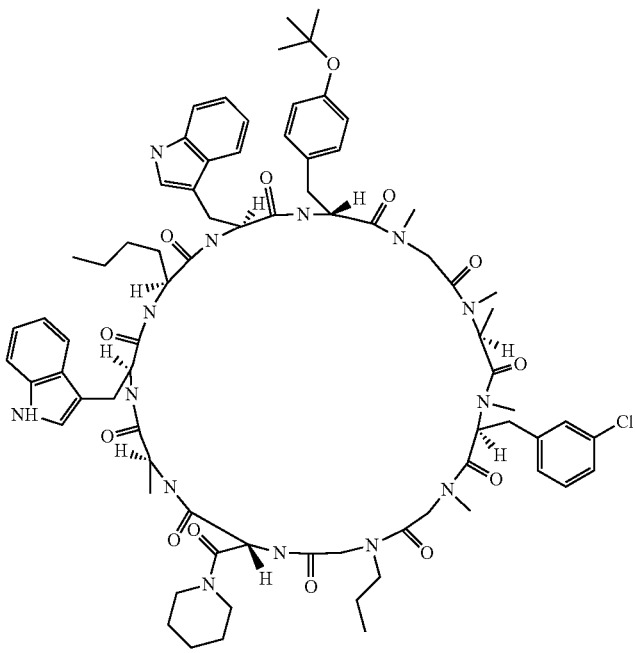 [SMILES: CCCC[C@@H]1NCC(=O)C[C@H](Cc2c[nH]c3ccccc23)NC(=O)CC[C@H](C)NC(=O)[C@@H](C(=O)N2CCCCC2)NC(=O)CN(CCC)C(=O)CN(C)C(=O)[C@H](Cc2cccc(Cl)c2)N(C)C(=O)[C@H](C)CN(C)C(=O)CN(C)C(=O)C[C@@H](Cc2ccc(OC(C)(C)C)cc2)NC(=O)[C@H](Cc2c[nH]c3ccccc23)CNC1=O]

TABLE 2-2-continued
Pep-2 Compound 102
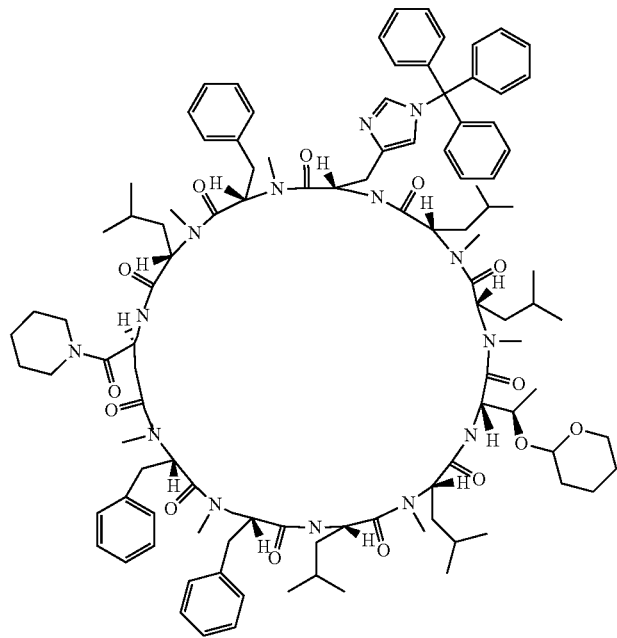
Pep-3 Compound 103
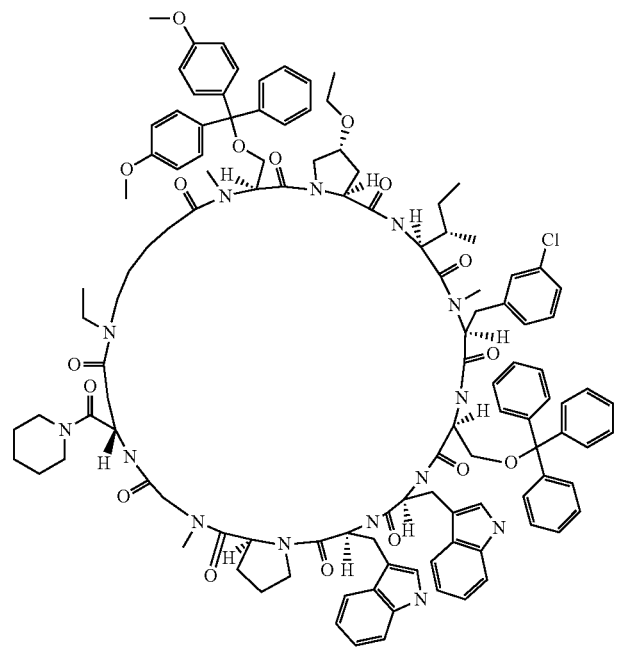 [SMILES: CCO[C@@H]1C[C@H]2C(=O)N[C@@H]([C@@H](C)CC)C(=O)N(C)[C@@H](Cc3cccc(Cl)c3)C(=O)N[C@@H](COC(c3ccccc3)(c3ccccc3)c3ccccc3)C(=O)N[C@@H](Cc3c[nH]c4ccccc34)C(=O)N[C@@H](Cc3c[nH]c4ccccc34)C(=O)N3CCC[C@H]3C(=O)N(C)CC(=O)N[C@H](C(=O)N3CCCCC3)CC(=O)N(CC)CCCCC(=O)N(C)[C@@H](COC(c3ccccc3)(c3ccc(OC)cc3)c3ccc(OC)cc3)C(=O)N2C1]

TABLE 2-2-continued
Pep-4 Compound 104
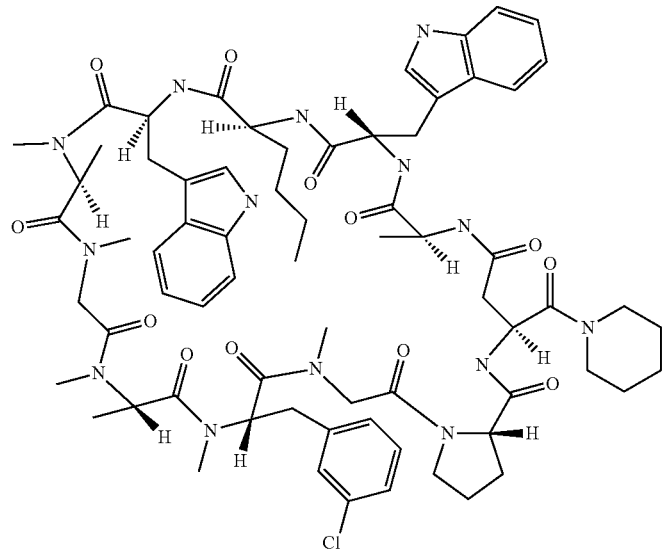 [SMILES: CCCC[C@@H]1NC(=O)[C@H](Cc2c[nH]c3ccccc23)NC(=O)[C@H](C)NC(=O)C[C@@H](C(=O)N2CCCCC2)NC(=O)[C@@H]2CCCN2C(=O)CN(C)C(=O)[C@H](Cc2cccc(Cl)c2)N(C)C(=O)[C@H](C)N(C)C(=O)CN(C)C(=O)[C@H](C)N(C)C(=O)[C@H](Cc2c[nH]c3ccccc23)NC1=O]
Pep-5 Compound 105
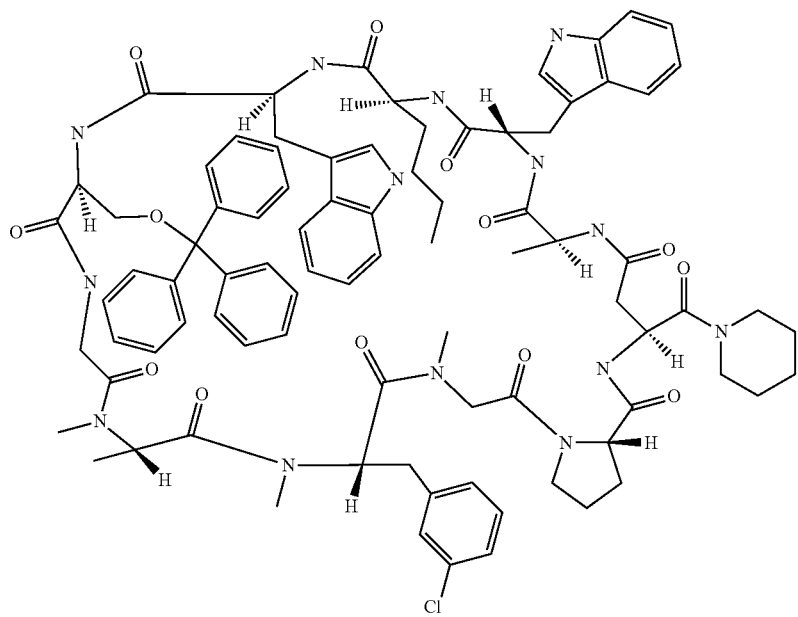 [SMILES: CCCC[C@@H]1NC(=O)[C@H](Cc2c[nH]c3ccccc23)NC(=O)[C@H](C)NC(=O)C[C@@H](C(=O)N2CCCCC2)NC(=O)[C@@H]2CCCN2C(=O)CN(C)C(=O)[C@H](Cc2cccc(Cl)c2)N(C)C(=O)[C@H](C)N(C)C(=O)CNC(=O)[C@H](COC(c2ccccc2)(c2ccccc2)c2ccccc2)NC(=O)[C@H](Cc2c[nH]c3ccccc23)NC1=O]

TABLE 2-2-continued
Pep-6 Compound 106
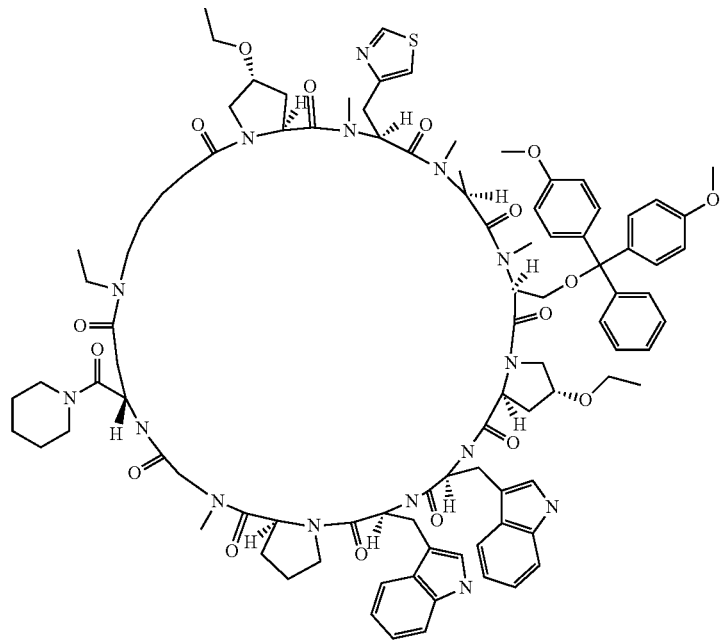
Pep-7 Compound 107
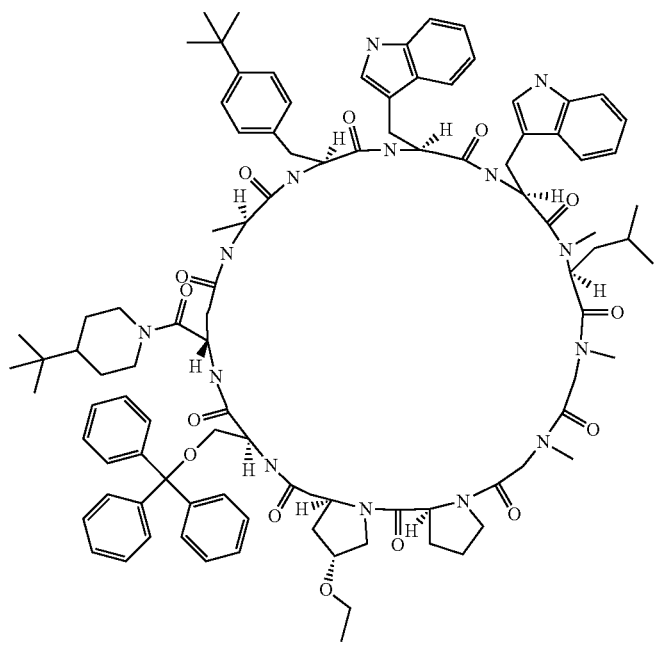
| | | TABLE 2-3 | | |
|---|---|---|---|---|
| | | LCMS Condition | Retention Time (min) | LCMS (ESI) m/z |
| Pep-1 | Compound 101 | SQDFA05 | 0.93 | 1480.1 (M + H)+ |
| Pep-2 | Compound 102 | SQDFA05 | 1.00 | 1852.3 (M + H)+ |
| Pep-3 | Compound 103 | SQDFA05 | 0.78 (30%), 1.06 (70%) | 1474.1, 1716.2 (M + H)+ |
| Pep-4 | Compound 104 | SQDFA05 | 0.78 | 1343.9 (M + H)+ |
| Pep-5 | Compound 105 | SQDFA05 | 1.01 | 1574.2 (M + H)+ |
| Pep-6 | Compound 106 | SQDFA05 | 0.98 | 1473.1 (M + H)+ |
| Pep-7 | Compound 107 | SQDFA05 | 1.10 | 1734.2 (M + H)+ |

Example 3 Deprotection of Protecting Groups on Peptide Side-Chain Functional Groups Using Weakly Acidic Solutions Produced from Weak Acids (Having Aqueous pKa of 0 to 9) and Solvents (Solvents which have Positive $Y_{OTs}$ Values, are Weakly Acidic (Aqueous pKa of 5 to 14) and have Low Nucleophilicity) (Step D)

Example 3-1. Possibility of Deprotection of Protecting Groups on Fmoc-Amino Acid Side-Chain Functional Groups Using the Above-Mentioned Weakly Acidic Solution Whether the protecting groups of side-chain functional groups of Fmoc-amino acids used in peptide synthesis can be deprotected under conditions of weaker acidity than TFA, more specifically, in a solution produced by dissolving a weak acid having an aqueous pKa of 0 to 9 in a solvent that has a positive YOTs value, is weakly acidic (aqueous pKa of 5 to 14), and has low nucleophilicity, was examined.

Specifically, tetramethylammonium hydrogen sulfate (pKa 2.0) was used as the weak acid and HFIP (having a YOTs value of 3.82 (value based on the literature: Prog. Phys. Org. Chem. 1990, 17, 121-158), and a pKa of 9.30) was used as the solvent. More specifically, either 0.1 M tetramethylammonium hydrogen sulfate/HFIP solution (2% TIPS) or 0.05 M tetramethylammonium hydrogen sulfate/HFIP solution (2% TIPS) was used.

Example 3-1-1: Preparation of 0.1 M tetramethylammonium hydrogen Sulfate/HFIP Solution (2% TIPS)

The 0.1 M tetramethylammonium hydrogen sulfate/HFIP solution (2% TIPS) was prepared by drawing 4 mL of a solution produced by mixing HFIP (11.66 mL), TIPS (0.24 mL), and DCE (0.10 mL), and dissolving 68.5 mg of tetramethylammonium hydrogen sulfate in this solution.

Example 3-1-2: Preparation of 0.05M tetramethylammonium hydrogen Sulfate/HFIP Solution (2% TIPS)

The 0.05 M tetramethylammonium hydrogen sulfate/HFIP solution (2% TIPS) was prepared by drawing 4 mL of a solution produced by mixing HFIP (11.66 mL), TIPS (0.24 mL), and DCE (0.10 mL), and dissolving 34.3 mg of tetramethylammonium hydrogen sulfate in this solution.

Fmoc-amino acids having side-chain protecting groups or peptides which comprise amino acid residues having side-chain protecting groups were deprotected by method A or method B described below.

Example 3-1-3: Method A

To a mixture of an Fmoc-amino acid (4.0 μmol) and a peptide (any one of the already synthesized cyclic peptides Pep 1 to Pep 6 (residue after cyclization); maximum concentration of 3.66 μmol) having protecting groups on their side chains, 0.1 M tetramethylammonium hydrogen sulfate/HFIP solution (2% TIPS) (0.20 mL) or 0.05 M tetramethylammonium hydrogen sulfate/HFIP solution (2% TIPS) (0.40 mL) was added and shaken for three minutes, then this was left to stand at 25° C. After a given amount of time, LCMS (FA05) analyses were carried out. Progress of the deprotection was calculated from the UV area ratio of the deprotected peptide to the protected peptide.

Example 3-1-4: Method B

To a peptide (any one of the already synthesized cyclic peptides Pep 1 to Pep 6 (residue after cyclization); maximum concentration of 3.66 μmol) comprising amino acid residues having protecting groups on their side chains, 0.1 M tetramethylammonium hydrogen sulfate/HFIP (2% TIPS) (0.20 mL) or 0.05 M tetramethylammonium hydrogen sulfate/HFIP (2% TIPS) (0.40 mL) was added and shaken for three minutes. This was left to stand at 25° C., and after a given amount of time, LCMS (FA05) analyses were carried out. Progress of the deprotection was calculated from the UV area ratio of the deprotected peptide to the protected peptide.

The peptides prepared as follows were used in method A and method B: elongation was performed and elongated peptides were cleaved off from the resin by the already described method and additionally subjected to a cyclization reaction by the already described method; then peptides were concentrated under reduced pressure, and the obtained residues were dissolved in dichloromethane, and this was aliquoted into 10 test tubes; and then concentrated again by removing the solvent under reduced pressure.

The results of evaluation are as shown below in Table 3.

TABLE 3

| run | Protected Amino Add | method | Coexisted Peptide | Condition | Time (h) | Deprotection (%) |
|---|---|---|---|---|---|---|
| 1 | D-Tyr (tBu) | B | Pep 1 (Compound 101) | 0.1M | 24 | >99% |
| 2 | | B | Pep 1 (Compound 101) | 0.05M | 24 | 81% |
| 3 | Tyr (3-F, tBu) | A | Pep 2 (Compound 102) | 0.1M | 22 | 65% |
| 4 | | A | Pep 2 (Compound 102) | 0.05M | 19 | 19% |
| 5 | MeHis (Trt) | A | Pep 2 (Compound 102) | 0.05M | 4 | >99% |
| 6 | Thr (THP) | B | Pep 2 (Compound 102) | 0.05M | 2 | >99% |
| 7 | MeSer (DMT) | B | Pep 3 (Compound 103) | 0.05M | 4 | >99% |
| 8 | MeSer (THP) | A | Pep 4 (Compound 104) | 0.05M | 1 | >99% |
| 9 | Ser (Trt) | B | Pep 5 (Compound 105) | 0.05M | 4 | >99% |
| 10 | Ser (THP) | A | Pep 3 (Compound 103) | 0.05M | 1 | >99% |
| 11 | Pro-OPis | A | Pep 2 (Compound 102) | 0.05M | 2 | >99% |
| 12 | D-Tyr (Clt) | A | Pep 5 (Compound 105) | 0.05M | 1 | >99% |
| 13 | D-Tyr (THP) | A | Pep 6 (Compound 106) | 0.05M | 1.25 | >99% |
| 14 | D-Tyr (Pis) | A | Pep 6 (Compound 106) | 0.05M | 1.25 | >99% |
| 15 | Tyr (3-F, Pis) | A | Pep 3 (Compound 103) | 0.05M | 1 | >99% |

Results of LCMS analyses taken on Fmoc-amino acids after deprotection are as follows:

Fmoc-Tyr(3-F)—OH (deprotection product of run 3, run 4, and run 15)
LCMS (ESI) m/z=422.3 (M+H)$^+$
Retention time: 0.73 minutes (analysis condition SQDFA05)

Fmoc-MeHis-OH (deprotection product of run 5)
LCMS (ESI) m/z=392.3 (M+H)$^+$
Retention time: 0.47 minutes (analysis condition SQDFA05)

Fmoc-MeSer-OH (deprotection product of run 8)
LCMS (ESI) m/z=342.3 (M+H)$^+$
Retention time: 0.67 minutes (analysis condition SQDFA05)

Fmoc-Ser-OH (deprotection product of run 10)
LCMS (ESI) m/z=328.2 (M+H)$^+$
Retention time: 0.64 minutes (analysis condition SQDFA05)

Fmoc-Pro-OH (deprotection product of run 11)
LCMS (ESI) m/z=338.3 (M+H)$^+$
Retention time: 0.75 minutes (analysis condition SQDFA05)

Fmoc-D-Tyr-OH (deprotection product of run 12 to run 14)
LCMS (ESI) m/z=404.3 (M+H)$^+$
Retention time: 0.72 minutes (analysis condition SQDFA05)

Deprotection product of Pep 1 (Compound 101) (deprotection product of run 1 and run 2; Compound 131)
LCMS (ESI) m/z=1424.0 (M+H)$^+$
Retention time: 0.79 minutes (analysis condition SQDFA05)

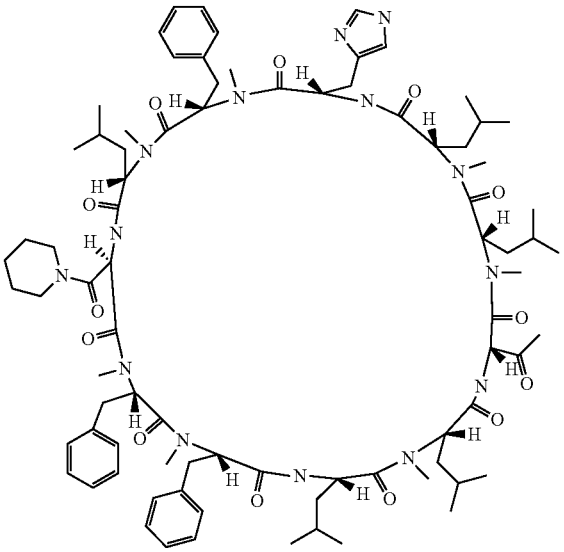

Compound 132

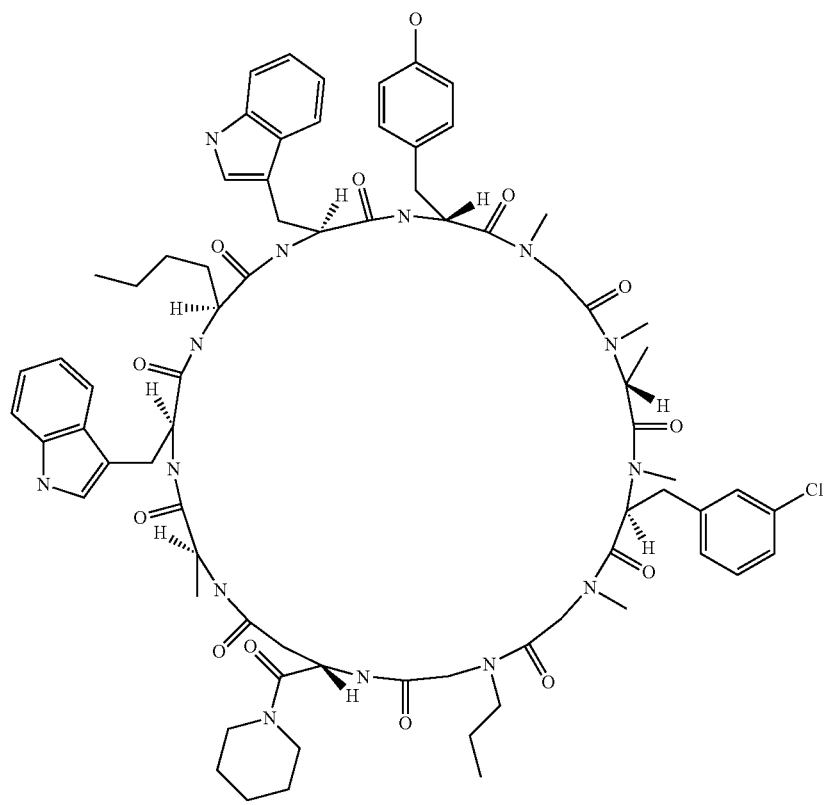

Compound 131

Deprotection product of Pep 2 (Compound 102) (deprotection product of run 6; Compound 132)

LCMS (ESI) m/z=1526.3 (M+H)+

Retention time: 0.89 minutes (analysis condition SQDFA05)

Compound 133

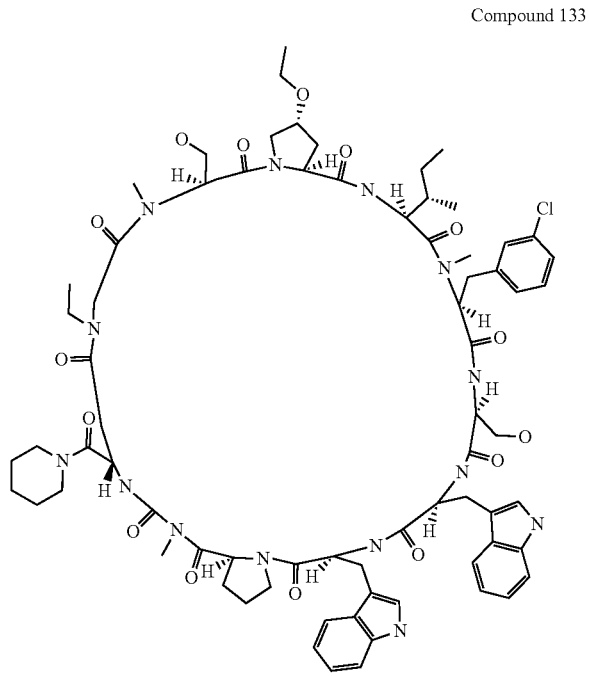 [SMILES: CCO[C@@H]1C[C@H]2C(=O)N[C@@H]([C@@H](C)CC)C(=O)N(C)[C@@H](Cc3cccc(Cl)c3)C(=O)N[C@@H](CO)C(=O)N[C@@H](Cc3c[nH]c4ccccc34)C(=O)N[C@@H](Cc3c[nH]c4ccccc34)C(=O)N3CCC[C@H]3C(=O)N(C)C(=O)N[C@H](C(=O)N3CCCCC3)CC(=O)N(CC)CC(=O)N(C)[C@@H](CO)CC(=O)N2C1]

Deprotection product of Pep 3 (Compound 103) (deprotection product of run 7; Compound 133)

LCMS (ESI) m/z=1474.1 (M+H)+

Retention time: 0.78 minutes (analysis condition SQDFA05)

Compound 135

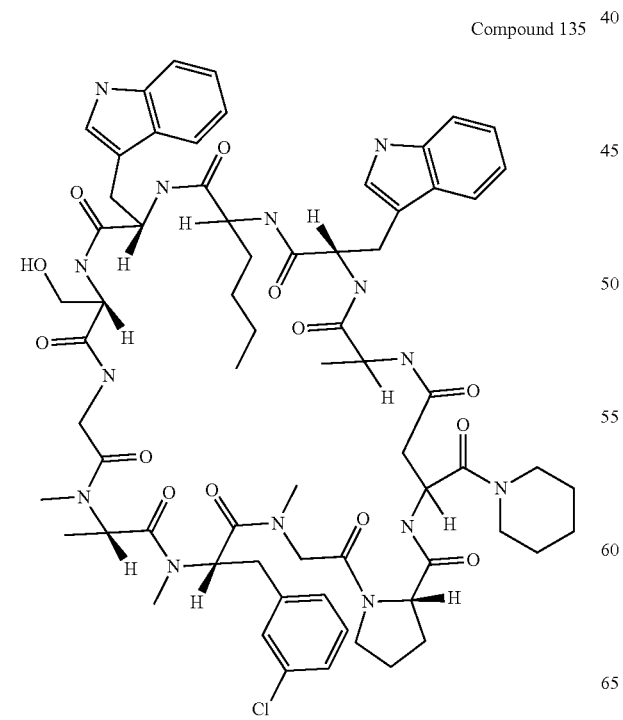

Deprotection product of Pep 5 (Compound 105) (deprotection product of run 9; Compound 135)

LCMS (ESI) m/z=1331.7 (M+H)+

Retention time: 0.74 minutes (analysis condition SQDFA05)

From these results, these protecting groups were confirmed to undergo deprotection under a condition of 0.1 M tetramethylammonium hydrogen sulfate/HFIP (2% TIPS) or 0.05 M tetramethylammonium hydrogen sulfate/HFIP (2% TIPS).

Protecting groups on the side chains are not affected by peptide cleavage conditions that use a TFE-DCM (1/1, v/v) solution or a TFE-DCM (1/1, v/v)/DIPEA (addition of 1.8 equivalents to the theoretical number of moles yielded by multiplying the loading rate of the resin used by the amount of resin used) solution. Therefore, in the intramolecular cyclization at the peptide main-chain N terminus and the Asp side-chain carboxylic acid portion after the cleavage step, the amino acid side-chain functional group is maintained in the protected form. As a result, undesired cyclization reactions in which the amino acid side-chain functional group functions as the nucleophilic species can be suppressed.

3-2. Possibility of Suppressing Hydrolysis and N-to O-Acyl Shift Product Generation which Take Place when Protecting Groups of Fmoc-Amino Acid Side-Chain Functional Groups are Deprotected Using the Above-Mentioned Weakly Acidic Solution Example 3-2-1

Deprotection of the Cyclic Compound (Compound 101, Pep1). In which an Amide Bond was Formed Between the N-Terminal Amino Group of H-Ala-Tp-Nle-Trp-D-Tvr(tBu)-MeGly-MeAla-MePhe(3-Cl)-MeGly-nPrGly-Asp-pip and the Side-Chain Carboxylic Acid of Asp, by Using 0.1 M Tetramethylammonium Hydrogen Sulfate/HFIP Solution (2% TIPS) as the Deprotection Condition Fmoc-Asp(O-Trt(2-Cl)-resin)-pip (Compound 50, resin loading rate: 0.342 mmol/g, 100 mg) was used as the resin, and cyclic compound (Compound 101) in which an amide bond is formed between the N-terminal amino group of H-Ala-Trp-Nle-Trp-D-Tyr(tBu)-MeGly-MeAla-MePhe(3-Cl)-MeGly-nPrGly-Asp-pip and the side-chain carboxylic acid of Asp was synthesized by the already described method. After cyclization, a residue formed by concentration under reduced pressure was dissolved in dichloromethane, then this was aliquoted into 10 test tubes, and then they were concentrated again by removing the solvent under reduced pressure.

Figure 2:
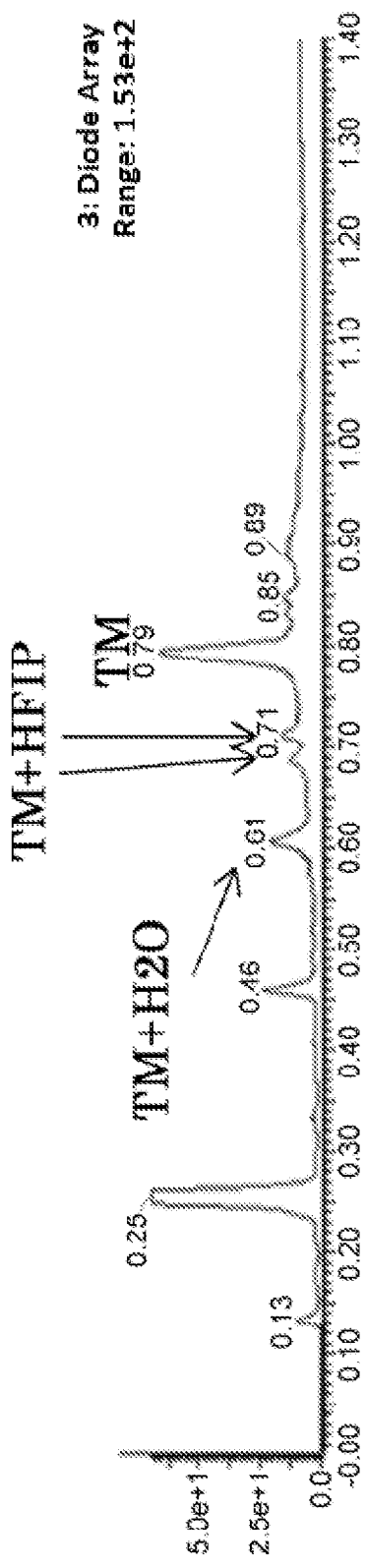
FIG. 2 shows the result showing detection of the desired peptide (Compound 131), hydrolysate of the target molecule (TM+H2O), and a solvolysis product of the target molecule by HFIP (TM+HFIP) under the deprotection condition using 0.1 M tetramethylammonium hydrogensulfate/HFIP solution (2% TIPS) analyzed by LCMS.

To one of the 10 test tubes aliquoted, 0.20 mL of 0.1 M tetramethylammonium hydrogen sulfate/HFIP solution (2% TIPS) (68.5 mg of tetramethylammonium hydrogen sulfate was dissolved in 4 mL of solution drawn out from a solution produced by mixing HFIP: 11.66 mL, TIPS: 0.24 mL, and DCE: 0.10 mL) was added. The test tube was capped using a rubber septum, shaken for three minutes, and then left to stand at 25° C. for 24 hours. When the reaction was confirmed by LCMS (FA05), completion of side-chain deprotection (deprotection of the tBu group of D-Tyr(tBu)) could be confirmed. Here, the ratio among the deprotected desired peptide (Compound 131), the solvolysis product (compound showing a mass spectrum in which any of the amide bonds of the peptide has undergone solvolysis by the solvent HFIP), and the hydrolysate (compound showing a mass spectrum in which any of the amide bonds of the peptide has undergone solvolysis by water) was 72:10:18 (FIG. 2). In the Examples, "TM+H2O" represents a compound in which any one of the amide bonds of the target molecule has undergone hydrolysis, and "TM+HFIP" represents a compound in which any one of the amide bonds of the target molecule has undergone solvolysis by HFIP.

The data of FIG. 2 are shown below:
Desired peptide (Compound 131)
LCMS (ESI) m/z=1424.0 (M+H)+
Retention time: 0.79 minutes (analysis condition SQDFA05)
Hydrolysate (TM+H2O)
LCMS (ESI) m/z=1442.0 (M+H)+
Retention time: 0.61 minutes (analysis condition SQDFA05)
Product of solvolysis by HFIP (TM+HFIP)
LCMS (ESI) m/z=1592.0 (M+H)+
Retention time: 0.69 minutes, 0.71 minutes (analysis condition SQDFA05)

Example 3-2-2

Figure 3:
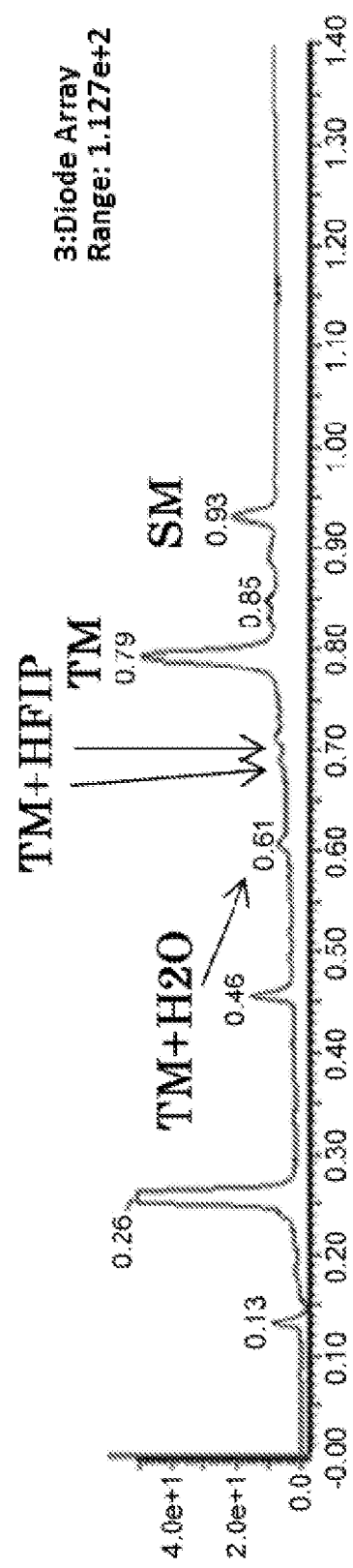
FIG. 3 shows the result showing detection of the desired peptide (Compound 131), hydrolysate of the target molecule (TM+H2O), and a solvolysis product of the target molecule by HFIP (TM+HFIP) under the deprotection condition using 0.05 M tetramethylammonium hydrogensulfate/HFIP solution (2% TIPS) analyzed by LCMS.

Deprotection of the Cyclic Compound (Compound 101, Pep1) in which an Amide Bond was Formed Between the N-Terminal Amino Group of H-Ala-Trp-Nle-Trp-D-Tyr(tBu)-MeGly-MeAla-MePhe(3-Cl)-MeGly-nPrGly-Asp-pip and the Side-Chain Carboxylic Acid of Asp, by Using 0.05 M Tetramethylammonium Hydrogen Sulfate/HFIP Solution (2% TIPS) as the Deprotection Condition After synthesizing Compound 101 (Pep1), 0.40 mL of 0.05 M tetramethylammonium hydrogen sulfate/HFIP solution (2% TIPS) (34.3 mg of tetramethylammonium hydrogen sulfate was dissolved in 4 mL of solution drawn out from a solution produced by mixing HFIP: 11.66 mL, TIPS: 0.24 mL, and DCE: 0.10 mL) was added to another one of the 10 test tubes aliquoted in the above-mentioned operation. The test tube was capped using a rubber septum, shaken for three minutes, and then left to stand at 25° C. for 24 hours, and then the reaction was checked by LCMS (FA05). As a result, side-chain deprotection (deprotection of the tBu group of D-Tyr(tBu)) had proceeded 81%, and at this time, the ratio among the deprotected desired peptide (Compound 131), the solvolysis product (compound showing a mass in which any of the amide bonds of the peptide has undergone solvolysis by the solvent HFIP), and the hydrolysate (compound showing a mass in which any of the amide bonds of the peptide has undergone hydrolysis by water) was 93:3:4 (FIG. 3). "TM+H$_2$O" represents a compound in which any one of the amide bonds of the target molecule has undergone hydrolysis. Similarly, "TM+HFIP" represents a compound in which any one of the amide bonds of the target molecule has undergone solvolysis by HFIP.

The data of FIG. 3 are shown below:
Desired peptide (Compound 131)
LCMS (ESI) m/z=1424.1 (M+H)+
Retention time: 0.79 minutes (analysis condition SQDFA05)
Hydrolysate
LCMS (ESI) m/z=1442.0 (M+H)+
Retention time: 0.61 minutes (analysis condition SQDFA05)
Product of solvolysis by HFIP
LCMS (ESI) m/z=1592.0 (M+H)+
Retention time: 0.69 minutes, 0.71 minutes (analysis condition SQDFA05)

As described in the comparative example below, when the cyclic compound (Compound 101, Pep1) in which an amide bond was formed between the N-terminal amino group of H-Ala-Trp-Nle-Trp-D-Tyr(tBu)-MeGly-MeAla-MePhe(3-Cl)-MeGly-nPrGly-Asp-pip and the side-chain carboxylic acid of Asp was deprotected under conditions of 5% TFA/DCE, deprotection for 2.5 hours at 25° C. resulted in 87% progress of the hydrolysis.

On the other hand, by using 0.1 M or 0.05 M tetramethylammonium hydrogen sulfate/HFIP solution (2% TIPS) instead of 5% TFA on the same peptide sequence, production of hydrolysates (and solvolysis products) could be reduced significantly. Furthermore, this result suggests the possibility that if a condition yielding weaker acidity than TFA can be satisfied, the concentration of the weak acid can be adjusted as one chooses.

Example 3-2-3

Deprotection of the Cyclic Compound (Compound 103, Pep3) in which an Amide Bond is Formed Between the N-Terminal Amino Group of H-g-EtAbu-MeSer(DMT)-Hyp(Et)-Ile-MePhe(3-Cl)-Ser(Trt)-Trp-Trp-Pro-MeGly-Asp-pip and the Side-Chain Carboxylic Acid of Asp, by Using 0.05 M Tetramethylammonium Hydrogen Sulfate/HFIP Solution (2% TIPS) as the Deprotection Condition Fmoc-Asp(O-Trt(2-Cl)-resin)-pip (Compound 50, loading: 0.316 mmol/g, 100 mg) was used as the resin, and the cyclic compound (Compound 103, Pep3) in which an amide bond was formed between the N-terminal amino group of H-g-EtAbu-MeSer(DMT)-Hyp(Et)-Ile-MePhe(3-Cl)-Ser(Trt)-Trp-Trp-Pro-MeGly-Asp-pip and the side-chain carboxylic acid of Asp was synthesized by the already described method. After cyclization, a residue formed by concentration under reduced pressure was dissolved in dichloromethane, then this was aliquoted into 10 test tubes, and then they were concentrated again by removing the solvent under reduced pressure.

To one of the 10 test tubes aliquoted, 0.40 mL of 0.05 M tetramethylammonium hydrogen sulfate/HFIP solution (2% TIPS) (34.3 mg of tetramethylammonium hydrogen sulfate was dissolved in 4 mL of solution drawn out from a solution produced by mixing HFIP: 11.66 mL, TIPS: 0.24 mL, and DCE: 0.10 mL) was added. The test tube was capped using a rubber septum, shaken for three minutes, and then left to stand at 25° C. At the stage of four hours, the reaction was checked by LCMS (SQDFA05). As a result, completion of side-chain deprotection (deprotection of the DMT group of MeSer(DMT) and deprotection of the Trt group of Ser(Trt)) could be confirmed. Here the UV area ratio according to LC of the deprotected desired peptide (Compound 133; cyclic compound in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp) and the N- to O-acyl shifted product of the desired peptide (depsipeptide) was 96:4. Taking LCMS (SQDFA05) analyses after leaving the reaction solution to stand at 25° C. for 22 hours from the start of the reaction resulted in UV area ratio according to LC of the deprotected desired peptide (Compound 133; cyclic compound in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp) and the N- to O-acyl shifted product of the desired peptide (depsipeptide) of 83:17 (FIG. 4).

Figure 4:
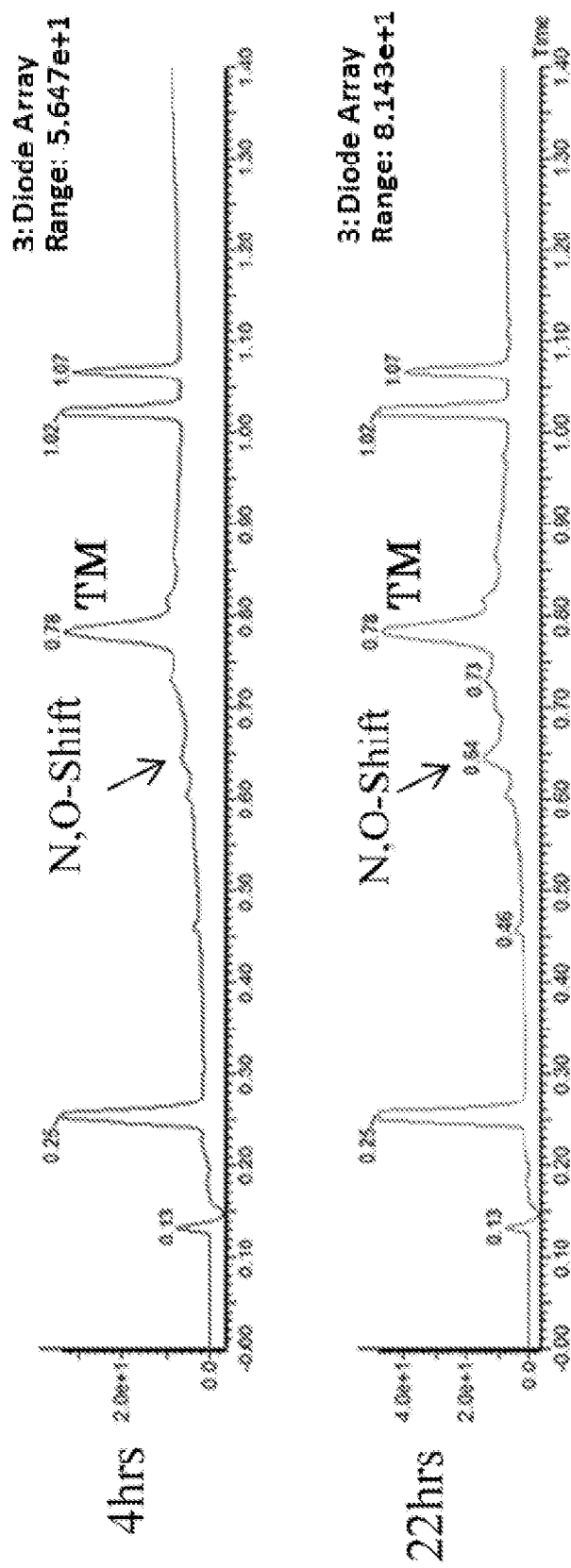
FIG. 4 shows the result showing detection of the desired peptide (Compound 133), and a N- to O-acyl shifted product of desired product under the deprotection condition using 0.05 M tetramethylammonium hydrogensulfate/HFIP solution (2% TIPS) analyzed by LCMS.

The data of FIG. 4 are shown below:

Desired peptide (Compound 133: cyclic compound in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp)

LCMS (ESI) m/z=1474.1 (M+H)+

Retention time: 0.78 minutes (analysis condition SQDFA05)

Product of N- to O-acyl shift

LCMS (ESI) m/z=1474.1 (M+H)+

Retention time: 0.64 minutes (analysis condition SQDFA05)

As described later, when the cyclic compound (Compound 103, Pep3) in which an amide bond was formed between the N-terminal amino group of H-g-EtAbu-MeSer(DMT)-Hyp(Et)-Ile-MePhe(3-Cl)-Ser(Trt)-Trp-Trp-Pro-MeGly-Asp-pip and the side-chain carboxylic acid of Asp was deprotected under conditions of 5% TFA/DCE, deprotection for two hours at 25° C. resulted in 70% progress of the N- to O-acyl shift.

On the other hand, by using 0.05 M tetramethylammonium hydrogen sulfate/HFIP solution (2% TIPS) instead of 5% TFA on the same peptide sequence, generation of N- to O-acyl shift products could be reduced significantly.

Example 3-2-4

Figure 5:
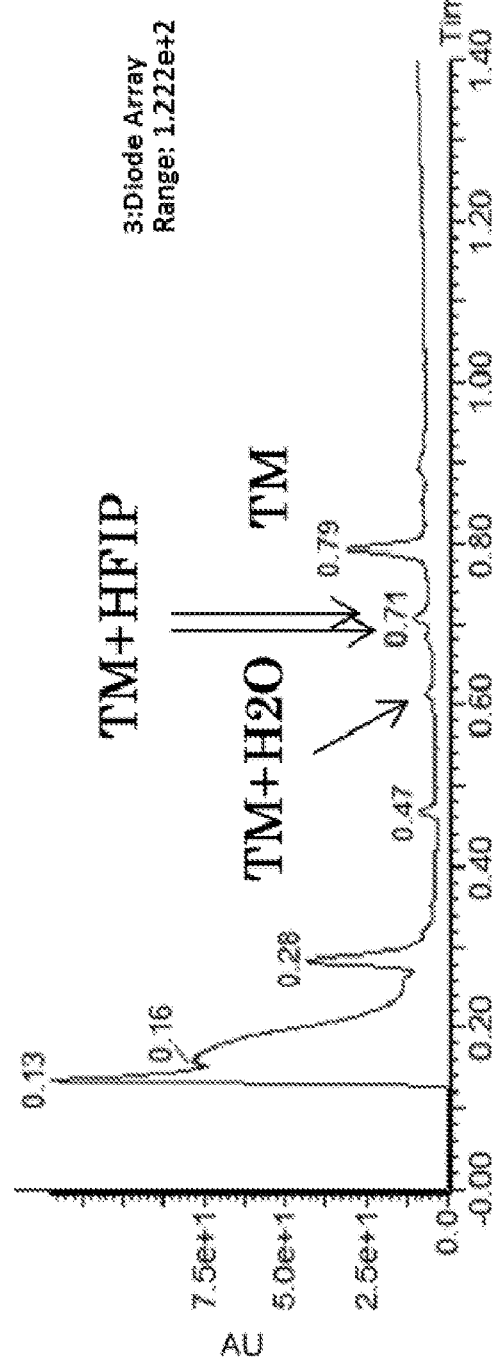
FIG. 5 shows the result showing detection of the desired peptide (Compound 131), hydrolysate of the target molecule (TM+H2O), and a solvolysis product of the target molecule by HFIP (TM+HFIP) under the deprotection condition using 0.05 M oxalic acid/HFIP solution (2% TIPS) analyzed by LCMS.

Deprotection of the Cyclic Compound (Compound 101, Pep1) in which an Amide Bond was Formed Between the N-Terminal Amino Group of H-Ala-Trp-Nle-Trp-D-Tyr(tBu)-MeGly-MeAla-MePhe(3-Cl)-MeGly-nPrGly-Asp-pip and the Side-Chain Carboxylic Acid of Asp, by Using 0.05 M Oxalic Acid/HFIP Solution (2% TIPS) as the Deprotection Condition After synthesizing Compound 101 (Pep1), 0.40 mL of 0.05 M oxalic acid/HFIP solution (2% TIPS) (18.0 mg of oxalic acid was dissolved in 4 mL of solution drawn out from a solution produced by mixing HFIP: 11.66 mL, TIPS: 0.24 mL, and DCE: 0.10 mL) was added to another one of 10 test tubes aliquoted in the above-mentioned operation. The test tube was capped using a rubber septum, shaken for three minutes, and then left to stand at 25° C. for four hours, and then the reaction was checked by LCMS (FA05). As a result, side-chain deprotection (deprotection of the tBu group of D-Tyr(tBu)) was completed, and at this time, the ratio among the deprotected desired peptide (Compound 131), the solvolysis product (compound showing a mass in which any of the amide bonds of the peptide has undergone solvolysis by the solvent HFIP), and the hydrolysate (compound showing a mass in which any of the amide bonds of the peptide has undergone hydrolysis by water) was 79:17:4 (FIG. 5). "TM+H2O" represents a compound in which any one of the amide bonds of the target molecule has undergone hydrolysis. Similarly, "TM+HFIP" represents a compound in which any one of the amide bonds of the target molecule has undergone solvolysis by HFIP.

The data of FIG. 5 are shown below:

Desired peptide (Compound 131)

LCMS (ESI) m/z=1423.5 (M+H)+

Retention time: 0.79 minutes (analysis condition SQDFA05)

Hydrolysate

LCMS (ESI) m/z=1441.5 (M+H)+

Retention time: 0.61 minutes (analysis condition SQDFA05)

Product of solvolysis by HFIP

LCMS (ESI) m/z=1591.5 (M+H)+

Retention time: 0.68 minutes, 0.71 minutes (analysis condition SQDFA05)

Example 3-2-5

Figure 6:
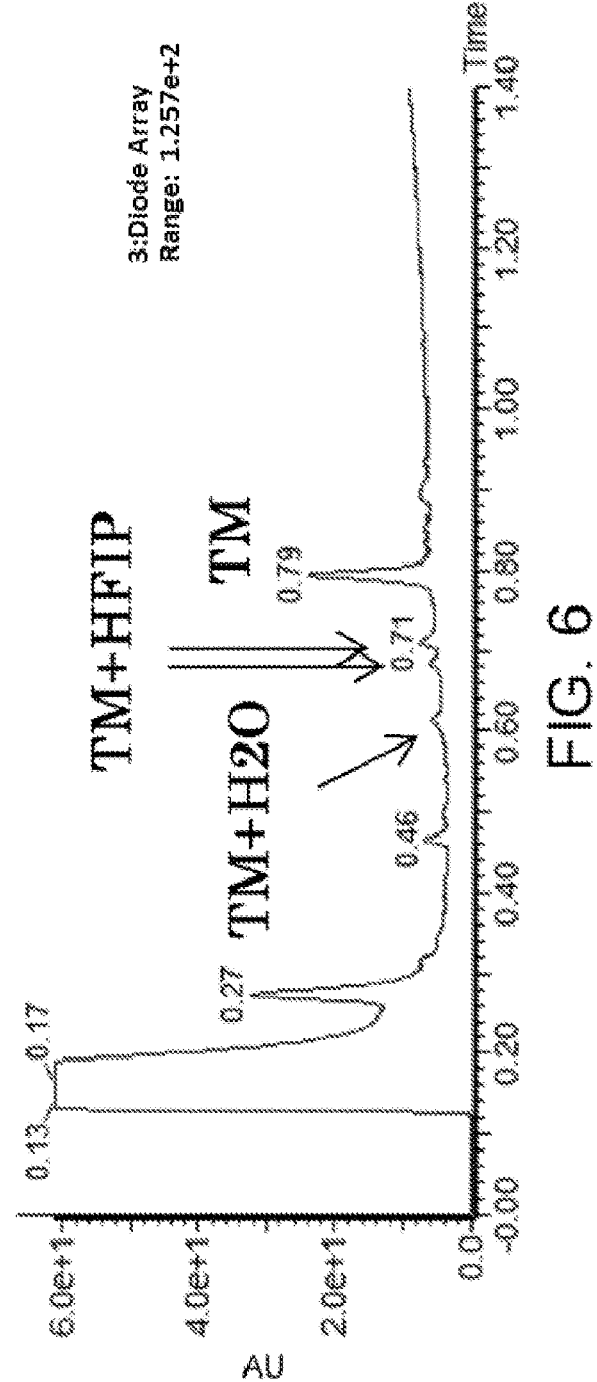
FIG. 6 shows the result showing detection of the desired peptide (Compound 131), hydrolysate of the target molecule (TM+H2O), and a solvolysis product of the target molecule by HFIP (TM+HFIP) under the deprotection condition using 0.05 M maleic acid/HFIP solution (2% TIPS) analyzed by LCMS.

Deprotection of Cyclic Compound (Compound 101, Pep 1) in which an Amide Bond was Formed Between the N-Terminal Amino Group of H-Ala-Trp-Nle-Trp-D-Tyr(tBu)-MeGly-MeAla-MePhe(3-Cl)-MeGly-nPrGly-Asp-Pip and the Side-Chain Carboxylic Acid of Asp, by Using 0.05 M Maleic Acid/HFIP Solution (2% TIPS) as the Deprotection Condition After synthesizing Compound 101 (Pep1), 0.40 mL of 0.05 M maleic acid/HFIP solution (2% TIPS) (23.2 mg of maleic acid was dissolved in 4 mL of solution drawn out from a solution produced by mixing HFIP: 11.66 mL, TIPS: 0.24 mL, and DCE: 0.10 mL) was added to another one of 10 test tubes aliquoted in the above-mentioned operation. The test tube was capped using a rubber septum, shaken for three minutes, and then left to stand at 25° C. for four hours, and then the reaction was checked by LCMS (FA05). As a result, side-chain deprotection (deprotection of the tBu group of D-Tyr(tBu)) was completed, and at this time, the ratio among the deprotected desired peptide (Compound 131), the solvolysis product (compound showing a mass in which any of the amide bonds of the peptide has undergone solvolysis by the solvent HFIP), and the hydrolysate (compound showing a mass in which any of the amide bonds of the peptide has undergone hydrolysis by water) was 81:12:7 (FIG. 6). "TM+H2O" represents a compound in which any one of the amide bonds of the target molecule has undergone hydrolysis. Similarly, "TM+HFIP" represents a compound in which any one of the amide bonds of the target molecule has undergone solvolysis by HFIP.

The data of FIG. 6 are shown below:

Desired peptide (Compound 131)

LCMS (ESI) m/z=1423.5 (M+H)+

Retention time: 0.79 minutes (analysis condition SQDFA05)

Hydrolysate

LCMS (ESI) m/z=1441.5 (M+H)+

Retention time: 0.61 minutes (analysis condition SQDFA05)

Product of solvolysis by HFIP

LCMS (ESI) m/z=1591.4 (M+H)+

Retention time: 0.68 minutes, 0.71 minutes (analysis condition SQDFA05)

Example 3-2-6

Deprotection of the Cyclic Compound (Compound 103, Pep3) in which an Amide Bond was Formed Between the N-Terminal Amino Group of H-n-EtAbu-MeSer(DMT)-Hyp(Et)-Ile-MePhe(3-Cl)-Ser(Trt)-Trp-Trp-Pro-MeGly-Asp-Pip and the Side-Chain Carboxylic Acid of Asp, By Using 0.05 M Oxalic Acid/HFIP Solution (2% TIPS) as the Deprotection Condition After synthesizing Compound 103 (Pep3), 0.40 mL of 0.05 M oxalic acid/HFIP solution (2% TIPS) (18.0 mg of oxalic acid was dissolved in 4 mL of solution drawn out from a solution produced by mixing HFIP: 11.66 mL, TIPS: 0.24 mL, and DCE: 0.10 mL) was added to another one of 10 test tubes aliquoted in the above-mentioned operation. The test tube was capped using a rubber septum, shaken for three minutes, and then left to stand at 25° C. for four hours, and then the reaction was checked by LCMS (SQDFA05). As a result, completion of side-chain deprotection (deprotection of the DMT group of MeSer(DMT) and deprotection of the Trt group of Ser(Trt)) could be confirmed. At this time, the UV area ratio according to LC of the deprotected desired peptide (Compound 133: cyclic compound in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp) and the N- to O-acyl shifted product of the desired peptide (depsipeptide) was 86:14 (FIG. 7).

Figure 7:
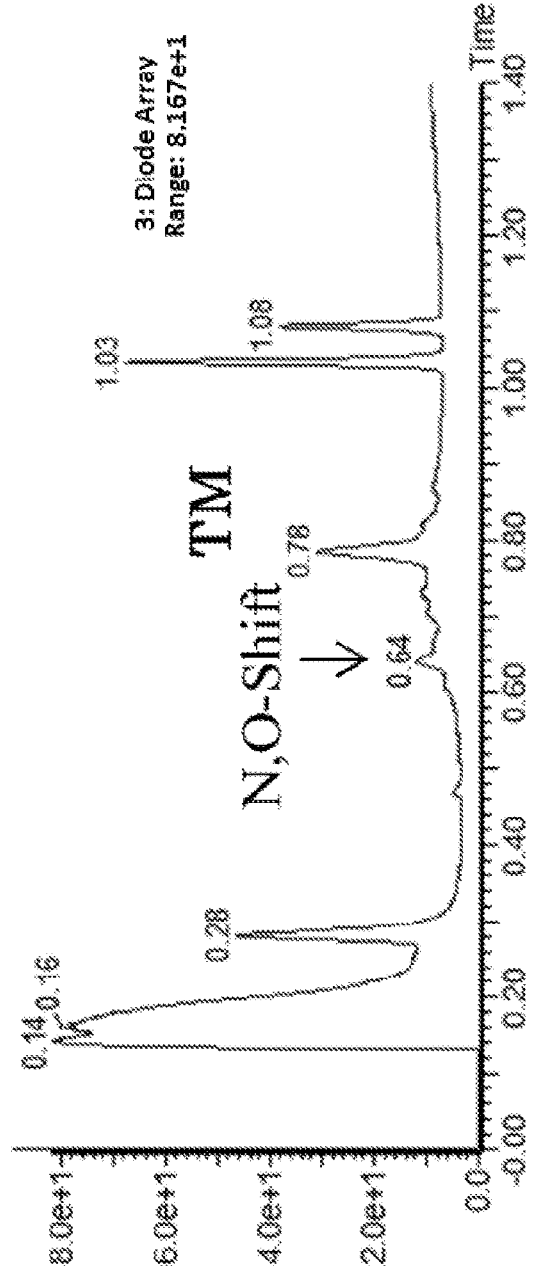
FIG. 7 shows the result showing detection of the desired peptide (Compound 133), and a N- to O-acyl shifted product of the target molecule under the deprotection condition using 0.05 M oxatic acid/HFIP solution (2% TIPS) analyzed by LCMS.

The data of FIG. 7 are shown below:
Desired peptide (Compound 133; cyclic compound in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp)
LCMS (ESI) m/z=1473.5 (M+H)+
Retention time: 0.78 minutes (analysis condition SQDFA05)
Product of N- to O-acyl shift
LCMS (ESI) m/z=1473.5 (M+H)+
Retention time: 0.64 minutes (analysis condition SQDFA05)

Example 3-2-7

Deprotection of the Cyclic Compound (Compound 103, Pep3) in which an Amide Bond was Formed Between the N-Terminal Amino Group of H-g-EtAbu-MeSer(DMT)-Hvp(Et)-Ile-MePhe(3-Cl)-Ser(Trt)-Trp-Trp-Pro-MeGly-Asp-Pip and the Side-Chain Carboxylic Acid of Asp, by Using 0.05 M Maleic Acid/HFIP Solution (2% TIPS) as the Deprotection Condition After synthesizing Compound 103 (Pep3), 0.40 mL of 0.05 M maleic acid/HFIP solution (2% TIPS) (23.2 mg of maleic acid was dissolved in 4 mL of solution drawn out from a solution produced by mixing HFIP: 11.66 mL, TIPS: 0.24 mL, and DCE: 0.10 mL) was added to another one of 10 test tubes aliquoted in the above-mentioned operation. The test tube was capped using a rubber septum, shaken for three minutes, and then left to stand at 25° C. for four hours, and then the reaction was checked by LCMS (SQDFA05). As a result, completion of side-chain deprotection (deprotection of the DMT group of MeSer(DMT) and deprotection of the Trt group of Ser(Trt)) could be confirmed. At this time, the UV area ratio according to LC of the deprotected desired peptide (Compound 133; cyclic compound in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp) and the N- to O-acyl shifted product of the desired peptide (depsipeptide) was 86:14 (FIG. 8).

Figure 8:
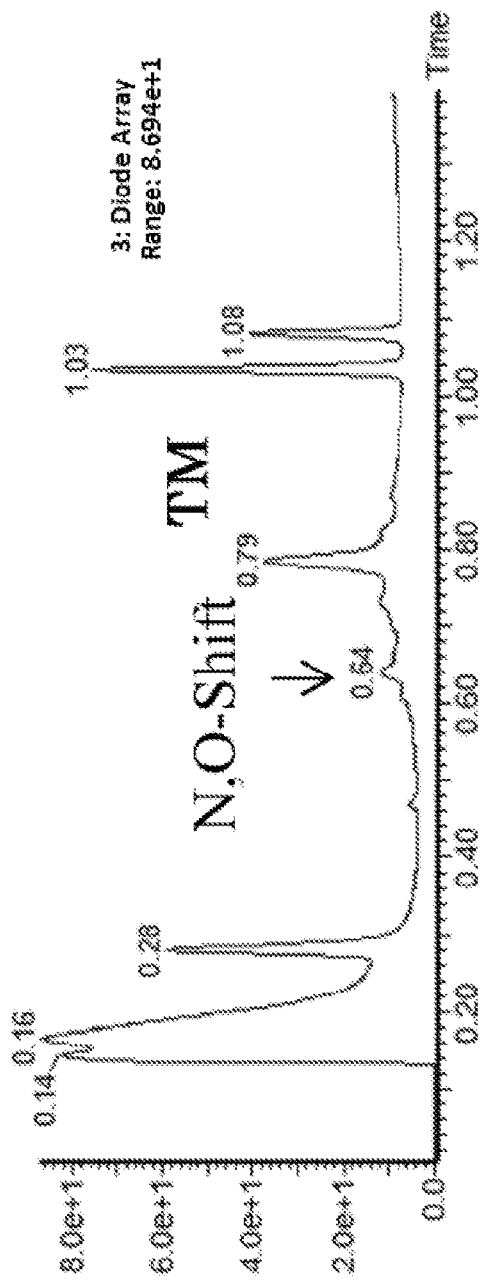
FIG. 8 shows the result showing detection of the desired peptide (Compound 133), and a N- to O-acyl shifted product of the target molecule under the deprotection condition using 0.05 M maleic acid/HFIP solution (2% TIPS) analyzed by LCMS.

The data of FIG. 8 are shown below:
Desired peptide (Compound 133; cyclic compound in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp)
LCMS (ESI) m/z=1473.5 (M+H)+
Retention time: 0.79 minutes (analysis condition SQDFA05)
Product of N- to O-acyl shift
LCMS (ESI) m/z=1473.5 (M+H)+
Retention time: 0.64 minutes (analysis condition SQDFA05)

These results showed that even when oxalic acid (pKa 1.23) or maleic acid (pKa 1.92) is used instead of tetramethylammonium hydrogen sulfate (pKa 2.0) as the weak acid, deprotection can be made to proceed while suppressing hydrolysis, solvolysis, and N- to O-acyl shift.

Example 3-2-8

Comparison Between the Use of 0.05 M Tetramethylammonium Hydrogen Sulfate/HFIP (2% TIPS) as the Deprotection Condition and the Use of 0.05 M Tetramethylammonium Hydrogen Sulfate/TFE (2% TIPS) as the Deprotection Condition in the Deprotection of the Cyclic Compound (Compound 107, Pep7) in which an Amide Bond was Formed Between the N-Terminal Amino Group of H-Ala-Phe(4-CF3)-Trp-Trp-MeLeu-MeGly-MeGly-Pro-Hyp(Et)-Ser(Trt)-Asp-Pip(tBu) and the Side-Chain Carboxylic Acid of Asp Using Fmoc-Asp(O-Trt(2-Cl)-resin)-piptBu (Compound 52, loading: 0.356 mmol/g, 100 mg) as the resin, cyclic compound (Compound 107) in which an amide bond was formed between the N-terminal amino group of H-Ala-Phe(4-CF3)-Trp-Trp-MeLeu-MeGly-MeGly-Pro-Hyp(Et)-Ser(Trt)-Asp-pip(tBu) and the side-chain carboxylic acid of Asp was synthesized by the already described method. After cyclization, a residue produced by concentration under reduced pressure was dissolved in dichloromethane, then this was aliquoted into 10 test tubes, and then the solvent was distilled off again under reduced pressure.

Figure 9:
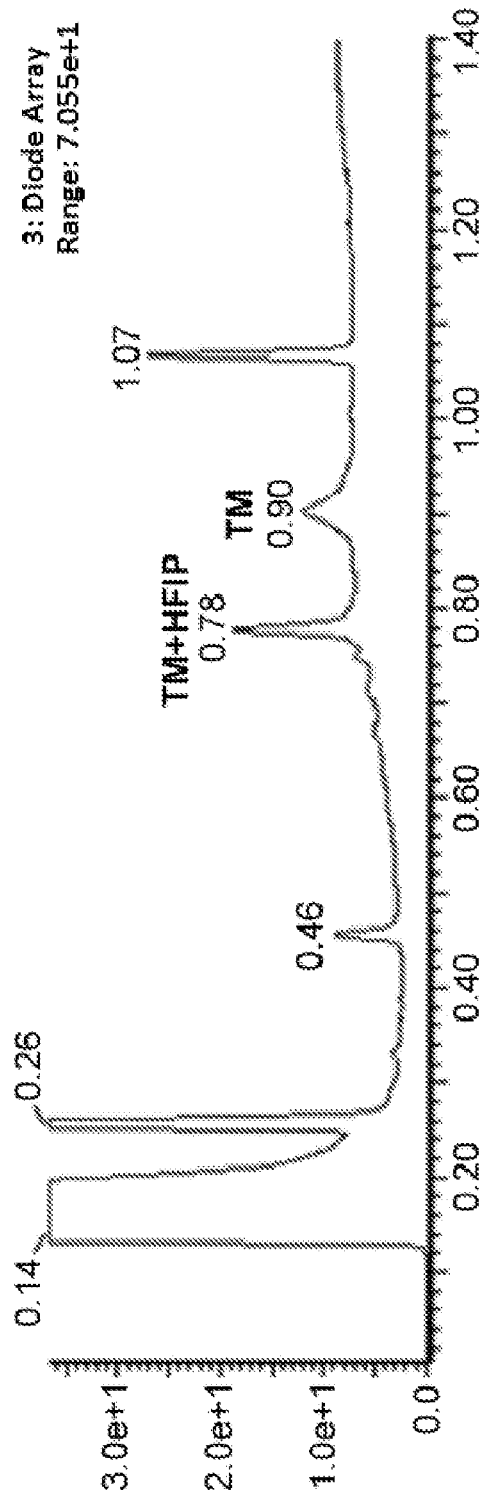
FIG. 9 shows the result showing detection of the desired peptide (Compound 137) and a solvolysis product of the target molecule by HFIP (product in which any one of the amide bonds has undergone solvolysis by HFIP) under the deprotection condition using 0.05 M tetramethylammonium hydrogensulfate/HFIP (2% TIPS) analyzed by LCMS.
Figure 10:
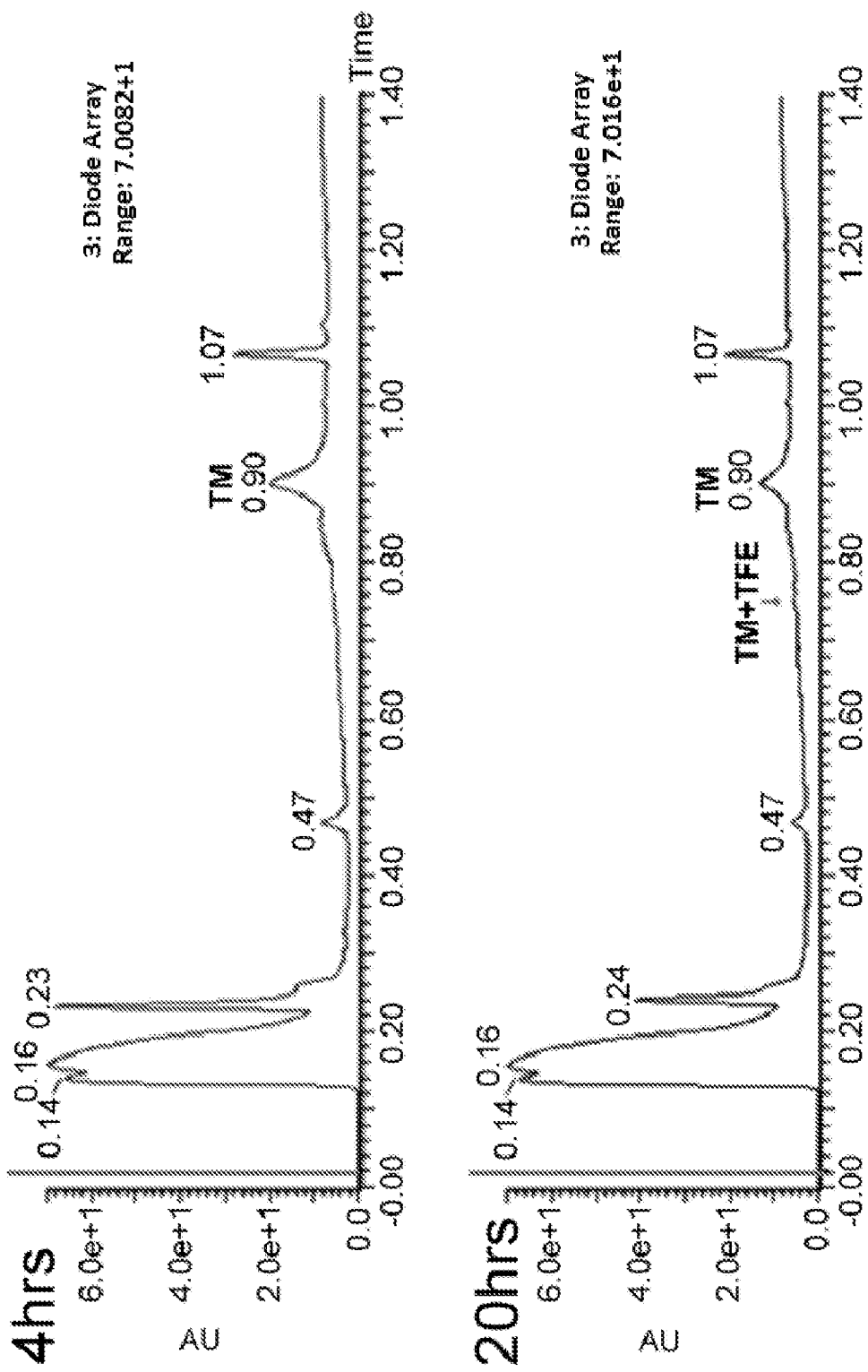
FIG. 10 shows the results showing detection of the desired peptide (Compound 137) and solvolysis product of the target molecule by TFE (product in which any one of the amide bonds has undergone solvolysis by TFE) under the deprotection condition using 0.05 M tetramethylammonium hydrogensulfate/TFE (2% TIPS) analyzed by LCMS.

To one of the 10 test tubes aliquoted, 0.40 mL of 0.05 M tetramethylammonium hydrogen sulfate/HFIP solution (2% TIPS) (a solution produced by dissolving 205.8 mg of tetramethylammonium hydrogen sulfate in a solution produced by mixing HFIP: 23.32 mL, TIPS: 0.48 mL, and DCE: 0.20 mL) was added. The test tube was capped using a rubber septum, and then left to stand at 25° C. for four hours, and the reaction was checked by LCMS (FA05). As a result, side-chain deprotection (deprotection of the Trt group of Ser(Trt)) was found to be completed, and at this point, the UV area ratio between the deprotected desired peptide (Compound 137) and the solvolysis product (compound showing a mass in which any of the amide bonds of the peptide has undergone solvolysis by the solvent HFIP) was 53:47 (FIG. 9). "TM+HFIP" represents a compound in which any one of the amide bonds of the target molecule has undergone solvolysis by HFIP.

the amide bonds of the peptide has undergone solvolysis by the solvent TFE) was 97:3 (FIG. 10). "TM+TFE" recited in Compound 137

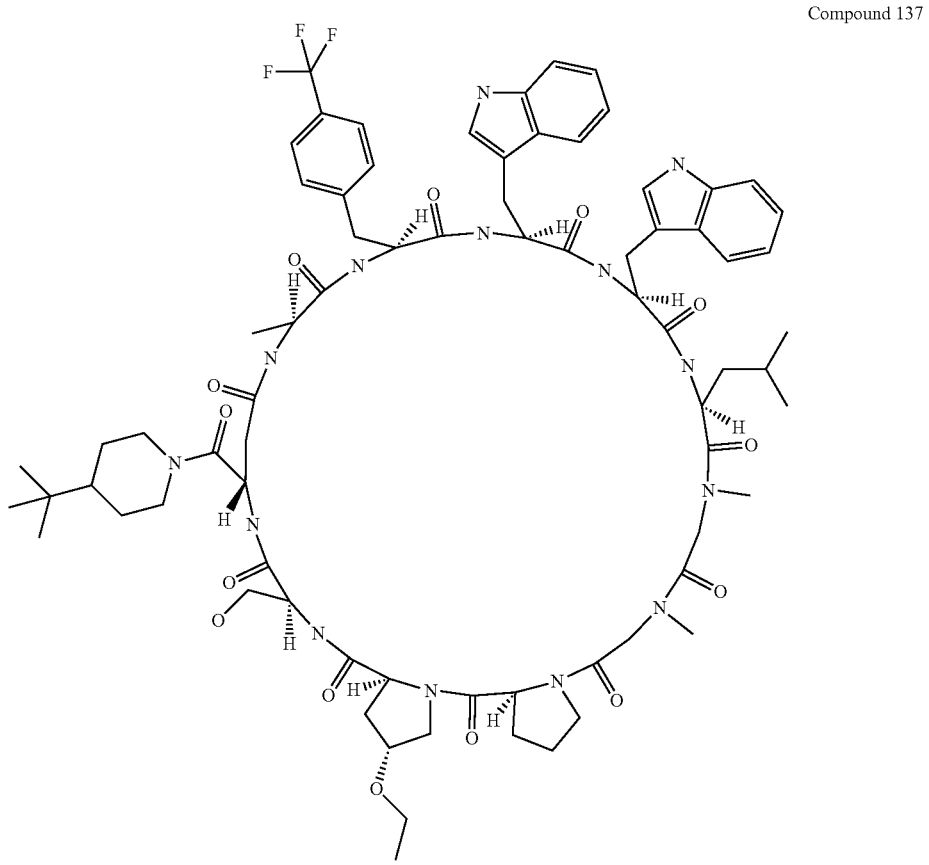 [SMILES: CCO[C@@H]1C[C@H]2C(=O)N[C@@H](CO)C(=O)N[C@H](C(=O)N3CCC(C(C)(C)C)CC3)CC(=O)N[C@@H](C)C(=O)N[C@@H](Cc3ccc(C(F)(F)F)cc3)C(=O)N[C@@H](Cc3c[nH]c4ccccc34)C(=O)N[C@@H](Cc3c[nH]c4ccccc34)C(=O)N[C@@H](CC(C)C)C(=O)N(C)CC(=O)N(C)CC(=O)N3CCC[C@H]3C(=O)N2C1]

The data of FIG. 9 are shown below:
Desired peptide (Compound 137)
LCMS (ESI) m/z=1492.1 (M+H)+
Retention time: 0.90 minutes (analysis condition SQDFA05)
Product of solvolysis by HFIP (product in which any one of the amide bonds has undergone solvolysis by HFIP)
LCMS (ESI) m/z=1660.1 (M+H)+
Retention time: 0.78 minutes (analysis condition SQDFA05)

To another test tube of 10 test tubes aliquoted, 0.40 mL of 0.05 M tetramethylamnmonium hydrogen sulfate/TFE solution (2% TIPS) (a solution produced by dissolving 205.8 mg of tetramethylammonium hydrogen sulfate in a solution produced by mixing TFE: 23.32 mL, TIPS: 0.48 mL, and DCE: 0.20 mL) was added. The test tube was capped using a rubber septum, and then left to stand at 25° C., and the reaction was checked by LCMS (FA05). As a result, four hours later, the side-chain deprotection (deprotection of the Trt group of Ser(Trt)) had proceeded 96%, and at this time, the solvolysis product (compound showing a mass in which any of the amide bonds of the peptide has undergone solvolysis by the solvent TFE) was detection limit or below by LCMS. When the reaction was checked 20 hours later, the side-chain deprotection (deprotection of the Trt group of Ser(Trt)) completed, and at this time, the UV area ratio of the deprotected desired peptide (Compound 137) and the solvolysis product (compound showing a mass in which any of this Example represents a compound in which the target molecule (TM) has undergone solvolysis by TFE (a compound in which any one of the amide bonds has undergone solvolysis by TFE).
The data of FIG. 10 are shown below:
Desired peptide (Compound 137)
LCMS (ESI) m/z=1492.2 (M+H)+
Retention time: 0.90 minutes (analysis condition SQDFA05)
Product of solvolysis by TFE (product in which any of the amide bonds has undergone solvolysis by TFE)
LCMS (ESI) m/z=1592.0 (M+H)+
Retention time: 0.75 minutes (analysis condition SQDFA05)

The above-mentioned results showed that TFE can be used instead of HFIP as the solvent for dissolving the weak acid. These results also suggest the possibility that any solvent may be used as long as the following conditions are met: YOTs value is positive, the solvent itself is weakly acidic (aqueous pKa of 5 to 14) and nucleophilicity is low.

Example 3-2-9

Deprotection Using 0.1 M Tetramethylammonium Hydrogen Sulfate/HFIP Solution (2% TIPS) as the Deprotection Condition. And Stopping the Reaction by Adding a Base (DIPEA) to this Solution Using Fmoc-Asp(O-Trt(2-Cl)-resin)-pip (Compound 50, loading: 0.342 mmol/g, 100 mg) as the resin, the cyclic compound (Compound 105, Pep5) in which an amide bond was formed between the N-terminal amino group of H-Ala-Trp-Nle-Trp-Ser(Trt)-Gly-MeAla-MePhe(3-Cl)-MeGly-Pro-Asp-pip and the side-chain carboxylic acid of Asp was synthesized by the already described method. After cyclization, a residue produced by concentration under reduced pressure was dissolved in dichloromethane, then this was aliquoted into 10 test tubes, and then they were concentrated again by removing the solvent under reduced pressure.

Figure 11:
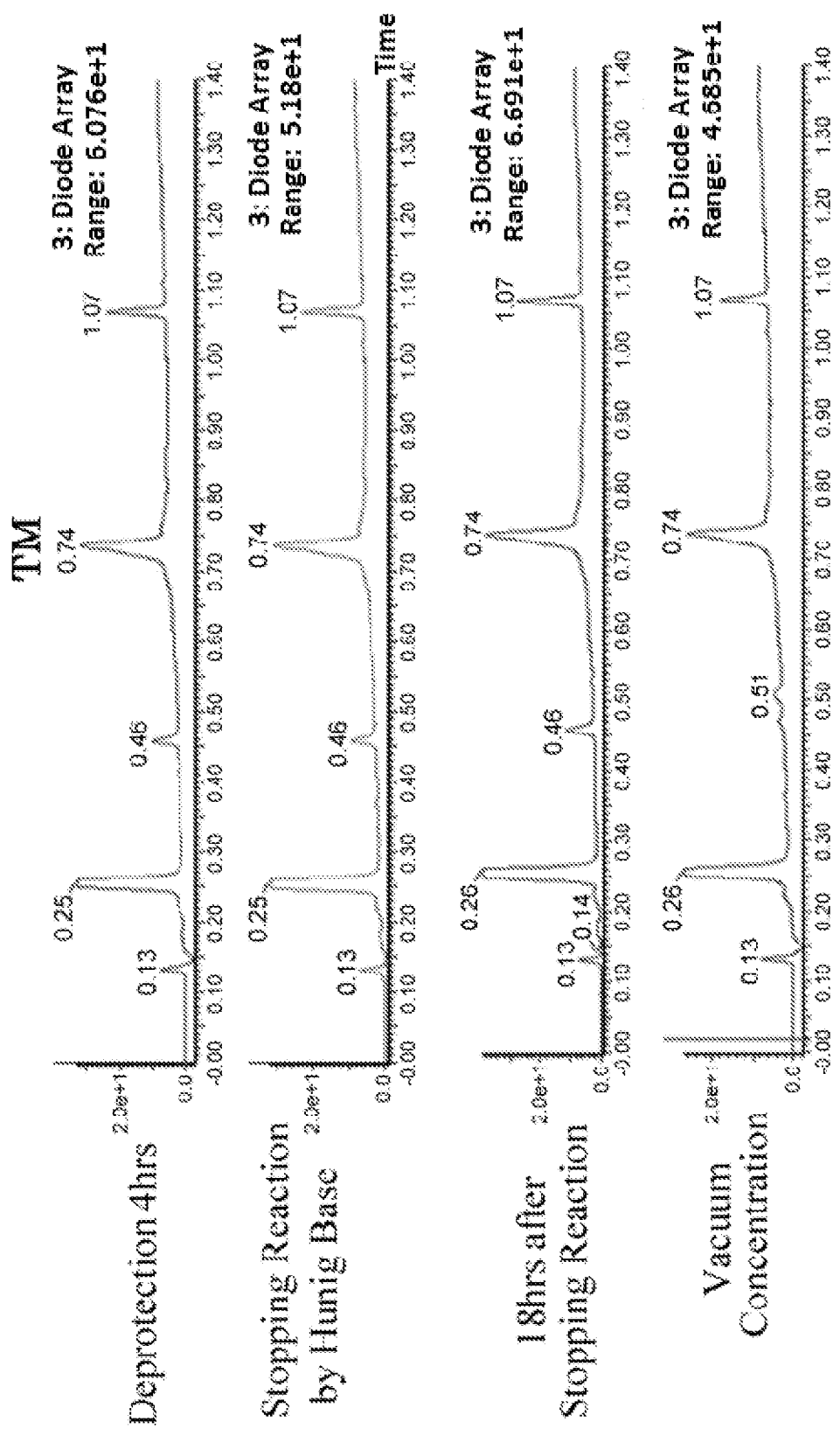
FIG. 11 shows the results showing detection of the desired peptide (Compound 135) analyzed by LCMS, when 0.1 M tetramethylanmonium hydrogen sulfate/HFIP solution (2% TIPS) was used as the deprotection condition, and a base (DIPEA) was added to this solution to stop the reaction.

To two of the 10 test tubes aliquoted, 0.40 mL of 0.1 M tetramethylammonium hydrogen sulfate/HFIP solution (2% TIPS) (68.5 mg of tetramethylammonium hydrogen sulfate was dissolved in 4 mL of solution drawn out from a solution produced by mixing HFIP: 11.66 mL, TIPS: 0.24 mL, and DCE: 0.10 mL) was added, respectively. The test tubes were capped respectively using a rubber septum, shaken for three minutes, and then left to stand at 25° C. for four hours, and the reactions were checked by LCMS (SQDFA05). As a result, side-chain deprotection (deprotection of the Trt group of Ser(Trt)) was completed, and at this time, peaks showing the masses of compounds other than the deprotected desired peptide (Compound 135), which are the solvolysis product (compound showing a mass in which any of the amide bonds of the peptide has undergone solvolysis by the solvent HFIP) and hydrolysate (compound showing a mass in which any of the amide bonds of the peptide was undergone solvolysis by water), were not detected (FIG. 11). To each of these reaction mixtures, diisopropylethylamine (DIPEA, 14 μL, two equivalents with respect to tetramethylammonium hydrogen sulfate) was added, and one of the test tubes was left to stand at 25° C. for 18 hours, the other test tube was subjected to concentration under reduced pressure. When their LCMS (SQDFA05) analyses were taken, peaks showing the masses of compounds other than the deprotected desired peptide, which are the solvolysis product and the hydrolysate, were not detected at this point as well (FIG. 11).

Compound 135

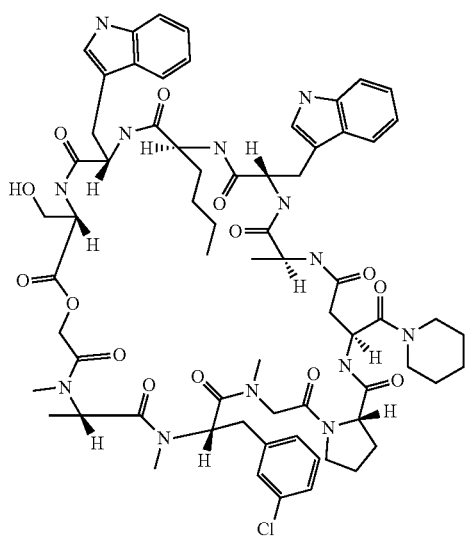

The data of FIG. 11 are shown below:
Desired peptide (Compound 135)
LCMS (ESI) m/z=1331.9 (M+H)+
Retention time: 0.74 minutes (analysis condition SQDFA05)

Example 3-2-10

Deprotection Using 0.1 M Tetramethylammonium Hydrogen Sulfate/HFIP Solution (2% TIPS) as the Deprotection Condition. And Stopping the Reaction by Adding a Base (DIPEA) to this Solution Using Fmoc-Asp(O-Trt(2-Cl)-resin)-pip (Compound 50, loading: 0.316 mmol/g, 100 mg) as the resin, the cyclic compound (Compound 103, Pep3) in which an amide bond was formed between the N-terminal amino group of H-g-EtAbu-MeSer(DMT)-Hyp(Et)-Ile-MePhe(3-Cl)-Ser(Trt)-Trp-Trp-Pro-MeGly-Asp-pip and the side-chain carboxylic acid of Asp was synthesized by the already described method. After cyclization, a residue produced by concentration under reduced pressure was dissolved in dichloromethane, then this was aliquoted into 10 test tubes, and then they were concentrated again by removing the solvent under reduced pressure.

To two of the 10 test tubes aliquoted, 0.40 mL of 0.1 M tetramethylammonium hydrogen sulfate/HFIP solution (2% TIPS) (68.5 mg of tetramethylammonium hydrogen sulfate was dissolved in 4 mL of solution drawn out from a solution produced by mixing HFIP: 11.66 mL, TIPS: 0.24 mL, and DCE: 0.10 mL) was added, respectively. The test tubes were capped respectively using a rubber septum, shaken for three minutes, and then left to stand at 25° C. for four hours, and the reactions were checked by LCMS (FA05). As a result, side-chain deprotections (deprotection of the DMT group of MeSer(DMT) and deprotection of the Trt group of Ser(Trt)) were completed, and the UV area ratio according to LC of the deprotected desired peptide (Compound 133) and the N- to O-acyl shifted product of the desired peptide (depsipeptide) was 93:7.

To each of these reaction mixtures, diisopropylethylamine (DIPEA, 14 μL, two equivalents with respect to tetramethylammonium hydrogen sulfate) was added, and one of the test tubes was left to stand at 25° C. for 18 hours, the other test tube was subjected to concentration under reduced pressure immediately after DIPEA addition. When their LCMS (FA05) analyses were taken, the mixture left to stand for 18 hours did not show change in the UV area ratio of the desired peptide to the N- to O-acyl shift product thereof; whereas the mixture which was concentrated under reduced pressure had a UV area ratio of the desired peptide to the N- to O-acyl shift product thereof of 98:2 (FIG. 12).

Figure 12:
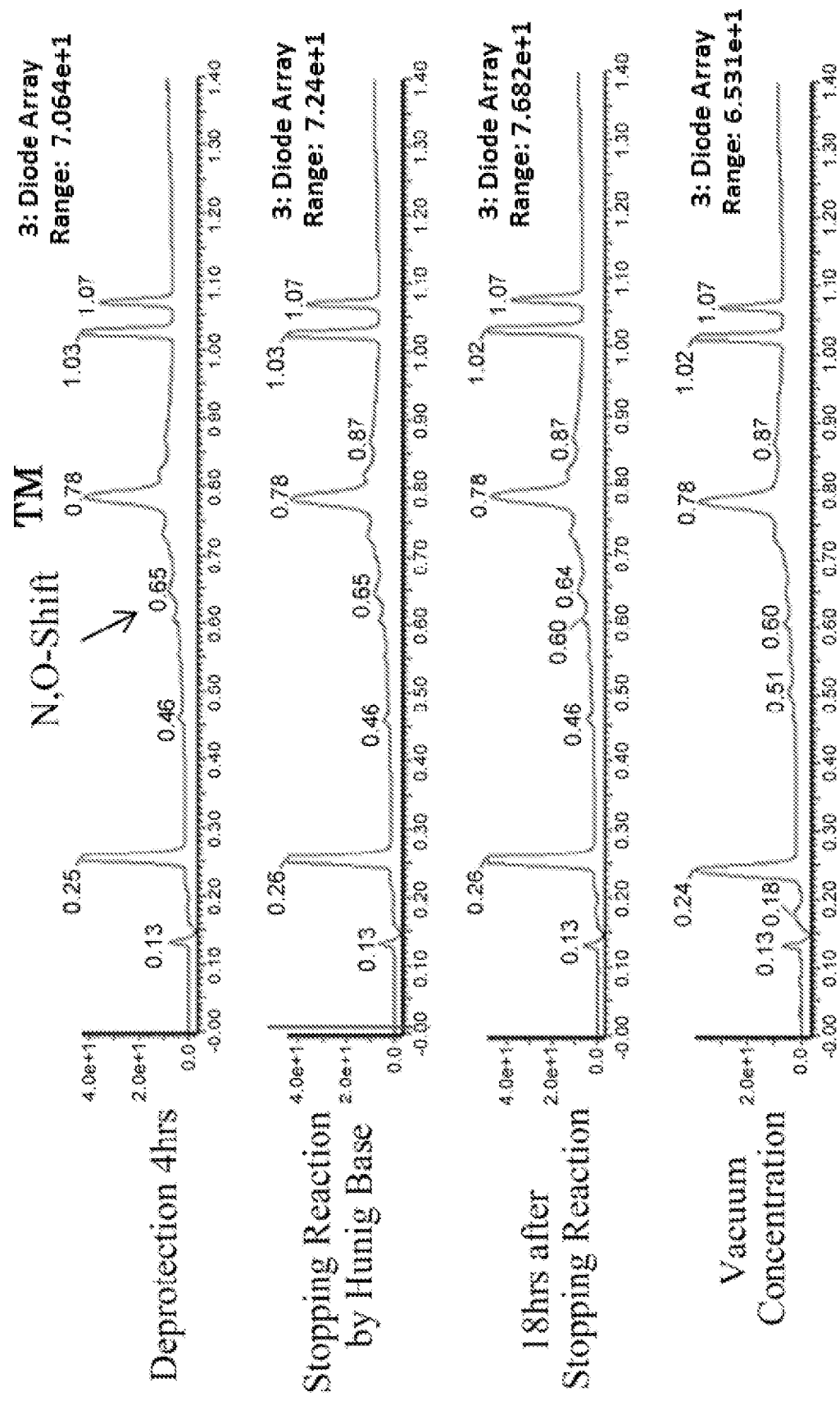
FIG. 12 shows the results showing detection of the desired peptide (Compound 133) analyzed by LCMS, when 0.1 M tetramethylamionium hydrogensulfate/HFIP solution (2% TIPS) was used as the deprotection condition, and abase (DIPEA) was added to this solution to stop the reaction.

The data of FIG. 12 are shown below:
Desired peptide (Compound 133)
LCMS (ESI) m/z=1474.1 (M+H)+
Retention time: 0.78 minutes (analysis condition SQDFA05)
N- to O-acyl shift product
LCMS (ESI) m/z=1474.1 (M+H)+
Retention time: 0.64 minutes (analysis condition SQDFA05)

The above-mentioned results showed that work-up is possible under conditions where the problems of hydrolysis (solvolysis) and N- to O-acyl shift are suppressed, by adding DIPEA after the deprotection reaction has been completed (or when one wants to stop the reaction).

Example 4 Reactivity of Thr and MeSer when Using THP Group as the Protecting Group for the Side-Chain Hydroxyl Groups The following experiments were performed for the reactivity when using THP group as the protecting group for the side-chain hydroxyl groups of Thr and MeSer for which low reactivity during the elongation reaction is of concern.

Example 4-1

Comparative Evaluation of the Elongation Reactivity of Fmoc-Thr(Trt)-OH and Fmoc-Thr(THP)—OH (Compound 2) on the Compound Having an N-methylamino Group at its N-Terminus (H-MePhe(3-Cl)-D-Tyr(tBu)-Trii-MePhe-Trp-MePhe-Ile-Asp(O-2-Cl-Trt-Resin)-Pip), which is a Peptide Elongated on a Resin Comparative evaluation of elongation reactivity was performed using a sequence having MePhe(3-Cl) at its N-terminus, which has low amino group reactivity due to steric hindrance.

Fmoc-MePhe(3-Cl)-D-Tyr(tBu)-Trp-MePhe-Trp-MePhe-Ile-Asp(O-Trt(2-Cl)-resin)-pip (Compound 108) was synthesized by the already described method, by using as the resin Fmoc-Asp(O-Trt(2-Cl)-resin)-pip (Compound 50, loading: 0.329 mmol/g, 100 mg) prepared by the already described method.

To the obtained Fmoc-MePhe(3-Cl)-D-Tyr(tBu)-Trp-MePhe-Trp-MePhe-Ile-Asp(O-Trt(2-Cl)-resin)-pip (Compound 108), dichloromethane (600 μL) was added, and this was left to stand for 30 minutes to allow swelling of the resin. After removing the liquid phase, the resin was washed three times with DMF (600 μL). To the obtained resin, 2% DBU/DMF (v/v, 600 μL) was added, this was shaken for 20 minutes, and the liquid phase was removed. The resin was washed three times with DMF (600 μL).

To this resin, a solution produced by mixing a solution of 0.60 M Fmoc-Thr(Trt)-OH/0.375 M oxyma in NMP (300 μL) and 10% (v/v) DIC/DMF (300 μL), or a solution produced by mixing a solution of 0.60 M Fmoc-Thr(THP)—OH (Compound 2)/0.375 M oxyma in NMP (300 μL) and 10% (v/v) DIC/DMF (300 μL) was added, and this was shaken. While shaking, approximately 10 mg of the reacting resin was collected at the stages of shaking for one hour, two hours, and four hours, respectively, the collected resins were washed three times with DMF (600 μL), 2% DBU/DMF (v/v, 600 μL) was additionally added and this was shaken for 20 minutes, and the liquid phase was removed. The resins were washed three times with DMF (600 μL), and then three times with dichloromethane (600 μL).

TFE/DCM (1/1, v/v, 1 mL) was added to the obtained resins, these were shaken for ten minutes. After removing the resins filtering, the liquid phases were concentrated under reduced pressure. The residues were analyzed by LCMS (analysis condition SQDFA05). The results are shown in Table 4.

TABLE 4

| Elongated Amino Add Residue | 1 h (Unreacted Form/ Elongated Form) | 2 h (Unreacted Form/ Elongated Form) | 4 h (Unreacted Form/ Elongated Form) |
|---|---|---|---|
| Thr (Trt) | 99/1 | 97/3 | 88/12 |
| Thr (THP) | 84/16 | 69/31 | 22/78 |

The ratios of the unreacted form/elongated form in the Table show the UV area ratios according to LC. In the Table, unreacted form means H-MePhe(3-Cl)-D-Tyr(tBu)-Trp-MePhe-Trp-MePhe-Ile-Asp-pip (Compound 109), and the elongated form means H-Thr(Trt)-MePhe(3-Cl)-D-Tyr(tBu)-Trp-MePhe-Trp-MePhe-Ile-Asp-pip (Compound 110; when Fmoc-Thr(Trt)-OH was added) or H-Thr(THP)-MePhe(3-Cl)-D-Tyr(tBu)-Trp-MePhe-Trp-MePhe-Ile-Asp-pip (Compound 111; when Fmoc-Thr(THP)—OH was added).

Compound 109

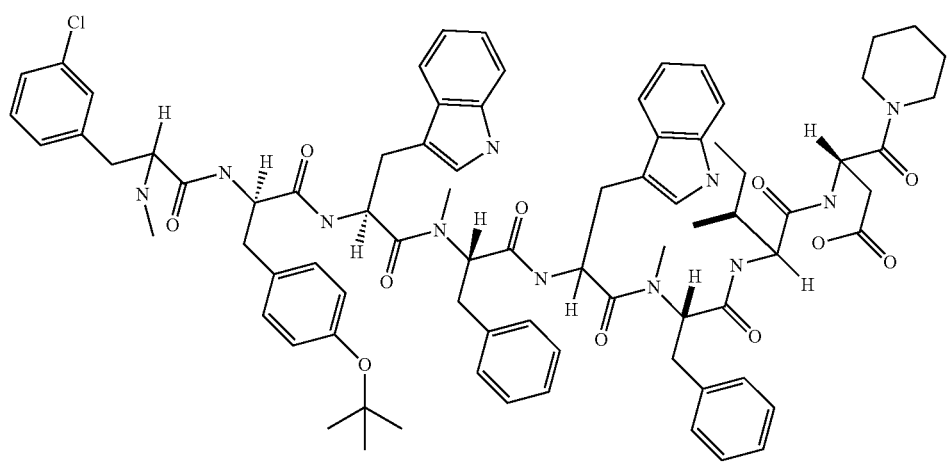

Unreacted form (Compound 109)
LCMS (ESI) m/z=1422.9 (M+H)+
Retention time: 0.77 minutes (analysis condition SQDFA05)
Compound 110
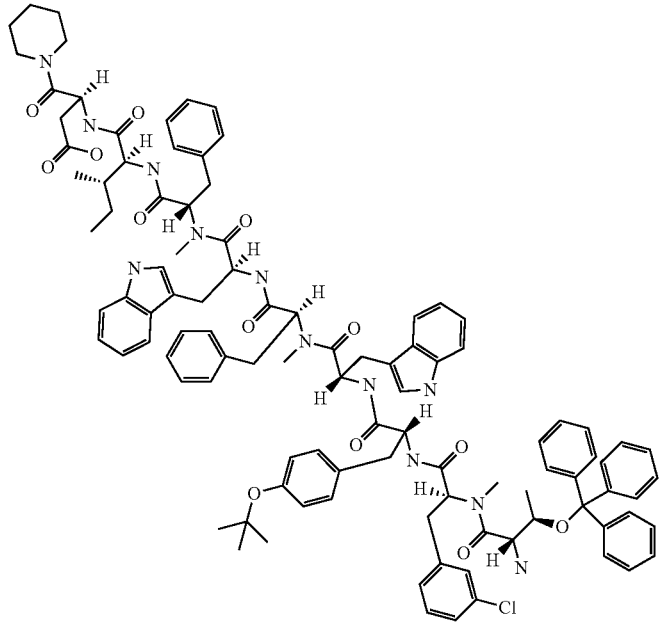
Elongated form (Thr(Trt)) (Compound 110)
LCMS (ESI) m/z=1766.2 (M+H)+
Retention time: 0.92 minutes (analysis condition SQDFA05)
Compound 111
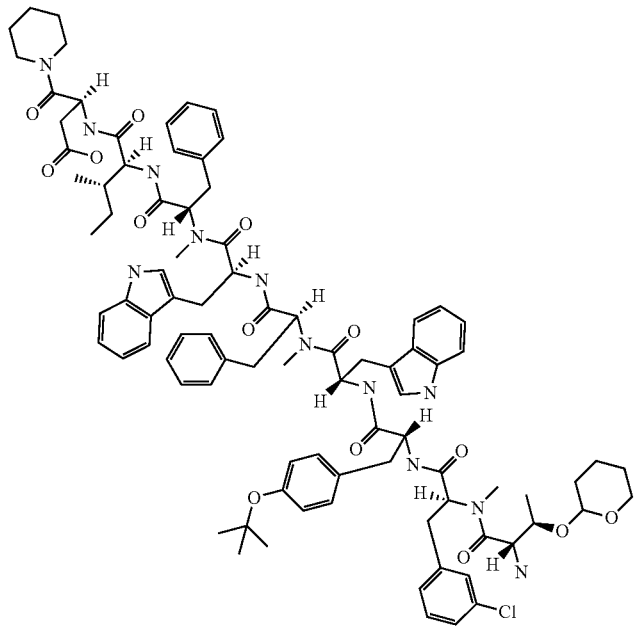

Elongated form (Thr(THP)) (Compound 111)
LCMS (ESI) m/z=1608.1 (M+H)+
Retention time: 0.80 minutes (analysis condition SQDFA05)

Example 4-2

Elongation Reactivity of Fmoc-Thr(Trt)-OH or Fmoc-Thr(THP)—OH (Compound 2) when Synthesizing H-b-MeAla-Ile-MeLeu-MeAla-MeLeu-Thr(PG)-MePhe-MeAla-MeLeu-MePhe-Asp(O-Trt(2-Cl)-resin)-pip by a Synthesizer Elongation reactivity was tested by elongating Thr to a sequence having MePhe at its N terminus, which has low reactivity due to steric hindrance, and to a sequence having MeLeu, which is sterically bulky with respect to the amino group of Thr, at its N terminus.

Peptide elongation of H-b-MeAla-Ile-MeLeu-MeAla-MeLeu-Thr(PG)-MePhe-MeAla-MeLeu-MePhe-Asp(O-Trt(2-Cl)-resin)-pip (wherein, PG on the Thr side chain represents a protecting group, and in this experiment, it represents protection by Trt or THP) was performed according to peptide synthesis method using the Fmoc method already described in the Examples, by using as the resin Fmoc-Asp(O-Trt(2-Cl)-resin)-pip (Compound 50, 100 mg) prepared by the already described method. In this case, Fmoc-Thr(Trt)-OH or Fmoc-Thr(THP)—OH (Compound 2) was used in the Thr elongation.

After the peptide elongation, removal of the N-terminal Fmoc group was performed on the peptide synthesizer, and the resin was washed with DMF and DCM.

After swelling the resin again with DCM, TFE/DCM (1/1, v/v, 2 mL) was added to the resin, this was shaken at room temperature for two hours, and the peptides were cleaved off from the resin. Next, the resin was removed by filtering the solution inside the tube through a column for synthesis, and the remaining resin was further washed twice with TFE/DCM (1/1, v/v, 1 mL).

After the cleavage, when using Fmoc-Thr(Trt)-OH, the Trt group of Thr(Trt) was deprotected by using a solution produced by mixing 4N HCl/1,4-dioxane (19.5 µL), TIPS (0.25 mL), and DCM (0.73 mL) and the mixture was shaken at 25° C. for five minutes. Then acid was neutralized by adding DIPEA (24 µL), and the elongation reactivity was tested by LCMS.

Figure 13:
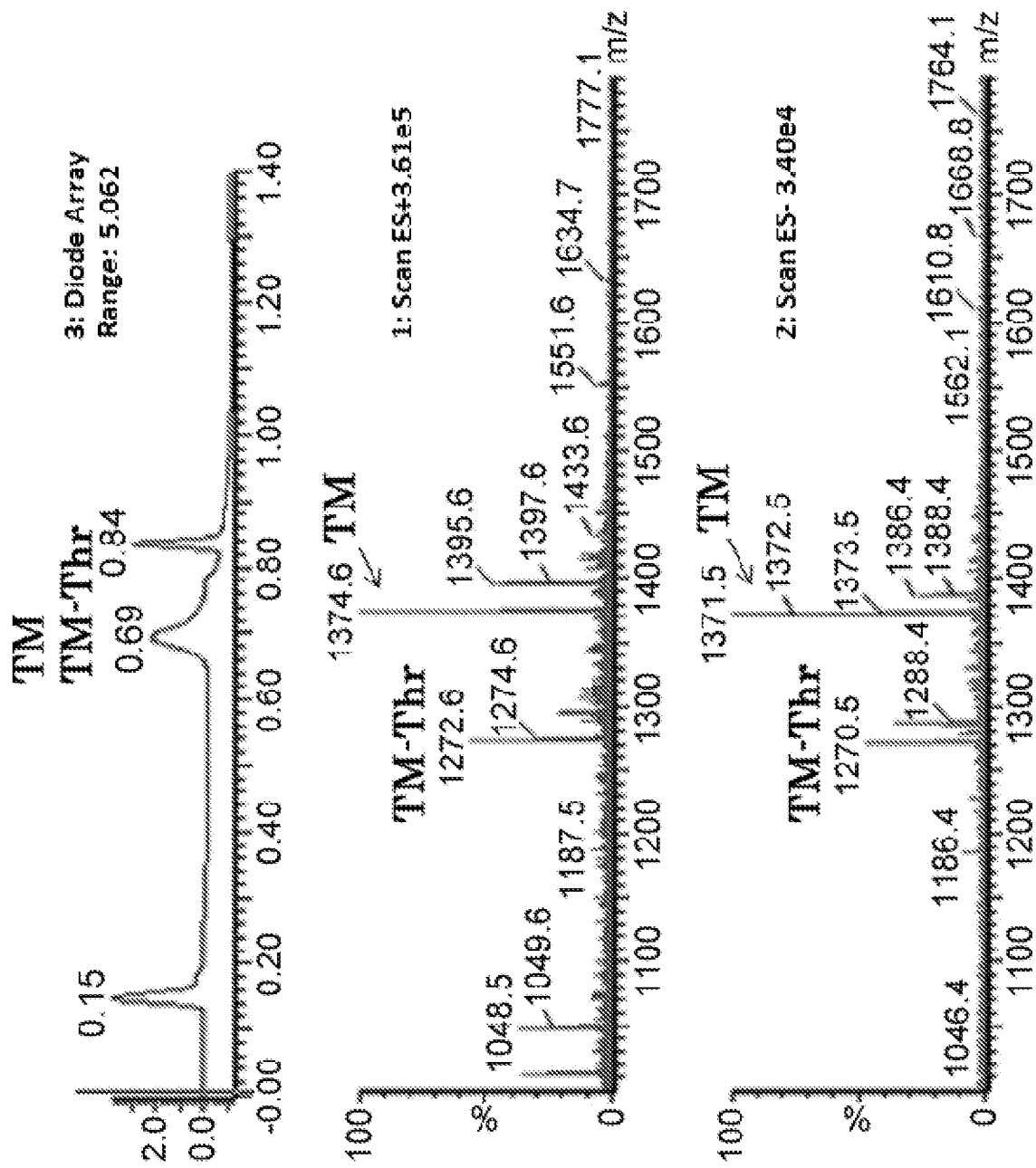
FIG. 13 shows the results showing detection of the desired peptide (Compound 112) and a product in which Thr has been removed from the desired peptide (Compound 113) analyzed by LCMS, when Fmoc-Thr(Trt)-OH was added.

The LCMS results for the products are shown in FIG. 13. The desired peptide (Compound 112, H-b-MeAla-Ile-MeLeu-MeAla-MeLeu-Thr-MePhe-MeAla-MeLeu-MePhe-Asp-pip) and the compound in which Thr was lost from the desired peptide (Compound 113, H-b-MeAla-Ile-MeLeu-MeAla-MeLeu-MePhe-MeAla-MeLeu-MePhe-Asp-pip) were observed at the same retention time of 0.69 minutes. Furthermore, according to MS (negative mode), Thr-lost peptide was included at a proportion of approximately 30%.

Compound 112

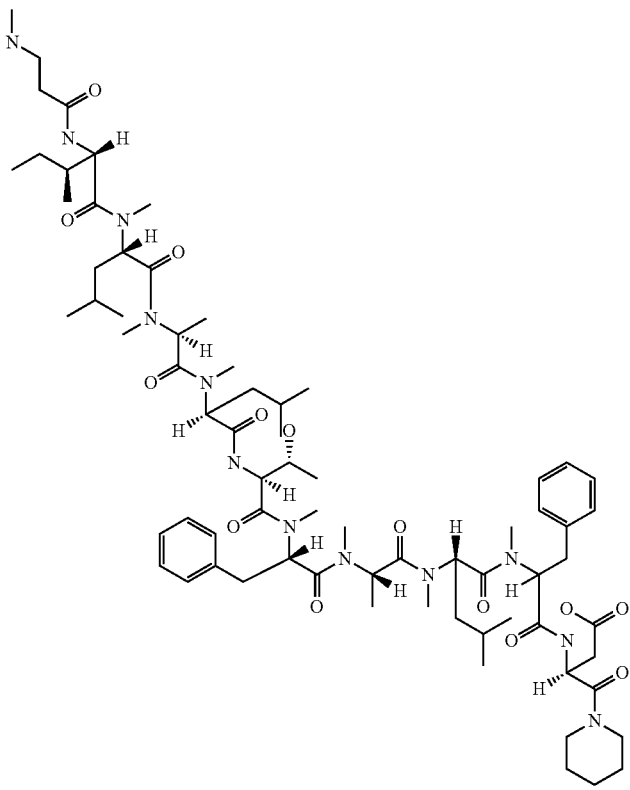

The data of FIG. 13 are shown below:
Target molecule (Compound 112, H-b-MeAla-Ile-MeLeu-MeAla-MeLeu-Thr-MePhe-MeAla-MeLeu-MePhe-Asp-pip)
LCMS (ESI) m/z=1373.6 (M+H)+
Retention time: 0.69 minutes (analysis condition SQDAA50)

Compound 113

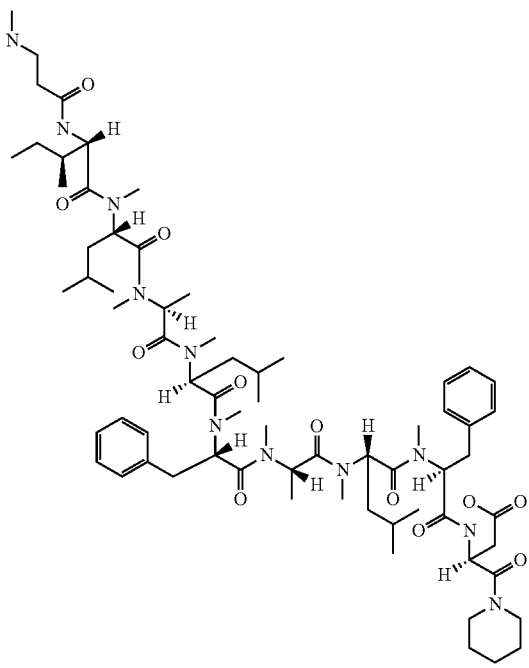

Target molecule—Thr (Compound 113, H-b-MeAla-Ile-MeLeu-MeAla-MeLeu-MePhe-MeAla-MeLeu-MePhe-Asp-pip)

LCMS (ESI) m/z=1272.6 (M+H)+

Retention time: 0.69 minutes (analysis condition SQDAA50)

Figure 14:
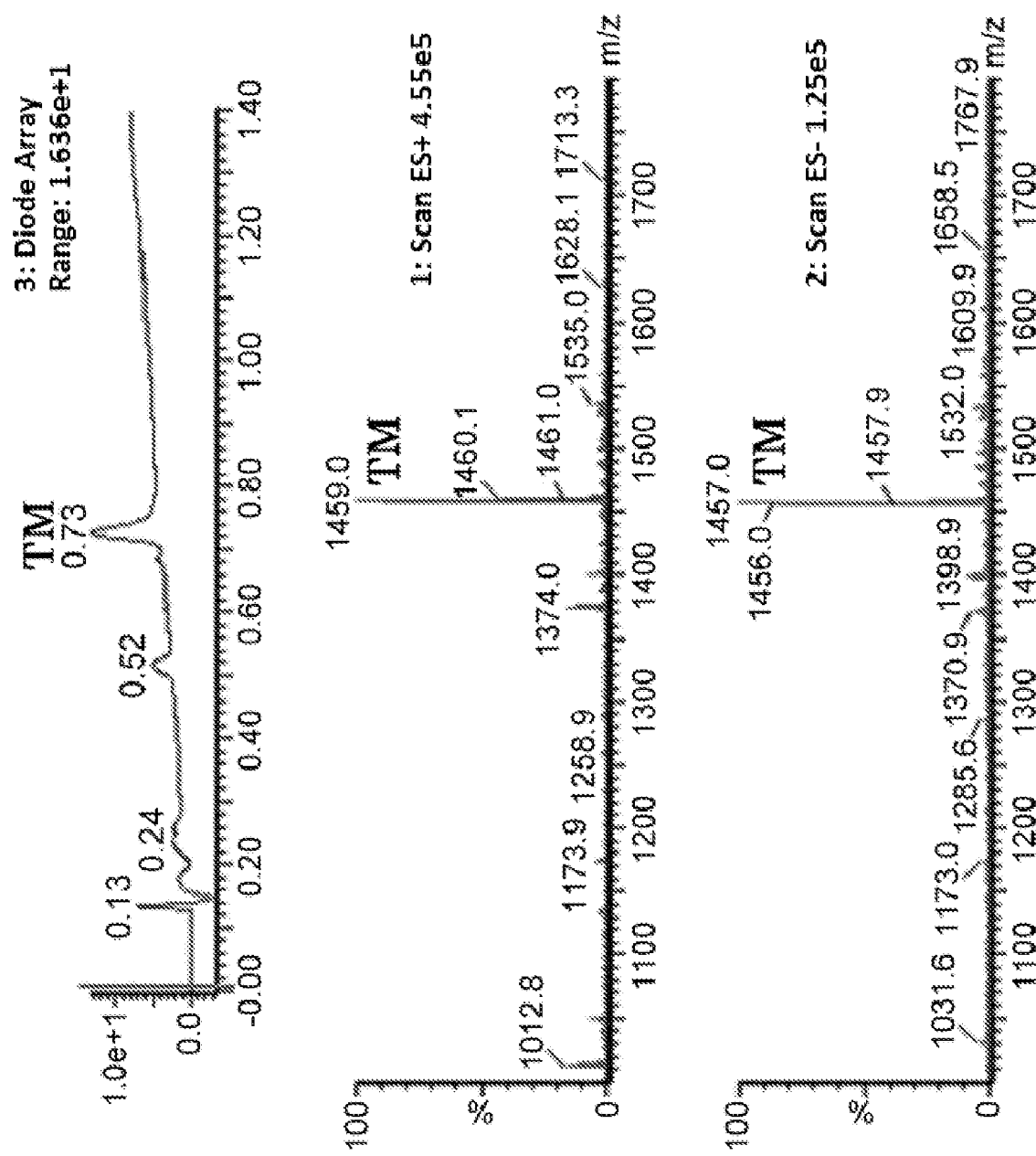
FIG. 14 shows the results showing detection of the desired peptide (Compound 114) analyzed by LCMS when Fmoc-Thr(THP)—OH was added. The product (Compound 113) in which Thr was missing from the desired peptide (Compound 114) was not detected.

The LCMS results for this product are shown in FIG. 14. In contrast to the case when Fmoc-Thr(Trt)-OH was added, when Fmoc-Thr(THP)—OH was added, the peptide (Compound 113, H-b-MeAla-Ile-MeLeu-MeAla-MeLeu-MePhe-MeAla-MeLeu-MePhe-Asp-pip) in which Thr was lost from the desired peptide (Compound 114, H-b-MeAla-Ile-MeLeu-MeAla-MeLeu-Thr(THP)-MePhe-MeAla-MeLeu-MePhie-Asp-pip) was not detected. When using Fmoc-Thr(THP)—OH (Compound 2), deprotection operation was not performed after cleavage from the resin, and the cleavage solution was directly subjected to LCMS analyses; therefore, the THP protection of the Thr side chain remained.

Compound 114

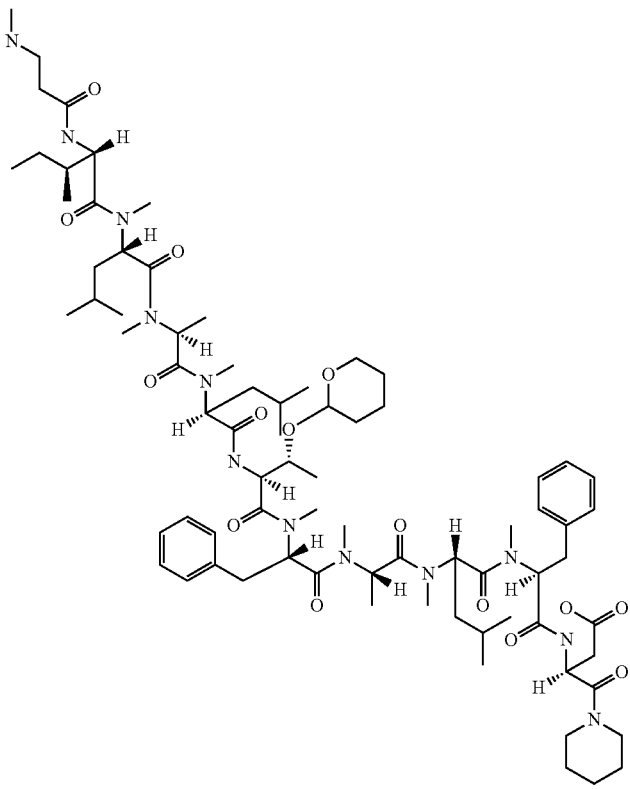

The data of FIG. 14 are shown below:
Target molecule (Compound 114)
LCMS (ESI) m/z=1458.1 (M+H)+
Retention time: 0.73 minutes (analysis condition SQDFA05)

The above-mentioned results showed that compared to Fmoc-Thr(Trt)-OH used for Thr elongation in standard peptide synthesis, Fmoc-Thr(THP)—OH (Compound 2) has higher reactivity. In particular, when elongating from a bulky amino group of an N-alkylated N terminus, high condensation efficiency was shown to be achievable. Furthermore, in the subsequent elongation reaction, it can be confirmed that elongation of an Fmoc-amino acid (Fmoc-MeLeu-OH in this case), which is bulky with respect to the N-terminal amino group of Thr(THP), proceeds without any problem.

Example 4-2

Confirmation of Elongation Reactivity of MeSer when Using Fmoc-MeSer(DMT)-OH or Fmoc-MeSer(THP)—OH (Compound 6) in the Synthesis of H-MeSer(PG)-MeVal-MeHis(Trt)-Tyr(3-F,tBu)-Pro-MeHis(Trt)-Pro-Trp-MePhe(4-Cl)-Asp(O-Trt(2-Cl)-resin)-Pro-OPis by a Synthesizer Peptide elongation of H-MeSer(PG)-MeVal-MeHis(Trt)-Tyr(3-F,tBu)-Pro-MeHis(Trt)-Pro-Trp-MePhe(4-Cl)-Asp(O-Trt(2-Cl)-resin)-Pro-OPis (wherein PG on the MeSer side chain represents a protecting group, and in this experiment, it represents protection by DMT or THP) was performed according to the peptide synthesis method using the Fmoc method already described in the Examples, by using as the resin Fmoc-Asp(O-Trt(2-Cl)-resin)-Pro-OPis (Compound 58, loading rate: 0.3736 mmol/g, 100 mg) prepared by the already described method. In this case, Fmoc-MeSer(DMT)-OH or Fmoc-MeSer(THP)—OH (Compound 6) was used in the MeSer elongation.

After the peptide elongation, N-terminal Fmoc group was removed on the peptide synthesizer, and the resin was washed using DMF and DCM.

After drying the obtained resin under reduced pressure, 30 mg each of the respective resins was collected. Each of the collected 30 mg of resin was swollen again with DCM, then TFE/DCM (1/1, v/v, 2 mL) was added to the resin, this was shaken at room temperature for two hours, and the peptides were cleaved off from the resin. Next, the resin was removed by filtering the solution inside the tube through a column for synthesis, and the remaining resin was further washed twice with TFE/DCM (1/1, v/v, 1 mL). All of the obtained cleavage solutions were mixed, and concentrated under reduced pressure.

To the obtained residue, 1.3 mL of 0.05 M tetramethylammonium hydrogen sulfate/HFIP solution (2% TIPS) prepared by the already described method was added to dissolve the residue, and then this was left to stand at room temperature for one hour. The side chain protecting groups other than the tBu protection of the Tyr(3-F) side chain (DMT or THP protection of the MeSer side chain and Trt protection of the Me His side chain) and main-chain C-terminal Pis protection were deprotected, and the reactions were checked by taking LCMS analyses.

Figure 15:
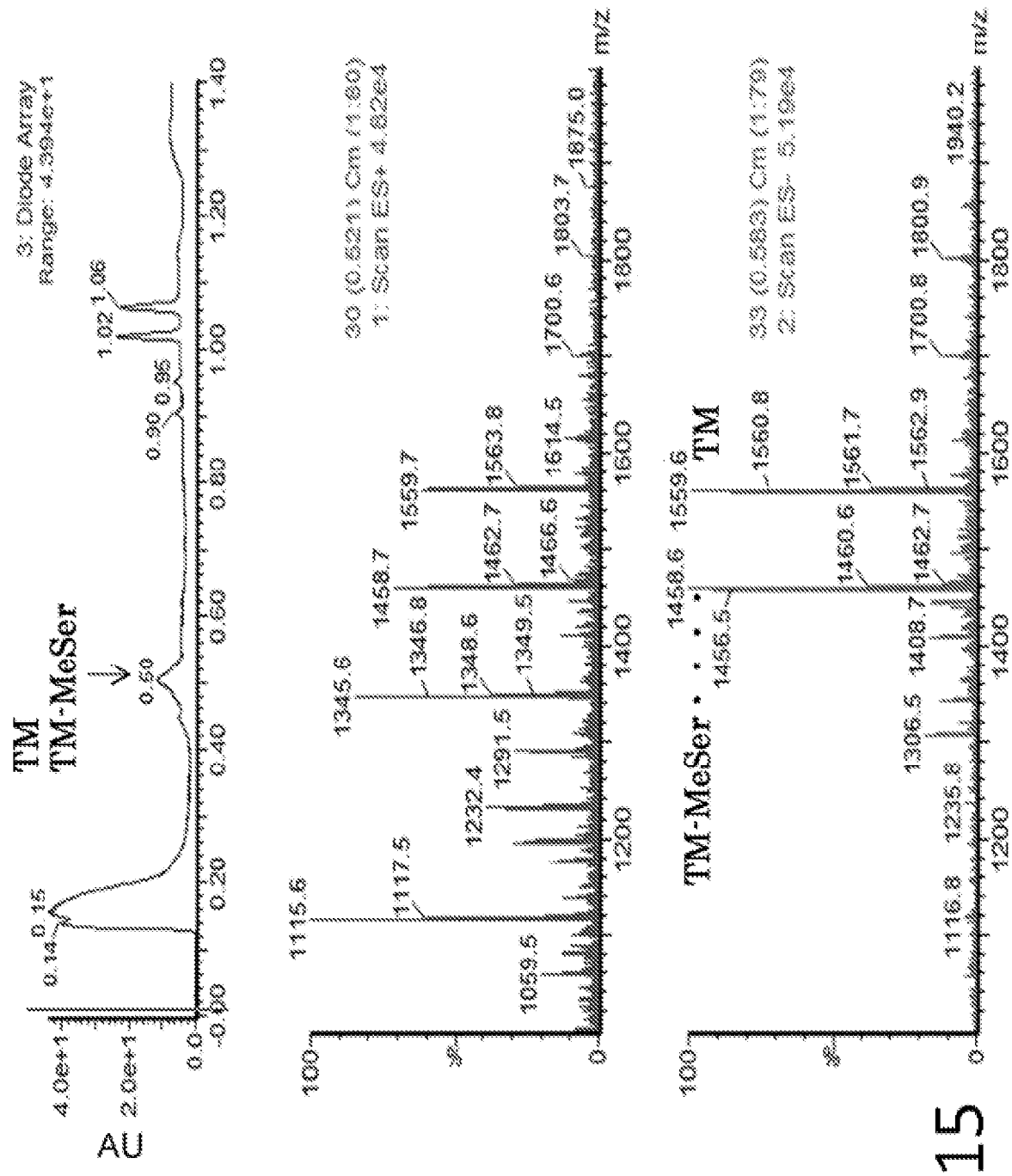
FIG. 15 shows the results showing detection of the desired peptide (Compound 115) and the product (Compound 116) in which MeSer was missing from the desired peptide analyzed by LCMS, when the synthesis was carried out using Fmoc-MeSer(DMT)-OH·0.75 DIPEA.

FIG. 15 shows the results of LCMS when the synthesis is carried out using Fmoc-MeSer(DMT)-OH·0.75 DIPEA. The desired peptide (Compound 115, H-MeSer-MeVal-MeHis-Tyr(3-F,tBu)-Pro-MeHis-Pro-Trp-MePhe(4-Cl)-Asp-Pro-OH) and the compound in which MeSer was lost from the desired peptide (Compound 116, H-MeVal-MeHis-Tyr(3-F,tBu)-Pro-MeHis-Pro-Trp-MePhe(4-Cl)-Asp-Pro-OH) were observed at the same retention time of 0.50 minutes.

Furthermore, according to MS (negative mode), MeSer-lost peptide (Compound 116, H-MeVal-MeHis-Tyr(3-F,tBu)-Pro-MeHis-Pro-Trp-MePhe(4-Cl)-Asp-Pro-OH) was found to be included at a proportion of 50%.

Compound 115

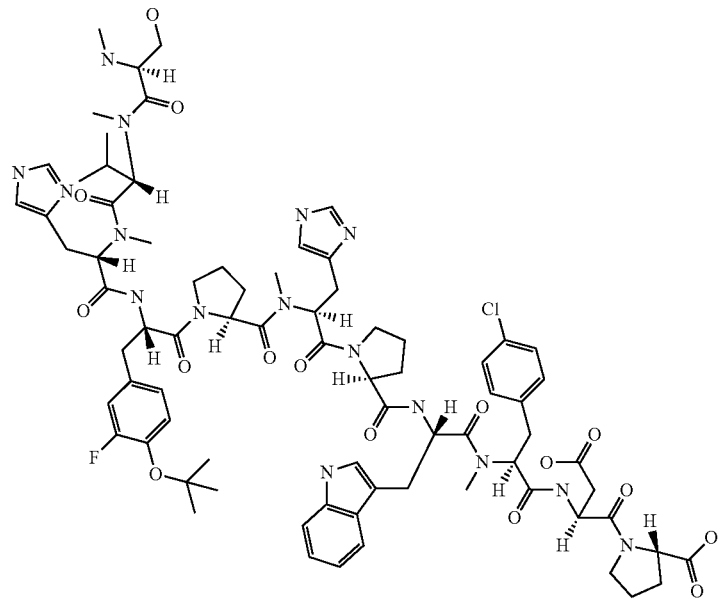

The data of FIG. 15 are shown below:
Target molecule (Compound 115)
LCMS (ESI) m/z=1559.7 (M+H)+
Retention time: 0.50 minutes (analysis condition SQDFA50)
Target molecule—MeSer (Compound 116)
LCMS (ESI) m/z=1458.8 (M+H)+
Retention time: 0.50 minutes (analysis condition SQDFA50)

Desired peptide—MeSer (Compound 116)
LCMS (ESI) m/z=1458.7 (M+H)+
Retention time: 0.50 minutes (analysis condition SQDFA50)

The above-mentioned results showed that compared to Fmoc-MeSer(DMT)-OH, Fmoc-MeSer(THP)—OH (Compound 6) has higher reactivity and can achieve high condensation efficiency when performing elongation from an amino group of an N-methylated N terminus.

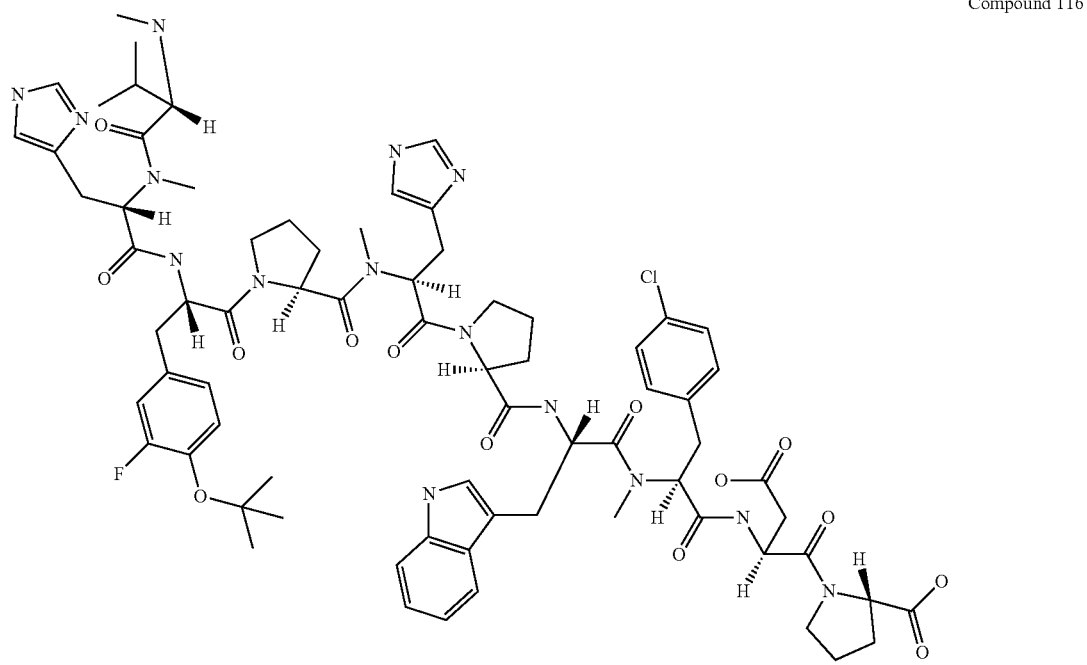 [SMILES: CN[C@H](C(=O)N(C)[C@@H](Cc1c[nH]cn1)C(=O)N[C@@H](Cc1ccc(OC(C)(C)C)c(F)c1)C(=O)N1CCC[C@H]1C(=O)N(C)[C@@H](Cc1c[nH]cn1)C(=O)N1CCC[C@H]1C(=O)N[C@@H](Cc1c[nH]c2ccccc12)C(=O)N(C)[C@@H](Cc1ccc(Cl)cc1)C(=O)N[C@@H](CC(=O)O)C(=O)N1CCC[C@H]1C(=O)O)C(C)C]

Compound 116

Figure 16:
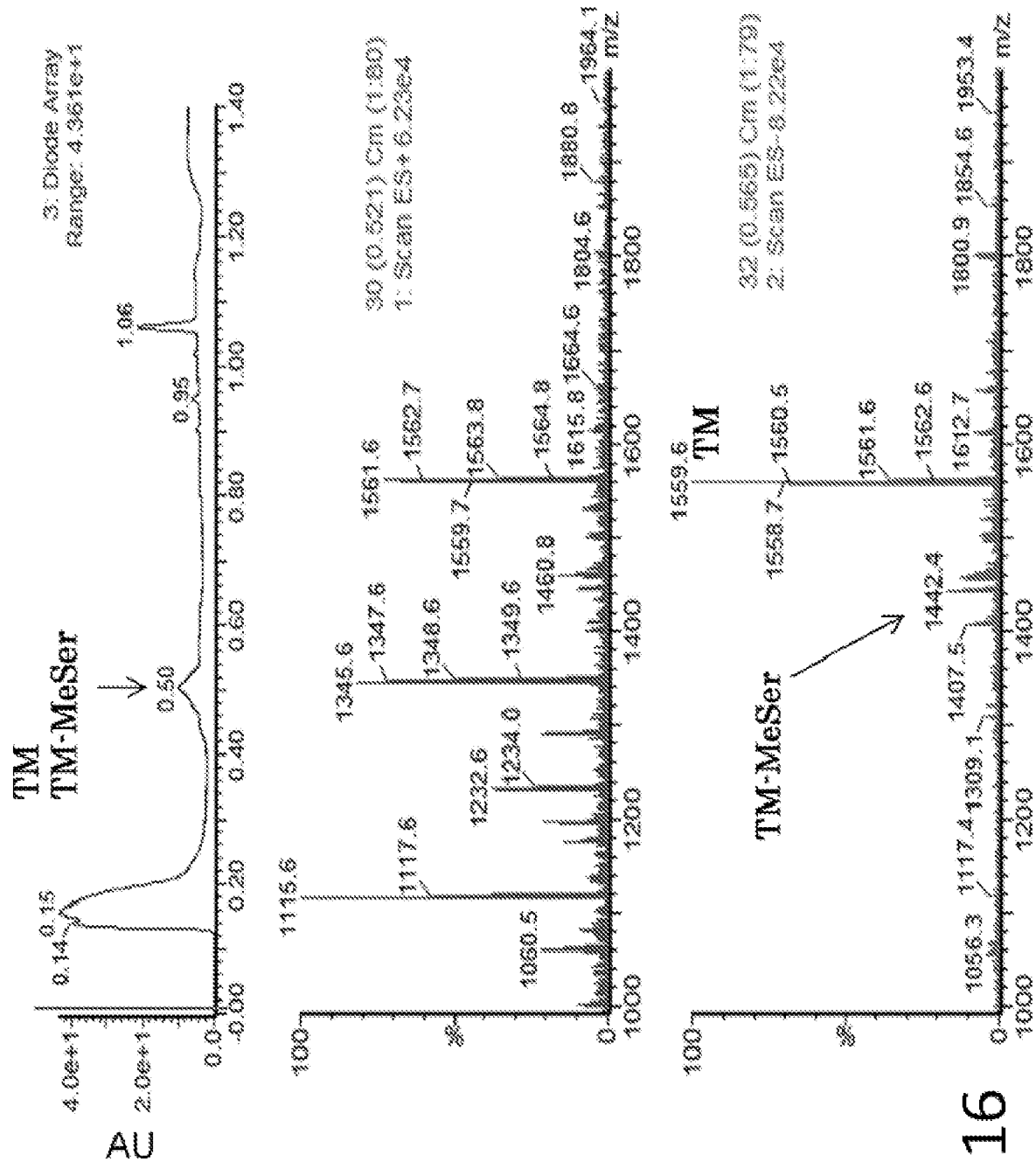
FIG. 16 shows the results showing detection of the desired peptide (Compound 115) and the product (Compound 116) in which MeSer was missing from the desired peptide analyzed by LCMS, when the synthesis was carried out using Fmoc-MeSer(THP)—OH (Compound 6).

In contrast, FIG. 16 shows the results of LCMS when the synthesis was carried out using Fmoc-MeSer(THP)—OH (Compound 6). The desired peptide (Compound 115, H-MeSer-MeVal-MeHis-Tyr(3-F,tBu)-Pro-MeHis-Pro-Trp-MePhe(4-Cl)-Asp-Pro-OH) and the compound in which MeSer was lost from the desired peptide (Compound 116) were observed at the same retention time of 0.50 minutes. However, according to MS (negative mode), the MeSer-lost peptide (Compound 116, H-MeVal-MeHis-Tyr(3-F,tBu)-Pro-MeHis-Pro-Trp-MePhe(4-Cl)-Asp-Pro-OH) was found to be included at a proportion of 10% or less.

The data of FIG. 16 are shown below:
Target molecule (Compound 115)
LCMS (ESI) m/z=1559.7 (M+H)+
Retention time: 0.50 minutes (analysis condition SQDFA50)

5. Deprotection of Cyclized Peptides in 5% TFA (Comparative Examples)

Comparative Example 1

Deprotection of the Side-Chain Protecting Group (Deprotection of the tBu Protection of D-Tyr(tBu)) of the Compound (Compound 101, Pep-1) in which an Amide Bond was Formed Between the N-Terminal Amino Group of H-Ala-Trp-Me-Trp-D-Tyr(tBu)-MeGly-MeAla-MePhe(3-Cl)-MeGly-nPrGly-Asp-Pip and the Side-Chain Carboxylic Acid of Asp (when Using 5% TFA/DCE (5% TIPS))

Using Fmoc-Asp(O-Trt(2-Cl)-resin)-pip (Compound 50, resin loading rate: 0.373 mmol/g, 100 mg) synthesized by the already described method, peptide elongation was performed on a synthesizer to obtain H-Ala-Trp-Nle-Trp-D-Tyr(tBu)-MeGly-MeAla-MePhe(3-Cl)-MeGly-nPrGly-Asp(O-Trt(2-Cl)-resin)-pip.

Then, after swelling the resin again with DCM, TFE/DCM (1/1, v/v, 2 mL) was added to the resin, this was shaken at room temperature for two hours, and then the peptide was cleaved off from the resin. Next, the resin was removed by filtering the solution inside the tube through a column for synthesis, and the remaining resin was further washed twice with TFE/DCM (1/1, v/v, 1 mL). All of the obtained cleavage solutions were mixed and concentrated under reduced pressure.

The obtained residue was dissolved in DMF/DCM (1/1, v/v, 8 mL), a 0-(7-aza-1H-benzotriazol-1-yl)-N,N,N,N-tetramethyluronium hexafluorophosphate (HATU, 21 mg)/DMF solution (0.5 M) and a DIPEA (12 μL)/DMF (88 μL) solution were added, and this was stirred at room temperature for two hours. The reaction was checked by LCMS analyses (analysis condition SQDFA05), and generation of the compound (Compound 101, Pep-1) in which an amide bond was formed between the N-terminal amino group of H-Ala-Trp-Nle-Trp-D-Tyr(tBu)-MeGly-MeAla-MePhe(3-Cl)-MeGly-nPrGly-Asp-pip and the side-chain carboxylic acid of Asp was confirmed.

LCMS (ESI) m/z=1480.0 (M+H)$^+$
Retention time: 0.93 minutes (analysis condition SQDFA05)

Figure 17:
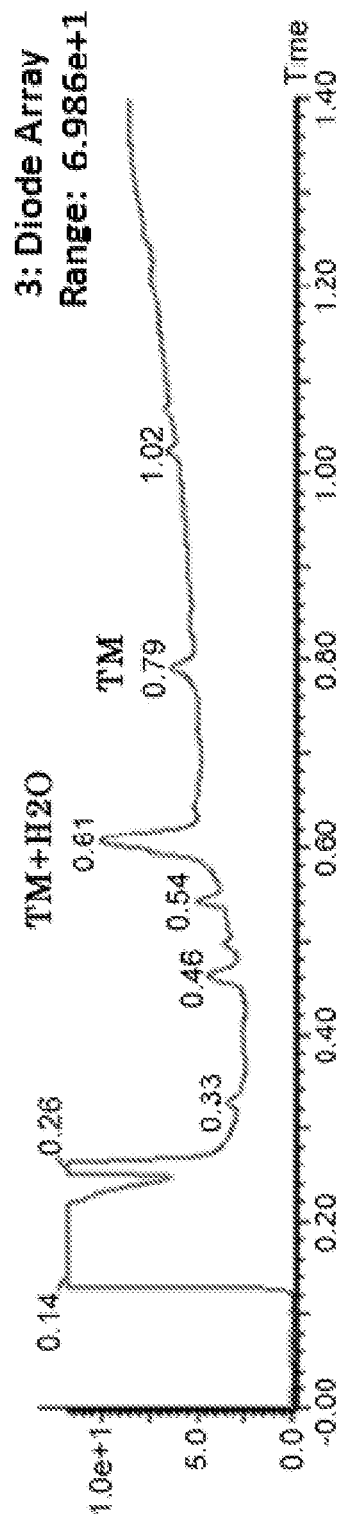
FIG. 17 shows the result showing detection of the desired peptide (Compound 131) and hydrolysate of the target molecule (TM+H2O) under the deprotection condition using 5% TFA/DCE (5% TIPS) analyzed by LCMS.

Thereafter, the solvent was distilled off under reduced pressure, 5% TFA/DCE (5% TIPS) (8 mL, moisture content was confirmed to be <200 ppm by the Karl Fischer titration) was added to the obtained residue, and this was stirred for 2.5 hours. The solvent was distilled off under reduced pressure, and when the residue was subjected to LCMS (FA05) analysis, masses corresponding to the compound (Compound 131) in which an amide bond was formed between the N-terminal amino group of H-Ala-Trp-Nle-Trp-D-Tyr-MeGly-MeAla-MePhe(3-Cl)-MeGly-nPrGly-Asp-pip and the side-chain carboxylic acid of Asp, which is a target molecule, and the hydrolysate thereof (product in which any of the amide bonds was hydrolyzed) were confirmed, and the UV area ratio corresponding to them was 13:87 (FIG. 17). The LC analysis results are shown in FIG. 17. "TM+H2O" in this Example represents a compound in which any one of the amide bonds of the target molecule has undergone hydrolysis.

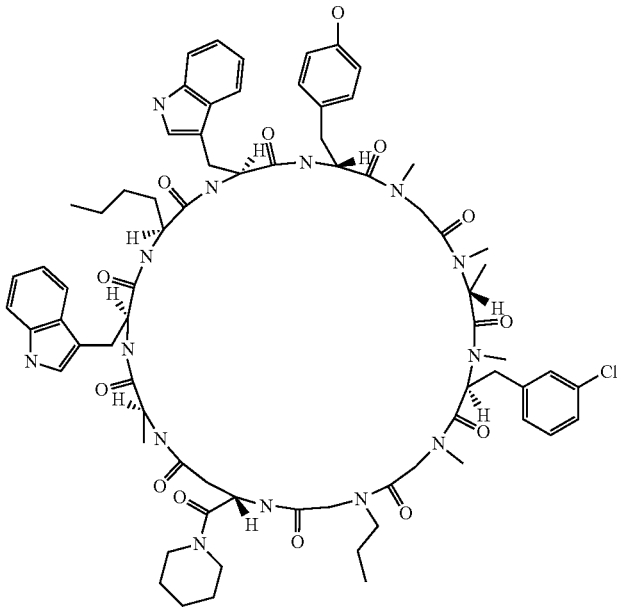

Compound 131

The data of FIG. 17 are shown below:
Target molecule (Compound 131, compound in which an amide bond was formed between the N-terminal amino group of H-Ala-Trp-Nle-Trp-D-Tyr-MeGly-MeAla-MePhe(3-Cl)-MeGly-nPrGly-Asp-pip and the side-chain carboxylic acid of Asp)
LCMS (ESI) m/z=1424.0 (M+H)+
Retention time: 0.79 minutes (analysis condition SQDFA05)
Hydrolysate (product in which any of the amide bonds of a compound has undergone hydrolysis, the compound in which an amide bond was formed between the N-terminal amino group of H-Ala-Trp-Nle-Trp-D-Tyr-MeGly-MeAla-MePhe(3-Cl)-MeGly-nPrGly-Asp-pip and the carboxylic acid of the Asp side chain)
LCMS (ESI) m/z=1442.0 (M+H)+
Retention time: 0.61 minutes (analysis condition SQDFA05)

These results confirmed that in deprotection using 5% TFA/DCE (5% TIPS), in case of cyclic peptides having sequences that are highly N-methylated, particularly sequences with consecutive N-methyl amino acids, approximately 90% of the target molecule is hydrolyzed, and obtaining the target molecule becomes difficult.

Comparative Example 2

Deprotection of the Side-Chain Protecting Groups (DMT Protection of MeSer Side Chain and Trt Protection of the Ser Side Chain) of the Compound (Compound 103. Pep3) in which an Amide Bond was Formed Between the N-Terminal Amino Group of H-g-EtAbu-MeSer(DMT)-Hyp(Et)-Ile-MePhe(3-Cl)-Ser(Trt)-Trp-Trp-Pro-MeGly-Asp-Pip and the Side-Chain Carboxylic Acid of Asp (when Using 5% TFA/DCE (5% TIPS))

Using Fmoc-Asp(O-Trt(2-Cl)-resin)-pip (Compound 50, resin loading rate: 0.316 mmol/g, 100 mg) synthesized by the already described method, peptide elongation was performed on a synthesizer to obtain H-g-EtAbu-MeSer(DMT)-Hyp(Et)-Ile-MePhe(3-Cl)-Ser(Trt)-Trp-Trp-Pro-MeGly-Asp(O-Trt(2-Cl)-resin)-pip.

Then, after swelling the resin again with DCM, TFE/DCM (1/1, v/v, 2 mL) was added to the resin, this was shaken at room temperature for two hours, and then the peptide was cleaved off from the resin. Next, the resin was removed by filtering the solution inside the tube through a column for synthesis, and the remaining resin was further washed twice with TFE/DCM (1/1, v/v, 1 mL).

The operation of cleaving the peptides off from the resin was repeated twice, and all of the obtained cleavage solutions were mixed and then concentrated under reduced pressure.

The obtained residue was dissolved in DMF/DCM (1/1, v/v, 8 mL), a 0-(7-aza-1H-benzotriazol-1-yl)-N,N,N,N-tetramethyluronium hexafluorophosphate (HATU, 18 mg)/DMF solution (0.5 M) and a DIPEA (9.9 µL)/DMF (39.6 µL) solution were added, and this was stirred at room temperature for two hours. The reaction was checked by LCMS analyses (SQDFA05), and the following compounds were confirmed: 70% of a compound formed by removal of DMT protection of the MeSer side chain from the compound (Compound 103, Pep3) in which an amide bond was formed between the N-terminal amino group of H-g-EtAbu-MeSer(DMT)-Hyp(Et)-Ile-MePhe(3-Ct)-Ser(Trt)-Trp-Trp-Pro-MeGly-Asp-pip and the side-chain carboxylic acid of Asp (LCMS (ESI) m/z=1716.2 (M+H)+; retention time: 1.06 minutes) and 30% of a compound in which both DMT protection of the MeSer side chain and Trt protection of the Ser side chain were removed from Compound 103 (LCMS (ESI) m/z=1474.1 (M+H)+; retention time: 0.78 minutes). The percentage was calculated from the UV area ratio according to LC. Thereafter, the solvent was distilled off under reduced pressure, the residue was dissolved in dichloromethane, and this was aliquoted into 10 test tubes. These were concentrated under reduced pressure to remove dichloromethane. The "residue after cyclization" used in the above-mentioned Examples refers to a residue obtained by concentration under reduced pressure after aliquoting it into 10 tubes.

To one of these test tubes, 5% TFA/DCE (5% TIPS) (0.8 mL, water content of 32.5 ppm determined by the Karl Fischer titration) was added and shaken for three minutes, and then this was left to stand at 25° C. for two hours. The solvent was distilled off under reduced pressure, and when the residue was subjected to LCMS (FA05) analysis, a compound (Compound 133) in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp, which is a target molecule, the N- to O-acyl shift product of the target molecule, a product in which one of the hydroxyl groups of the target molecule was esterified with TFA, and a product in which two of the hydroxyl groups of the target molecule were esterified with TFA were confirmed to have a UV area ratio of 17:46:32:5. The LC analysis results are shown in FIG. 18.

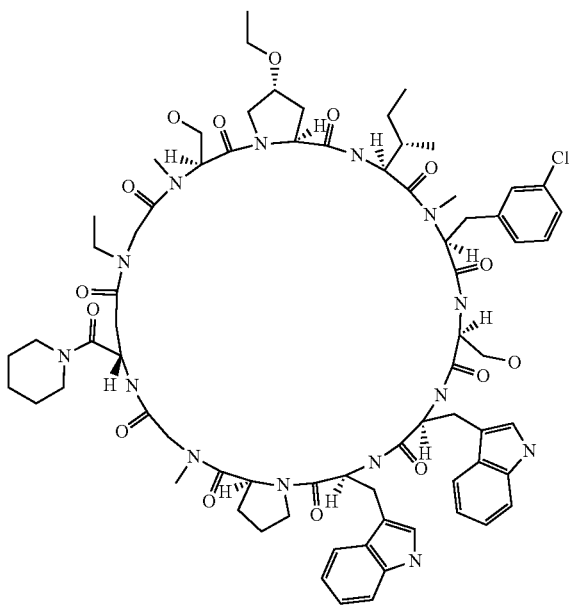

Compound 133

Figure 18:
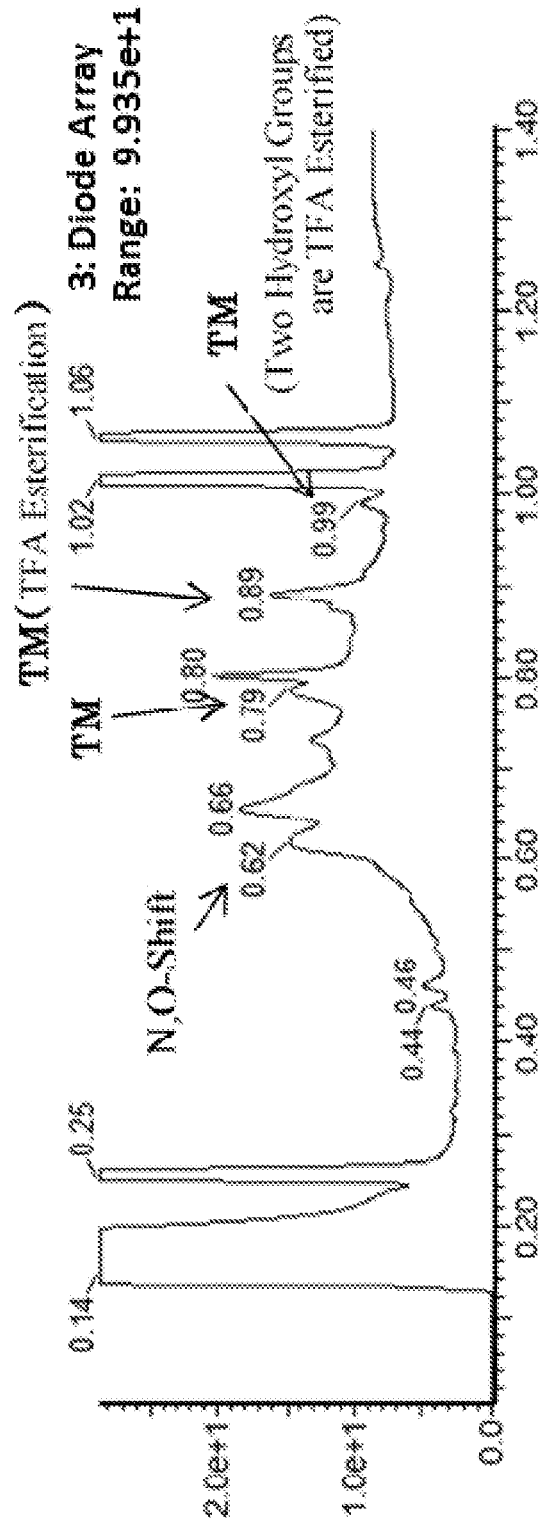
FIG. 18 shows the result showing detection of the desired peptide (Compound 133), a N- to O-acyl shifted product of the target molecule, a compound in which one hydroxyl group of the target molecule has been TFA esterified, and a compound in which two hydroxyl groups of the target molecule have been TFA esterified under the deprotection condition using 5% TFA/DCE (5% TIPS) analyzed by LCMS.

The data of FIG. 18 are shown below:
Desired peptide (Compound 133, compound in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp) LCMS (ESI) m/z=1473.8 (M+H)+
Retention time: 0.79 minutes (analysis condition SQDFA05)
N- to O-acyl shift product of the target molecule (a compound in which N- to O-acyl shift progressed at either one or both of the two hydroxyl groups of the target molecule)
LCMS (ESI) m/z=1473.8 (M+H)+
Retention time: 0.62 minutes (analysis condition SQDFA05)
Compound in which one of the hydroxyl groups of the target molecule was esterified with TFA
LCMS (ESI) m/z=1569.8 (M+H)+
Retention time: 0.89 minutes (analysis condition SQDFA05)
Compound in which two of the hydroxyl groups of the target molecule were esterified with TFA
LCMS (ESI) m/z=1665.9 (M+H)+
Retention time: 0.99 minutes (analysis condition SQDFA05)

These results confirmed that when β-hydroxyl group-containing amino acids such as MeSer and Ser are included in a sequence, deprotection using 5% TFA/DCE (5% TIPS)

causes N- to O-acyl shift to progress. Furthermore, deprotection under this condition was confirmed to cause TFA esterification to take place on one or both of the two side-chain hydroxyl groups. It was confirmed that obtaining the target molecule becomes difficult due to these undesired reactions.

Examinations in which the reaction temperature is lowered to 0° C., and examinations in which the TFA concentration is lowered were carried out with the objective of suppressing generation of N- to O-acyl shift products and suppressing TFA esterification of hydroxyl groups.

Comparative Example 3

Deprotection of the Side-Chain Protecting Groups (DMT Protection of the MeSer Side Chain and Trt Protection of the Ser Side Chain) of the Compound (Compound 103, Pep3) in which an Amide Bond was Formed Between the N-Terminal Amino Group of H-g-EtAbu-MeSer(DMT)-Hyp(Et)-Ile-MePhe(3-Cl)-Ser(Trt)-Trp-Trp-Pro-MeGly-Asp-Pip and the Side-Chain Carboxylic Acid of Asp (when Performing the Deprotection at 0° C. Using 5% TFA/DCE (5% TIPS))

After the above-mentioned cyclization, 5% TFA/DCE (5% TIPS) (0.8 ml, moisture content of 36.6 ppm determined by the Karl Fischer titration) was added at 0° C. to one of the 10 test tubes aliquoted, this was shaken for one minute, and then this was left to stand at 0° C. for four hours. When the reaction solution was subjected to LCMS (FA05) analysis, the compound (Compound 133) in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp, which is a target molecule, the N- to O-acyl shift product of the target molecule, a product in which one of the hydroxyl groups of the target molecule was esterified with TFA, and a product in which one of the hydroxyl groups of the N- to O-acyl shift product of the target molecule was esterified with TFA were confirmed to have a UV area ratio of 56:12:21:11. The LC analysis results are shown in FIG. 19.

Figure 19:
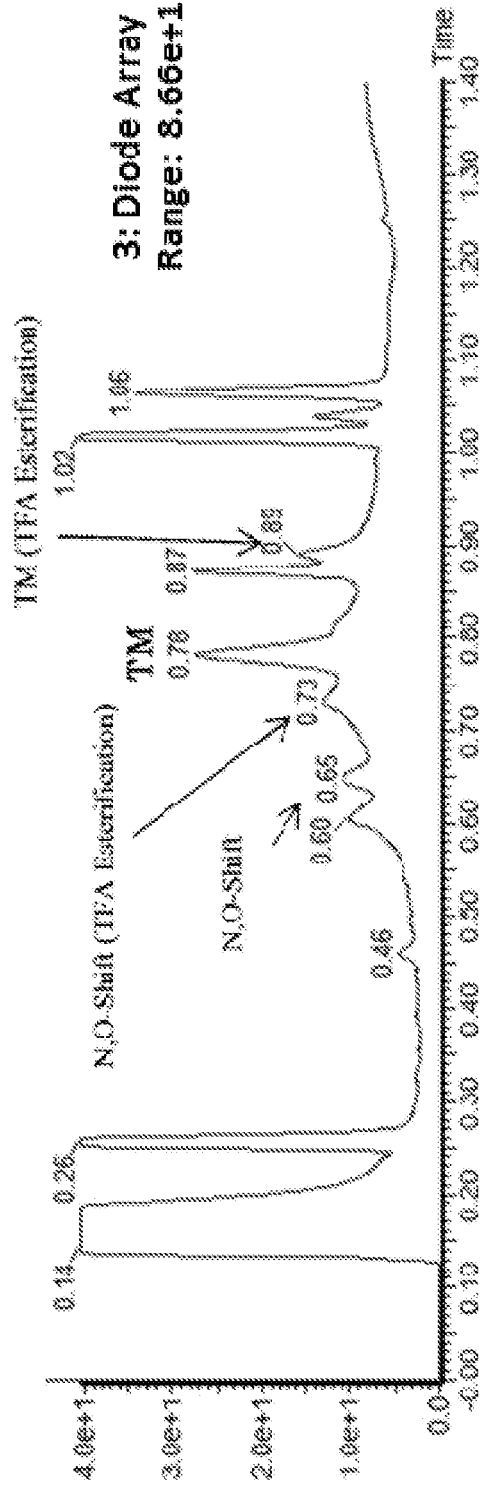
FIG. 19 shows the result showing detection of the desired peptide (Compound 133), a N- to O-acyl shifted product of the target molecule, a compound in which one hydroxyl group of the target molecule has been TFA esterified, and a compound in which two hydroxyl groups of the target molecule have been TFA esterified under the deprotection condition using 5% TFA/DCE (5% TIPS) (0° C.) analyzed by LCMS.

The data of FIG. 19 are shown below:
Desired peptide (Compound 133, compound in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp)
LCMS (ESI) m/z=1473.7 (M+H)+
Retention time: 0.78 minutes (analysis condition SQDFA05)
N- to O-acyl shift product of the target molecule (a compound in which N- to O-acyl shift progressed at either one or both of the two hydroxyl groups of the target molecule)
LCMS (ESI) m/z=1473.7 (M+H)+
Retention time: 0.65 minutes (analysis condition SQDFA05)
Compound in which one of the hydroxyl groups of the target molecule was esterified with TFA
LCMS (ESI) m/z=1569.7 (M+H)+
Retention time: 0.89 minutes (analysis condition SQDFA05)
Compound in which one of the hydroxyl groups of the N- to O-acyl shift product of the target molecule was esterified with TFA
LCMS (ESI) m/z=1569.7 (M+H)+
Retention time: 0.73 minutes (analysis condition SQDFA05)

Comparative Example 4

Deprotection of the Side-Chain Protecting Groups (DMT Protection of the MeSer Side Chain and Trt Protection of the Ser Side Chain) of the Compound (Compound 103, Pep3) in which an Amide Bond was Formed Between the N-Terminal Amino Group of H-g-EtAbu-MeSer(DMT)-Hyp(Et)-Ile-MePhe(3-Cl)-Ser(Trt)-Trp-Trp-Pro-MeGly-Asp-Pip and the Side-Chain Carboxylic Acid of Asp (when Performing the Deprotection at 25° C. and Using 2% TFA/DCE (5% TIPS))

After the above-mentioned cyclization, 2% TFA/DCE (5% TIPS) (0.8 mL, water content of 30.1 ppm determined by the Karl Fischer titration) was added at 25° C. to one of the 10 test tubes aliquoted, this was shaken for one minute, and then this was left to stand at room temperature for four hours. When the reaction solution was subjected to LCMS (FA05) analysis, a compound (Compound 133) in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp, which is a target molecule, a N- to O-acyl shift product of the target molecule, a product in which one of the hydroxyl groups of the target molecule was esterified with TFA, a product in which two of the hydroxyl groups of the target molecule were esterified with TFA, and a product in which one of the hydroxyl groups of the N- to O-acyl shift product of the target molecule was esterified with TFA were confirmed to have a UV area ratio of 30:34:24:3:9. The LC analysis results are shown in FIG. 20.

Figure 20:
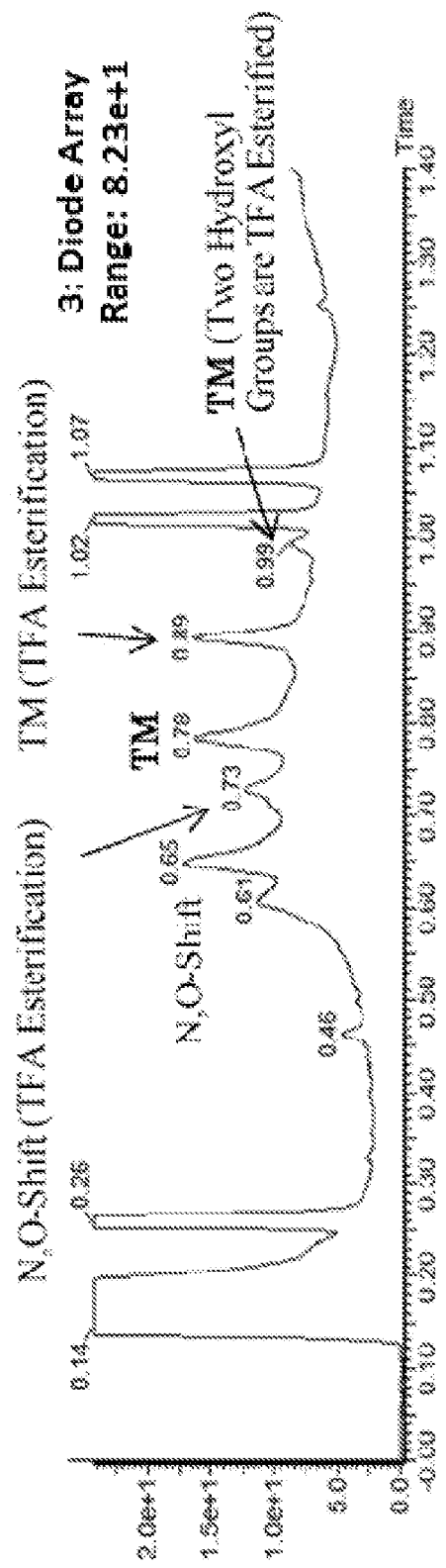
FIG. 20 shows the result showing detection of the desired peptide (Compound 133), a N- to O-acyl shifted product of the target molecule, a compound in which one hydroxyl group of the target molecule has been TFA esterified, and a compound in which two hydroxyl groups of the target molecule have been TFA esterified under the deprotection condition using 5% TFA/DCE (5% TIPS) (25° C.) analyzed by LCMS.

The data of FIG. 20 are shown below:
Desired peptide (Compound 133, compound in which an amide bond was formed between the N-terminal amino group of H-g-EtAbu-MeSer-Hyp(Et)-Ile-MePhe(3-Cl)-Ser-Trp-Trp-Pro-MeGly-Asp-pip and the side-chain carboxylic acid of Asp)
LCMS (ESI) m/z=1473.8 (M+H)+
Retention time: 0.78 minutes (analysis condition SQDFA05)
N- to O-acyl shift product of the target molecule (a compound in which N- to O-acyl shift progressed at either one or both of the two hydroxyl groups of the target molecule)
LCMS (ESI) m/z=1473.8 (M+H)+
Retention time: 0.65 minutes (analysis condition SQDFA05)
Compound in which one of the hydroxyl groups of the target molecule was esterified with TFA
LCMS (ESI) m/z=1569.8 (M+H)+
Retention time: 0.89 minutes (analysis condition SQDFA05)
Compound in which two of the hydroxyl groups of the target molecule were esterified with TFA
LCMS (ESI) m/z=1665.7 (M+H)+
Retention time: 0.99 minutes (analysis condition SQDFA05)

Compound in which one of the hydroxyl groups of the N- to O-acyl shift product of the target molecule was esterified with TFA
LCMS (ESI) m/z=1569.8 (M+H)+
Retention time: 0.73 minutes (analysis condition SQDFA05)

According to the above-mentioned results, the problems of N- to O-acyl shift and the problems of TFA esterification of the hydroxyl groups included in the compounds could not be completely solved simply by decreasing the reaction temperature and by using a lower concentration of the TFA solution.

Example 6 Application to Parallel Synthesis (Solid Phase Method) of the Present Invention Example 6-1

Synthesis of a Group of Peptides in which Cyclization by an Amide Bond was Performed Between the N-Terminal Amino Group and the Side-Chain Carboxylic Acid Group of Aspartic Acid A group of peptides in which cyclization by an amide bond was performed between the N-terminal main chain amino group and the side-chain carboxylic acid group of an aspartic acid to which proline is bonded to its C terminus or its C terminus is amidated (amidated by any one of piperidine, 4-(tert-butyl)piperidine, and N-methyloctan-1-amine) was synthesized.

Using 100 mg of any one of Compound 50 (2-chlorotrityl resin made to support Compound 48 (Fmoc-Asp-pip)), Compound 52 (2-chlorotrityl resin made to support Compound 51 (Fmoc-Asp-piptBu)), Compound 55 (2-chlorotrityl resin made to support Compound 54 (Fmoc-Asp-MeOctyl)), and Compound 58 (2-chlorotrityl resin made to support Compound 57 (Fmoc-Asp-Pro-OPis)), peptide elongation was carried out using as an Fmoc amino acid Fmoc-MeVal-OH, Fmoc-MePhe(3-Cl)—OH (Compound 15), Fmoc-MePhe(4-Cl)—OH (Compound 16), Fmoc-MeHis(Trt)-OH (Compound 7), Fmoc-MePhe-OH, Fmoc-MeSer(DMT)-OH (Compound 5), Fmoc-MeSer(THP)—OH (Compound 6), Fmoc-MeAla-OH, Fmoc-nPrGly-OH (Compound 20), Fmoc-MeGly-OH, Fmoc-Hyp(Et)-OH (Compound 18), Fmoc-Pro-OH, Fmoc-Thr(THP)—OH (Compound 2), Fmoc-Ile-OH, Fmoc-Val-OH, Fmoc-Trp-OH, Fmoc-Tyr(3-F,tBu)-OH (Compound 13), Fmoc-Phe(4-CF3)-OH, Fmoc-Phe(3-Cl)—OH. Fmoc-Ser(Trt)-OH. Fmoc-Met(O2)-OH, Fmoc-b-Ala-OH, Fmoc-Ala-OH, Fmoc-Gly-OH, and such. (In MeSer elongation, Fmoc-MeSer(DMT)-OH (Compound 5) was used for PS-53 and PS-54 (Table 5-1), and Fmoc-MeSer(THP)—OH (Compound 6) was used for the other cases.) Peptide elongation was performed according to the peptide synthesis method by the Fmoc method already described in the Examples. After peptide elongation, the N-terminal Fmoc group was removed on the peptide synthesizer, and then the resin was washed with DMF.

Then, after swelling the resin again with DCM, TFE/DCM (1/1, v/v, 2 mL) and diisopropylethylamine (DIPEA, at an amount of 1.8 equivalents with respect to the number of moles on the resin used (number of moles resulting from multiplying the loading rate (mmol/g) by the amount of resin used (normally 0.10 g))) were added to the resin, this was shaken at room temperature for two hours, and then the peptides were cleaved off from the resin. Next, the resin was removed by filtering the solution inside the tube through a column for synthesis, and the remaining resin was further washed twice with TFE/DCM (1/1, v/v, 1 mL). All of the obtained cleavage solutions were mixed, and concentrated under reduced pressure.

The obtained residue was dissolved in DMF/DCM (1/1, v/v, 8 mL), a 0.5 M O-(7-aza-1H-benzotriazol-1-yl)-N,N,N,N-tetramethyluronium hexafluorophosphate (HATU)/DMF solution (at an amount of 1.5 equivalents with respect to the number of moles on the resin used (number of moles resulting from multiplying the loading rate (mmol/g) of the resin by the amount of resin used (0.1 g))) and DIPEA (1.8 equivalents with respect to the number of moles on the resin used) were added, and this was stirred at room temperature for two hours. Thereafter, the solvent was distilled off under reduced pressure.

Deprotection was performed as follows on the obtained residue.

When the sequence includes Tyr(3-F,tBu), 2 mL of 0.1 M tetramethylammonium hydrogen sulfate/HFIP solution (2% TIPS) prepared by the already described method was added to dissolve the residue, and then this was left to stand at room temperature or at 30° C. for 24 hours. When the sequence does not contain Tyr(3-F), 4 mL of 0.05 M tetramethylammonium hydrogen sulfate/HFIP solution (2% TIPS) prepared by the already described method was added to dissolve the residue, and then this was left to stand at room temperature for four hours. After allowing the reaction to stand for a certain amount of time, diisopropylethylamine (DIPEA, 70 µL) was added, and the solvent was distilled off under reduced pressure.

After distilling off the solvent under reduced pressure, the resulting material was dissolved in DMF. After removing the insoluble material by filtration, this was purified by preparative HPLC, and the amide-cyclized cyclic peptides in the title (PS-1 to PS-54) were obtained. The sequences of PS-1 to PS-54 are shown in Table 5-1 and their structures are shown in 5-2. The mass spectral values, liquid chromatography retention times, purities, and yields of each of the obtained peptides are shown in Table 5-3.

TABLE 5-1

| | MW | 11 | 10 | 9 | 8 | 7 | 6 | 5 | 4 | 3 | 2 | 1 | H-1 | Used resin | Resin Loading Amount |
|---|---|---|---|---|---|---|---|---|---|---|---|---|---|---|---|
| PS-1 | 1683.8 | Ala | Pro | Met(O2) | Tyr(3-F) | MeHis | Thr | Thr | Trp | MePhe(4-Cl) | MePhe(4-Cl) | Asp | MeOctyl | Compound 55 | 0.368 mmol/g |
| PS-2 | 1691.8 | Ala | Thr | Met(O2) | MePhe | Thr | MePhe(4-Cl) | Phe(3-Cl) | MePhe(4-Cl) | Thr | Phe(3-Cl) | Asp | piptBu | Compound 52 | 0.356 mmol/g |
| PS-3 | 1722.9 | Ala | Thr | Phe(3-Cl) | MePhe | Thr | Trp | Phe(3-Cl) | MePhe | Tyr(3-F) | Phe(3-Cl) | Asp | piptBu | Compound 52 | 0.358 mmol/g |
| PS-4 | 1652.2 | Ala | Thr | Thr | MeAla | Met(O2) | Trp | Phe(3-Cl) | MePhe | Thr | Phe(3-Cl) | Asp | piptBu | Compound 52 | 0.356 mmol/g |
| PS-5 | 1699.8 | Ser | Pro | Met(O2) | Tyr(3-F) | MeHis | Thr | Thr | Trp | MePhe(4-Cl) | MePhe(4-Cl) | Asp | MeOctyl | Compound 55 | 0.368 mmol/g |
| PS-6 | 1707.8 | Ser | Thr | Met(O2) | MePhe | Thr | MePhe(4-Cl) | Phe(3-Cl) | MePhe(4-Cl) | Thr | Phe(3-Cl) | Asp | piptBu | Compound 52 | 0.356 mmol/g |
| PS-7 | 1745.8 | Ala | Thr | Met(O2) | MePhe | Thr | Trp | Phe(3-Cl) | MePhe | Tyr(3-F) | MePhe(4-Cl) | Asp | Meoctyl | Compound 55 | 0.368 mmol/g |
| PS-8 | 1655.8 | Ala | Pro | Met(O2) | Tyr(3-F) | MeHis | Thr | Thr | Trp | MePhe(4-Cl) | MePhe(4-Cl) | Asp | Pro | Compound 58 | 0.3885 mmol/g |
| PS-9 | 1665.3 | Ala | Thr | Met(O2) | MePhe | Thr | MePhe(4-Cl) | Phe(3-Cl) | MePhe(4-Cl) | Thr | Phe(3-Cl) | Asp | Pro | Compound 58 | 0.3885 mmol/g |
| PS-10 | 1701.7 | Ala | Thr | Met(O2) | MePhe | Thr | Trp | Phe(3-Cl) | MePhe | Tyr(3-F) | Phe(3-Cl) | Asp | Pro | Compound 58 | 0.3885 mmol/g |
| PS-11 | 1626.1 | Ala | Thr | Phe(3-Cl) | MeAla | Thr | Trp | Phe(3-Cl) | MePhe | Thr | Phe(3-Cl) | Asp | Pro | Compound 58 | 0.3885 mmol/g |
| PS-12 | 1671.8 | Ser | Pro | Met(O2) | Tyr(3-F) | MeHis | Thr | Thr | Trp | MePhe(4-Cl) | MePhe(4-Cl) | Asp | Pro | Compound 58 | 0.3885 mmol/g |
| PS-13 | 1681.8 | Ser | Thr | Met(O2) | MePhe | Thr | MePhe(3-Cl) | Phe(3-Cl) | MePhe(4-Cl) | Thr | Phe(3-Cl) | Asp | Pro | Compound 58 | 0.3885 mmol/g |
| PS-14 | 1717.7 | Ser | Thr | Met(O2) | MePhe | Thr | Trp | Phe(3-Cl) | MePhe | Tyr(3-F) | Phe(3-Cl) | Asp | Pro | Compound 58 | 0.3885 mmol/g |
| PS-15 | 1642.1 | Ser | Thr | Phe(3-Cl) | MeAla | Thr | Trp | Phe(3-Cl) | MePhe | Thr | Phe(3-Cl) | Asp | Pro | Compound 58 | 0.3885 mmol/g |
| PS-16 | 1543.09 | Ala | MePhe(O2) | MePhe(3-Cl) | Met(O2) | Hyp(Et) | Th | MePhe(3-Cl) | MePhe(4-Cl) | bAla | Trp | Asp | piptBu | Compound 52 | 0.356 mmol/g |
| PS-17 | 1690.3 | Ala | Met(O2) | MePhe | Trp | Pro | MeGly | MePhe(4-Cl) | Met(O2) | MeVal | Phe(3-Cl) | Asp | pip | Compound 50 | 0.338 mmol/g |
| PS-18 | 1808.4 | Ala | Met(O2) | Met(O2) | MePhe | Met(O2) | Trp | Phe(3-Cl) | MePhe(4-Cl) | Thr | Phe(3-Cl) | Asp | MeOctyl | Compound 55 | 0.366 mmol/g |
| PS-19 | 1664.23 | Ala | Ile | Phe(3-Cl) | MeAla | Thr | Trp | Phe(3-Cl) | MePhe | Met(O2) | Phe(3-Cl) | Asp | piptBu | Compound 52 | 0.336 mmol/g |
| PS-20 | 1561.11 | Ser | MePhe(3-Cl) | MePhe(3-Cl) | Met(O2) | Hyp(Et) | Thr | MePhe(3-Cl) | nPrGly | bAla | MeGly | Asp | MeOctyl | Compound 55 | 0.366 mmol/g |
| PS-21 | 1864.43 | Ala | Met(O2) | MePhe | Trp | Pro | MeGly | MePhe(3-Cl) | Met(O2) | MeVal | Trp | Asp | MeOctyl | Compound 55 | 0.368 mmol/g |
| PS-22 | 1824.4 | Ser | Met(O2) | Met(O2) | MePhe | Met(O2) | Trp | Phe(3-Cl) | MePhe(4-Cl) | Thr | Phe(3-Cl) | Asp | MeOctyl | Compound 55 | 0.388 mmol/g |
| PS-23 | 1680.23 | Ser | Ile | Phe(3-Cl) | MeAla | Thr | Trp | Phe(3-Cl) | MePhe | Met(O2) | Phe(3-Cl) | Asp | piptBu | Compound 52 | 0.358 mmol/g |
| PS-24 | 1518.97 | Ala | MePhe(3-Cl) | MePhe(3-Cl) | Met(O2) | Hyp(Et) | Thr | MePhe(3-Cl) | nPrGly | bAla | MnGly | Asp | Pro | Compound 58 | 0.3885 mmol/g |
| PS-25 | 1620.29 | Ala | Met(O2) | MePhe | Trp | Pro | MeGly | MePhe(3-Cl) | Met(O2) | MeVal | Trs | Asp | Pro | Compound 58 | 0.3885 mmol/g |
| PS-26 | 1780.25 | Ala | Met(O2) | Met(O2) | MePhe | Met(O2) | Trp | Phe(3-Cl) | MePhe(4-Cl) | Thr | Phe(3-Cl) | Asp | Pro | Compound 58 | 0.3885 mmol/g |
| PS-27 | 1838.11 | Ala | Ile | MeAla | MeAla | Thr | Trp | Phe(3-Cl) | MePhe | Met(O2) | Phe(3-Cl) | Asp | Pro | Compound 58 | 0.3885 mmol/g |
| PS-28 | 1532.97 | Ser | MePhe(3-Cl) | MePhe(3-Cl) | Met(O2) | Hyp(Et) | Thr | MePhe(3-Cl) | MePhe(4-Cl) | Thr | MeGly | Asp | Pro | Compound 58 | 0.3885 mmol/g |
| PS-29 | 1636.29 | Ser | Met(O2) | MePhe | Trp | Pro | Trp | MePhe(3-Cl) | MePhe(4-Cl) | Thr | Trp | Asp | Pro | Compound 58 | 0.3885 mmol/g |
| PS-30 | 1796.25 | Ser | Met(O2) | Met(O2) | MePhe | Met(O2) | Trp | Phe(3-Cl) | MePhe(4-Cl) | Thr | Phe(3-Cl) | Asp | Pro | Compound 58 | 0.3885 mmol/g |
| PS-31 | 1654.11 | Ser | Ile | Thr | MeAla | Thr | Trp | Phe(3-Cl) | MePhe | Thr | Phe(3-Cl) | Asp | Pro | Compound 58 | 0.3885 mmol/g |
| PS-32 | 1575.57 | Ala | Thr | Met(O2) | MePhe | Thr | Trp | Phe(3-Cl) | MePhe(4-Cl) | MeSer | MeSer | Asp | Pro | Compound 58 | 0.3885 mmol/g |
| PS-33 | 1678.8 | Ala | Met(O2) | Phe(3-Cl) | MeSer | Thr | Trp | Phe(3-Cl) | MePhe(4-Cl) | Thr | Phe(3-Cl) | Asp | Pro | Compound 58 | 0.3885 mmol/g |
| PS-34 | 1808.04 | Ala | Thr | Met(O2) | Ile | Thr | Trp | Phe(3-Cl) | MePhe(4-Cl) | Thr | Phe(3-Cl) | Asp | Pro | Compound 58 | 0.3885 mmol/g |
| PS-35 | 1513.95 | Ala | Ile | Gly | Ile | Thr | Trp | Phe(3-Cl) | MePhe(4-Cl) | Thr | Phe(3-Cl) | Asp | Pro | Compound 58 | 0.3885 mmol/g |
| PS-36 | 1379.94 | Ser | bAla | MePhe(3-Cl) | Gly | MePhe(3-Cl) | Pro | bAla | MePhe(4-Cl) | Thr | MePhe | Asp | Pro | Compound 58 | 0.3885 mmol/g |
| PS-37 | 1591.87 | Ser | Thr | Met(O2) | MePhe | Thr | Trp | Phe(3-Cl) | MePhe(4-Cl) | MeSer | MeSer | Asp | Pro | Compound 58 | 0.3885 mmol/g |
| PS-38 | 1682.5 | Ser | Met(O2) | Phe(3-Cl) | MeSer | Thr | Trp | Phe(3-Cl) | MePhe(4-Cl) | Thr | Phe(3-Cl) | Asp | Pro | Compound 58 | 0.3885 mmol/g |
| PS-39 | 1624.04 | Ser | Thr | Met(O2) | Ile | Thr | Trp | Phe(3-Cl) | MePhe(4-Cl) | Thr | Phe(3-Cl) | Asp | Pro | Compound 58 | 0.3885 mmol/g |
| PS-40 | 1529.9 | Ser | Ile | Gly | Ile | Thr | Trp | Phe(3-Cl) | MePhe(4-Cl) | Thr | Phe(3-Cl) | Asp | Pro | Compound 58 | 0.3885 mmol/g |

TABLE 5-1-continued

| | MW | 11 | 10 | 9 | 8 | 7 | 6 | 5 | 4 | 3 | 2 | 1 | H-1 | Used resin | Resin Loading Amount |
|---|---|---|---|---|---|---|---|---|---|---|---|---|---|---|---|
| PS-41 | 1382.08 | Ala | bAla | Met(O2) | Gly | MePhe(3-Cl) | Pro | bAla | MePhe(4-Cl) | Thr | MePhe | Asp | MeOctyl | Compound 55 | 0.366 mmol/g |
| PS-42 | 1693.7 | Ala | Thr | Met(O2) | MePhe | Thr | Trp | Phe(3-Cl) | MePhe(4-Cl) | MeSer | MeSer | Asp | MeOctyl | Compound 55 | 0.366 mmol/g |
| PS-43 | 1702.62 | Ala | Met(O2) | Phe(3-Cl) | MeSer | Thr | Trp | Phe(3-Cl) | MePhe(4-Cl) | Thr | Phe(3-Cl) | Asp | piptBu | Compound 52 | 0.361 mmol/g |
| PS-44 | 1619.7 | Ser | Thr | Met(O2) | MePhe | Thr | Trp | Phe(3-Cl) | MePhe(4-Cl) | Thr | MeSer | Asp | MeOctyl | Compound 55 | 0.366 mmol/g |
| PS-45 | 1718.62 | Ser | Met(O2) | Phe(3-Cl) | MeSer | Thr | Trp | Phe(3-Cl) | MePhe(4-Cl) | Thr | Phe(3-Cl) | Asp | piptBu | Compound 52 | 0.361 mmol/g |
| PS-46 | 1650.16 | Ser | Met(O2) | MeSer | MeVal | Thr | Trp | Phe(3-Cl) | MePhe(4-Cl) | Thr | Phe(3-Cl) | Asp | piptBu | Compound 52 | 0.361 mmol/g |
| PS-47 | 1634.16 | Ala | Thr | Met(O2) | Ile | Thr | Trp | Phe(3-Cl) | MePhe(4-Cl) | Thr | Phe(3-Cl) | Asp | piptBu | Compound 52 | 0.361 mmol/g |
| PS-48 | 1483.97 | Ala | Ile | Gly | Ile | Thr | Trp | Phe(3-Cl) | MePhe(4-Cl) | Thr | Phe(3-Cl) | Asp | Pip | Compound 50 | 0.320 mmol/g |
| PS-49 | 1650.16 | Ser | Thr | Met(O2) | Ile | Thr | Trp | Phe(3-Cl) | MePhe(4-Cl) | Thr | Phe(3-Cl) | Asp | piptBu | Compound 52 | 0.361 mmol/g |
| PS-50 | 1558.07 | Ser | Ile | Gly | Ile | Thr | Trp | Phe(3-Cl) | MePhe(4-Cl) | Thr | Phe(3-Cl) | Asp | piptBu | Compound 52 | 0.361 mmol/g |
| PS-51 | 1397.47 | Ala | Pro | bAla | Phe(4-CF3) | Thr | Ser | bAla | Try | Trp | Val | Asp | Pro | Compound 58 | 0.3573 mmol/g |
| PS-52 | 1579.00 | Ala | Phe(3-Cl) | MePhe(4-Cl) | MeHis | MeGly | Phe(3-Cl) | MePhe | Thr | MeHis | Thr | Asp | Pro | Compound 58 | 0.3573 mmol/g |
| PS-53 | 1789.9 | Ala | Met(O2) | Phe(3-Cl) | MeSer | Met(O2) | Trp | MePhe | MePhe | Tyr(3-F) | Phe(3-Cl) | Asp | piptBu | Compound 52 | 0.361 mmol/g |
| PS-54 | 1763.8 | Ala | Met(O2) | Phe(3-Cl) | MeSer | Met(O2) | Trp | MePhe | MePhe | Tyr(3-F) | Phe(3-Cl) | Asp | Pro | Compound 58 | 0.375 mmol/g |

TABLE 5-2
PS-1
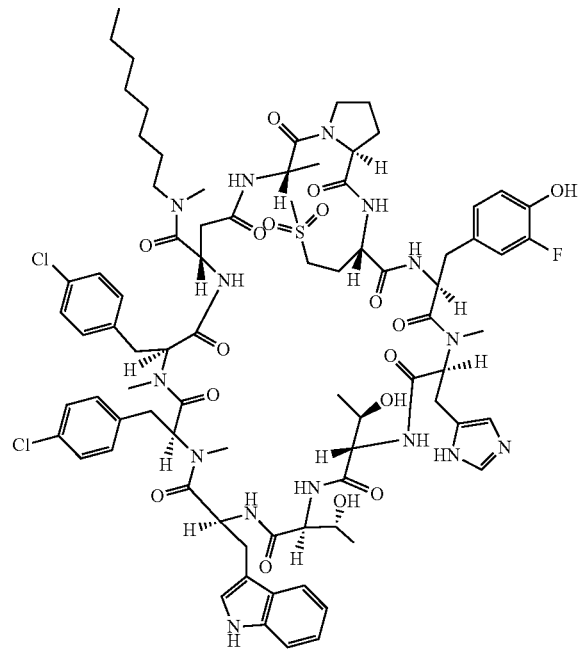 [SMILES: CCCCCCCCN(C)C(=O)[C@@H]1CC(=O)N[C@@H](C)C(=O)N2CCC[C@H]2C(=O)N[C@@H](CCS(C)(=O)=O)C(=O)N[C@@H](Cc2ccc(O)c(F)c2)C(=O)N(C)[C@@H](Cc2cnc[nH]2)C(=O)CN[C@@H]([C@@H](C)O)C(=O)N[C@@H]([C@@H](C)O)C(=O)N[C@@H](Cc2c[nH]c3ccccc23)C(=O)N(C)[C@@H](Cc2ccc(Cl)cc2)C(=O)N(C)[C@@H](Cc2ccc(Cl)cc2)C(=O)N1]
PS-2
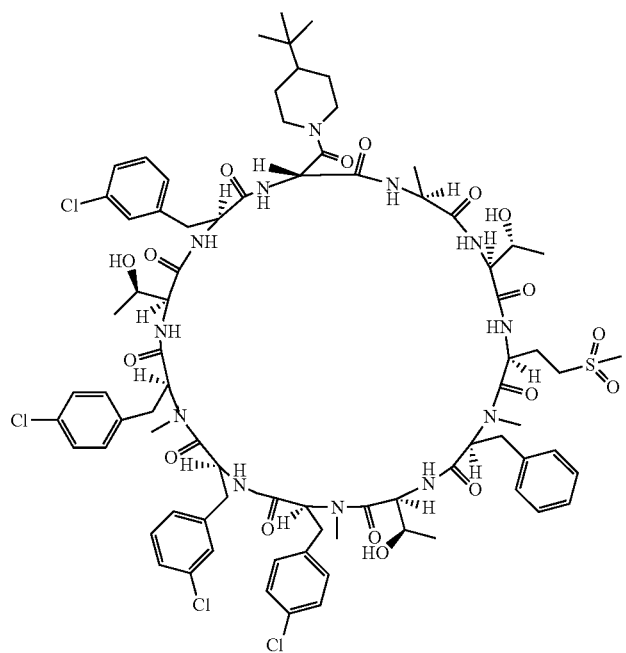 [SMILES: C[C@@H]1NC(=O)C[C@@H](C(=O)N2CCC(C(C)(C)C)CC2)CNC(=O)[C@H](Cc2cccc(Cl)c2)NC(=O)C[C@H]([C@@H](C)O)CNC(=O)[C@H](Cc2ccc(Cl)cc2)CCN(C)C(=O)[C@H](Cc2cccc(Cl)c2)NCC(=O)[C@H](Cc2ccc(Cl)cc2)N(C)C(=O)[C@H]([C@@H](C)O)NC(=O)[C@H](Cc2ccccc2)N(C)C(=O)[C@H](CCS(C)(=O)=O)NC(=O)[C@H]([C@@H](C)O)NC1=O]

TABLE 5-2-continued
PS-3
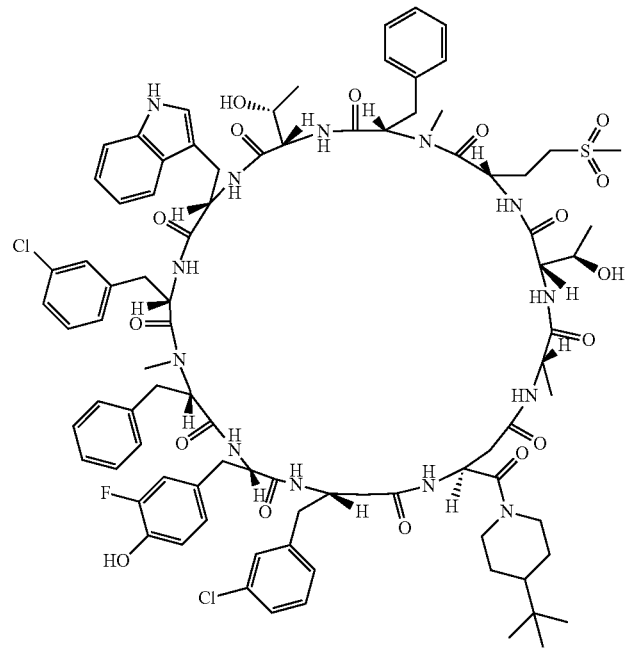
PS-4
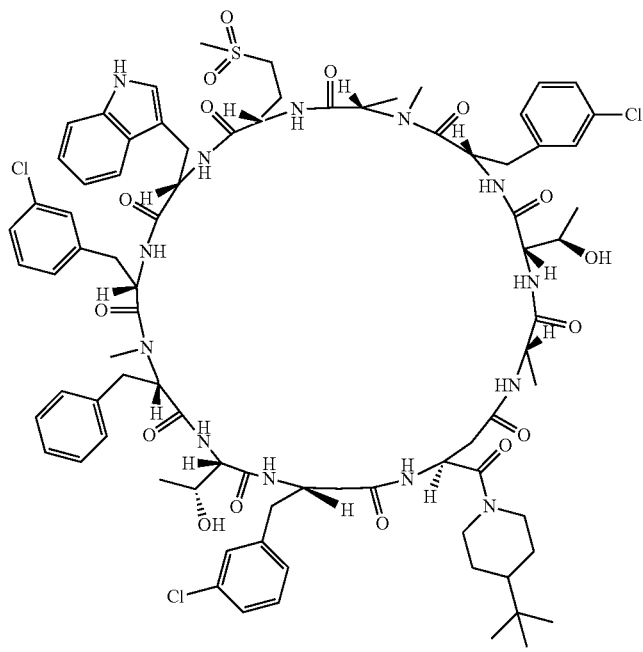

TABLE 5-2-continued
PS-5
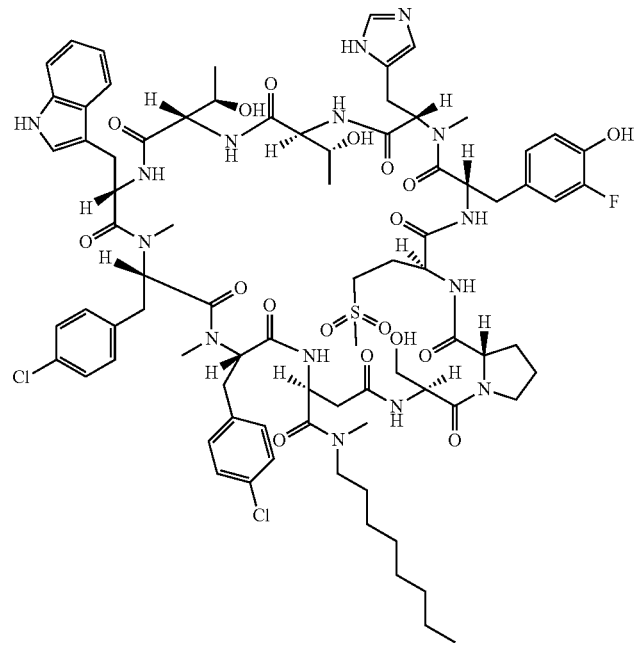 [SMILES: CCCCCCCCN(C)C(=O)[C@@H]1CC(=O)N[C@@H](CO)C(=O)N2CCC[C@H]2C(=O)N[C@@H](CCS(C)(=O)=O)C(=O)N[C@@H](Cc2ccc(O)c(F)c2)C(=O)N(C)[C@@H](Cc2cnc[nH]2)C(=O)N[C@@H]([C@@H](C)O)C(=O)N[C@@H]([C@@H](C)O)C(=O)N[C@@H](Cc2c[nH]c3ccccc23)C(=O)N(C)[C@@H](Cc2ccc(Cl)cc2)C(=O)N(C)[C@@H](Cc2ccc(Cl)cc2)C(=O)N1]
PS-6
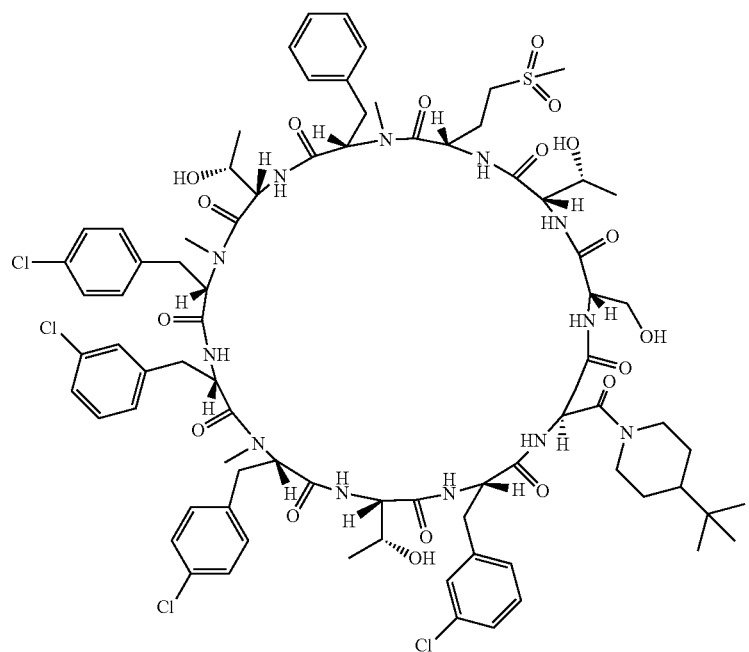 [SMILES: C[C@@H](O)[C@@H]1NC(=O)[C@H](CO)NC(=O)C[C@@H](C(=O)N2CCC(C(C)(C)C)CC2)NC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2ccc(Cl)cc2)N(C)C(=O)[C@H]([C@@H](C)O)NC(=O)[C@H](Cc2ccccc2)N(C)C(=O)[C@H](CCS(C)(=O)=O)NC1=O]

TABLE 5-2-continued
PS-7
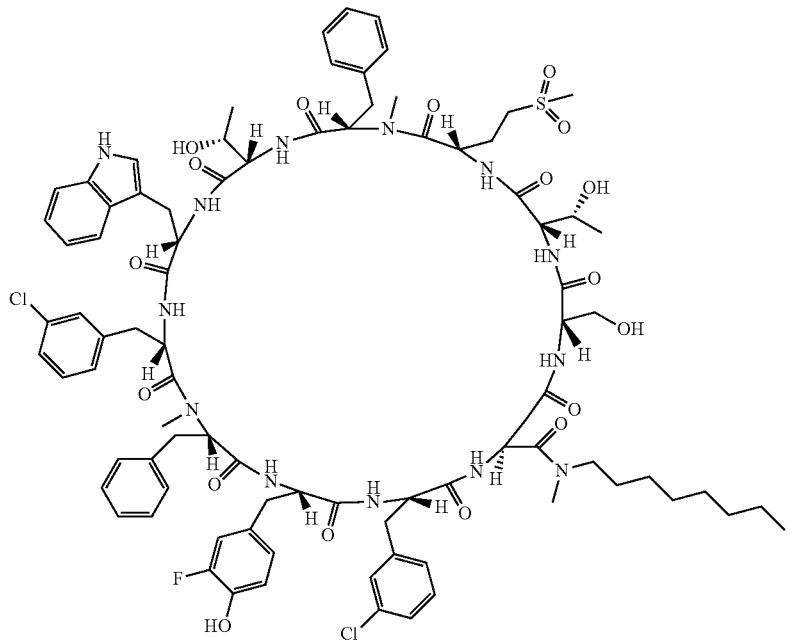 [SMILES: CCCCCCCCN(C)C(=O)[C@@H]1CC(=O)N[C@@H](CO)C(=O)N[C@@H]([C@@H](C)O)C(=O)N[C@@H](CCS(C)(=O)=O)C(=O)N(C)[C@@H](Cc2ccccc2)C(=O)N[C@@H]([C@@H](C)O)C(=O)N[C@@H](Cc2c[nH]c3ccccc23)C(=O)N[C@@H](Cc2cccc(Cl)c2)C(=O)N(C)[C@@H](Cc2ccccc2)C(=O)N[C@@H](Cc2ccc(O)c(F)c2)C(=O)N[C@@H](Cc2cccc(Cl)c2)C(=O)N1]
PS-8
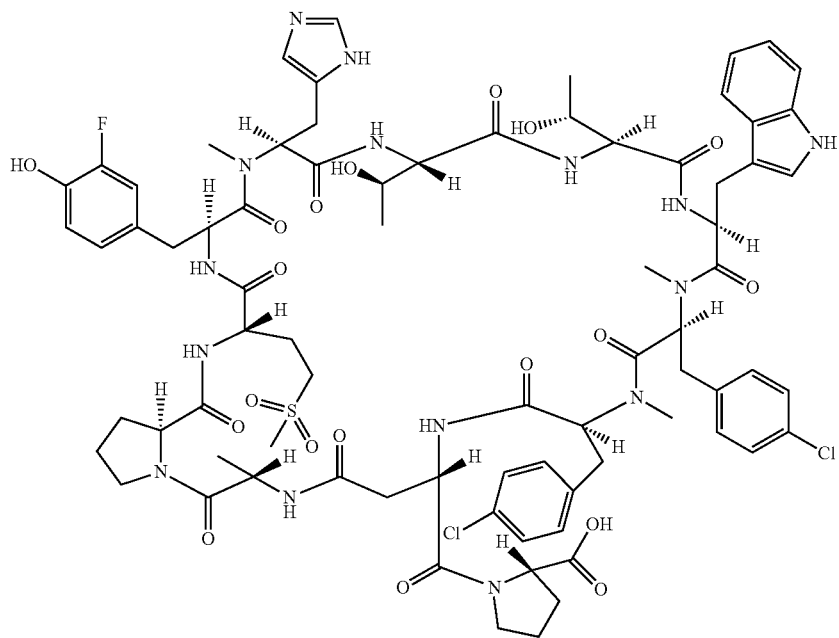 [SMILES: C[C@@H]1NC(=O)C[C@@H](C(=O)N2CCC[C@H]2C(=O)O)NC(=O)[C@H](Cc2ccc(Cl)cc2)N(C)C(=O)[C@H](Cc2ccc(Cl)cc2)N(C)C(=O)[C@H](Cc2c[nH]c3ccccc23)NC(=O)[C@H]([C@@H](C)O)NC(=O)[C@H]([C@@H](C)O)NC(=O)[C@H](Cc2cnc[nH]2)N(C)C(=O)[C@H](Cc2ccc(O)c(F)c2)NC(=O)[C@H](CCS(C)(=O)=O)NC(=O)[C@@H]2CCCN2C1=O]

TABLE 5-2-continued
PS-9
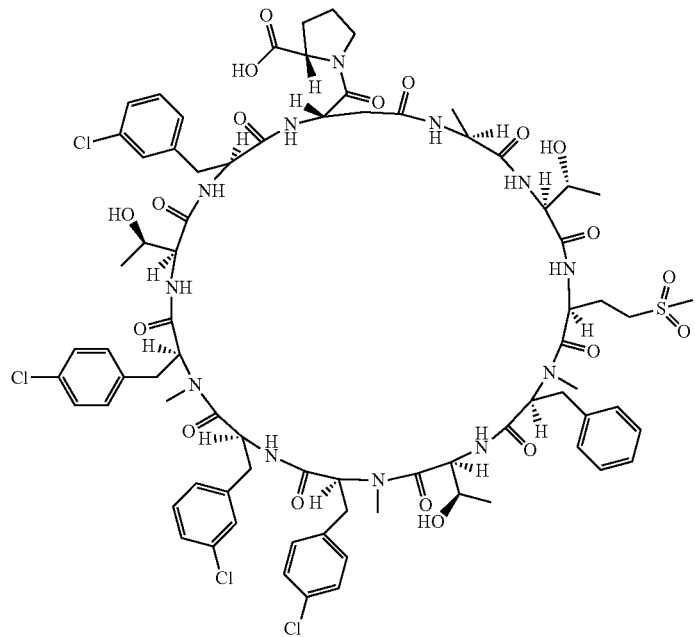 [SMILES: C[C@@H]1NC(=O)C[C@@H](C(=O)N2CCC[C@H]2C(=O)O)NC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2ccc(Cl)cc2)N(C)C(=O)[C@H]([C@@H](C)O)NC(=O)[C@H](Cc2ccccc2)N(C)C(=O)[C@H](CCS(C)(=O)=O)NC(=O)[C@H]([C@@H](C)O)NC1=O]
PS-10
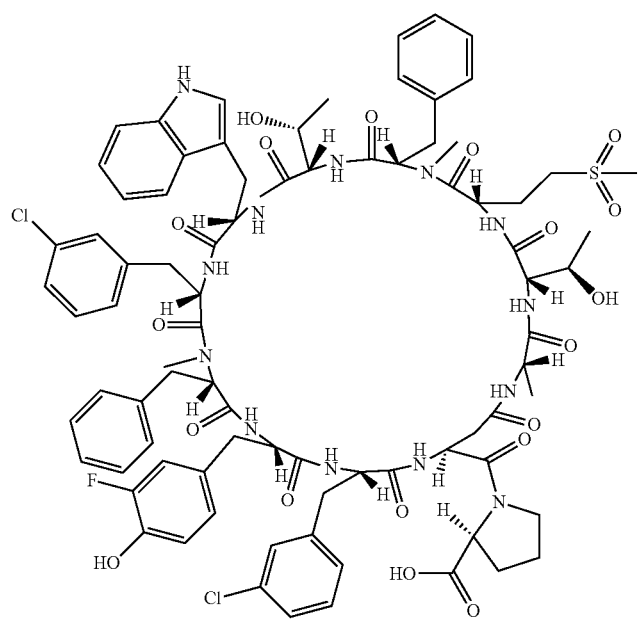 [SMILES: C[C@@H]1NC(=O)C[C@@H](C(=O)N2CCC[C@H]2C(=O)O)NC(=O)[C@H](Cc2cccc(Cl)c2)NC(=O)[C@H](Cc2ccc(O)c(F)c2)NC(=O)[C@H](Cc2ccccc2)N(C)C(=O)[C@H](Cc2cccc(Cl)c2)NC(=O)[C@H](Cc2c[nH]c3ccccc23)NC(=O)[C@H]([C@@H](C)O)NC(=O)[C@H](Cc2ccccc2)N(C)C(=O)[C@H](CCS(C)(=O)=O)NC(=O)[C@H]([C@@H](C)O)NC1=O]

TABLE 5-2-continued
PS-11
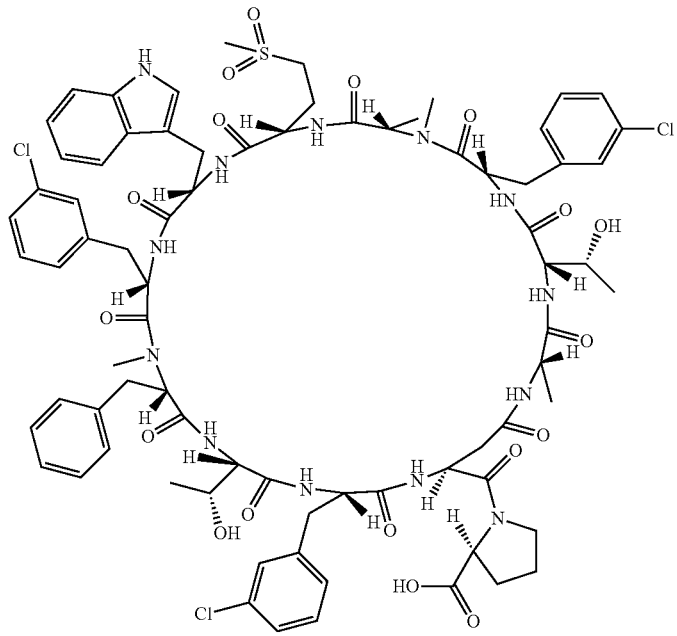 [SMILES: C[C@@H]1NC(=O)C[C@@H](C(=O)N2CCC[C@H]2C(=O)O)NC(=O)[C@H](Cc2cccc(Cl)c2)NC(=O)[C@H]([C@@H](C)O)NC(=O)[C@H](Cc2ccccc2)N(C)C(=O)[C@H](Cc2cccc(Cl)c2)NC(=O)[C@H](Cc2c[nH]c3ccccc23)NC(=O)[C@H](CCS(C)(=O)=O)NC(=O)[C@H](C)N(C)C(=O)[C@H](Cc2cccc(Cl)c2)NC(=O)[C@H]([C@@H](C)O)NC1=O]
PS-12
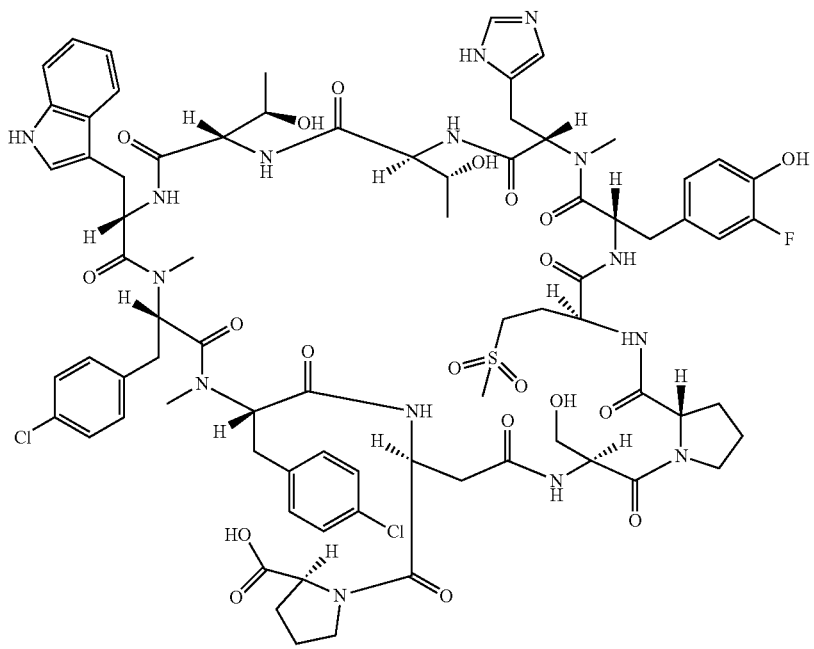 [SMILES: C[C@@H](O)[C@@H]1NC(=O)[C@H]([C@@H](C)O)NC(=O)[C@H](Cc2cnc[nH]2)N(C)C(=O)[C@H](Cc2ccc(O)c(F)c2)NC(=O)[C@H](CCS(C)(=O)=O)NC(=O)[C@@H]2CCCN2C(=O)[C@H](CO)NC(=O)C[C@@H](C(=O)N2CCC[C@H]2C(=O)O)NC(=O)[C@H](Cc2ccc(Cl)cc2)N(C)C(=O)[C@H](Cc2ccc(Cl)cc2)N(C)C(=O)[C@H](Cc2c[nH]c3ccccc23)NC1=O]

TABLE 5-2-continued
PS-13
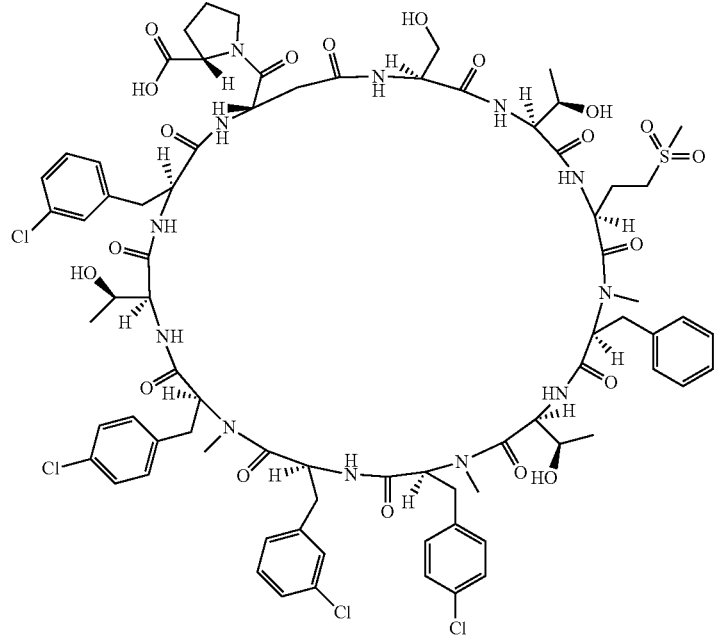 [SMILES: C[C@@H](O)[C@@H]1NC(=O)[C@H](CO)NC(=O)C[C@@H](C(=O)N2CCC[C@H]2C(=O)O)NC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2ccc(Cl)cc2)N(C)C(=O)[C@H]([C@@H](C)O)NC(=O)[C@H](Cc2ccccc2)N(C)C(=O)[C@H](CCS(C)(=O)=O)NC1=O]
PS-14
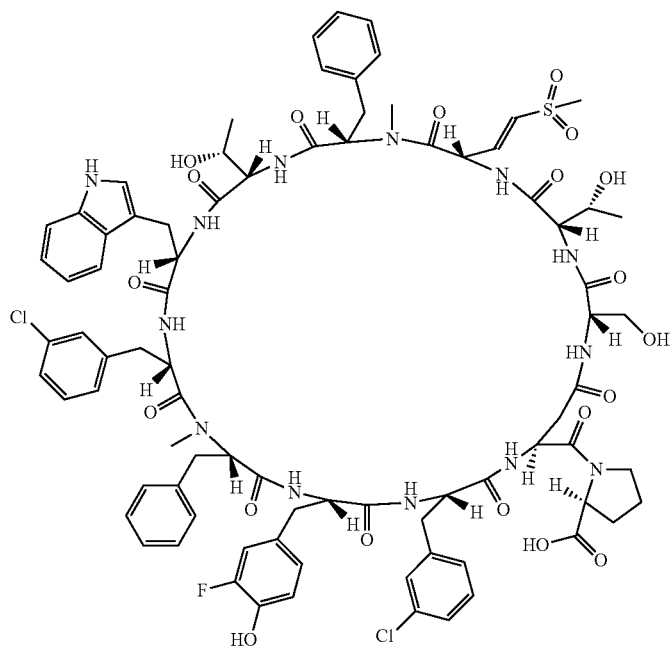 [SMILES: C[C@@H](O)[C@@H]1NC(=O)[C@H](CO)NC(=O)C[C@@H](C(=O)N2CCC[C@H]2C(=O)O)NC(=O)[C@H](Cc2cccc(Cl)c2)NC(=O)[C@H](Cc2ccc(O)c(F)c2)NC(=O)[C@H](Cc2ccccc2)N(C)C(=O)[C@H](Cc2cccc(Cl)c2)NC(=O)[C@H](Cc2c[nH]c3ccccc23)NC(=O)[C@H]([C@@H](C)O)NC(=O)[C@H](Cc2ccccc2)N(C)C(=O)[C@H](/C=C/S(C)(=O)=O)NC1=O]

TABLE 5-2-continued
PS-15
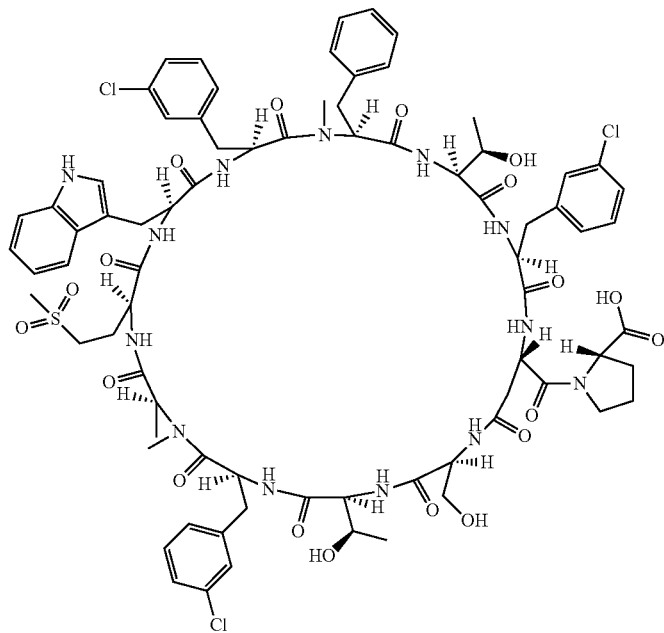 [SMILES: C[C@@H](O)[C@@H]1NC(=O)[C@H](CO)NC(=O)C[C@@H](C(=O)N2CCC[C@H]2C(=O)O)NC(=O)[C@H](Cc2cccc(Cl)c2)NC(=O)[C@H]([C@@H](C)O)NC(=O)[C@H](Cc2ccccc2)N(C)C(=O)[C@H](Cc2cccc(Cl)c2)NC(=O)[C@H](Cc2c[nH]c3ccccc23)NC(=O)[C@H](CCS(C)(=O)=O)NC(=O)[C@H](C)N(C)C(=O)[C@H](Cc2cccc(Cl)c2)NC1=O]
PS-16
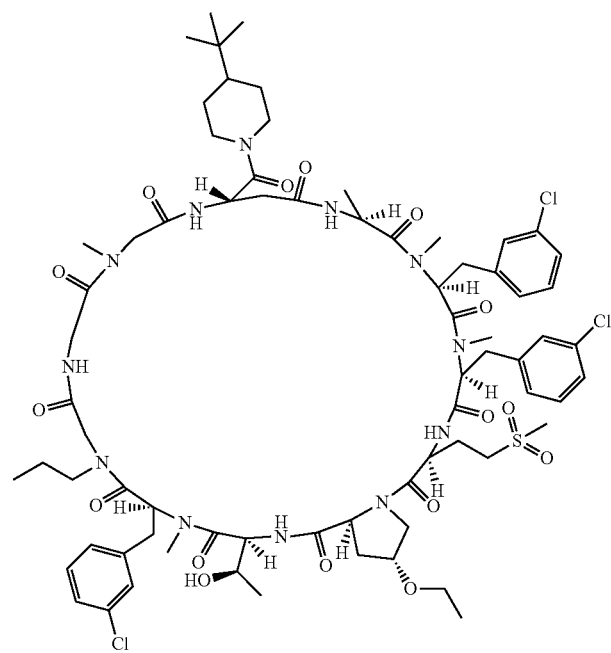 [SMILES: CCCN1CC(=O)NCCC(=O)N(C)CC(=O)N[C@H](C(=O)N2CCC(C(C)(C)C)CC2)CC(=O)N[C@@H](C)C(=O)N(C)[C@@H](Cc2cccc(Cl)c2)C(=O)N(C)[C@@H](Cc2cccc(Cl)c2)C(=O)N[C@@H](CCS(C)(=O)=O)C(=O)N2C[C@H](OCC)C[C@H]2C(=O)N[C@@H]([C@@H](C)O)C(=O)N(C)[C@@H](Cc2cccc(Cl)c2)C1=O]

TABLE 5-2-continued
PS-17
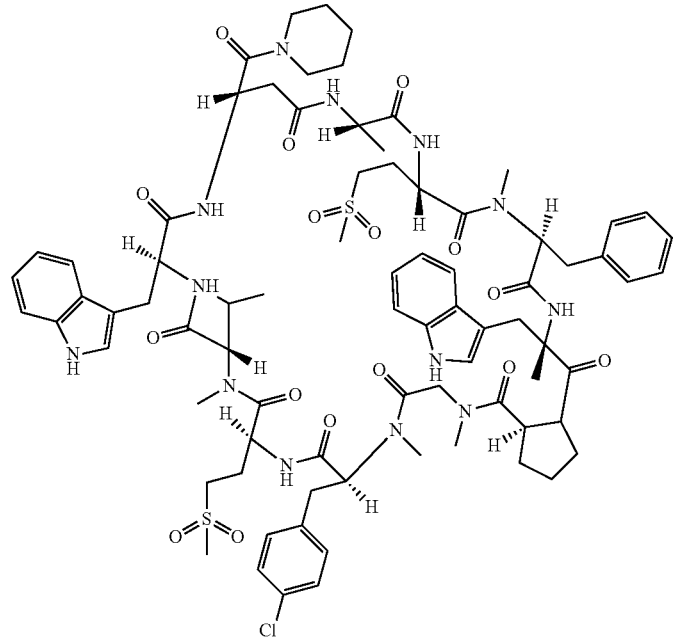 [SMILES: CC1[C@H]2C(=O)N1[C@@H](Cc1c[nH]c3ccccc13)C(=O)N[C@H](C(=O)N1CCCCC1)CC(=O)N[C@@H](C)C(=O)N[C@@H](CCS(C)(=O)=O)C(=O)N(C)[C@@H](Cc1ccccc1)C(=O)N[C@@](C)(Cc1c[nH]c3ccccc13)C(=O)C1CCC[C@H]1C(=O)N(C)CC(=O)N(C)[C@@H](Cc1ccc(Cl)cc1)C(=O)N[C@@H](CCS(C)(=O)=O)C(=O)N2C]
PS-18
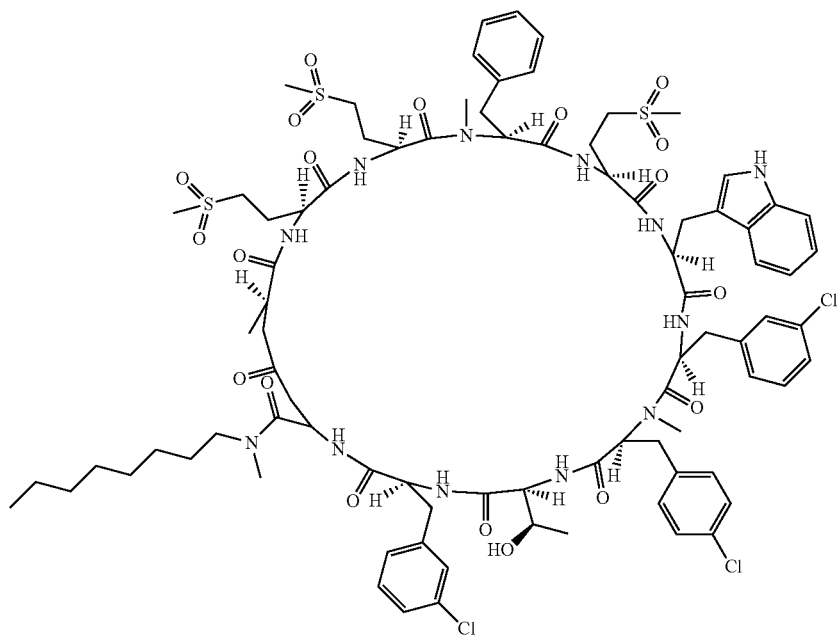 [SMILES: CCCCCCCCN(C)C(=O)C1CC(=O)C[C@@H](C)C(=O)N[C@@H](CCS(C)(=O)=O)C(=O)N[C@@H](CCS(C)(=O)=O)C(=O)N(C)[C@@H](Cc2ccccc2)C(=O)N[C@@H](CCS(C)(=O)=O)C(=O)N[C@@H](Cc2c[nH]c3ccccc23)C(=O)N[C@@H](Cc2cccc(Cl)c2)C(=O)N(C)[C@@H](Cc2ccc(Cl)cc2)C(=O)N[C@@H]([C@@H](C)O)C(=O)N[C@@H](Cc2cccc(Cl)c2)C(=O)N1]

TABLE 5-2-continued
PS-19
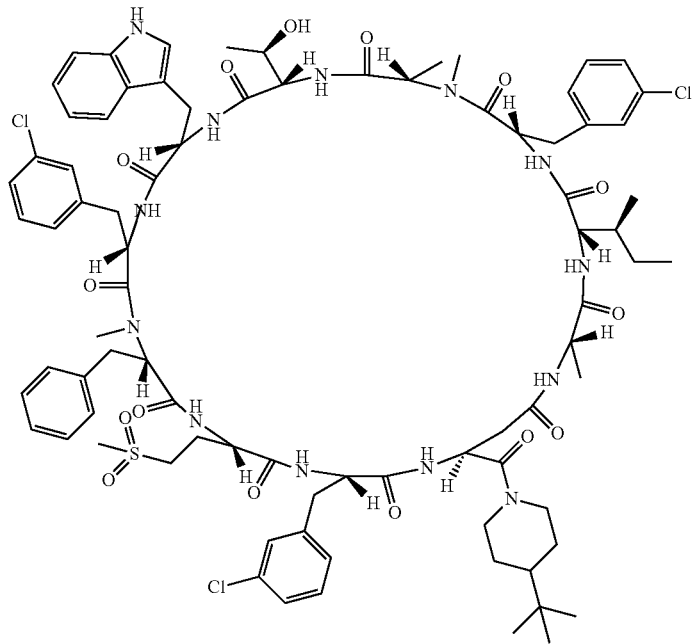
PS-20
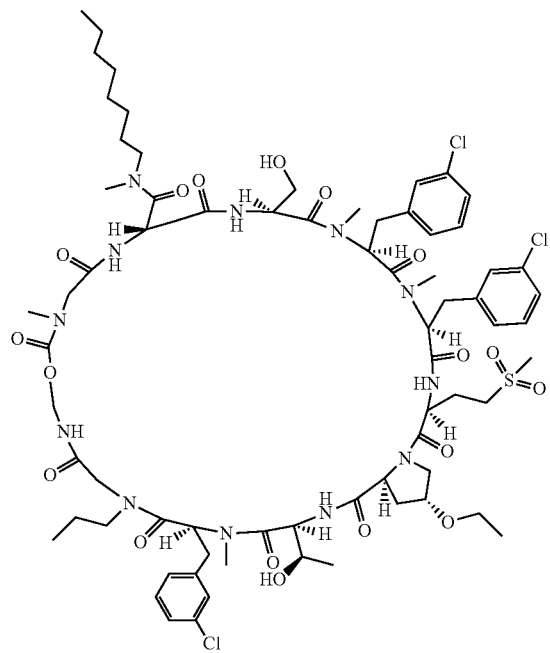 [SMILES: CCCCCCCCN(C)C(=O)[C@@H]1CC(=O)N[C@@H](CO)C(=O)N(C)[C@@H](Cc2cccc(Cl)c2)C(=O)N(C)[C@@H](Cc2cccc(Cl)c2)C(=O)N[C@@H](CCS(C)(=O)=O)C(=O)N2C[C@H](OCC)C[C@H]2C(=O)N[C@@H]([C@@H](C)O)C(=O)N(C)[C@@H](Cc2cccc(Cl)c2)C(=O)N(CCC)CC(=O)NCOC(=O)N(C)CC(=O)N1]

TABLE 5-2-continued
PS-21
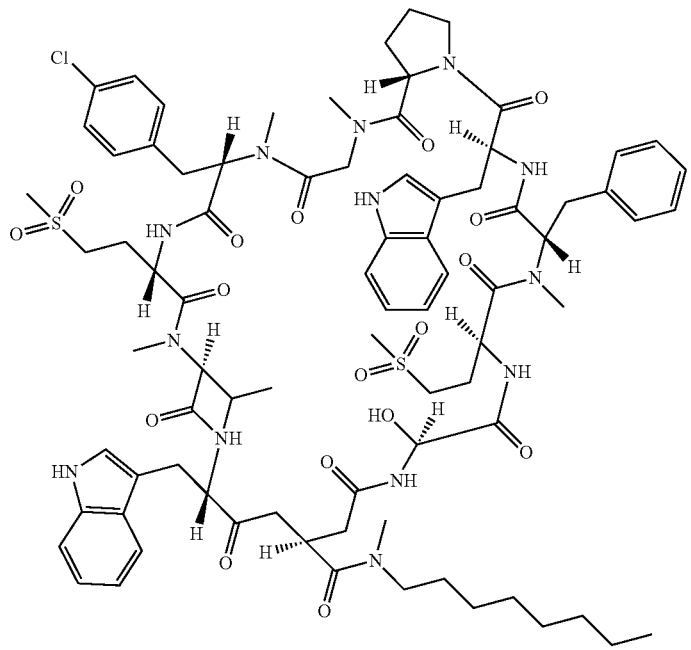 [SMILES: CCCCCCCCN(C)C(=O)[C@@H]1CC(=O)N[C@@H](O)CC(=O)N[C@@H](CCS(C)(=O)=O)C(=O)N(C)[C@@H](Cc2ccccc2)C(=O)N[C@@H](Cc2c[nH]c3ccccc23)C(=O)N2CCC[C@H]2C(=O)N(C)CC(=O)N(C)[C@@H](Cc2ccc(Cl)cc2)C(=O)N[C@@H](CCS(C)(=O)=O)C(=O)N(C)[C@@H]2C(=O)N(C2C)[C@@H](Cc2c[nH]c3ccccc23)C(=O)C1]
PS-22
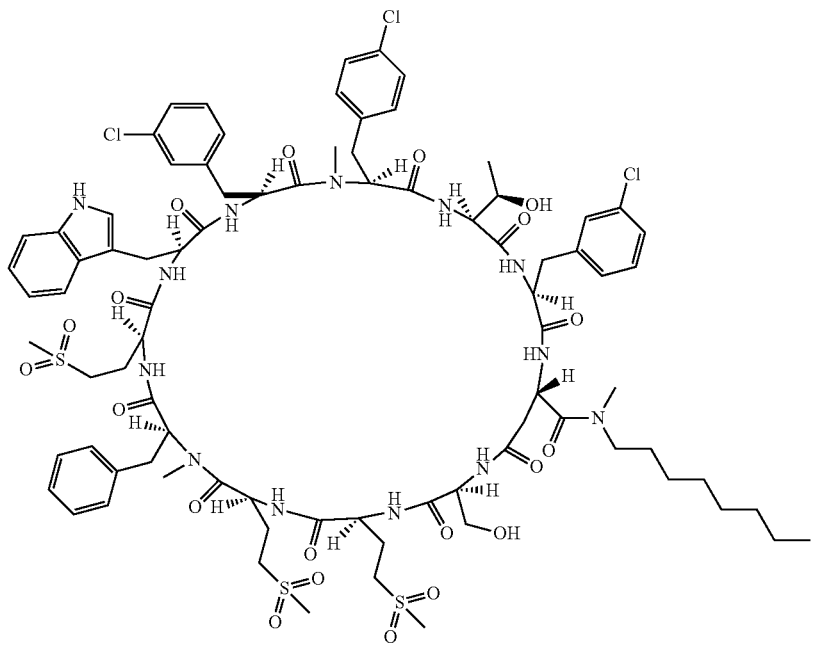 [SMILES: CCCCCCCCN(C)C(=O)[C@@H]1CC(=O)N[C@@H](CO)C(=O)N[C@@H](CCS(C)(=O)=O)C(=O)N[C@@H](CCS(C)(=O)=O)C(=O)N(C)[C@@H](Cc2ccccc2)C(=O)N[C@@H](CCS(C)(=O)=O)C(=O)N[C@@H](Cc2c[nH]c3ccccc23)C(=O)N[C@@H](Cc2cccc(Cl)c2)C(=O)N(C)[C@@H](Cc2ccc(Cl)cc2)C(=O)N[C@@H]([C@@H](C)O)C(=O)N[C@@H](Cc2cccc(Cl)c2)C(=O)N1]

TABLE 5-2-continued
PS-23
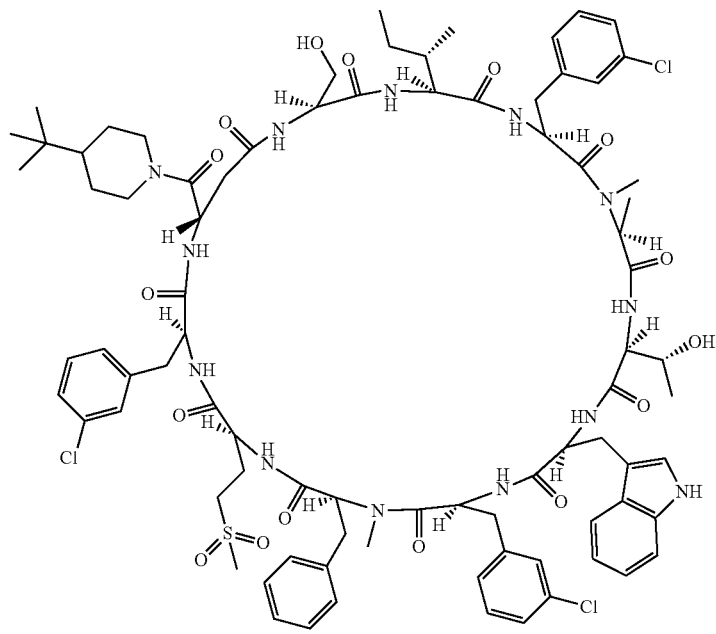 [SMILES: CC[C@H](C)[C@@H]1NC(=O)[C@H](CO)NC(=O)C[C@@H](C(=O)N2CCC(C(C)(C)C)CC2)NC(=O)[C@H](Cc2cccc(Cl)c2)NC(=O)[C@H](CCS(C)(=O)=O)NC(=O)[C@H](Cc2ccccc2)N(C)C(=O)[C@H](Cc2cccc(Cl)c2)NC(=O)[C@H](Cc2c[nH]c3ccccc23)NC(=O)[C@H]([C@@H](C)O)NC(=O)[C@H](C)N(C)C(=O)[C@H](Cc2cccc(Cl)c2)NC1=O]
PS-24
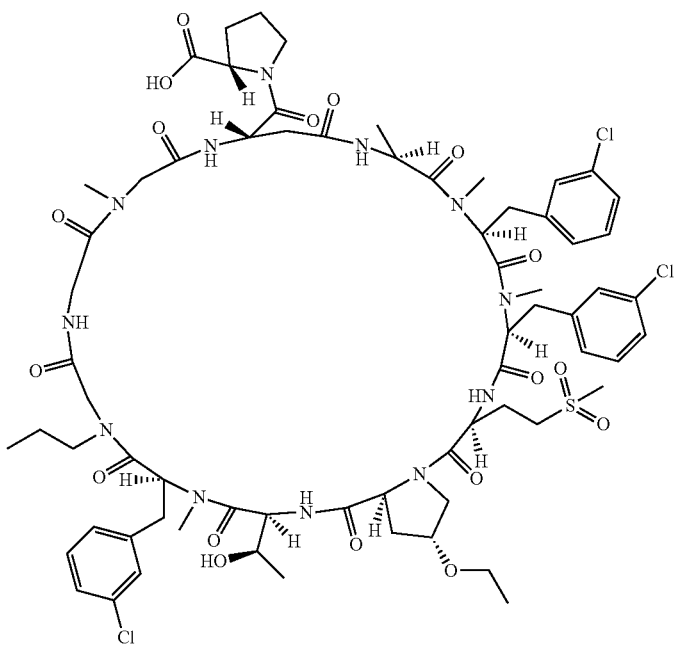 [SMILES: CCCN1CC(=O)NCCC(=O)N(C)CC(=O)N[C@H](C(=O)N2CCC[C@H]2C(=O)O)CC(=O)N[C@@H](C)C(=O)N(C)[C@@H](Cc2cccc(Cl)c2)C(=O)N(C)[C@@H](Cc2cccc(Cl)c2)C(=O)N[C@@H](CCS(C)(=O)=O)C(=O)N2C[C@H](OCC)C[C@H]2C(=O)N[C@@H]([C@@H](C)O)C(=O)N(C)[C@@H](Cc2cccc(Cl)c2)C1=O]

TABLE 5-2-continued
PS-25
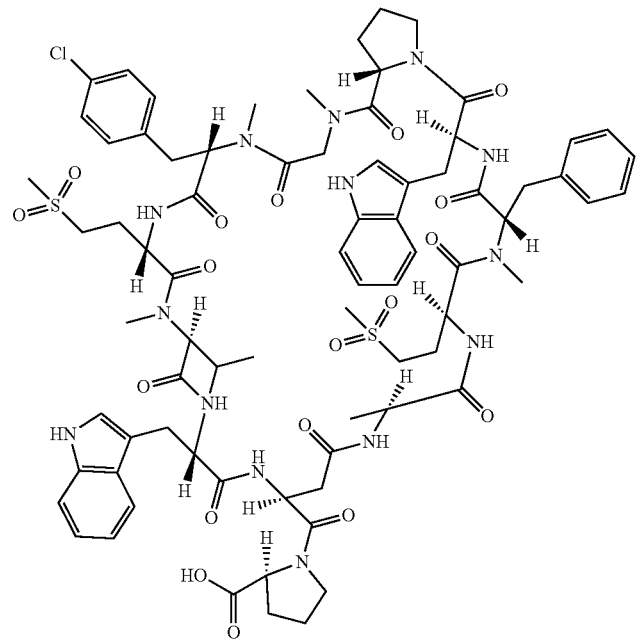 [SMILES: CC1[C@H]2C(=O)N1[C@@H](Cc1c[nH]c3ccccc13)C(=O)N[C@H](C(=O)N1CCC[C@H]1C(=O)O)CC(=O)N[C@@H](C)CC(=O)N[C@@H](CCS(C)(=O)=O)C(=O)N(C)[C@@H](Cc1ccccc1)C(=O)N[C@@H](Cc1c[nH]c3ccccc13)C(=O)N1CCC[C@H]1C(=O)N(C)CC(=O)N(C)[C@@H](Cc1ccc(Cl)cc1)C(=O)N[C@@H](CCS(C)(=O)=O)C(=O)N2C]
PS-26
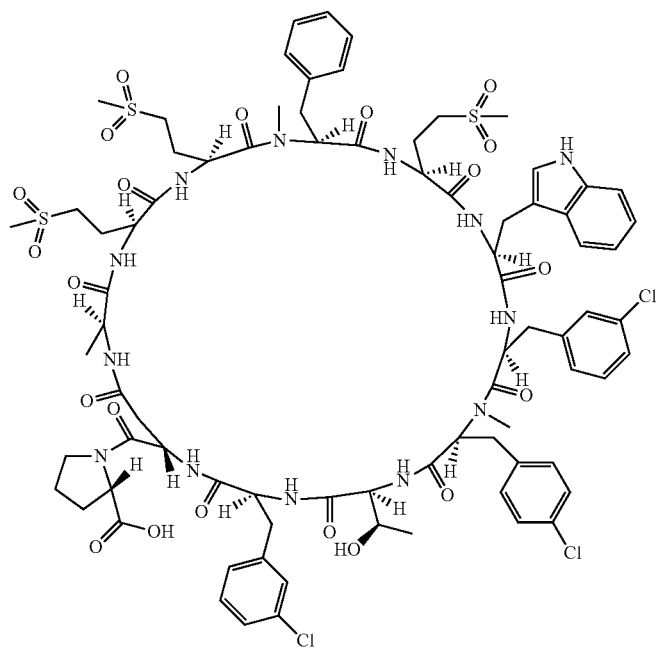 [SMILES: C[C@@H]1NC(=O)C[C@@H](C(=O)N2CCC[C@H]2C(=O)O)NC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H](CCS(C)(=O)=O)NC(=O)[C@H](Cc2ccccc2)N(C)C(=O)[C@H](CCS(C)(=O)=O)NC(=O)[C@H](CCS(C)(=O)=O)NC1=O]

TABLE 5-2-continued
PS-27
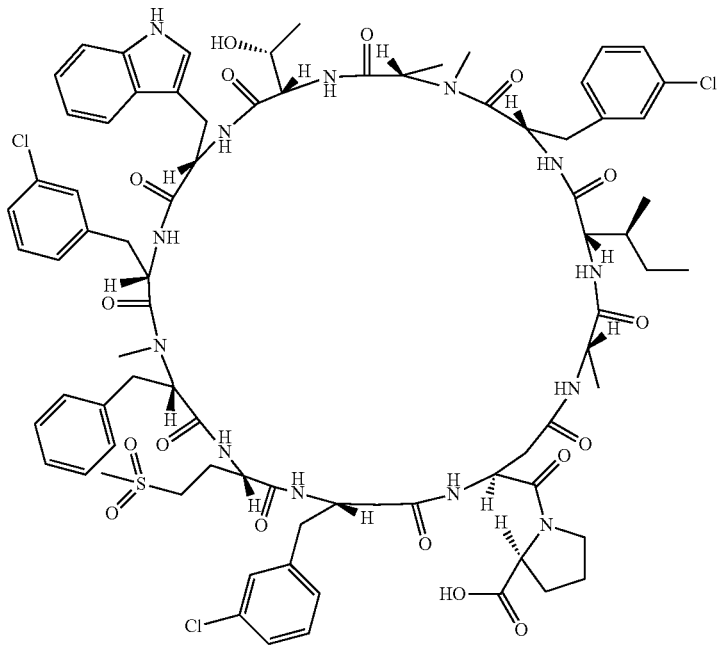
PS-28
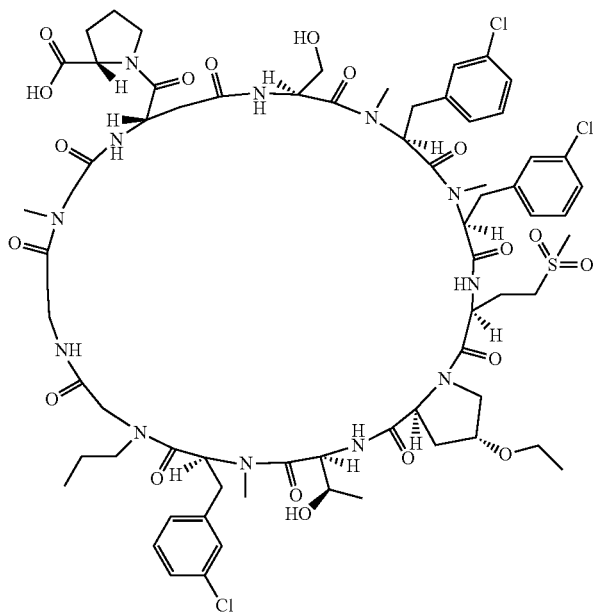 [SMILES: CCCN1CC(=O)NCCC(=O)N(C)CC(=O)N[C@H](C(=O)N2CCC[C@H]2C(=O)O)CC(=O)N[C@@H](CO)C(=O)N(C)[C@@H](Cc2cccc(Cl)c2)C(=O)N(C)[C@@H](Cc2cccc(Cl)c2)C(=O)N[C@@H](CCS(C)(=O)=O)C(=O)N2C[C@H](OCC)C[C@H]2C(=O)N[C@@H]([C@@H](C)O)C(=O)N(C)[C@@H](Cc2cccc(Cl)c2)C1=O]

TABLE 5-2-continued
PS-29
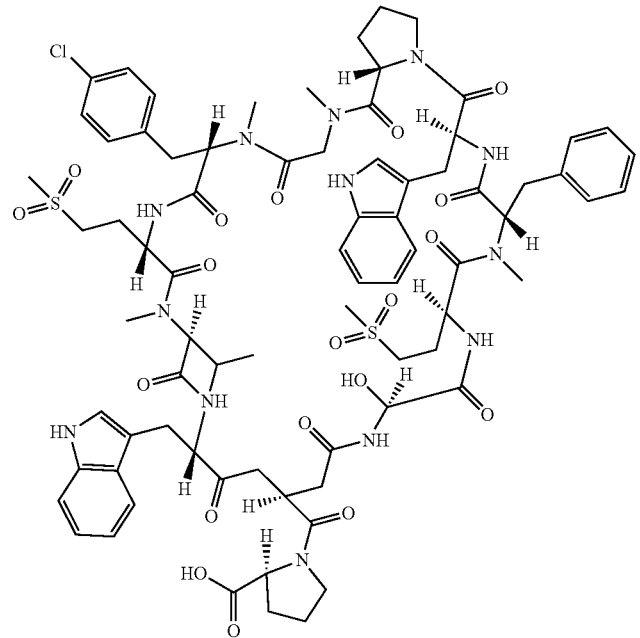 [SMILES: CC1[C@H]2C(=O)N1[C@@H](Cc1c[nH]c3ccccc13)C(=O)C[C@H](C(=O)N1CCC[C@H]1C(=O)O)CC(=O)N[C@@H](O)CC(=O)N[C@@H](CCS(C)(=O)=O)C(=O)N(C)[C@@H](Cc1ccccc1)C(=O)N[C@@H](Cc1c[nH]c3ccccc13)C(=O)N1CCC[C@H]1C(=O)N(C)CC(=O)N(C)[C@@H](Cc1ccc(Cl)cc1)C(=O)N[C@@H](CCS(C)(=O)=O)C(=O)N2C]
PS-30
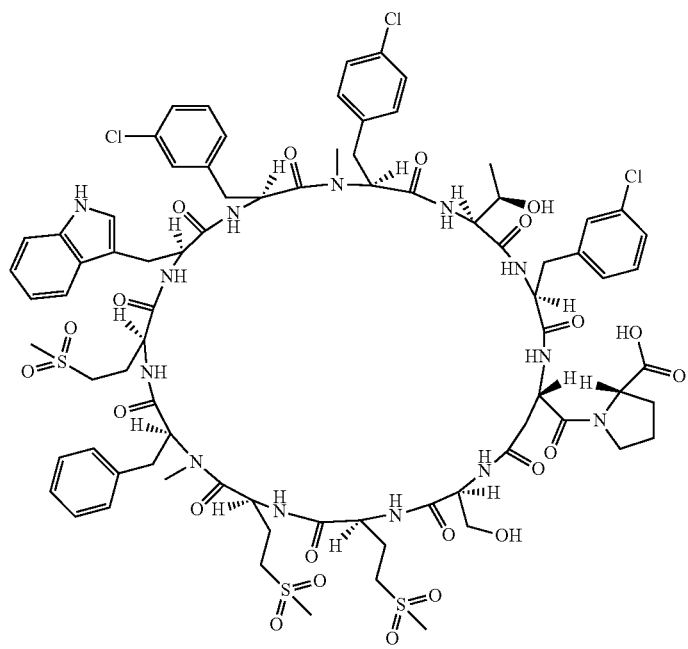 [SMILES: C[C@@H](O)[C@@H]1NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H](CCS(C)(=O)=O)NC(=O)[C@H](Cc2ccccc2)N(C)C(=O)[C@H](CCS(C)(=O)=O)NC(=O)[C@H](CCS(C)(=O)=O)NC(=O)[C@H](CO)NC(=O)C[C@@H](C(=O)N2CCC[C@H]2C(=O)O)NC(=O)[C@H](Cc2cccc(Cl)c2)NC1=O]

TABLE 5-2-continued
PS-31
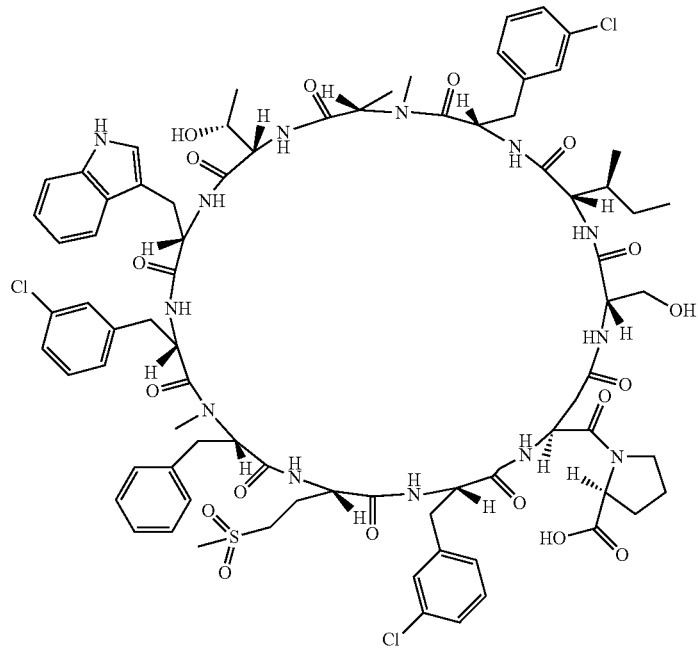 [SMILES: CC[C@H](C)[C@@H]1NC(=O)[C@H](CO)NC(=O)C[C@@H](C(=O)N2CCC[C@H]2C(=O)O)NCC(=O)[C@H](Cc2cccc(Cl)c2)NC(=O)[C@H](CCS(C)(=O)=O)NC(=O)[C@H](Cc2ccccc2)N(C)C(=O)[C@H](Cc2cccc(Cl)c2)NC(=O)[C@H](Cc2c[nH]c3ccccc23)NC(=O)[C@H]([C@@H](C)O)NC(=O)[C@H](C)N(C)C(=O)[C@H](Cc2cccc(Cl)c2)NC1=O]
PS-32
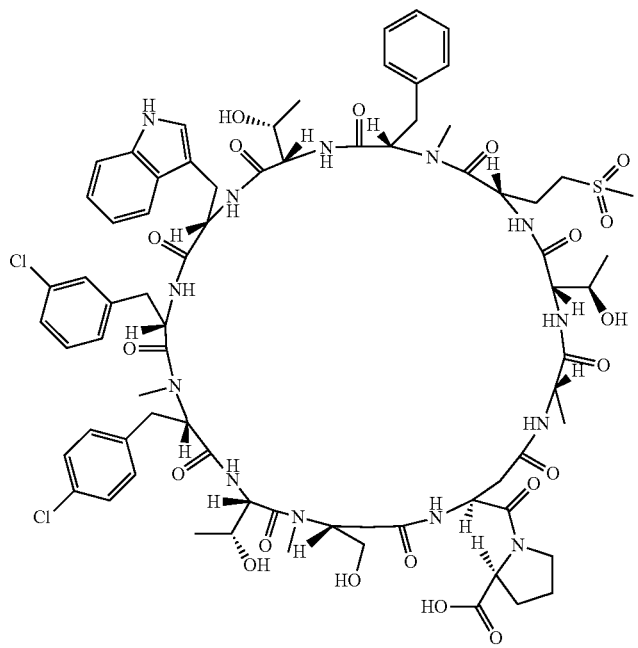

TABLE 5-2-continued
PS-33
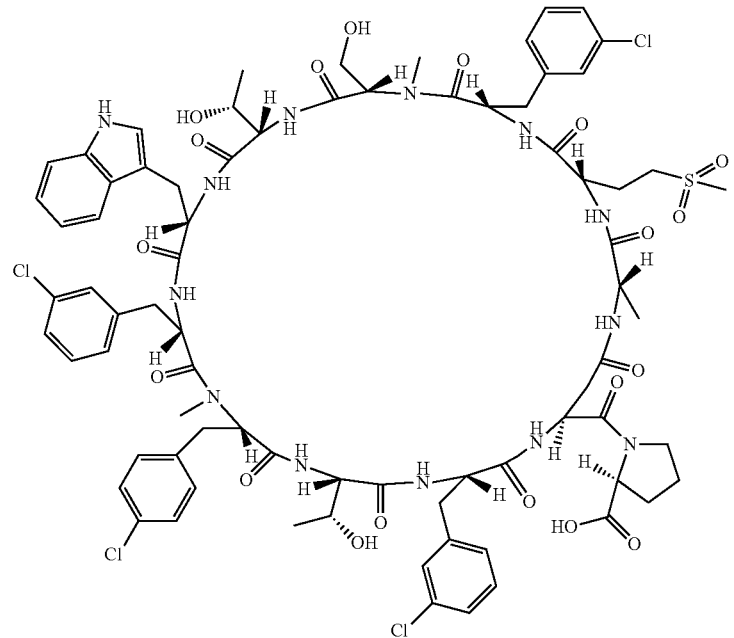 [SMILES: C[C@@H]1NC(=O)C[C@@H](C(=O)N2CCC[C@H]2C(=O)O)NCC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H]([C@@H](C)O)NC(=O)[C@H](CO)N(C)C(=O)[C@H](Cc2cccc(Cl)c2)NC(=O)[C@H](CCS(C)(=O)=O)NC1=O]
PS-34
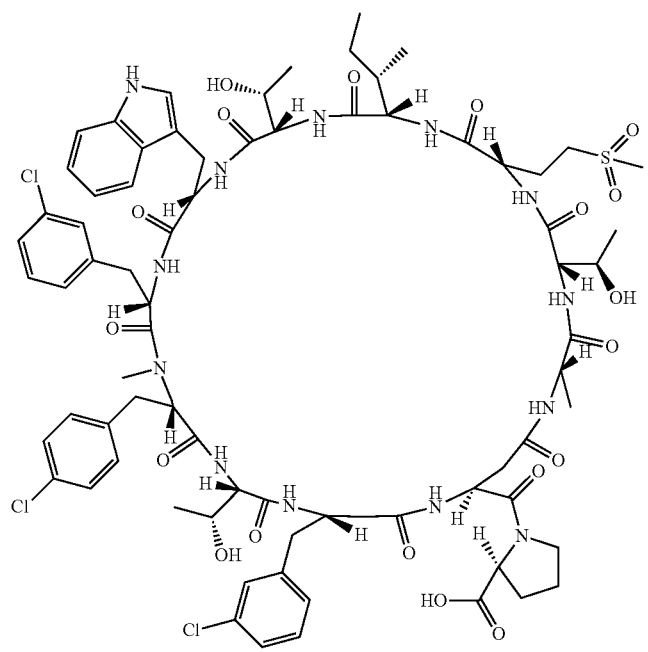

TABLE 5-2-continued
PS-35
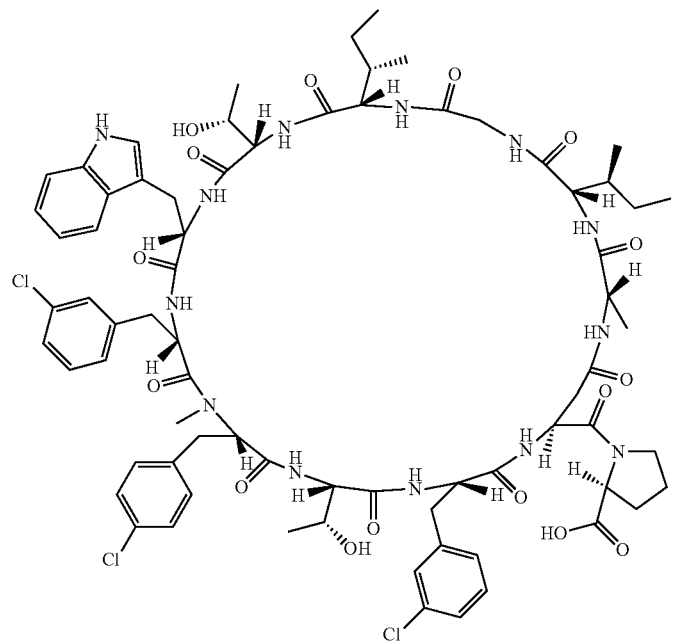 [SMILES: CC[C@H](C)[C@@H]1NC(=O)CNC(=O)[C@H]([C@@H](C)CC)NC(=O)[C@H](C)NC(=O)C[C@@H](C(=O)N2CCC[C@H]2C(=O)O)NCC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H]([C@@H](C)O)NC1=O]
PS-36
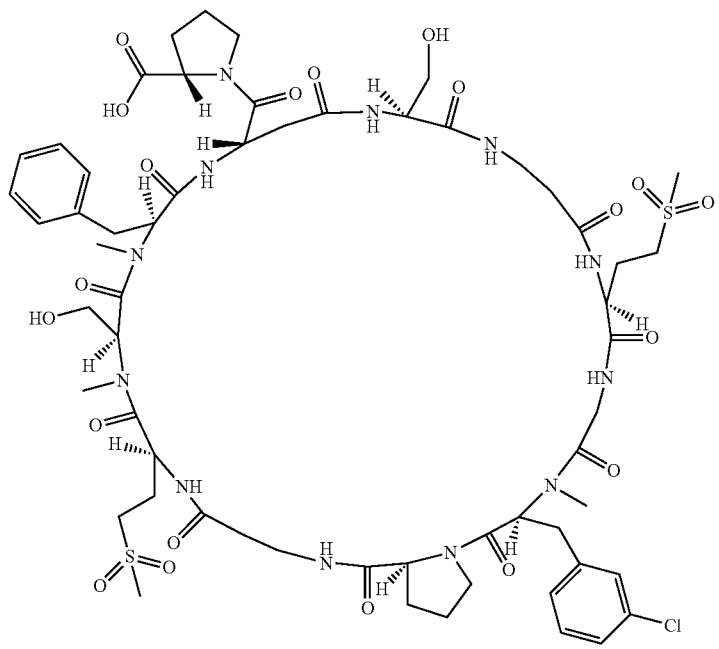 [SMILES: CN1C(=O)CNC(=O)[C@H](CCS(C)(=O)=O)NC(=O)CCNC(=O)[C@H](CO)NC(=O)C[C@@H](C(=O)N2CCC[C@H]2C(=O)O)NC(=O)[C@H](Cc2ccccc2)N(C)C(=O)[C@H](CO)N(C)C(=O)[C@H](CCS(C)(=O)=O)NC(=O)CCNC(=O)[C@@H]2CCCN2C(=O)[C@@H]1Cc1cccc(Cl)c1]

TABLE 5-2-continued
PS-37
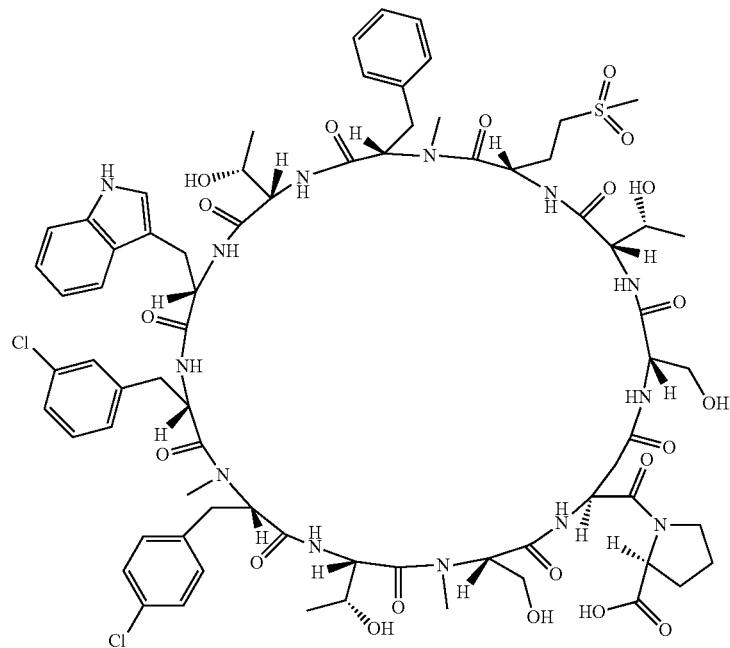 [SMILES: C[C@@H](O)[C@@H]1NC(=O)[C@H](CO)NC(=O)C[C@@H](C(=O)N2CCC[C@H]2C(=O)O)NCC(=O)[C@H](CO)N(C)C(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H]([C@@H](C)O)NC(=O)[C@H](Cc2ccccc2)N(C)C(=O)[C@H](CCS(C)(=O)=O)NC1=O]
PS-38
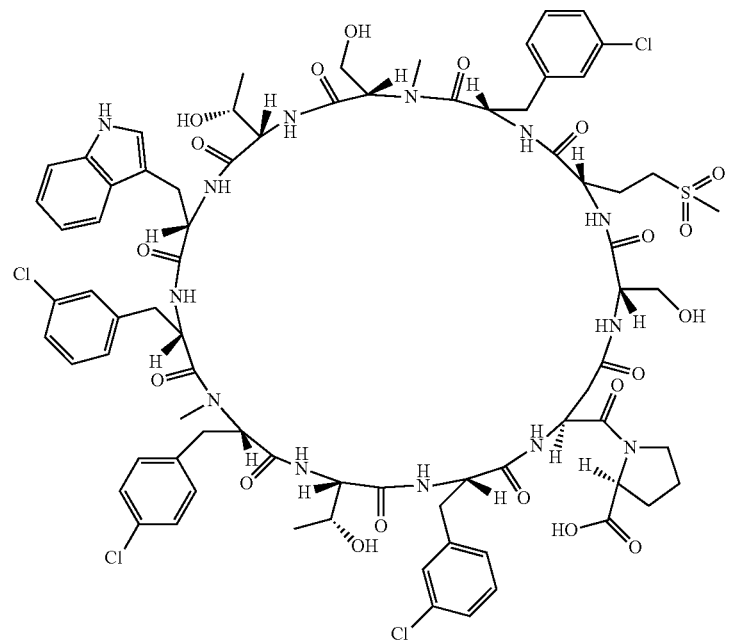 [SMILES: C[C@@H](O)[C@@H]1NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H]([C@@H](C)O)NC(=O)[C@H](CO)N(C)C(=O)[C@H](Cc2cccc(Cl)c2)NC(=O)[C@H](CCS(C)(=O)=O)NC(=O)[C@H](CO)NC(=O)C[C@@H](C(=O)N2CCC[C@H]2C(=O)O)NCC(=O)[C@H](Cc2cccc(Cl)c2)NC1=O]

TABLE 5-2-continued
PS-39
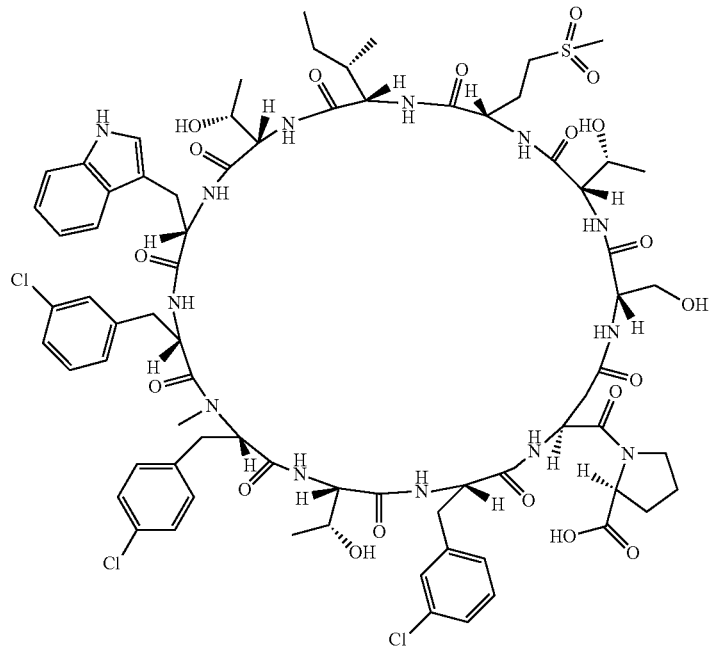 [SMILES: CC[C@H](C)[C@@H]1NC(=O)[C@H](CCS(C)(=O)=O)NC(=O)[C@H]([C@@H](C)O)NC(=O)[C@H](CO)NC(=O)C[C@@H](C(=O)N2CCC[C@H]2C(=O)O)NCC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H]([C@@H](C)O)NC1=O]
PS-40
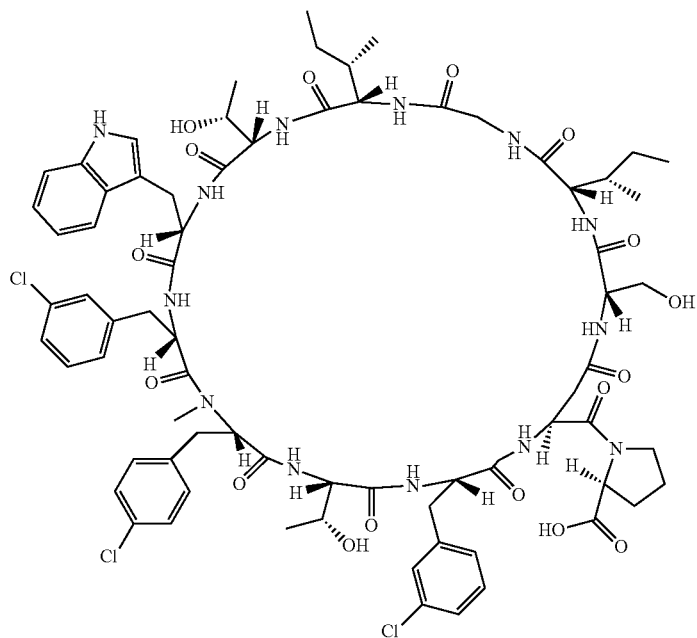 [SMILES: CC[C@H](C)[C@@H]1NC(=O)CNC(=O)[C@H]([C@@H](C)CC)NC(=O)[C@H](CO)NC(=O)C[C@@H](C(=O)N2CCC[C@H]2C(=O)O)NCC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H]([C@@H](C)O)NC1=O]

TABLE 5-2-continued
PS-41
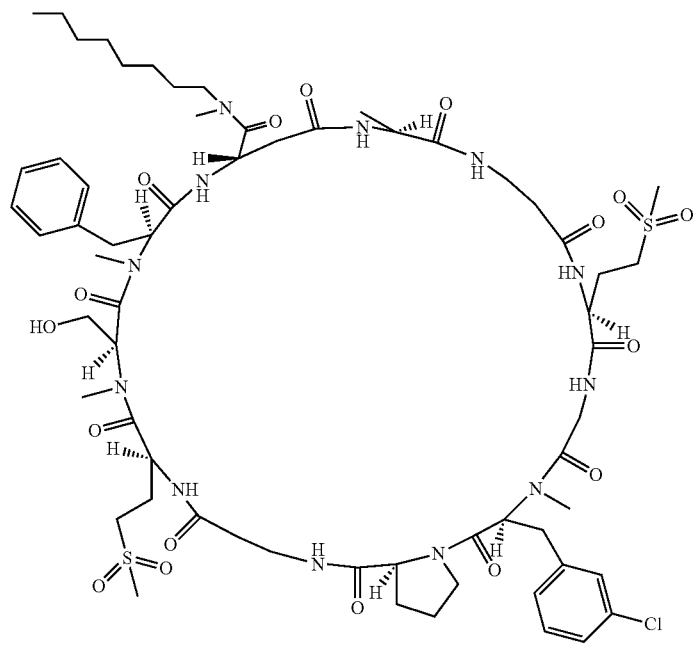 [SMILES: CCCCCCCCN(C)C(=O)[C@@H]1CC(=O)N[C@@H](C)C(=O)NCCC(=O)N[C@@H](CCS(C)(=O)=O)C(=O)NCC(=O)N(C)[C@@H](Cc2cccc(Cl)c2)C(=O)N2CCC[C@H]2C(=O)NCCC(=O)N[C@@H](CCS(C)(=O)=O)C(=O)N(C)[C@@H](CO)C(=O)N(C)[C@@H](Cc2ccccc2)C(=O)N1]
PS-42
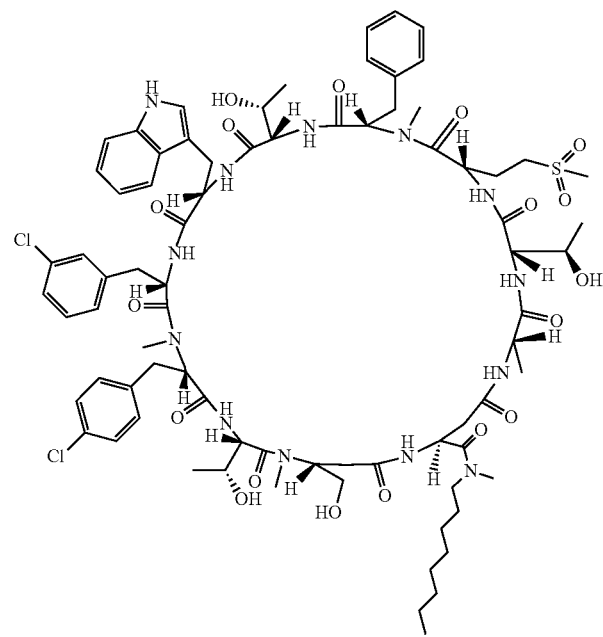

TABLE 5-2-continued
PS-43
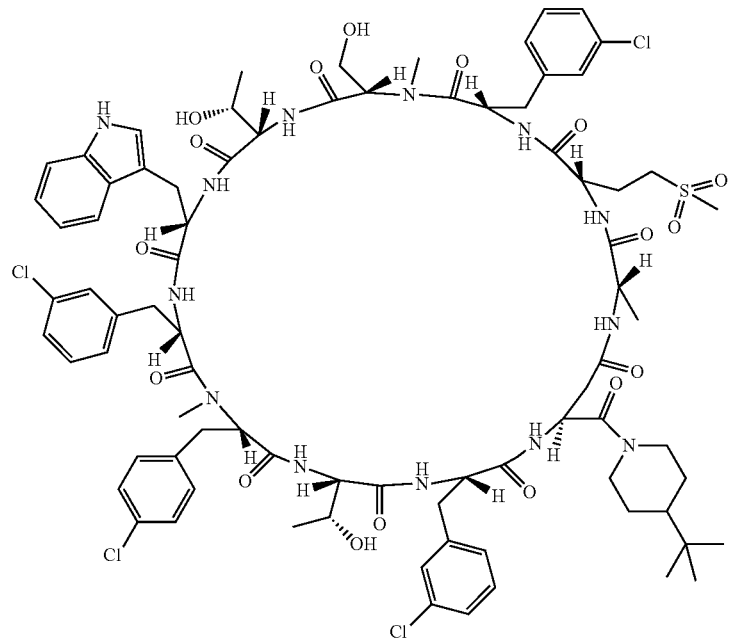 [SMILES: C[C@@H]1NC(=O)C[C@@H](C(=O)N2CCC(C(C)(C)C)CC2)NCC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H]([C@@H](C)O)NC(=O)[C@H](CO)N(C)C(=O)[C@H](Cc2cccc(Cl)c2)NC(=O)[C@H](CCS(C)(=O)=O)NC1=O]
PS-44
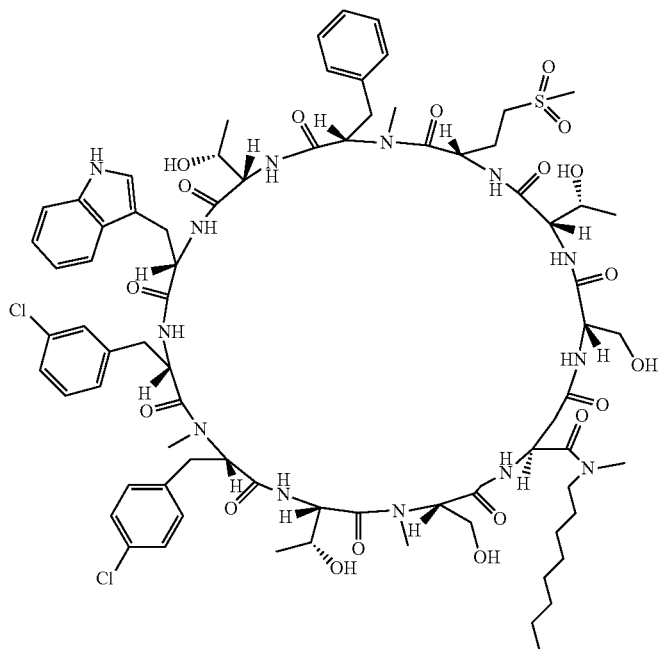 [SMILES: CCCCCCCCN(C)C(=O)[C@@H]1CC(=O)N[C@@H](CO)C(=O)N[C@@H]([C@@H](C)O)C(=O)N[C@@H](CCS(C)(=O)=O)C(=O)N(C)[C@@H](Cc2ccccc2)C(=O)N[C@@H]([C@@H](C)O)C(=O)N[C@@H](Cc2c[nH]c3ccccc23)C(=O)N[C@@H](Cc2cccc(Cl)c2)C(=O)N(C)[C@@H](Cc2ccc(Cl)cc2)C(=O)N[C@@H]([C@@H](C)O)C(=O)N(C)[C@@H](CO)C(=O)CN1]

TABLE 5-2-continued
PS-45
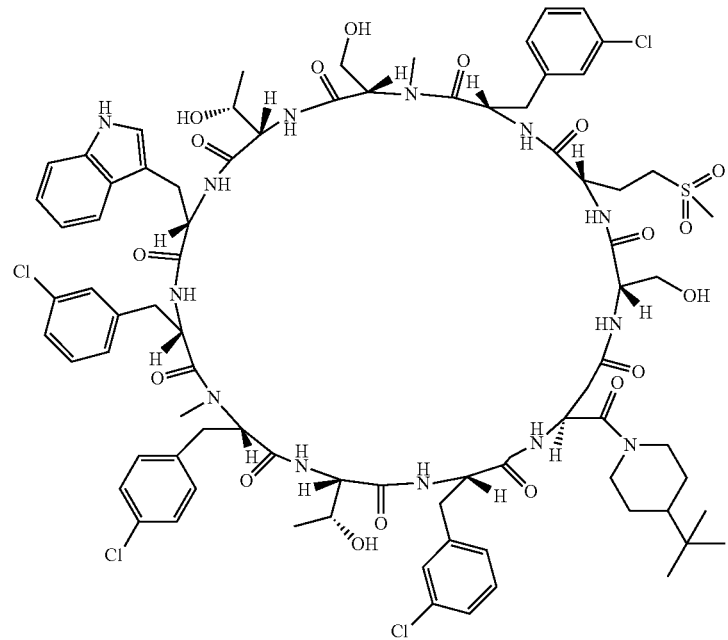 [SMILES: C[C@@H](O)[C@@H]1NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H]([C@@H](C)O)NC(=O)[C@H](CO)N(C)C(=O)[C@H](Cc2cccc(Cl)c2)NC(=O)[C@H](CCS(C)(=O)=O)NC(=O)[C@H](CO)NC(=O)C[C@@H](C(=O)N2CCC(C(C)(C)C)CC2)NCC(=O)[C@H](Cc2cccc(Cl)c2)NC1=O]
PS-46
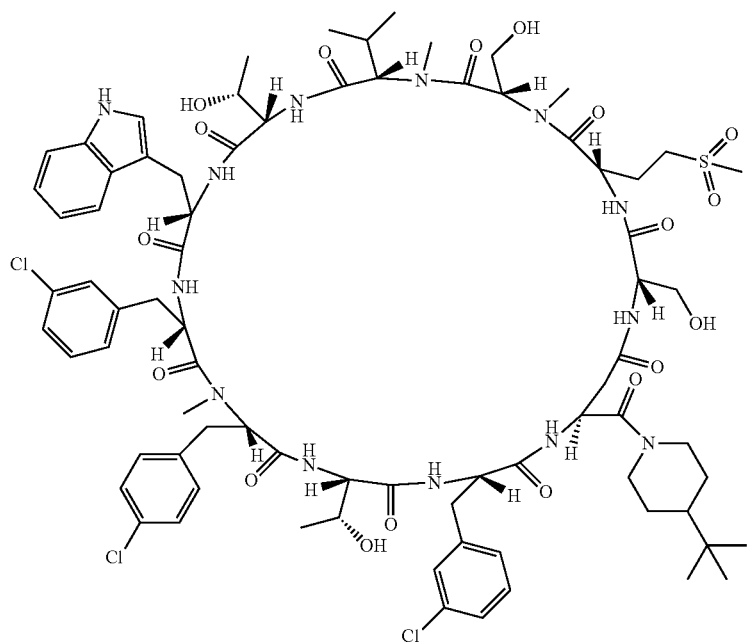 [SMILES: CC(C)[C@H]1C(=O)N[C@@H]([C@@H](C)O)C(=O)N[C@@H](Cc2c[nH]c3ccccc23)C(=O)N[C@@H](Cc2cccc(Cl)c2)C(=O)N(C)[C@@H](Cc2ccc(Cl)cc2)C(=O)N[C@@H]([C@@H](C)O)C(=O)N[C@@H](Cc2cccc(Cl)c2)C(=O)CN[C@H](C(=O)N2CCC(C(C)(C)C)CC2)CC(=O)N[C@@H](CO)C(=O)N[C@@H](CCS(C)(=O)=O)C(=O)N(C)[C@@H](CO)C(=O)N1C]

TABLE 5-2-continued
PS-47
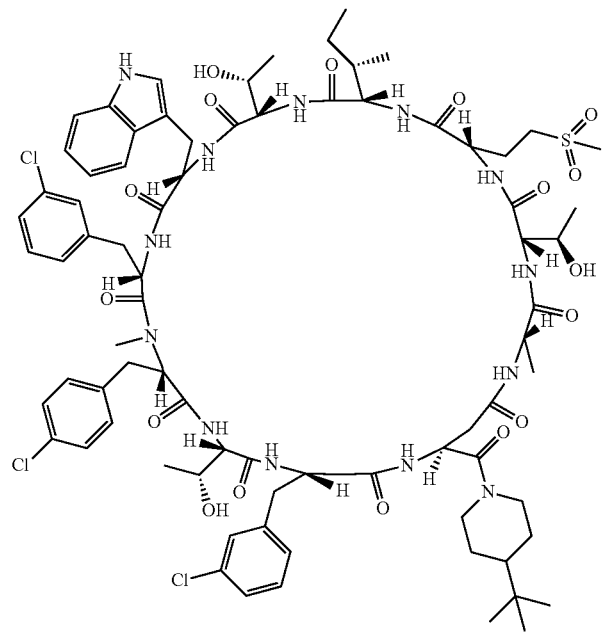
PS-48
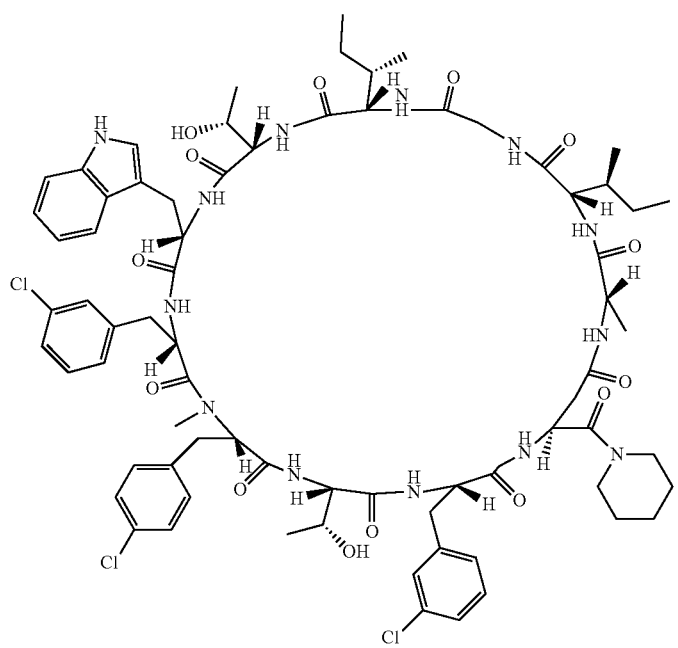 [SMILES: CC[C@H](C)[C@@H]1NC(=O)CNC(=O)[C@H]([C@@H](C)CC)NC(=O)[C@H](C)NC(=O)C[C@@H](C(=O)N2CCCCC2)NCC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H]([C@@H](C)O)NC1=O]

TABLE 5-2-continued
PS-49
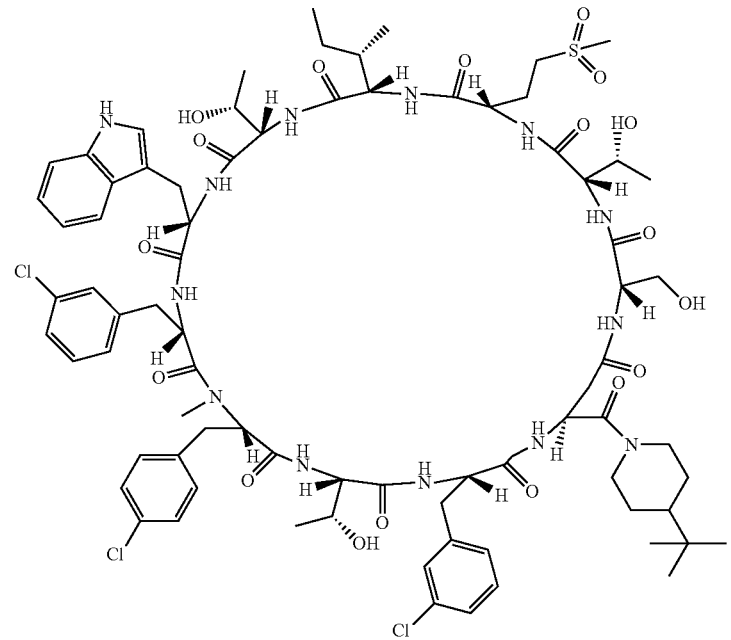 [SMILES: CC[C@H](C)[C@@H]1NC(=O)[C@H](CCS(C)(=O)=O)NC(=O)[C@H]([C@@H](C)O)NC(=O)[C@H](CO)NC(=O)C[C@@H](C(=O)N2CCC(C(C)(C)C)CC2)NCC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H]([C@@H](C)O)NC1=O]
PS-50
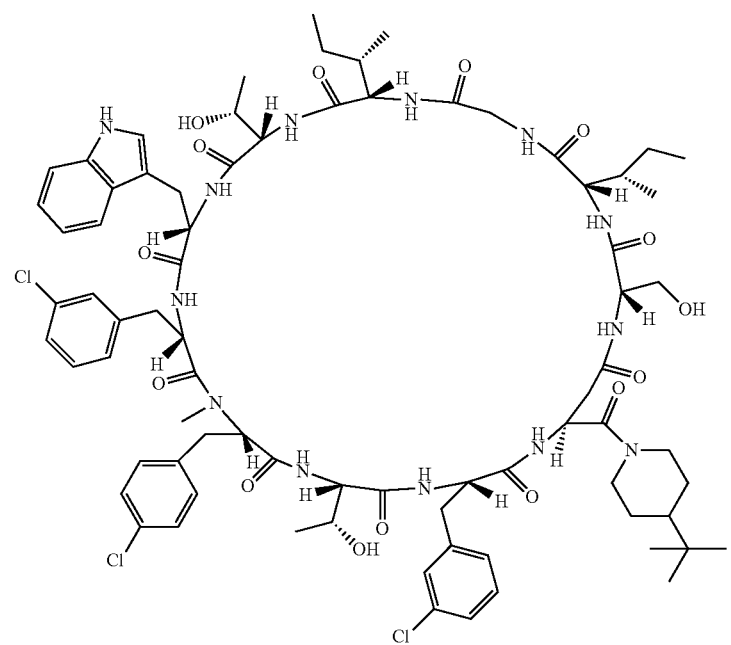 [SMILES: CC[C@H](C)[C@@H]1NC(=O)CNC(=O)[C@H]([C@@H](C)CC)NC(=O)[C@H](CO)NC(=O)C[C@@H](C(=O)N2CCC(C(C)(C)C)CC2)NCC(=O)[C@H](Cc2cccc(Cl)c2)NC(=O)[C@H]([C@@H](C)O)NC(=O)[C@H](Cc2ccc(Cl)cc2)N(C)C(=O)[C@H](Cc2cccc(Cl)c2)NC(=O)[C@H](Cc2c[nH]c3ccccc23)NC(=O)[C@H]([C@@H](C)O)NC1=O]

TABLE 5-2-continued
PS-51
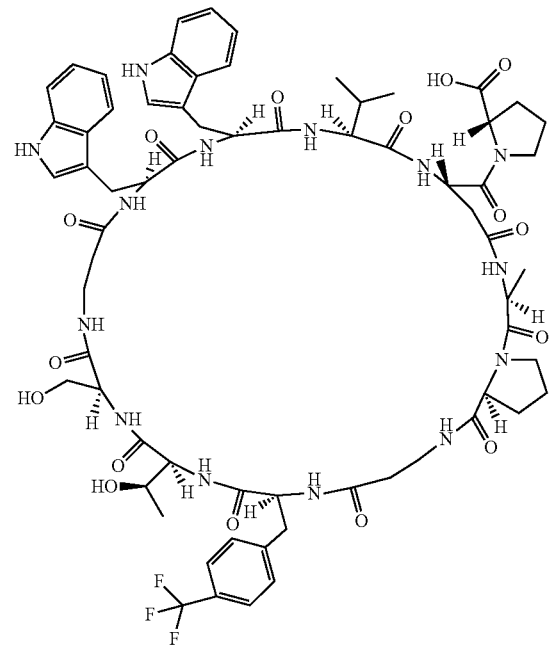 [SMILES: CC(C)[C@@H]1NC(=O)[C@H](Cc2c[nH]c3ccccc23)NC(=O)[C@H](Cc2c[nH]c3ccccc23)NC(=O)CCNC(=O)[C@H](CO)NC(=O)[C@H]([C@@H](C)O)NC(=O)[C@H](Cc2ccc(C(F)(F)F)cc2)NC(=O)CCNC(=O)[C@@H]2CCCN2C(=O)[C@H](C)NC(=O)C[C@@H](C(=O)N2CCC[C@H]2C(=O)O)NC1=O]
PS-52
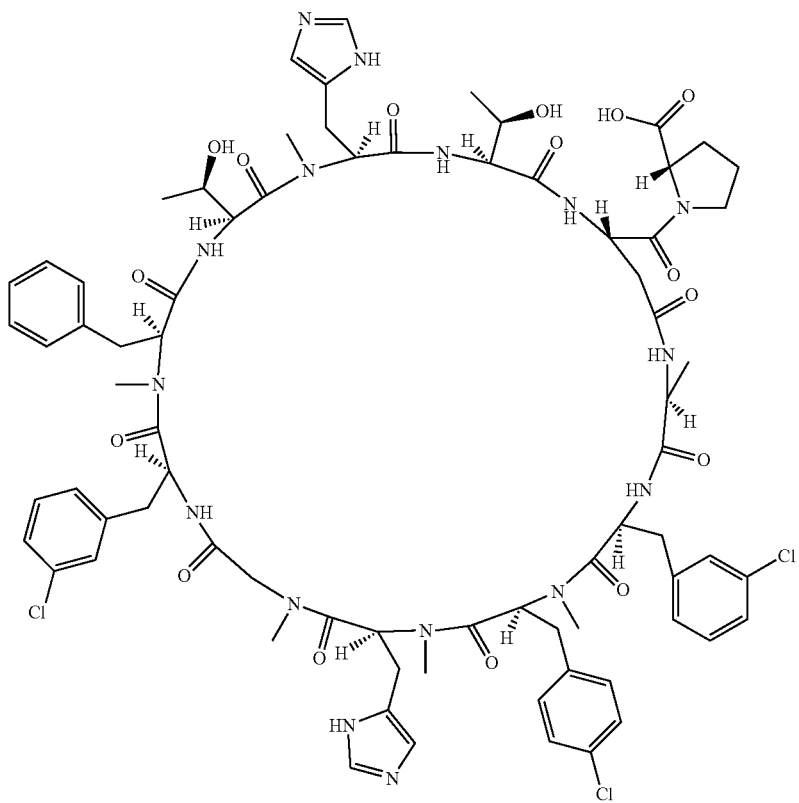 [SMILES: C[C@@H]1NC(=O)C[C@@H](C(=O)N2CCC[C@H]2C(=O)O)NC(=O)[C@H]([C@@H](C)O)NC(=O)[C@H](Cc2cnc[nH]2)N(C)C(=O)[C@H]([C@@H](C)O)NC(=O)[C@H](Cc2ccccc2)N(C)C(=O)[C@H](Cc2cccc(Cl)c2)NC(=O)CN(C)C(=O)[C@H](Cc2cnc[nH]2)N(C)C(=O)[C@H](Cc2ccc(Cl)cc2)N(C)C(=O)[C@H](Cc2cccc(Cl)c2)NC1=O]

TABLE 5-2-continued
PS-53
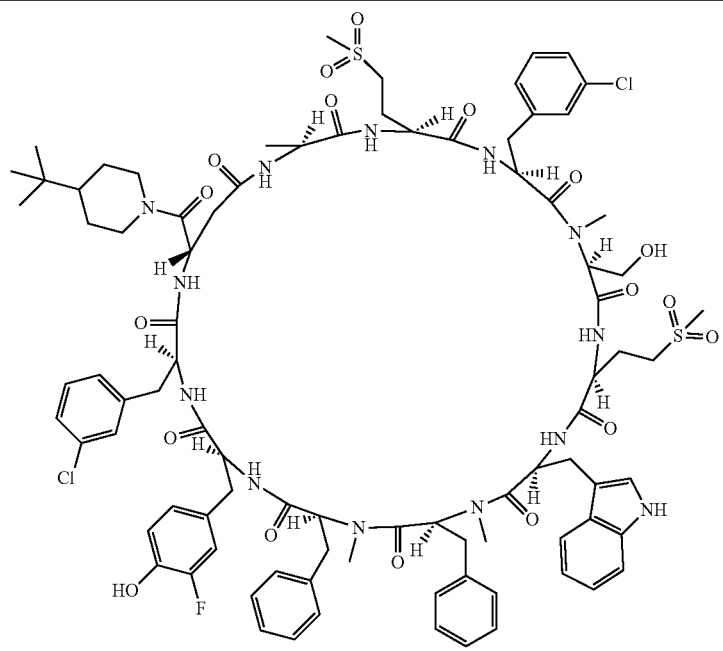
PS-54
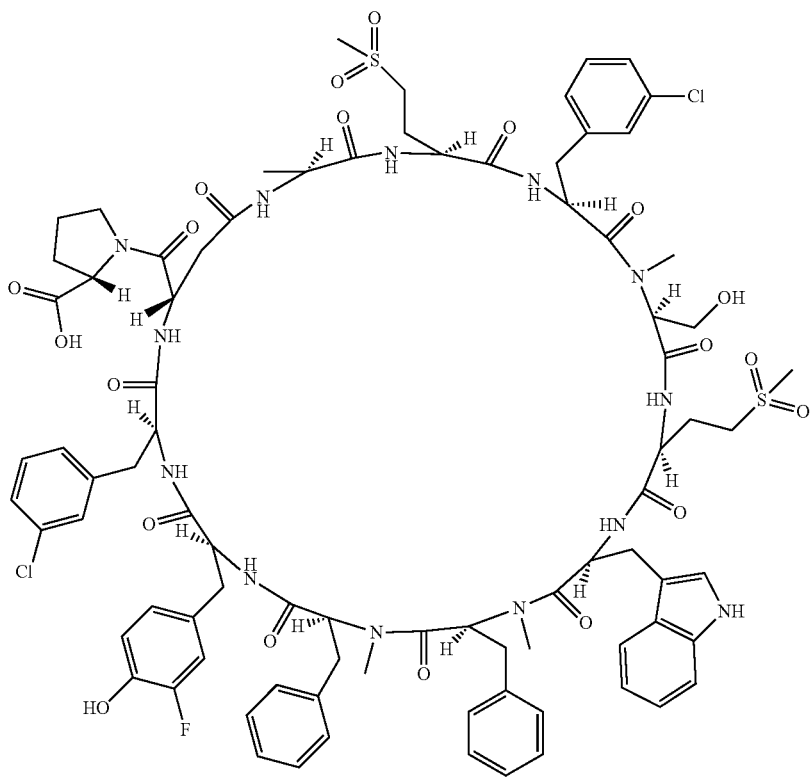 [SMILES: C[C@@H]1NC(=O)C[C@@H](C(=O)N2CCC[C@H]2C(=O)O)NC(=O)[C@H](Cc2cccc(Cl)c2)NC(=O)[C@H](Cc2ccc(O)c(F)c2)NC(=O)[C@H](Cc2ccccc2)N(C)C(=O)[C@H](Cc2ccccc2)N(C)C(=O)[C@H](Cc2c[nH]c3ccccc23)NC(=O)[C@H](CCS(C)(=O)=O)NC(=O)[C@H](CO)N(C)C(=O)[C@H](Cc2cccc(Cl)c2)NC(=O)[C@H](CCS(C)(=O)=O)NC1=O]
| | TABLE 5-3 | | | | | | TABLE 5-3-continued | | | |
|---|---|---|---|---|---|---|---|---|---|---|
| | LCMS Condition | Retention Time (min) | LCMS (ESI) m/z | Purity (%) | Yield (mg) | | LCMS Condition | Retention Time (min) | LCMS (ESI) m/z | Purity (%) | Yield (mg) |
| PS-1 | SQDFA05 | 0.75 | 1682.8 (M + H)+ | 85 | 4.81 | PS-3 | SQDFA05 | 0.98 | 1726.7 (M + H)+ | 90 | 8.08 |
| PS-2 | SQDFA05 | 1.09 | 1689.7 (M + H)+ | 95 | 5.15 | PS-4 | SQDFA05 | 1.04 | 1650.8 (M + H)+ | 95 | 13.82 |

TABLE 5-3-continued

| | LCMS Condition | Retention Time (min) | LCMS (ESI) m/z | | Purity (%) | Yield (mg) |
|---|---|---|---|---|---|---|
| PS-5 | SQDFA05 | 0.74 | 1698.8 | (M + H)+ | 95 | 4.9 |
| PS-6 | SQDFA05 | 1.08 | 1705.9 | (M + H)+ | 95 | 10.61 |
| PS-7 | SQDFA05 | 1.02 | 1744.7 | (M + H)+ | 95 | 6.53 |
| PS-8 | SQDFA05 | 6.57 | 1654.7 | (M + H)+ | 95 | 8.86 |
| PS-9 | SQDFA05 | 0.93 | 1663.5 | (M + H)+ | 95 | 9.09 |
| PS-10 | SQDFA05 | 0.84 | 1700.7 | (M + H)+ | 90 | 10.5 |
| PS-11 | SQDFA05 | 0.89 | 1624.7 | (M + H)+ | 95 | 11.32 |
| PS-12 | SQDFA05 | 0.58 | 1670.7 | (M + H)+ | 95 | 3.32 |
| PS-13 | SQDFA05 | 0.92 | 1679.6 | (M + H)+ | 95 | 8.71 |
| PS-14 | SQDFA05 | 0.83 | 1716.7 | (M + H)+ | 95 | 7.4 |
| PS-15 | SQDFA05 | 0.88 | 1640.7 | (M + H)+ | 95 | 7.9 |
| PS-16 | SQDFA05 | 0.99 | 1541.9 | (M + H)+ | 70 | 4.94 |
| PS-17 | SQDFA05 | 0.81 | 1589.9 | (M + H)+ | 85 | 11.3 |
| PS-18 | SQDFA05 | 1.06 | 1806.8 | (M + H)+ | 90 | 11.94 |
| PS-19 | SQDFA05 | 1.08 | 1662.8 | (M + H)+ | 90 | 13.25 |
| PS-20 | SQDFA05 | 1.02 | 1559.7 | (M + H)+ | 60 | 1.77 |
| PS-21 | SQDFA05 | 0.93 | 1663.9 | (M + H)+ | 90 | 4.33 |
| PS-22 | SQDFA05 | 1.05 | 1822.8 | (M + H)+ | 90 | 11.56 |
| PS-23 | SQDFA05 | 1.07 | 1678.8 | (M + H)+ | 95 | 6.02 |
| PS-24 | SQDFA05 | 0.79 | 1515.7 | (M + H)+ | 75 | 3.52 |
| PS-25 | SQDFA05 | 0.76 | 1619.9 | (M + H)+ | 70 | 8.35 |
| PS-26 | SQDFA05 | 0.88 | 1778.5 | (M + H)+ | 80 | 11.88 |
| PS-27 | SQDFA05 | 0.91 | 1636.8 | (M + H)+ | 80 | 13.93 |
| PS-28 | SQDFA05 | 0.77 | 1531.7 | (M + H)+ | 70 | 6.43 |
| PS-29 | SQDFA05 | 0.73 | 1635.7 | (M + H)+ | 91 | 3.78 |
| PS-30 | SQDFA05 | 0.87 | 1794.7 | (M + H)+ | 95 | 11.86 |
| PS-31 | SQDFA05 | 0.91 | 1652.7 | (M + H)+ | 83 | 10.33 |
| PS-32 | SQDFA05 | 0.74 | 1574.7 | (M + H)+ | 95 | 13.75 |
| PS-33 | SQDFA05 | 0.86 | 1674.6 | (M + H)+ | 94 | 15.42 |
| PS-34 | SQDFA05 | 0.84 | 1606.6 | (M + H)+ | 95 | 12.53 |
| PS-35 | SGDFA05 | 0.89 | 1512.7 | (M + H)+ | 95 | 16.18 |
| PS-36 | SQDFA05 | 0.53 | 1379.7 | (M + H)+ | 80 | 2.12 |
| PS-37 | SQDFA05 | 0.73 | 1590.7 | (M + H)+ | 95 | 15.65 |
| PS-38 | SQDFA05 | 0.85 | 1690.4 | (M + H)+ | 95 | 11.25 |
| PS-39 | SQDFA05 | 0.82 | 1622.6 | (M + H)+ | 95 | 11.33 |
| PS-40 | SQDFA05 | 0.87 | 1528.7 | (M + H)+ | 94 | 11.61 |
| PS-41 | SQDFA05 | 0.73 | 1391.7 | (M + H)+ | 90 | 2.32 |
| PS-42 | SQDFA05 | 0.92 | 1602.7 | (M + H)+ | 90 | 6.54 |
| PS-43 | SQDFA05 | 1.02 | 1700.6 | (M + H)+ | 90 | 5.83 |
| PS-44 | SQDFA05 | 0.91 | 1618.9 | (M + H)+ | 90 | 4.85 |
| PS-45 | SQDFA05 | 1.00 | 1716.7 | (M + H)+ | 90 | 3.93 |
| PS-46 | SQDFA05 | 0.98 | 1648.7 | (M + H)+ | 90 | 4.77 |
| PS-47 | SQDFA05 | 0.99 | 1632.7 | (M + H)+ | 90 | 3.64 |
| PS-48 | SQDFA05 | 0.96 | 1482.7 | (M + H)+ | 90 | 4.81 |
| PS-49 | SQDFA05 | 0.97 | 1648.7 | (M + H)+ | 90 | 3.15 |
| PS-50 | SQDFA05 | 1.05 | 1554.8 | (M + H)+ | 90 | 6.01 |
| PS-51 | SQDFA05 | 0.62 | 1396.7 | (M + H)+ | 71 | 2.98 |
| PS-52 | SQDFA05 | 0.56 | 1577.6 | (M + H)+ | 95 | 6.4 |
| PS-53 | SQDFA05 | 0.93 | 1788.7 | (M + H)+ | 89 | 7.4 |
| PS-54 | SQDFA05 | 0.78 | 1762.7 | (M + H)+ | 85 | 2.8 |

Example 7 Application of the Present Invention to the Liquid Phase Method

Synthesis including elongation reaction by the liquid phase method is shown below.

Partial Application to Liquid Phase Methods

Figure 21:
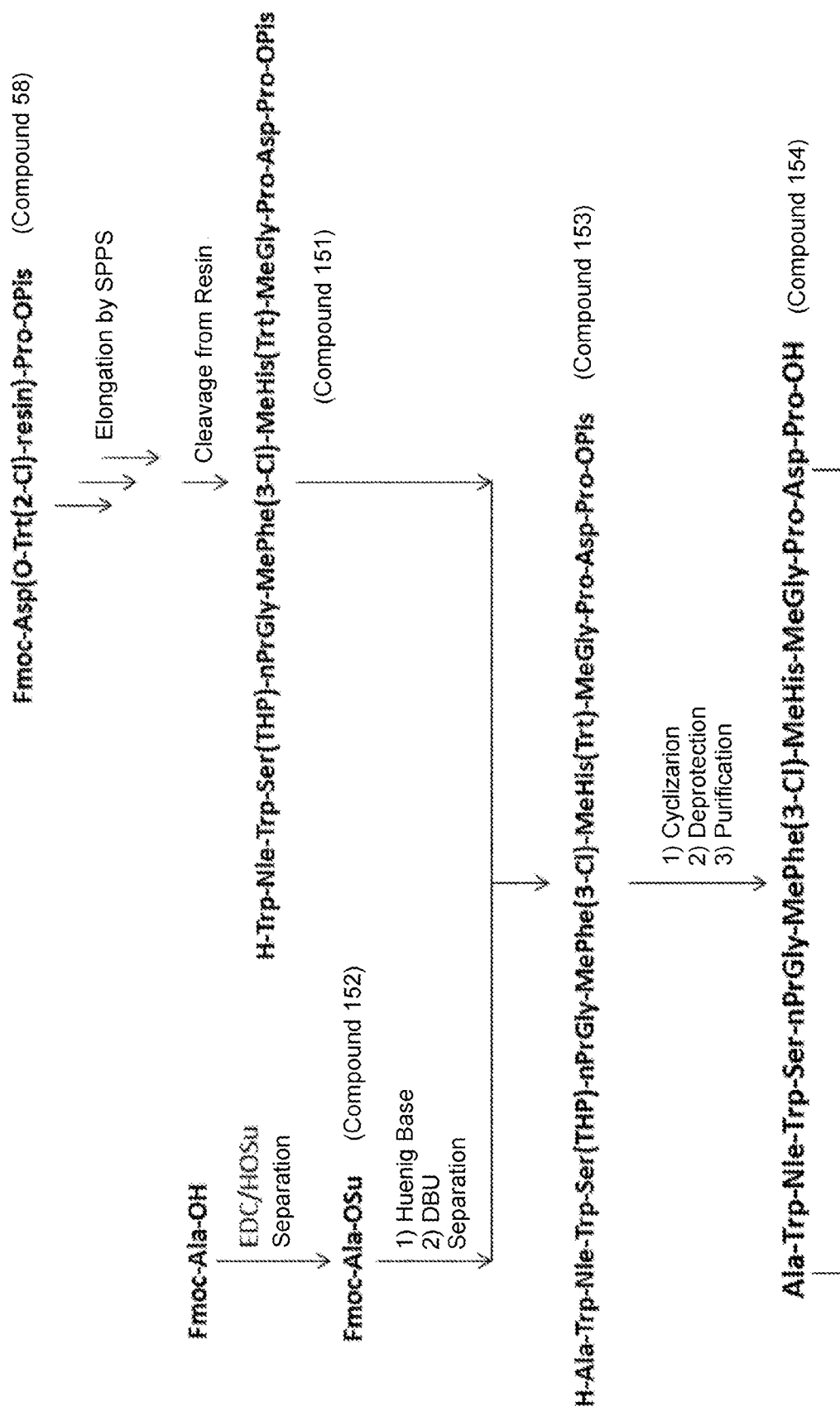
FIG. 21 shows the synthesis method including elongation reaction in the liquid phase.

Synthesis of the Cyclic Peptide (Compound 154. Cyclic Peptide in which an Amide Bond was Formed Between the Main Chain N-Terminal Amino Group of H-Ala-Trp-Nle-Trp-Ser-nPrGly-MePhe(3-Cl)-MeHis-MeGly-Pro-Asp-Pro-OH and the Side-Chain Carboxylic Acid Group of Asp), Which Includes Coupling of Fmoc-Ala-OSu (Compound 152) with H-Trp-Nle-Trp-Ser(THP)-nPrGly-MePhe(3-Cl)-MeHis(Trt)-MeGly-Pro-Asp-Pro-OPis (Compound 151) in the Liquid Phase The peptide was synthesized by the synthetic route described in FIG. 21 which includes elongation reaction by the liquid phase method.

Example 7-1

Synthesis of H-Trp-Nle-Trp-Ser(THP)-nPrGly-MePhe(3-Cl)-MeHis(Trt)-MeGly-Pro-Asp-Pro-OPis (Compound 151)

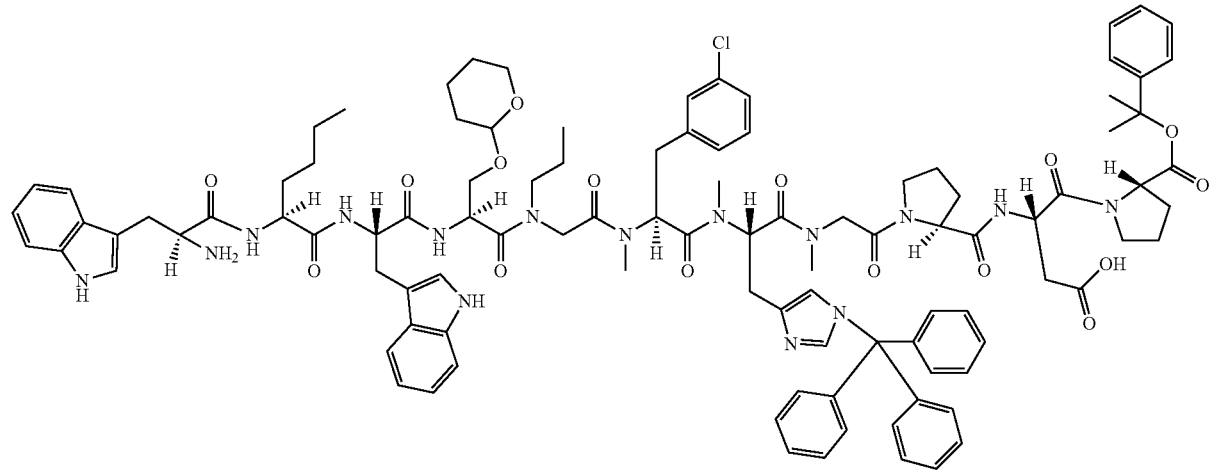

Compound 151

Peptide elongation was performed according to the peptide synthesis method by the Fmoc method already described in the Examples, using Fmoc-Asp(O-Trt(2-Cl)-resin)-Pro-OPis (Compound 58, loading rate: 0.3736 mmol/g, 200 mg) synthesized by the already described method. After peptide elongation, removal of the N-terminal Fmoc group was performed on the peptide synthesizer, and the resin was washed using DMF.

Then, after swelling the resin again with DCM, TFE/DCM (1/1, v/v, 4 mL) and diisopropylethylamine (24 µL) were added to the resin, this was shaken at room temperature for two hours, and the peptide was cleaved off from the resin. Next, the resin was removed by filtering the solution inside the tube through a column for synthesis, and the remaining resin was further washed twice with TFE/DCM (1/1, v/v, 2 mL). All of the obtained cleavage solutions were mixed, concentrated under reduced pressure, and the titled compound (Compound 151, H-Trp-Nle-Trp-Ser(THP)-nPr-Gly-MePhe(3-Cl)-MeHis(Trt)-MeGly-Pro-Asp-Pro-OPis: 113.8 mg) was obtained. This was used in the next step without purification.

LCMS (ESI) m/z=1860.9 (M+H)$^+$

Retention time: 0.72 minutes (analysis condition SQDFA05)

Example 7-2

Synthesis of (S)-2,5-dioxopyrrolidin-1-yl 2-((((9H-fluoren-9-yl)methoxy)carbonyl)amino)propanoate (Compound 152, Fmoc-Ala-OSu)

Compound 152

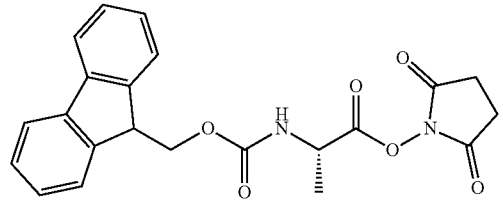

(S)-2-((((9H-fluoren-9-yl)methoxy)carbonyl)amino)propanoic acid (Fmoc-Ala-OH; 1.00 g, 3.21 mmol), 1-hydroxypyrrolidin-2,5-dione (HOSu; 0.554 g, 4.82 mmol), and dichloromethane (6.4 mL) were mixed under nitrogen atmosphere. This mixture was cooled on ice to 0° C., 1-ethyl-3-(3-dimethylaminopropyl)carbodiimide hydrochloride (WSCI·HCl, 0.924 g, 4.82 mmol) was added, and the obtained reaction solution was stirred at 0° C. for one hour and at room temperature for 15 hours. Next, the solvent was distilled off under reduced pressure, and the obtained residue was purified by reverse-phase silica gel chromatography (0.1% aqueous formic acid solution/0.1% formic acid solution in acetonitrile) to obtain (S)-2,5-dioxopyrrolidin-1-yl 2-((((9H-fluoren-9-yl)methoxy)carbonyl)amino)propanoate (Compound 152, Fmoc-Ala-OSu, 1.05 g)

LCMS (ESI) m/z=409.3 (M+H)$^+$

Retention time: 0.80 minutes (analysis condition SQDFA05)

Example 7-3

Coupling Between (S)-2,5-dioxopyrrolidin-1-yl 2-((((9H-fluoren-9-yl)methoxy)carbonyl)amino) propanoate (Compound 152, Fmoc-Ala-OSu) and H-Trp-Nle-Trp-Ser(THP)-nPrGly-MePhe(3-Cl)-MeHis(Trt)-MeGly-Pro-Asp-Pro-OPis (Compound 151), and the Subsequent Fmoc Removal Reaction

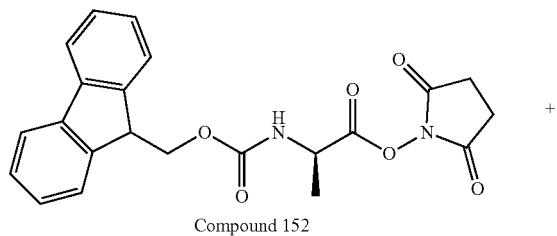

Compound 152

+

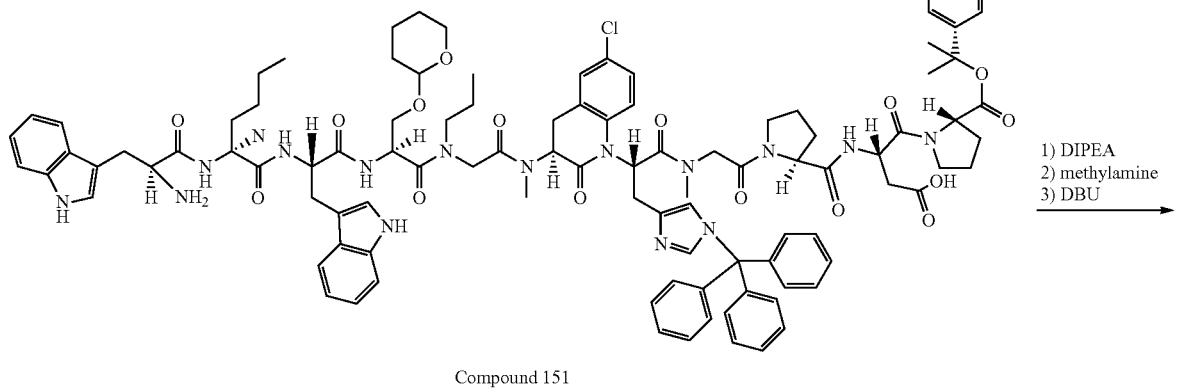

Compound 151

1) DIPEA
2) methylamine
3) DBU

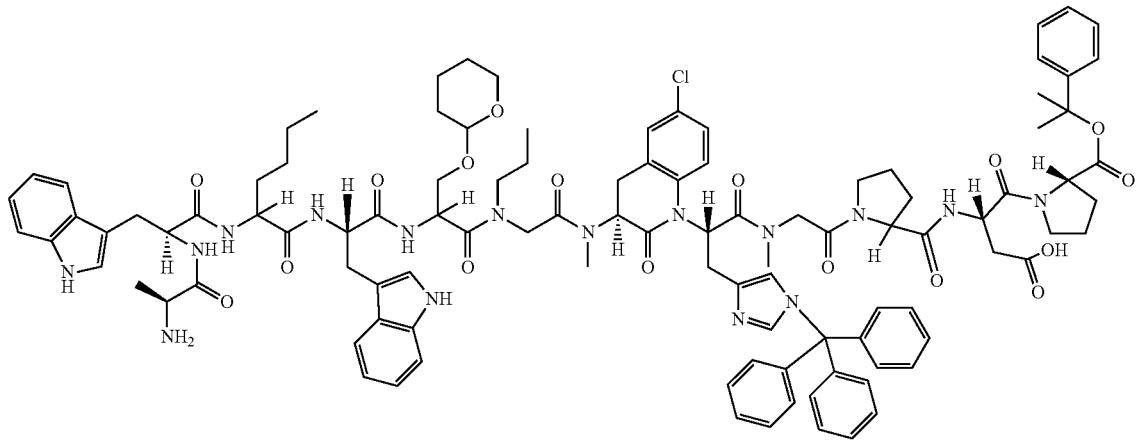

Compound 153

(S)-2,5-Dioxopyrrolidin-1-yl 2-((((9H-fluoren-9-yl)methoxy)carbonyl)-amino)propanoate (Compound 152, Fmoc-Ala-OSu, 26.2 mg) and diisopropylethylamine (DIPEA, 12.8 µL) were added to a solution of the obtained H-Trp-Nle-Trp-Ser(THP)-nPrGly-MePhe(3-Cl)-MeHis(Trt)-MeGly-Pro-Asp-Pro-OPis (Compound 151, 113.8 mg) in dichloromethane (245 µL), and this was stirred at 25° C. for one hour. Next, methylamine (40% solution in methanol, 11.9 µL) was added to the reaction solution, this was stirred for 30 minutes. Then, DBU (11.1 µL) was added, and this was stirred for another 30 minutes. The obtained reaction solution was purified by reverse-phase silica gel column chromatography (0.1% aqueous formic acid solution/0.1% formic acid solution in acetonitrile), and the obtained fractions were freeze-dried. The obtained residue was dissolved in dichloromethane, and this washed with saturated aqueous sodium hydrogen carbonate solution and saturated aqueous sodium chloride solution to obtain H-Ala-Trp-Nle-Trp-Ser(THP)-nPrGly-MePhe(3-Cl)-MeHis(Trt)-MeGly-Pro-Asp-Pro-OPis (Compound 153: 79.3 mg, 0.041 mmol).

LCMS (ESI) m/z=1931.8 (M+H)$^+$

Retention time: 0.73 minutes (analysis condition SQDFA05)

Example 7-4

Synthesis of the Compound in which Amide Cyclization is Accomplished Between the N-Terminal Amino Group of H-Ala-Trp-Nle-Trp-Ser-nPrGly-MePhe(3-Cl)-MeHis-MeGly-Pro-Asp-Pro-OH and the Side-Chain Carboxylic Acid Group of Asp (Compound 154) (Cyclization Reaction of Compound 153, and the Subsequent Deprotection Reaction)

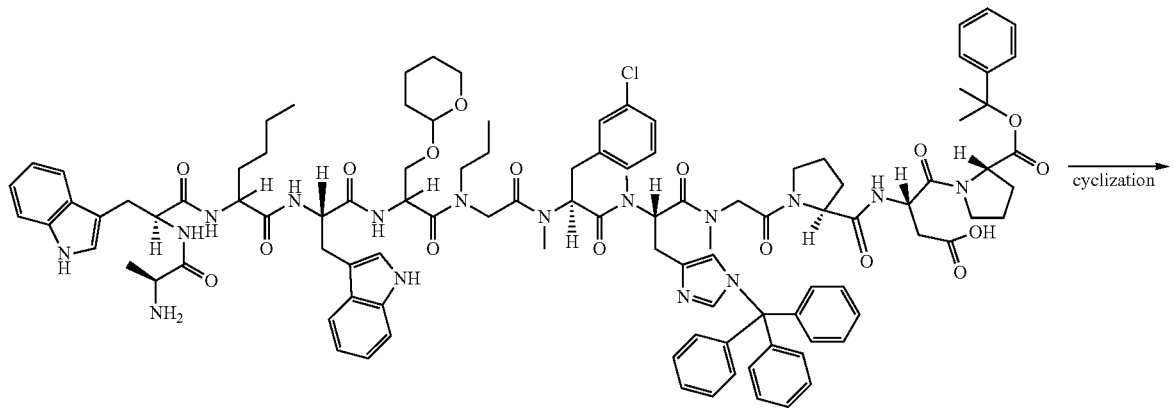

Compound 153

-continued

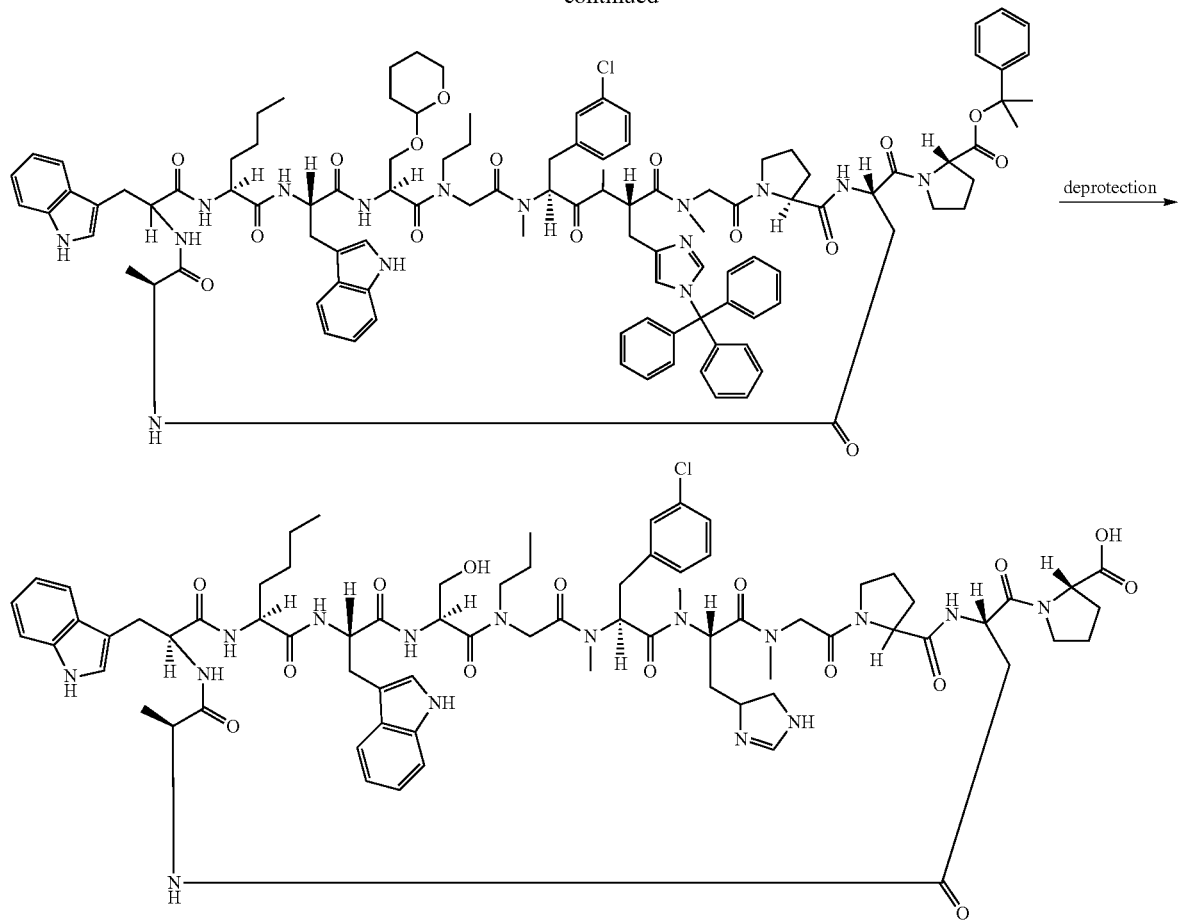

Compound 154

The obtained H-Ala-Trp-Nle-Trp-Ser(THP)-nPrGly-MePhe(3-CO-MeHis(Trt)-MeGly-Pro-Asp-Pro-OPis (Compound 153; 79.3 mg, 0.041 mmol) was dissolved in DMF (20 mL) and dichloromethane (20 mL), HATU (17.2 mg, 0.045 mmol) and diisopropylethylamine (10.8 μL, 0.062 mmol) were added, and this was stirred at 25° C. for two hours. Subsequently, the solvent was distilled off under reduced pressure. Then, 0.05 M tetramethylammonium hydrogen sulfate/HFIP (2% TIPS) solution (prepared by the method already described in the Examples, 8 mL) was added and this was left to stand at 25° C. for one hour. Diisopropylethylamine (140 μL) was added to the obtained reaction solution and the solvent was distilled off under reduced pressure. The obtained residue was purified by reverse-phase silica gel column chromatography (0.1% aqueous formic acid solution/0.1% formic acid solution in acetonitrile), and the obtained fractions were freeze-dried to obtain the compound in which amide cyclization is accomplished between the N-terminal amino group of H-Ala-Trp-Nle-Trp-Ser-nPrGly-MePhe(3-Cl)-MeHis-MeGly-Pro-Asp-Pro-OH and the side-chain carboxylic acid group of Asp (Compound 154; 59 mg, 0.040 mmol, 98%).

LCMS (ESI) m/z=1469.7 (M+H)+
Retention time: 0.61 minutes (analysis condition SQDFA05)

As in the above-described peptide syntheses which include segment coupling in the liquid phase, the synthesis methods of the present invention can be applied to liquid-phase methods as well.

INDUSTRIAL APPLICABILITY

According to the present invention, peptides containing N-substituted amino acids, which are expected to be useful as pharmaceuticals, can be synthesized with high purity and high synthetic efficiency. The present invention is useful in fields such as industrial production of peptides comprising N-substituted amino acids, which may become raw materials for pharmaceuticals.

The invention claimed is:
1. A method of producing a peptide comprising at least one N-alkylated amino acid or proline, wherein the N-alkyl of the N-alkylated amino acid and the proline are optionally substituted with a substituent independently selected from the group consisting of a halogen group, an ether group, and a hydroxyl group;
wherein the method comprises the steps of:
1) preparing an (Fmoc-protected amino acid comprising at least one each of following functional groups i) and ii), an Fmoc-protected peptide comprising the Fmoc-protected amino acid:

i) a main chain amino group protected by at least one protecting group having an Fmoc skeleton; and
ii) at least one free carboxylic acid group or active esterified carboxylic acid group;
2) converting at least one free carboxylic acid group or active esterified carboxylic acid group in the Fmoc-protected amino acid, or the Fmoc-protected peptide prepared in step 1) into an ester group;
3) deprotecting the protecting group having the Fmoc-skeleton of the Fmoc-protected amino acid, or the Fmoc-protected peptide, by using a base to expose its amino group;
4) forming an amide bond by adding a new Fmoc-protected amino acid, or a new Fmoc-protected peptide; and
5) converting the ester group into a carboxylic acid group under a condition having weaker acidity than TFA, and the step performed under the condition having weaker acidity than TFA is performed using a weakly acidic solution containing a fluoroalcohol.

2. The production method of claim 1, wherein peptide production is carried out by a solid phase method.

3. The production method of claim 1, wherein peptide production is carried out by a liquid phase method.

4. The production method of claim 1, wherein step 4) further comprises the steps of:
deprotecting the protecting group having the Fmoc skeleton on the newly added Fmoc-protected amino acid, or the newly added Fmoc-protected peptide, by using a base to expose its amino group; and
forming an amide bond by further adding a new Fmoc-protected amino acid, or a new Fmoc-protected peptide, and wherein these steps are repeated once or multiple times.

5. The production method of any one of claims 1, 2, 3, and 4, wherein the produced peptide comprises on its C-terminal side an amino acid residue comprising one reactive site, and comprises on its N-terminal side an amino acid residue comprising the other reactive site.

6. The production method of claim 5, which further comprises the step of bonding said reactive site and said other reactive site to cyclize the peptide.

7. The production method of claim 6, wherein the amino acid residue having said other reactive site is at the N terminus and the bonding is an amide bonding.

8. The production method of claim 1, wherein at least one side chain of the amino acid constituting a peptide obtained in step 4) has a protecting group that is not deprotected under a basic condition and is deprotected under a condition having weaker acidity than TFA, and the step performed under the condition having weaker acidity than TFA is performed using a weakly acidic solution comprising a weak acid having an aqueous pKa value of 0 to 9 in a solvent having an aqueous pKa value of 5 to 14 and whose ionization ability value $Y_{OTs}$ is positive.

9. The production method of claim 8, wherein the solvent having an aqueous pKa value of 5 to 14 and whose ionization ability value $Y_{OTs}$ is positive is fluoroalcohol.

10. The production method of claim 9, wherein the fluoroalcohol is TFE or HFIP.

11. The production method of claim 8, wherein the side chain protecting group is a protecting group which is capable of being deprotected in the range of pH 1 to pH 7, or a protecting group which is capable of being deprotected in 10% or lower concentration of TFA.

12. The production method of claim 8, wherein the side chain protecting group is selected from following a) to d):

a) when the side chain protecting group is a protecting group for the side chain hydroxyl group of Ser, Thr, Hyp, and derivatives thereof, any one protecting group selected from a MOM skeleton, a Bn skeleton, a Dpm skeleton, a Trt skeleton, a silyl skeleton, and a Boc skeleton represented by the general formulae below;
b) when the side chain protecting group is a protecting group for the side chain hydroxyl group of Tyr and derivatives thereof, any one protecting group selected from a MOM skeleton, a Bn skeleton, a Dpm skeleton, a Trt skeleton, a silyl skeleton, a Boc skeleton, and a tBu skeleton represented by the general formulae below;
c) when the side chain protecting group is a protecting group for the side chain imidazole ring of His and derivatives thereof, any one protecting group selected from a MOM skeleton, a Bn skeleton, and a Trt skeleton represented by the general formulae below; and
d) when the side chain protecting group is a protecting group for the side chain carboxylic acid group of Asp, Glu, and derivatives thereof, any one protecting group selected from a MOM skeleton, a Bn skeleton, a Dpm skeleton, a Trt skeleton, a tBu skeleton, a phenyl-EDOTn skeleton, which are represented by the following general formulae, and an orthoester skeleton in which a carbon atom of the carboxylic acid group to be protected is substituted with three alkoxy groups:
wherein the protecting group having a MOM skeleton has the following formula:

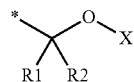

wherein
R1 is H, R2 is H, and X is methyl, benzyl, 4-methoxybenzyl, 2,4-dimethoxybenzyl, 3,4-dimethoxybenzyl, or 2-trimethylsilylethyl;
R1 is methyl, R2 is H, and X is ethyl;
R1, R2, and R3 are all methyl; or
R1 and X together form —CH$_2$—CH$_2$—CH$_2$— or —CH$_2$—CH$_2$—CH$_2$—CH$_2$—, and R2 is H,
wherein when any one of R1, R2, and X is methyl or ethyl, these groups may further be substituted with alkyl, benzyl, or aryl;
wherein the protecting group having a Bn skeleton has the following formula:

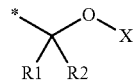

wherein
R1 to R5 are each independently H, alkyl, aryl, or halogen, and R6 and R7 are alkyl;
R1, R2, R4, and R5 are each independently H, alkyl, aryl, or halogen, R3 is methoxy, and R6 and R7 are H;
R1 and R3 are methoxy, R2, R4, and R5 are each independently H, alkyl, aryl, or halogen, and R6 and R7 are H; or R1, R4, and R5 are each independently H, alkyl, aryl, or halogen, and R2 and R3 together form —O—CH2-O—;

wherein the protecting group having a Dpm skeleton has the following formula:

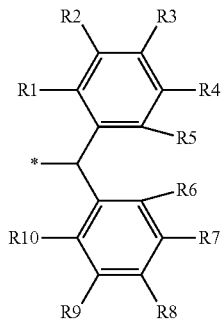

wherein
R1 to R10 are each independently H, alkyl, aryl, alkoxy, or halogen; or
R1 to R4 and R7 to R10 are each independently H, alkyl, aryl, alkoxy, or halogen, and R5 and R6 together form —O— or —CH2-CH2-;

wherein the protecting group having a Trt skeleton has the following formula:

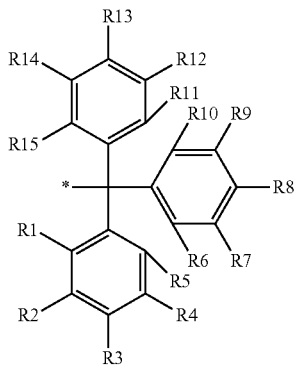

wherein
R1 to R15 are each independently H, alkyl, aryl, alkoxy, or halogen;
R1, R2, and R4 to R15 are each independently H, alkyl, aryl, alkoxy, or halogen, and R3 is methyl or methoxy;
R1 is Cl, and R2 to R15 are each independently H, alkyl, aryl, alkoxy, or halogen; or
R1 to R4 and R7 to R15 are each independently H, alkyl, aryl, alkoxy, or halogen, and R5 and R6 together form —O—;

wherein the protecting group having a silyl skeleton has the following formula:

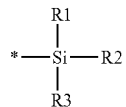

wherein R1 to R3 are each independently alkyl or aryl;
wherein the protecting group having a Boc skeleton has the following formula:

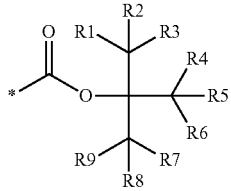

wherein R1 to R9 are each independently H, alkyl, or aryl;
wherein the protecting group having a tBu skeleton has the following formula:

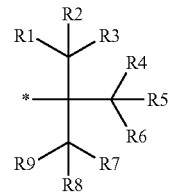

wherein
R1 to R9 are each independently H, alkyl, or aryl; and
wherein the protecting group having a phenyl-EDOTn skeleton has the following formula:

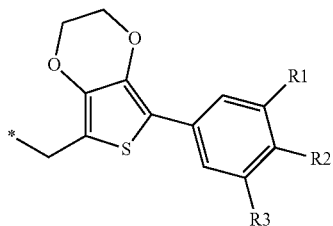

wherein R1 to R3 are each independently H or methoxy.

* * * * *